US007919320B2

(12) United States Patent
Metz et al.

(10) Patent No.: US 7,919,320 B2
(45) Date of Patent: *Apr. 5, 2011

(54) PUFA POLYKETIDE SYNTHASE SYSTEMS AND USES THEREOF

(75) Inventors: James G. Metz, Longmont, CO (US); James H. Flatt, Colorado Springs, CO (US); Jerry M. Kuner, Longmont, CO (US); William R. Barclay, Boulder, CO (US)

(73) Assignee: Martek Biosciences Corporation, Columbia, MD (US)

( * ) Notice: Subject to any disclaimer, the term of this patent is extended or adjusted under 35 U.S.C. 154(b) by 605 days.

This patent is subject to a terminal disclaimer.

(21) Appl. No.: 11/777,277

(22) Filed: Jul. 12, 2007

(65) Prior Publication Data
US 2010/0024050 A1  Jan. 28, 2010

Related U.S. Application Data

(63) Continuation of application No. 10/124,800, filed on Apr. 16, 2002, now Pat. No. 7,247,461, and a continuation-in-part of application No. 09/231,899, filed on Jan. 14, 1999, now Pat. No. 6,566,583.

(60) Provisional application No. 60/323,269, filed on Sep. 18, 2001, provisional application No. 60/298,796, filed on Jun. 15, 2001, provisional application No. 60/284,066, filed on Apr. 16, 2001.

(51) Int. Cl.
*C12N 5/02* (2006.01)
*C12N 1/00* (2006.01)
*C12N 15/00* (2006.01)
*C12N 15/82* (2006.01)
*C07H 21/04* (2006.01)
*A01H 9/00* (2006.01)

(52) U.S. Cl. .................. 435/410; 435/252.3; 435/254.1; 435/320.1; 536/23.2; 800/278; 800/295

(58) Field of Classification Search .......................... None
See application file for complete search history.

(56) References Cited

U.S. PATENT DOCUMENTS

| | | | |
|---|---|---|---|
| 5,130,242 A | 7/1992 | Barclay et al. |
| 5,246,841 A | 9/1993 | Yazawa et al. |
| 5,310,242 A | 5/1994 | Golder |
| 5,639,790 A | 6/1997 | Voelker et al. |
| 5,672,491 A | 9/1997 | Khosla et al. |
| 5,683,898 A | 11/1997 | Yazawa et al. |
| 5,798,259 A | 8/1998 | Yazawa et al. |
| 5,908,622 A | 6/1999 | Barclay |
| 6,033,883 A | 3/2000 | Barr et al. |
| 6,140,486 A | 10/2000 | Facciotti et al. |
| 6,503,706 B1 | 1/2003 | Abken et al. |
| 6,566,583 B1 | 5/2003 | Facciotti et al. |
| 6,677,145 B2 | 1/2004 | Mukerji et al. |
| 7,001,772 B2 | 2/2006 | Roessler et al. |
| 7,087,432 B2 | 8/2006 | Qiu et al. |
| 7,125,672 B2 | 10/2006 | Picataggio et al. |
| 7,208,590 B2 | 4/2007 | Mukerji et al. |
| 7,211,418 B2 | 5/2007 | Metz et al. |
| 7,214,853 B2 | 5/2007 | Facciotti et al. |
| 7,217,856 B2 | 5/2007 | Weaver et al. |
| 7,247,461 B2 | 7/2007 | Metz et al. |
| 7,256,022 B2 | 8/2007 | Metz et al. |
| 7,256,023 B2 | 8/2007 | Metz et al. |
| 7,259,295 B2 | 8/2007 | Metz et al. |
| 7,271,315 B2 | 9/2007 | Metz et al. |
| 2004/0005672 A1 | 1/2004 | Santi et al. |
| 2004/0010817 A1 | 1/2004 | Shockey et al. |
| 2004/0139498 A1 | 7/2004 | Jaworski et al. |
| 2004/0172682 A1 | 9/2004 | Kinney et al. |
| 2005/0089865 A1 | 4/2005 | Napier et al. |
| 2005/0164192 A1 | 7/2005 | Graham et al. |
| 2007/0244192 A1 | 10/2007 | Metz |
| 2007/0245431 A1 | 10/2007 | Metz et al. |
| 2007/0256146 A1 | 11/2007 | Metz et al. |
| 2007/0266455 A1 | 11/2007 | Weaver et al. |
| 2007/0270494 A1 | 11/2007 | Metz et al. |
| 2008/0022422 A1 | 1/2008 | Weaver et al. |
| 2008/0026434 A1 | 1/2008 | Weaver et al. |
| 2008/0026435 A1 | 1/2008 | Weaver et al. |
| 2008/0026436 A1 | 1/2008 | Weaver et al. |
| 2008/0026437 A1 | 1/2008 | Weaver et al. |
| 2008/0032296 A1 | 2/2008 | Weaver et al. |
| 2008/0032338 A1 | 2/2008 | Weaver et al. |
| 2008/0032367 A1 | 2/2008 | Weaver et al. |

(Continued)

FOREIGN PATENT DOCUMENTS

CA  2520795  10/2004

(Continued)

OTHER PUBLICATIONS

U.S. Appl. No. 11/674,574, filed Feb. 13, 2007, Facciotti et al. U.S. Appl. No. 11/778,594, filed Jul. 16, 2007, Metz et al.
U.S. Appl. No. 11/781,861, filed Jul. 23, 2007, Weaver et al.
U.S. Appl. No. 11/781,882, filed Jul. 23, 2007, Weaver et al.
Allen E.A. et al. 2002 "Structure and regulation of the omega-3 polyunsaturated fatty acid synthase genes from the deep-sea bacterium *Photobacterium profundum* strain SS9" Microbiology vol. 148 pp. 1903-1913.
GenBank Accession No. AF4091 00, (Allen et al.) 2002.
Kaulmann et al. "Biosynthesis of Polyunsaturated Fatty Acids by Polyketide Synthases", Angew. Chem. Int. Ed. 2002, 41, No. 11, pp. 1866-1869.

(Continued)

*Primary Examiner* — Nashaat T Nashed
(74) *Attorney, Agent, or Firm* — Sterne, Kessler, Goldstein & Fox P.L.L.C.

(57) ABSTRACT

The invention generally relates to polyunsaturated fatty acid (PUFA) polyketide synthase (PKS) systems isolated from or derived from non-bacterial organisms, to homologues thereof, to isolated nucleic acid molecules and recombinant nucleic acid molecules encoding biologically active domains of such a PUFA PKS system, to genetically modified organisms comprising PUFA PKS systems, to methods of making and using such systems for the production of bioactive molecules of interest, and to novel methods for identifying new bacterial and non-bacterial microorganisms having such a PUFA PKS system.

8 Claims, 3 Drawing Sheets

U.S. PATENT DOCUMENTS

| | | | |
|---|---|---|---|
| 2008/0032368 | A1 | 2/2008 | Weaver et al. |
| 2008/0032369 | A1 | 2/2008 | Weaver et al. |
| 2008/0038379 | A1 | 2/2008 | Metz et al. |
| 2008/0038793 | A1 | 2/2008 | Metz et al. |
| 2008/0038794 | A1 | 2/2008 | Metz et al. |
| 2008/0038795 | A1 | 2/2008 | Metz et al. |
| 2008/0038796 | A1 | 2/2008 | Metz et al. |
| 2008/0038797 | A1 | 2/2008 | Metz et al. |
| 2008/0038798 | A1 | 2/2008 | Weaver et al. |
| 2008/0038799 | A1 | 2/2008 | Weaver et al. |
| 2008/0040822 | A1 | 2/2008 | Metz et al. |
| 2008/0044868 | A1 | 2/2008 | Metz et al. |
| 2008/0044869 | A1 | 2/2008 | Metz et al. |
| 2008/0044870 | A1 | 2/2008 | Metz et al. |
| 2008/0044871 | A1 | 2/2008 | Metz et al. |
| 2008/0044872 | A1 | 2/2008 | Metz et al. |
| 2008/0044873 | A1 | 2/2008 | Metz et al. |
| 2008/0044874 | A1 | 2/2008 | Weaver et al. |
| 2008/0050790 | A1 | 2/2008 | Metz et al. |
| 2008/0050791 | A1 | 2/2008 | Weaver et al. |
| 2008/0148433 | A1 | 6/2008 | Metz et al. |

FOREIGN PATENT DOCUMENTS

| | | |
|---|---|---|
| EP | 0594868 | 5/1994 |
| EP | 0823475 | 2/1998 |
| WO | WO 93/23545 | 11/1993 |
| WO | WO 96/21735 | 7/1996 |
| WO | WO 98/46764 | 10/1998 |
| WO | WO 98/55625 | 12/1998 |
| WO | WO 00/42195 | 7/2000 |
| WO | WO 02/083870 | 10/2002 |
| WO | WO 2004/087879 | 10/2004 |
| WO | WO 2006/008099 | 1/2006 |
| WO | WO 2006/034228 | 3/2006 |

OTHER PUBLICATIONS

Khosla et al., "Tolerance and Specificity of Polyketide Synthases", Annu. Rev. Biochem. 1999. 68:219-253.
Nakahara et al. Production of docosahexaenoic and docosapentaenoic acids by *Schizochytrium* sp. isloated from Yap Islands. 1996 J. Am. Oil Chem. Soc. 1996, vol. 73, No. 11, pp. 1421-1426.
Nasu et al., "Efficient Transformation of *Marchantia polymorpha* That is Haploid and Has Very Small Genome DNA," Journal of Fermentation and Bioengineering vol. 84, No. 6, 519-523 1997.
Orikasa et al. Characterization of the eicosapentaenoic acid biosynthesis gene cluster from *Shewanella* sp. strain SCRC-2738, Cellular and Molecular Biology (Noisy-le-grand), Jul. 2004, vol. 50, No. 5, pp. 625-630.
Qiu et al. Identification of a delta4 fatty acid desaturase from *Thraustochytrium* sp. involved in the biosynthesis. J. Biol. Chem. Aug. 24, 2001, vol. 276, No. 34, pp. 31561-31566.
Satomi et al. *Shewanella marinintesina* sp. nov., *Shewanella schlegeliana* sp. nov. and *Shewanelia sairae* sp. nov., novel eicosapentaenoic-acid-producing marine bacteria isolated from seeanimal intestines. Internat. J. Syst. Evol. Microbiol. 2003, vol. 53, pp. 491-499.
Singh et al. Microbial Production of Docosahexaenoic Acid (DHA, C22:6) Adv. Appl. Microbial, 1997. vol. 45, pp. 271-312.
Takeyama et al. Expression of eicosapentaenoic acid synthesis gene clustter from *Shewanella* sp. in transgenic marine cyanobacterium. *Synechecoccus* sp. Microbiology. 1997, vol. 143, pp. 2725-2731.
UniProt Accession No. Q93CG6_PHOPR, (Allen et al.) 2002.
Weete et al. Lipids and Ultrastructure of *Thrauchytrium* sp. ATCC26185. 1997, Am Oil Chem. Soc. vol. 32, No. 8, pp. 839-845.
Yokochi et al. Optimization of docosahexaenoic acid production. App. Microbiol. Biotechnol. 1998, vol. 49, pp. 72-76.
International Search Report for International (PCT) Patent Application No. PCT/US00/00956, mailed Jul. 6, 2000.
Written Opinion for International (PCT) Patent Application No. PCT/US00/00956, mailed Dec. 19, 2000.
International Preliminary Examination Report for International (PCT) Patent Application No. PCT/US00/00956, mailed Apr. 19, 2001.
International Search Report for International (PCT) Patent Application No. PCT/US04/09323, mailed Apr. 4, 2007.
Written Opinion for International (PCT) Patent Application No. PCT/US04/09323, mailed Apr. 4, 2007.
International Preliminary Report on Patentability for International (PCT) Patent Application No. PCT/US04/09323, mailed May 9, 2007.
International Search Report for International (PCT) Patent Application No. PCT/US05/36998, mailed Mar. 22, 2007.
Written Opinion for International (PCT) Patent Application No. PCT/US05/36998, mailed Mar. 22, 2007.
International Search Report for International (PCT) Patent Application No. PCT/US08/63835, mailed Nov. 3, 2008.
Written Opinion for International (PCT) Patent Application No. PCT/US08/63835, mailed Nov. 3, 2008.
International Search Report for International (PCT) Patent Application No. PCT/US06/22893, mailed Feb. 29, 2008.
Written Opinion for International (PCT) Patent Application No. PCT/US06/22893, mailed Feb. 29, 2008.
International Search Report for International (PCT) Patent Application No. PCT/US07/64105, mailed Nov. 23, 2007.
Written Opinion for International (PCT) Patent Application No. PCT/US07/64105, mailed Nov. 23, 2007.
International Preliminary Report on Patentabililty for International (PCT) Patent Application No. PCT/US07/64105, mailed Sep. 25, 2008.
International Search Report for International (PCT) Patent Application No. PCT/US07/64104, mailed Dec. 5, 2008.
Written Opinion for International (PCT) Patent Application No. PCT/US07/64104, mailed Dec. 5, 2008.
International Search Report for International (PCT) Patent Application No. PCT/US2007/064106, mailed Sep. 16, 2008.
Written Opinion for International (PCT) Patent Application No. PCT/US2007/064106, mailed Sep. 16, 2008.
International Preliminary Report on Patentability for International (PCT) Patent Application No. PCT/US2007/064106, mailed Oct. 30, 2008.
Fan K W et al: "Eicosapentaenoic and docosahexaenoic acids production by and okara-utilizing potential of thraustochytrids" Journal of Industrial Microbiology and Biotechnology, Basingstoke, GB, vol. 27, No. 4, Oct. 1, 2001, pp. 199-202, XP002393382 ISSN: 1367-5435.
Wolff et al, Arachidonic, Eicosapentaenoic and Biosynthetically Related Fatty Acids in Seed Lipids from a primitive Gymnosperm, *Agathis robusta*. Lipids 34(10), 1994, 1083-1097.
Grimsley et al, "Fatty acid composition of mutants of the moss *Physcomitrella patens*" Phytochemistry 20(7): 1519-1524, 1981.
Bedford et al, "A functional chimeric modular polyketide synthase generated via domain replacement." Chemistry & Biology 3: 827-831, Oct. 1996.
U.S. Appl. No. 11/689,587, filed Mar. 22, 2007, Metz et al.
U.S. Appl. No. 11/689,596, filed Mar. 22, 2007, Metz et al.
U.S. Appl. No. 11/689,598, filed Mar. 22, 2007, Metz et al.
U.S. Appl. No. 11/689,605, filed Mar. 22, 2007, Metz et al.
U.S. Appl. No. 11/689,608, filed Mar. 22, 2007, Metz et al.
U.S. Appl. No. 11/777,220, filed Jul. 12, 2007, Metz et al.
U.S. Appl. No. 11/777,275, filed Jul. 12, 2007, Metz et al.
U.S. Appl. No. 11/777,278, filed Jul. 12, 2007, Metz et al.
U.S. Appl. No. 11/777,279, filed Jul. 12, 2007, Metz et al.
Abbadi et al., Eur. J. Lipid Sci. Technol., 103:106-113 (2001).
Allen et al., Appl. Envir. Microbiol., 65(4):1710-1720 (1999).
Bateman et al., Nucl. Acids Res., 30(1):276-280 (2002).
Bentley et al., Annu. Rev. Microbiol., 53:411-46 (1999).
Bisang et al., Nature, 401:502-505 (1999).
Bork, TIG, 12(10):425-427 (1996).
Brenner, TIG, 15(4):132-133 (1999).
Broun et al., Science, 282:1315-1317 (1998).
Chuck et al., Chem. and Bio., Current Bio. (London, GB), 4:10 (1997) pp. 757-766.
Creelman et al., Annu. Rev. Plan Physiol. Plant Mol. Biol., 48:355-81 (1997).
Database Geneseq 'Online! Dec. 11, 2000, "*S. aggregatum* PKS cluster ORF6 homolog DNA." XP002368912, retrieved from EBI accession No. GSN:AAA71567Database accession No. AAA71567—& Database Geneseq 'Online! Dec. 11, 2000, "*S. aggregatum* PKS cluster ORF6 homolog protein." XP002368914 retrieved from EBI accession No. GSP:AAB10482 Database accession No. AAB10482 & WO 00/42195 A (Calgene, LLC) Jul. 20, 2000.

DeLong & Yayanos, Appl. Environ. Microbiol., 51(4):730-737 (1986).

Doerks, TIG, 14(6):248-250 (1998).

Facciotti et al., "Cloning and Characterization of Polyunsaturated Fatty Acids (PUFA) Genes from Marine Bacteria" in Proceedings of the international symposium on progress and prospect of marine biotechnology (China Ocean Pres 1999), pp. 404-405 Abstract.

GenBank Accession No. U09865. *Alcaligenes eutrophus* pyruvate dehydrogenase (pdhA), dihydrolipoamide acetyltransferase (pdhB), dihydrolipoamide dehydrogenase (pdhL), and ORF3 genes, complete cds (1994).

Harlow et al. Antibodies: A Laboratory Manual (1988) Cold Spring Harbor Laboratory Press, p. 76.

Heath et al., J. Biol. Chem., 271(44):27795-27801 (1996).

Hopwood & Sherman, Annu. Rev. Genet., 24:37-66 (1990).

Hutchinson, Annu. Rev. Microbiol., 49:201-238 (1995).

Jez et al., Chem. and Bio. (London), 7:12 (2000) pp. 919-930.

Jostensen & Landfald, FEMS Microbiology Letters, 151:95-101 (1997).

Katz & Donadio, Annu. Rev. Microbiol., 47:875-912 (1993).

Kealey et al., "Production of a polyketide natural product in non-polyketide-producing prokaryotic and eukaryotic hosts", Proceedings of the National Academy of Sciences of the United States of America, vol. 95, No. 2, Jan. 20, 1998, pp. 505-509, XP002338563.

Keating et al., Curr. Opin. Chem. Biol., 3:598-606 (1999).

Kyle et al., HortScience, 25:1523-26 (1990).

Leadlay PF. Current Opinion in Chemical Biology (1997) 1: 162-168.

Magnuson, Microbil. Rev., 57(3):522-542 (1993) Abstract.

Metz et al., Science, 293:290-293 2001.

Nakahara, Yukagaku, 44(10):821-7 (1995).

Nasu et al., J. Ferment. Bioeng., 122:467-473 (1997).

Nichols et al., Curr. Opin. Biotechnol., 10:240-246 (1999).

Nicholson et al., Chemistry and Biology (London), 8:2 (2001) pp. 157-178.

Nogi et al., Extremophiles, 2:1-7 (1998).

Oliynyk et al. Chemistry & Biology (1996) 3: 833-839.

Parker-Barnes et al., PNAS, 97(15):8284-8289 (2000).

Sanchez et al., Chemistry & Biolosy, 8:725-738 (2001).

Shanklin et al., Annu. Rev. Plant Physiol. Plant Mol. Biol., 49:611-41 (1998).

Smith et al., Nature Biotechnol., 15:1222-1223 (1997).

Somerville Am. J. Clin. Nutr., 58(2 supp):270S-275S (1993).

Van de Loo, Proc. Natl. Acad. Sci. USA, 92:6743-6747 (1995).

Wallis et al., "Polyunsaturated fatty acid synthesis: what will they think of next?", Tibs Trends in Bio Sciences, Elsevier Publ., Cambridge, EN, vol. 27, No. 9, Sep. 2002, pp. 467-473, XP004378766.

Watanabe et al., J. Biochem., 122:467-473 (1997).

Yalpani et al., The Plant Cell, 13:1401-1409 (2001).

Yazawa, Lipids, 31(supp):S297-S300 (1996).

Cane et al., "Harnessing the Biosynthetic Code: Combinations, Permutations, and Mutations." Science 1998, vol. 282, pp. 63-68.

Napier "Plumbing the depths of PUFA biosynthesis: a novel polyketide synthase-like pathway from marine organisms." Trends in Plant Science. Feb. 2002, vol. 7, No. 2, pp. 51-54.

International Search Report for International (PCT) Patent Application No. PCT/US02/12254, mailed Nov. 15, 2002.

International Preliminary Examination Report for International (PCT) Patent Application No. PCT/US02/12254, mailed Oct. 16, 2006.

Examiner's First Report for Australian Patent Application No. 2002303394, mailed Dec. 20, 2006.

Supplementary Partial European Search Report for European Patent Application No. 02731415, dated Sep. 20, 2005.

Supplementary European Search Report for European Patent Application No. 02731415, dated Mar. 13, 2006.

Examiner's Report for European Patent Application No. 02731415, dated Aug. 1, 2007.

Sequence alignment for SEQ ID No. 5 with SEQID No. 17 from US Patent 5,683,898. Search resulted dated Aug. 5, 2009.

Sequence alignment for SEQ ID No. 1 with SEQID No. 16 from US Patent 5,683,898. Search resulted dated Aug. 5, 2009.

Sequence alignment of SEQ ID No. 7 with SEQ ID No. 1 of Yazawa, US Patent 5,798,259, search result date Aug. 10, 2009.

Sequence alignment of SEQ ID No. 11 with SEQ ID No. 16 of Yazawa, US Patent 5,798,259, search result date Aug. 10, 2009.

Weissmann et al. Biochemistry (1997) 36: 13849-13855.

Weissmann et al. Biochemistry (1998) 37: 11012-11017.

Wiesmann et al. Chemistry & Biology (Sep. 1995) 2: 583-589.

Comparison of PKS Orfs/domains:
*Schizochytrium vs Shewanella*

PUFA POLYKETIDE SYNTHASE SYSTEMS AND USES THEREOF

CROSS-REFERENCE TO RELATED APPLICATIONS

This application is a continuation of U.S. application Ser. No. 10/124,800, filed Apr. 16, 2002, now U.S. Pat. No. 7,247,461, entitled "PUFA Polyketide Synthase Systems and Uses Thereof," which claims the benefit of priority under 35 U.S.C. §119(e) to: U.S. Provisional Application Ser. No. 60/284,066, filed Apr. 16, 2001, entitled "A Polyketide Synthase System and Uses Thereof"; U.S. Provisional Application Ser. No. 60/298,796, filed Jun. 15, 2001, entitled "A Polyketide Synthase System and Uses Thereof"; and U.S. Provisional Application Ser. No. 60/323,269, filed Sep. 18, 2001, entitled "*Thraustochytrium* PUFA PKS System and Uses Thereof". U.S. application Ser. No. 10/124,800, is also a continuation-in-part of copending U.S. application Ser. No. 09/231,899, filed Jan. 14, 1999, entitled "*Schizochytrium* PKS Genes". Each of the above-identified patent applications is incorporated herein by reference in its entirety.

This application does not claim the benefit of priority from U.S. application Ser. No. 09/090,793, filed Jun. 4, 1998, now U.S. Pat. No. 6,140,486, although U.S. application Ser. No. 09/090,793 is incorporated herein by reference in its entirety.

REFERENCE TO SEQUENCE LISTING

This application contains a Sequence Listing submitted as an electronic text file named "2997-29_corrected_ST25.txt", having a size in bytes of 280 kb, and created on 4 Mar. 2007. The information contained in this electronic file is hereby incorporated by reference in its entirety pursuant to 37 CFR §1.52(e)(5).

FIELD OF THE INVENTION

This invention relates to polyunsaturated fatty acid (PUFA) polyketide synthase (PKS) systems from microorganisms, including eukaryotic organisms, such as Thraustochytrid microorganisms. More particularly, this invention relates to nucleic acids encoding non-bacterial PUFA PKS systems, to non-bacterial PUFA PKS systems, to genetically modified organisms comprising non-bacterial PUFA PKS systems, and to methods of making and using the non-bacterial PUFA PKS systems disclosed herein. This invention also relates to a method to identify bacterial and non-bacterial microorganisms comprising PUFA PKS systems.

BACKGROUND OF THE INVENTION

Polyketide synthase (PKS) systems are generally known in the art as enzyme complexes derived from fatty acid synthase (FAS) systems, but which are often highly modified to produce specialized products that typically show little resemblance to fatty acids. Researchers have attempted to exploit polyketide synthase (PKS) systems that have been described in the literature as falling into one of three basic types, typically referred to as: Type II, Type I and modular. The Type II system is characterized by separable proteins, each of which carries out a distinct enzymatic reaction. The enzymes work in concert to produce the end product and each individual enzyme of the system typically participates several times in the production of the end product. This type of system operates in a manner analogous to the fatty acid synthase (FAS) systems found in plants and bacteria. Type I PKS systems are similar to the Type II system in that the enzymes are used in an iterative fashion to produce the end product. The Type I differs from Type II in that enzymatic activities, instead of being associated with separable proteins, occur as domains of larger proteins. This system is analogous to the Type I FAS systems found in animals and fungi.

In contrast to the Type I and II systems, in modular PKS systems, each enzyme domain is used only once in the production of the end product. The domains are found in very large proteins and the product of each reaction is passed on to another domain in the PKS protein. Additionally, in all of the PKS systems described above, if a carbon-carbon double bond is incorporated into the end product, it is always in the trans configuration.

In the Type I and Type II PKS systems described above, the same set of reactions is carried out in each cycle until the end product is obtained. There is no allowance for the introduction of unique reactions during the biosynthetic procedure. The modular PKS systems require huge proteins that do not utilize the economy of iterative reactions (i.e., a distinct domain is required for each reaction). Additionally, as stated above, carbon-carbon double bonds are introduced in the trans configuration in all of the previously described PKS systems.

Polyunsaturated fatty acids (PUFAs) are critical components of membrane lipids in most eukaryotes (Lauritzen et al., *Prog. Lipid Res.* 40 1 (2001); McConn et al., *Plant J.* 15, 521 (1998)) and are precursors of certain hormones and signaling molecules (Heller et al., *Drugs* 55, 487 (1998); Creelman et al., *Annu. Rev. Plant Physiol. Plant Mol. Biol.* 48, 355 (1997)). Known pathways of PUFA synthesis involve the processing of saturated 16:0 or 18:0 fatty acids (the abbreviation X:Y indicates an acyl group containing X carbon atoms and Y cis double bonds; double-bond positions of PUFAs are indicated relative to the methyl carbon of the fatty acid chain (ω3 or ω6) with systematic methylene interruption of the double bonds) derived from fatty acid synthase (FAS) by elongation and aerobic desaturation reactions (Sprecher, *Curr. Opin. Clin. Nutr. Metab. Care* 2, 135 (1999); Parker-Barnes et al., *Proc. Natl. Acad. Sci. USA* 97, 8284 (2000); Shanklin et al., *Annu. Rev. Plant Physiol. Plant Nol. Biol.* 49, 611 (1998)). Starting from acetyl-CoA, the synthesis of DHA requires approximately 30 distinct enzyme activities and nearly 70 reactions including the four repetitive steps of the fatty acid synthesis cycle. Polyketide synthases (PKSs) carry out some of the same reactions as FAS (Hopwood et al., *Annu. Rev. Genet.* 24, 37 (1990); Bentley et al., *Annu. Rev. Microbiol.* 53, 411 (1999)) and use the same small protein (or domain), acyl carrier protein (ACP), as a covalent attachment site for the growing carbon chain. However, in these enzyme systems, the complete cycle of reduction, dehydration and reduction seen in FAS is often abbreviated so that a highly derivatized carbon chain is produced, typically containing many keto- and hydroxy-groups as well as carbon-carbon double bonds in the trans configuration. The linear products of PKSs are often cyclized to form complex biochemicals that include antibiotics and many other secondary products (Hopwood et al., (1990) supra; Bentley et al., (1999), supra; Keating et al., *Curr. Opin. Chem. Biol.* 3, 598 (1999)).

Very long chain PUFAs such as docosahexaenoic acid (DHA; 22:6ω3) and eicosapentaenoic acid (EPA; 20:5ω3) have been reported from several species of marine bacteria, including *Shewanella* sp (Nichols et al., *Curr. Op. Biotechnol.* 10, 240 (1999); Yazawa, *Lipids* 31, S (1996); DeLong et al., *Appl. Environ. Microbiol.* 51, 730 (1986)). Analysis of a genomic fragment (cloned as plasmid pEPA) from *Shewanella* sp. strain SCRC2738 led to the identification of five open reading frames (Orfs), totaling 20 Kb, that are necessary and sufficient for EPA production in *E. coli* (Yazawa, (1996), supra). Several of the predicted protein domains were homologues of FAS enzymes, while other regions showed no homology to proteins of known function. On the basis of these observations and biochemical studies, it was suggested that PUFA synthesis in *Shewanella* involved the elongation of 16- or 18-carbon fatty acids produced by FAS and the insertion of double bonds by undefined aerobic desaturases (Watanabe et al., *J. Biochem.* 122, 467 (1997)). The recognition that this hypothesis was incorrect began with a reexamination of the protein sequences encoded by the five *Shewanella* Orfs. At least 11 regions within the five Orfs were identifiable as putative enzyme domains (See Metz et al., *Science* 293:290-293 (2001)). When compared with sequences in the gene databases, seven of these were more strongly related to PKS proteins than to FAS proteins. Included in this group were domains putatively encoding malonyl-CoA:ACP acyltransferase (MAT), 3-ketoacyl-ACP synthase (KS), 3-ketoacyl-ACP reductase (KR), acyltransferase (AT), phosphopantetheine transferase, chain length (or chain initiation) factor (CLF) and a highly unusual cluster of six ACP domains (i.e., the presence of more than two clustered ACP domains has not previously been reported in PKS or FAS sequences). However, three regions were more highly homologous to bacterial FAS proteins. One of these was similar to the newly-described Triclosan-resistant enoyl reductase (ER) from *Streptococcus pneumoniae* (Heath et al., *Nature* 406, 145 (2000)); comparison of ORF8 peptide with the *S. pneumoniae* enoyl reductase using the LALIGN program (matrix, BLOSUM50; gap opening penalty, −10; elongation penalty −1) indicated 49% similarity over a 386aa overlap). Two regions were homologues of the *E. coli* FAS protein encoded by fabA, which catalyzes the synthesis of trans-2-decenoyl-ACP and the reversible isomerization of this product to cis-3-decenoyl-ACP (Heath et al., *J. Biol. Chem.*, 271, 27795 (1996)). On this basis, it seemed likely that at least some of the double bonds in EPA from *Shewanella* are introduced by a dehydrase-isomerase mechanism catalyzed by the FabA-like domains in Orf7.

Anaerobically-grown *E. coli* cells harboring the pEPA plasmid accumulated EPA to the same levels as aerobic cultures (Metz et al., 2001, supra), indicating that an oxygen-dependent desaturase is not involved in EPA synthesis. When pEPA was introduced into a fabB⁻ mutant of *E. coli*, which is unable to synthesize monounsaturated fatty acids and requires unsaturated fatty acids for growth, the resulting cells lost their fatty acid auxotrophy. They also accumulated much higher levels of EPA than other pEPA-containing strains, suggesting that EPA competes with endogenously produced monounsaturated fatty acids for transfer to glycerolipids. When pEPA-containing *E. coli* cells were grown in the presence of [$^{13}$C]-acetate, the data from $^{13}$C-NMR analysis of purified EPA from the cells confirmed the identity of EPA and provided evidence that this fatty acid was synthesized from acetyl-CoA and malonyl-CoA (See Metz et al., 2001, supra). A cell-free homogenate from pEPA-containing fabB⁻ cells synthesized both EPA and saturated fatty acids from [$^{14}$C]-malonyl-CoA. When the homogenate was separated into a 200,000×g high-speed pellet and a membrane-free supernatant fraction, saturated fatty acid synthesis was confined to the supernatant, consistent with the soluble nature of the Type II FAS enzymes (Magnuson et al., *Microbiol. Rev.* 57, 522 (1993)). Synthesis of EPA was found only in the high-speed pellet fraction, indicating that EPA synthesis can occur without reliance on enzymes of the *E. coli* FAS or on soluble intermediates (such as 16:0-ACP) from the cytoplasmic fraction. Since the proteins encoded by the *Shewanella* EPA genes are not particularly hydrophobic, restriction of EPA synthesis activity to this fraction may reflect a requirement for a membrane-associated acyl acceptor molecule. Additionally, in contrast to the *E. coli* FAS, EPA synthesis is specifically NADPH-dependent and does not require NADH. All these results are consistent with the pEPA genes encoding a multifunctional PKS that acts independently of FAS, elongase, and desaturase activities to synthesize EPA directly. It is likely that the PKS pathway for PUFA synthesis that has been identified in *Shewanella* is widespread in marine bacteria. Genes with high homology to the *Shewanella* gene cluster have been identified in *Photobacterium profundum* (Allen et al., *Appli. Environ. Microbiol.* 65:1710 (1999)) and in *Moritella marina* (*Vibrio marinus*) (Tanaka et al., *Biotechnol. Lett.* 21:939 (1999)).

The biochemical and molecular-genetic analyses performed with *Shewanella* provide compelling evidence for polyketide synthases that are capable of synthesizing PUFAs from malonyl-CoA. A complete scheme for synthesis of EPA by the *Shewanella* PKS has been proposed. The identification of protein domains homologous to the *E. coli* FabA protein, and the observation that bacterial EPA synthesis occurs anaerobically, provide evidence for one mechanism wherein the insertion of cis double bonds occurs through the action of a bifunctional dehydratase/2-trans, 3-cis isomerase (DH/2, 3I). In *E. coli*, condensation of the 3-cis acyl intermediate with malonyl-ACP requires a particular ketoacyl-ACP synthase and this may provide a rationale for the presence of two KS in the *Shewanella* gene cluster (in Orf 5 and Orf 7). However, the PKS cycle extends the chain in two-carbon increments while the double bonds in the EPA product occur at every third carbon. This disjunction can be solved if the double bonds at C-14 and C-8 of EPA are generated by 2-trans, 2-cis isomerization (DH/2,2I) followed by incorporation of the cis double bond into the elongating fatty acid chain. The enzymatic conversion of a trans double bond to the cis configuration without bond migration is known to occur, for example, in the synthesis of 11-cis-retinal in the retinoid cycle (Jang et al., *J. Biol. Chem.* 275, 28128 (2000)). Although such an enzyme function has not yet been identified in the *Shewanella* PKS, it may reside in one of the unassigned protein domains.

The PKS pathways for PUFA synthesis in *Shewanella* and another marine bacteria, *Vibrio marinus*, are described in detail in U.S. Pat. No. 6,140,486 (issued from U.S. application Ser. No. 09/090,793, filed Jun. 4, 1998, entitled "Production of Polyunsaturated Fatty Acids by Expression of Polyketide-like Synthesis Genes in Plants", which is incorporated herein by reference in its entirety).

Polyunsaturated fatty acids (PUFAs) are considered to be useful for nutritional, pharmaceutical, industrial, and other purposes. An expansive supply of PUFAs from natural sources and from chemical synthesis are not sufficient for commercial needs. Because a number of separate desaturase and elongase enzymes are required for fatty acid synthesis from linoleic acid (LA, 18:2 Δ 9, 12), common in most plant species, to the more saturated and longer chain PUFAs, engineering plant host cells for the expression of PUFAs such as EPA and DHA may require expression of five or six separate enzyme activities to achieve expression, at least for EPA and DHA. Additionally, for production of useable quantities of such PUFAs, additional engineering efforts may be required, for instance the down regulation of enzymes competing for substrate, engineering of higher enzyme activities such as by mutagenesis or targeting of enzymes to plastid organelles. Therefore it is of interest to obtain genetic material involved in PUFA biosynthesis from species that naturally produce these fatty acids and to express the isolated material alone or in combination in a heterologous system which can be manipulated to allow production of commercial quantities of PUFAs.

The discovery of a PUFA PKS system in marine bacteria such as *Shewanella* and *Vibrio marinus* (see U.S. Pat. No. 6,140,486, ibid.) provides a resource for new methods of commercial PUFA production. However, these marine bacteria have limitations which will ultimately restrict their usefulness on a commercial level. First, although U.S. Pat. No. 6,140,486 discloses that the marine bacteria PUFA PKS systems can be used to genetically modify plants, the marine bacteria naturally live and grow in cold marine environments and the enzyme systems of these bacteria do not function well above 30° C. In contrast, many crop plants, which are attractive targets for genetic manipulation using the PUFA PKS system, have normal growth conditions at temperatures above 30° C. and ranging to higher than 40° C. Therefore, the marine bacteria PUFA PKS system is not predicted to be readily adaptable to plant expression under normal growth conditions. Moreover, the marine bacteria PUFA PKS genes, being from a bacterial source, may not be compatible with the genomes of eukaryotic host cells, or at least may require significant adaptation to work in eukaryotic hosts. Additionally, the known marine bacteria PUFA PKS systems do not directly produce triglycerides, whereas direct production of triglycerides would be desirable because triglycerides are a lipid storage product in microorganisms and as a result can be accumulated at very high levels (e.g. up to 80-85% of cell weight) in microbial/plant cells (as opposed to a "structural" lipid product (e.g. phospholipids) which can generally only accumulate at low levels (e.g. less than 10-15% of cell weight at maximum)).

Therefore, there is a need in the art for other PUFA PKS systems having greater flexibility for commercial use.

SUMMARY OF THE INVENTION

One embodiment of the present invention relates to an isolated nucleic acid molecule comprising a nucleic acid sequence chosen from: (a) a nucleic acid sequence encoding an amino acid sequence selected from the group consisting of: SEQ ID NO:2, SEQ ID NO:4, SEQ ID NO:6, and biologically active fragments thereof; (b) a nucleic acid sequence encoding an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and biologically active fragments thereof; (c) a nucleic acid sequence encoding an amino acid sequence that is at least about 60% identical to at least 500 consecutive amino acids of the amino acid sequence of (a), wherein the amino acid sequence has a biological activity of at least one domain of a polyunsaturated fatty acid (PUFA) polyketide synthase (PKS) system; (d) a nucleic acid sequence encoding an amino acid sequence that is at least about 60% identical to the amino acid sequence of (b), wherein the amino acid sequence has a biological activity of at least one domain of a polyunsaturated fatty acid (PUFA) polyketide synthase (PKS) system; and (e) a nucleic acid sequence that is fully complementary to the nucleic acid sequence of (a), (b), (c), or (d). In alternate aspects, the nucleic acid sequence encodes an amino acid sequence that is at least about 70% identical, or at least about 80% identical, or at least about 90% identical, or is identical to: (1) at least 500 consecutive amino acids of an amino acid sequence selected from the group consisting of: SEQ ID NO:2, SEQ ID NO:4, and SEQ ID NO:6; and/or (2) a nucleic acid sequence encoding an amino acid sequence that is at least about 70% identical to an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, and SEQ ID NO:32. In a preferred embodiment, the nucleic acid sequence encodes an amino acid sequence chosen from: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32 and/or biologically active fragments thereof. In one aspect, the nucleic acid sequence is chosen from: SEQ ID NO:1, SEQ ID NO:3, SEQ ID NO:5, SEQ ID NO:7, SEQ ID NO:9, SEQ ID NO: 12, SEQ ID NO:17, SEQ ID NO:19, SEQ ID NO:21, SEQ ID NO:23, SEQ ID NO:25, SEQ ID NO:27, SEQ ID NO:29, and SEQ ID NO:31.

Another embodiment of the present invention relates to a recombinant nucleic acid molecule comprising the nucleic acid molecule as described above, operatively linked to at least one transcription control sequence. In another embodiment, the present invention relates to a recombinant cell transfected with the recombinant nucleic acid molecule described directly above.

Yet another embodiment of the present invention relates to a genetically modified microorganism, wherein the microorganism expresses a PKS system comprising at least one biologically active domain of a polyunsaturated fatty acid (PUFA) polyketide synthase (PKS) system. The at least one domain of the PUFA PKS system is encoded by a nucleic acid sequence chosen from: (a) a nucleic acid sequence encoding at least one domain of a polyunsaturated fatty acid (PUFA) polyketide synthase (PKS) system from a Thraustochytrid microorganism; (b) a nucleic acid sequence encoding at least one domain of a PUFA PKS system from a microorganism identified by the screening method of the present invention; (c) a nucleic acid sequence encoding an amino acid sequence selected from the group consisting of: SEQ ID NO:2, SEQ ID NO:4, SEQ ID NO:6, and biologically active fragments thereof; (d) a nucleic acid sequence encoding an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and biologically active fragments thereof; (e) a nucleic acid sequence encoding an amino acid sequence that is at least about 60% identical to at least 500 consecutive amino acids of an amino acid sequence selected from the group consisting of: SEQ ID NO:2, SEQ ID NO:4, and SEQ ID NO:6; wherein the amino acid sequence has a biological activity of at least one domain of a PUFA PKS system; and, (f) a nucleic acid sequence encoding an amino acid sequence that is at least about 60% identical to an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; wherein the amino acid sequence has a biological activity of at least one domain of a PUFA PKS system. In this embodiment, the microorganism is genetically modified to affect the activity of the PKS system. The screening method of the present invention referenced in (b) above comprises: (i) selecting a microorganism that produces at least one PUFA; and, (ii) identifying a microorganism from (i) that has an ability to produce increased PUFAs under dissolved oxygen conditions of less than about 5% of saturation in the fermentation medium, as compared to production of PUFAs by the microorganism under dissolved oxygen conditions of greater than 5% of saturation, and more preferably 10% of saturation, and more preferably greater than 15% of saturation, and more preferably greater than 20% of saturation in the fermentation medium.

In one aspect, the microorganism endogenously expresses a PKS system comprising the at least one domain of the PUFA PKS system, and wherein the genetic modification is in a nucleic acid sequence encoding the at least one domain of the PUFA PKS system. For example, the genetic modification can be in a nucleic acid sequence that encodes a domain having a biological activity of at least one of the following proteins: malonyl-CoA:ACP acyltransferase (MAT), β-keto acyl-ACP synthase (KS), ketoreductase (KR), acyltransferase (AT), FabA-like β-hydroxy acyl-ACP dehydrase (DH), phosphopantetheine transferase, chain length factor (CLF), acyl carrier protein (ACP), enoyl ACP-reductase (ER), an enzyme that catalyzes the synthesis of trans-2-decenoyl-ACP, an enzyme that catalyzes the reversible isomerization of trans-2-decenoyl-ACP to cis-3-decenoyl-ACP, and an enzyme that catalyzes the elongation of cis-3-decenoyl-ACP to cis-vaccenic acid. In one aspect, the genetic modification is in a nucleic acid sequence that encodes an amino acid sequence selected from the group consisting of: (a) an amino acid sequence that is at least about 70% identical, and preferably at least about 80% identical, and more preferably at least about 90% identical and more preferably identical to at least 500 consecutive amino acids of an amino acid sequence selected from the group consisting of: SEQ ID NO:2, SEQ ID NO:4, and SEQ ID NO:6; wherein the amino acid sequence has a biological activity of at least one domain of a PUFA PKS system; and, (b) an amino acid sequence that is at least about 70% identical, and preferably at least about 80% identical, and more preferably at least about 90% identical and more preferably identical to an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; wherein the amino acid sequence has a biological activity of at least one domain of a PUFA PKS system.

In one aspect, the genetically modified microorganism is a Thraustochytrid, which can include, but is not limited to, a Thraustochytrid from a genus chosen from *Schizochytrium* and *Thraustochytrium*. In another aspect, the microorganism has been further genetically modified to recombinantly express at least one nucleic acid molecule encoding at least one biologically active domain from a bacterial PUFA PKS system, from a Type I PKS system, from a Type II PKS system, and/or from a modular PKS system.

In another aspect of this embodiment, the microorganism endogenously expresses a PUFA PKS system comprising the at least one biologically active domain of a PUFA PKS system, and wherein the genetic modification comprises expression of a recombinant nucleic acid molecule selected from the group consisting of a recombinant nucleic acid molecule encoding at least one biologically active domain from a second PKS system and a recombinant nucleic acid molecule encoding a protein that affects the activity of the PUFA PKS system. Preferably, the recombinant nucleic acid molecule comprises any one of the nucleic acid sequences described above.

In one aspect of this embodiment, the recombinant nucleic acid molecule encodes a phosphopantetheine transferase. In another aspect, the recombinant nucleic acid molecule comprises a nucleic acid sequence encoding at least one biologically active domain from a bacterial PUFA PKS system, from a type I PKS system, from a type II PKS system, and/or from a modular PKS system.

In another aspect of this embodiment, the microorganism is genetically modified by transfection with a recombinant nucleic acid molecule encoding the at least one domain of a polyunsaturated fatty acid (PUFA) polyketide synthase (PKS) system. Such a recombinant nucleic acid molecule can include any recombinant nucleic acid molecule comprising any of the nucleic acid sequences described above. In one aspect, the microorganism has been further genetically modified to recombinantly express at least one nucleic acid molecule encoding at least one biologically active domain from a bacterial PUFA PKS system, from a Type I PKS system, from a Type II PKS system, or from a modular PKS system.

Yet another embodiment of the present invention relates to a genetically modified plant, wherein the plant has been genetically modified to recombinantly express a PKS system comprising at least one biologically active domain of a polyunsaturated fatty acid (PUFA) polyketide synthase (PKS) system. The domain can be encoded by any of the nucleic acid sequences described above. In one aspect, the plant has been further genetically modified to recombinantly express at least one nucleic acid molecule encoding at least one biologically active domain from a bacterial PUFA PKS system, from a Type I PKS system, from a Type II PKS system, and/from a modular PKS system.

Another embodiment of the present invention relates to a method to identify a microorganism that has a polyunsaturated fatty acid (PUFA) polyketide synthase (PKS) system. The method includes the steps of: (a) selecting a microorganism that produces at least one PUFA; and, (b) identifying a microorganism from (a) that has an ability to produce increased PUFAs under dissolved oxygen conditions of less than about 5% of saturation in the fermentation medium, as compared to production of PUFAs by the microorganism under dissolved oxygen conditions of greater than 5% of saturation, more preferably 10% of saturation, more preferably greater than 15% of saturation and more preferably greater than 20% of saturation in the fermentation medium. A microorganism that produces at least one PUFA and has an ability to produce increased PUFAs under dissolved oxygen conditions of less than about 5% of saturation is identified as a candidate for containing a PUFA PKS system.

In one aspect of this embodiment, step (b) comprises identifying a microorganism from (a) that has an ability to produce increased PUFAs under dissolved oxygen conditions of less than about 2% of saturation, and more preferably under dissolved oxygen conditions of less than about 1% of saturation, and even more preferably under dissolved conditions of about 0% of saturation.

In another aspect of this embodiment, the microorganism selected in (a) has an ability to consume bacteria by phagocytosis. In another aspect, the microorganism selected in (a) has a simple fatty acid profile. In another aspect, the microorganism selected in (a) is a non-bacterial microorganism. In another aspect, the microorganism selected in (a) is a eukaryote. In another aspect, the microorganism selected in (a) is a member of the order Thraustochytriales. In another aspect, the microorganism selected in (a) has an ability to produce PUFAs at a temperature greater than about 15° C., and preferably greater than about 20° C., and more preferably greater than about 25° C., and even more preferably greater than about 30° C. In another aspect, the microorganism selected in (a) has an ability to produce bioactive compounds (e.g., lipids) of interest at greater than 5% of the dry weight of the organism, and more preferably greater than 10% of the dry weight of the organism. In yet another aspect, the microorganism selected in (a) contains greater than 30% of its total fatty acids as C14:0, C16:0 and C16:1 while also producing at least one long chain fatty acid with three or more unsaturated bonds, and preferably, the microorganism selected in (a) contains greater than 40% of its total fatty acids as C14:0, C16:0 and C16:1 while also producing at least one long chain fatty acid with three or more unsaturated bonds. In another aspect, the microorganism selected in (a) contains greater than 30% of its total fatty acids as C14:0, C16:0 and C16:1 while also producing at least one long chain fatty acid with four or more unsaturated bonds, and more preferably while also producing at least one long chain fatty acid with five or more unsaturated bonds.

In another aspect of this embodiment, the method further comprises step (c) of detecting whether the organism comprises a PUFA PKS system. In this aspect, the step of detecting can include detecting a nucleic acid sequence in the microorganism that hybridizes under stringent conditions with a nucleic acid sequence encoding an amino acid sequence from a Thraustochytrid PUFA PKS system. Alternatively, the step of detecting can include detecting a nucleic acid sequence in the organism that is amplified by oligonucleotide primers from a nucleic acid sequence from a Thraustochytrid PUFA PKS system.

Another embodiment of the present invention relates to a microorganism identified by the screening method described above, wherein the microorganism is genetically modified to regulate the production of molecules by the PUFA PKS system.

Yet another embodiment of the present invention relates to a method to produce a bioactive molecule that is produced by a polyketide synthase system. The method includes the step of culturing under conditions effective to produce the bioactive molecule a genetically modified organism that expresses a PKS system comprising at least one biologically active domain of a polyunsaturated fatty acid (PUFA) polyketide synthase (PKS) system. The domain of the PUFA PKS system is encoded by any of the nucleic acid sequences described above.

In one aspect of this embodiment, the organism endogenously expresses a PKS system comprising the at least one domain of the PUFA PKS system, and the genetic modification is in a nucleic acid sequence encoding the at least one domain of the PUFA PKS system. For example, the genetic modification can change at least one product produced by the endogenous PKS system, as compared to a wild-type organism.

In another aspect of this embodiment, the organism endogenously expresses a PKS system comprising the at least one biologically active domain of the PUFA PKS system, and the genetic modification comprises transfection of the organism with a recombinant nucleic acid molecule selected from the group consisting of: a recombinant nucleic acid molecule encoding at least one biologically active domain from a second PKS system and a recombinant nucleic acid molecule encoding a protein that affects the activity of the PUFA PKS system. For example, the genetic modification can change at least one product produced by the endogenous PKS system, as compared to a wild-type organism.

In yet another aspect of this embodiment, the organism is genetically modified by transfection with a recombinant nucleic acid molecule encoding the at least one domain of the polyunsaturated fatty acid (PUFA) polyketide synthase (PKS) system. In another aspect, the organism produces a polyunsaturated fatty acid (PUFA) profile that differs from the naturally occurring organism without a genetic modification. In another aspect, the organism endogenously expresses a non-bacterial PUFA PKS system, and wherein the genetic modification comprises substitution of a domain from a different PKS system for a nucleic acid sequence encoding at least one domain of the non-bacterial PUFA PKS system.

In yet another aspect, the organism endogenously expresses a non-bacterial PUFA PKS system that has been modified by transfecting the organism with a recombinant nucleic acid molecule encoding a protein that regulates the chain length of fatty acids produced by the PUFA PKS system. For example, the recombinant nucleic acid molecule encoding a protein that regulates the chain length of fatty acids can replace a nucleic acid sequence encoding a chain length factor in the non-bacterial PUFA PKS system. In another aspect, the protein that regulates the chain length of fatty acids produced by the PUFA PKS system is a chain length factor. In another aspect, the protein that regulates the chain length of fatty acids produced by the PUFA PKS system is a chain length factor that directs the synthesis of C20 units.

In one aspect, the organism expresses a non-bacterial PUFA PKS system comprising a genetic modification in a domain chosen from: a domain encoding FabA-like β-hydroxy acyl-ACP dehydrase (DH) domain and a domain encoding β-ketoacyl-ACP synthase (KS), wherein the modification alters the ratio of long chain fatty acids produced by the PUFA PKS system as compared to in the absence of the modification. In one aspect, the modification comprises substituting a DH domain that does not possess isomerization activity for a FabA-like β-hydroxy acyl-ACP dehydrase (DH) in the non-bacterial PUFA PKS system. In another aspect, the modification is selected from the group consisting of a deletion of all or a part of the domain, a substitution of a homologous domain from a different organism for the domain, and a mutation of the domain.

In another aspect, the organism expresses a PKS system and the genetic modification comprises substituting a FabA-like β-hydroxy acyl-ACP dehydrase (DH) domain from a PUFA PKS system for a DH domain that does not posses isomerization activity.

In another aspect, the organism expresses a non-bacterial PUFA PKS system comprising a modification in an enoyl-ACP reductase (ER) domain, wherein the modification results in the production of a different compound as compared to in the absence of the modification. For example, the modification can be selected from the group consisting of a deletion of all or a part of the ER domain, a substitution of an ER domain from a different organism for the ER domain, and a mutation of the ER domain.

In one aspect, the bioactive molecule produced by the present method can include, but is not limited to, an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, and a cholesterol lowering formulation. In one aspect, the bioactive molecule is a polyunsaturated fatty acid (PUFA). In another aspect, the bioactive molecule is a molecule including carbon-carbon double bonds in the cis configuration. In another aspect, the bioactive molecule is a molecule including a double bond at every third carbon.

In one aspect of this embodiment, the organism is a microorganism, and in another aspect, the organism is a plant.

Another embodiment of the present invention relates to a method to produce a plant that has a polyunsaturated fatty acid (PUFA) profile that differs from the naturally occurring plant, comprising genetically modifying cells of the plant to express a PKS system comprising at least one recombinant nucleic acid molecule comprising a nucleic acid sequence encoding at least one biologically active domain of a PUFA PKS system. The domain of the PUFA PKS system is encoded by any of the nucleic acid sequences described above.

Yet another embodiment of the present invention relates to a method to modify an endproduct containing at least one fatty acid, comprising adding to the endproduct an oil produced by a recombinant host cell that expresses at least one recombinant nucleic acid molecule comprising a nucleic acid sequence encoding at least one biologically active domain of a PUFA PKS system. The domain of a PUFA PKS system is encoded by any of the nucleic acid sequences described above. In one aspect, the endproduct is selected from the group consisting of a dietary supplement, a food product, a pharmaceutical formulation, a humanized animal milk, and an infant formula. A pharmaceutical formulation can include, but is not limited to: an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, and a cholesterol lowering formulation. In one aspect, the endproduct is used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, and peroxisomal disorder.

Yet another embodiment of the present invention relates to a method to produce a humanized animal milk, comprising genetically modifying milk-producing cells of a milk-producing animal with at least one recombinant nucleic acid molecule comprising a nucleic acid sequence encoding at least one biologically active domain of a PUFA PKS system. The domain of the PUFA PKS system is encoded by any of the nucleic acid sequences described above.

Yet another embodiment of the present invention relates to a method produce a recombinant microbe, comprising genetically modifying microbial cells to express at least one recombinant nucleic acid molecule comprising a comprising a nucleic acid sequence encoding at least one biologically active domain of a PUFA PKS system. The domain of the PUFA PKS system is encoded by any of the nucleic acid sequences described above.

Yet another embodiment of the present invention relates to a recombinant host cell which has been modified to express a polyunsaturated fatty acid (PUFA) polyketide synthase (PKS) system, wherein the PKS catalyzes both iterative and non-iterative enzymatic reactions. The PUFA PKS system comprises: (a) at least two enoyl ACP-reductase (ER) domains; (b) at least six acyl carrier protein (ACP) domains; (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; and (h) at least one malonyl-CoA:ACP acyltransferase (MAT) domain. In one aspect, the PUFA PKS system is a eukaryotic PUFA PKS system. In another aspect, the PUFA PKS system is an algal PUFA PKS system, and preferably a Thraustochytriales PUFA PKS system, which can include, but is not limited to, a *Schizochytrium* PUFA PKS system or a *Thraustochytrium* PUFA PKS system.

In this embodiment, the PUFA PKS system can be expressed in a prokaryotic host cell or in a eukaryotic host cell. In one aspect, the host cell is a plant cell. Accordingly, one embodiment of the invention is a method to produce a product containing at least one PUFA, comprising growing a plant comprising such a plant cell under conditions effective to produce the product. The host cell is a microbial cell and in this case, one embodiment of the present invention is a method to produce a product containing at least one PUFA, comprising culturing a culture containing such a microbial cell under conditions effective to produce the product. In one aspect, the PKS system catalyzes the direct production of triglycerides.

Yet another embodiment of the present invention relates to a genetically modified microorganism comprising a polyunsaturated fatty acid (PUFA) polyketide synthase (PKS) system, wherein the PKS catalyzes both iterative and non-iterative enzymatic reactions. The PUFA PKS system comprises: (a) at least two enoyl ACP-reductase (ER) domains; (b) at least six acyl carrier protein (ACP) domains; (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; and (h) at least one malonyl-CoA:ACP acyltransferase (MAT) domain. The genetic modification affects the activity of the PUFA PKS system. In one aspect of this embodiment, the microorganism is a eukaryotic microorganism.

Yet another embodiment of the present invention relates to a recombinant host cell which has been modified to express a non-bacterial polyunsaturated fatty acid (PUFA) polyketide synthase (PKS) system, wherein the non-bacterial PUFA PKS catalyzes both iterative and non-iterative enzymatic reactions. The non-bacterial PUFA PKS system comprises: (a) at least one enoyl ACP-reductase (ER) domain; (b) multiple acyl carrier protein (ACP) domains; (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; and (h) at least one malonyl-CoA:ACP acyltransferase (MAT) domain.

DETAILED DESCRIPTION OF THE INVENTION

Figure 1:
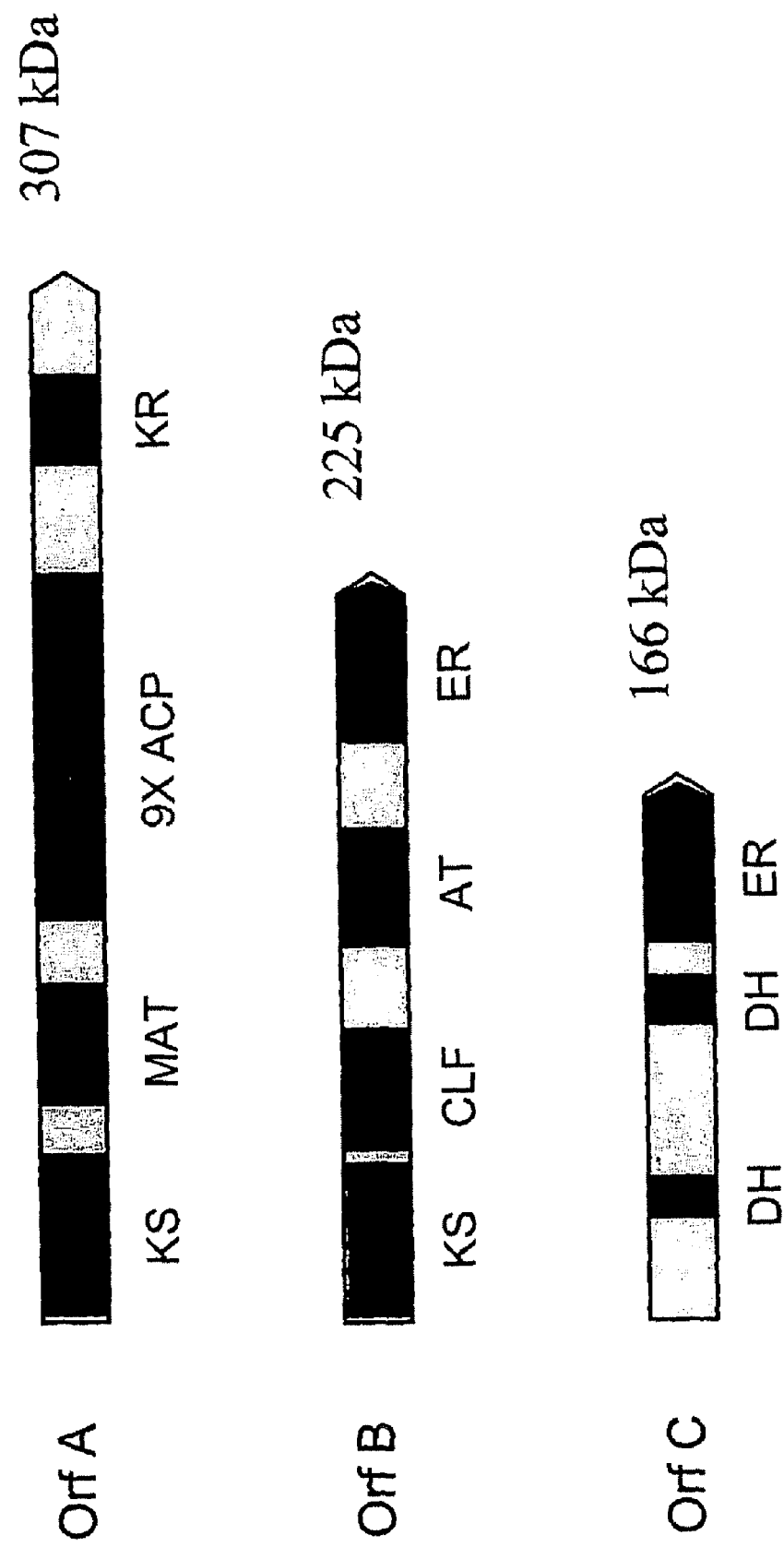
FIG. 1 is a graphical representation of the domain structure of the *Schizochytrium* PUFA PKS system.

The present invention generally relates to non-bacterial derived polyunsaturated fatty acid (PUFA) polyketide synthase (PKS) systems, to genetically modified organisms comprising non-bacterial PUFA PKS systems, to methods of making and using such systems for the production of products of interest, including bioactive molecules, and to novel methods for identifying new eukaryotic microorganisms having such a PUFA PKS system. As used herein, a PUFA PKS system generally has the following identifying features: (1) it produces PUFAs as a natural product of the system; and (2) it comprises several multifunctional proteins assembled into a complex that conducts both iterative processing of the fatty acid chain as well non-iterative processing, including trans-cis isomerization and enoyl reduction reactions in selected cycles (See FIG. 1, for example).

More specifically, first, a PUFA PKS system that forms the basis of this invention produces polyunsaturated fatty acids (PUFAs) as products (i.e., an organism that endogenously (naturally) contains such a PKS system makes PUFAs using this system). The PUFAs referred to herein are preferably polyunsaturated fatty acids with a carbon chain length of at least 16 carbons, and more preferably at least 18 carbons, and more preferably at least 20 carbons, and more preferably 22 or more carbons, with at least 3 or more double bonds, and preferably 4 or more, and more preferably 5 or more, and even more preferably 6 or more double bonds, wherein all double bonds are in the cis configuration. It is an object of the present invention to find or create via genetic manipulation or manipulation of the endproduct, PKS systems which produce polyunsaturated fatty acids of desired chain length and with desired numbers of double bonds. Examples of PUFAs include, but are not limited to, DHA (docosahexaenoic acid (C22:6, ω-3)), DPA (docosapentaenoic acid (C22:5, ω-6)), and EPA (eicosapentaenoic acid (C20:5, ω-3)).

Second, the PUFA PKS system described herein incorporates both iterative and non-iterative reactions, which distinguish the system from previously described PKS systems (e.g., type I, type II or modular). More particularly, the PUFA PKS system described herein contains domains that appear to function during each cycle as well as those which appear to function during only some of the cycles. A key aspect of this may be related to the domains showing homology to the bacterial Fab A enzymes. For example, the Fab A enzyme of E. coli has been shown to possess two enzymatic activities. It possesses a dehydration activity in which a water molecule ($H_2O$) is abstracted from a carbon chain containing a hydroxy group, leaving a trans double bond in that carbon chain. In addition, it has an isomerase activity in which the trans double bond is converted to the cis configuration. This isomerization is accomplished in conjunction with a migration of the double bond position to adjacent carbons. In PKS (and FAS) systems, the main carbon chain is extended in 2 carbon increments. One can therefore predict the number of extension reactions required to produce the PUFA products of these PKS systems. For example, to produce DHA (C22:6, all cis) requires 10 extension reactions. Since there are only 6 double bonds in the end product, it means that during some of the reaction cycles, a double bond is retained (as a cis isomer), and in others, the double bond is reduced prior to the next extension.

Before the discovery of a PUFA PKS system in marine bacteria (see U.S. Pat. No. 6,140,486), PKS systems were not known to possess this combination of iterative and selective enzymatic reactions, and they were not thought of as being able to produce carbon-carbon double bonds in the cis configuration. However, the PUFA PKS system described by the present invention has the capacity to introduce cis double bonds and the capacity to vary the reaction sequence in the cycle.

Therefore, the present inventors propose to use these features of the PUFA PKS system to produce a range of bioactive molecules that could not be produced by the previously described (Type II, Type I and modular) PKS systems. These bioactive molecules include, but are limited to, polyunsaturated fatty acids (PUFAs), antibiotics or other bioactive compounds, many of which will be discussed below. For example, using the knowledge of the PUFA PKS gene structures described herein, any of a number of methods can be used to alter the PUFA PKS genes, or combine portions of these genes with other synthesis systems, including other PKS systems, such that new products are produced. The inherent ability of this particular type of system to do both iterative and selective reactions will enable this system to yield products that would not be found if similar methods were applied to other types of PKS systems.

In one embodiment, a PUFA PKS system according to the present invention comprises at least the following biologically active domains: (a) at least two enoyl ACP-reductase (ER) domains; (b) at least six acyl carrier protein (ACP) domains; (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; and (h) at least one malonyl-CoA:ACP acyltransferase (MAT) domain. The functions of these domains are generally individually known in the art and will be described in detail below with regard to the PUFA PKS system of the present invention.

In another embodiment, the PUFA PKS system comprises at least the following biologically active domains: (a) at least one enoyl ACP-reductase (ER) domain; (b) multiple acyl carrier protein (ACP) domains (at least four, and preferably at least five, and more preferably at least six, and even more preferably seven, eight, nine, or more than nine); (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; and (h) at least one malonyl-CoA:ACP acyltransferase (MAT) domain. Preferably, such a PUFA PKS system is a non-bacterial PUFA-PKS system.

In one embodiment, a PUFA PKS system of the present invention is a non-bacterial PUFA PKS system. In other words, in one embodiment, the PUFA PKS system of the present invention is isolated from an organism that is not a bacteria, or is a homologue of or derived from a PUFA PKS system from an organism that is not a bacteria, such as a eukaryote or an archaebacterium. Eukaryotes are separated from prokaryotes based on the degree of differentiation of the cells. The higher group with more differentiation is called eukaryotic. The lower group with less differentiated cells is called prokaryotic. In general, prokaryotes do no possess a nuclear membrane, do not exhibit mitosis during cell division, have only one chromosome, their cytoplasm contains 70S ribosomes, they do not possess any mitochondria, endoplasmic reticulum, chloroplasts, lysosomes or golgi apparatus, their flagella (if present) consists of a single fibril. In contrast eukaryotes have a nuclear membrane, they do exhibit mitosis during cell division, they have many chromosomes, their cytoplasm contains 80S ribosomes, they do possess mitochondria, endoplasmic reticulum, chloroplasts (in algae), lysosomes and golgi apparatus, and their flagella (if present) consists of many fibrils. In general, bacteria are prokaryotes, while algae, fungi, protist, protozoa and higher plants are eukaryotes. The PUFA PKS systems of the marine bacteria (e.g., *Shewanella* and *Vibrio marinus*) are not the basis of the present invention, although the present invention does contemplate the use of domains from these bacterial PUFA PKS systems in conjunction with domains from the non-bacterial PUFA PKS systems of the present invention. For example, according to the present invention, genetically modified organisms can be produced which incorporate non-bacterial PUFA PKS functional domains with bacteria PUFA PKS functional domains, as well as PKS functional domains or proteins from other PKS systems (type I, type II, modular) or FAS systems.

*Schizochytrium* is a Thraustochytrid marine microorganism that accumulates large quantities of triacylglycerols rich in DHA and docosapentaenoic acid (DPA; 22:5 ω-6); e.g., 30% DHA+DPA by dry weight (Barclay et al., *J. Appl. Phycol.* 6, 123 (1994)). In eukaryotes that synthesize 20- and 22-carbon PUFAs by an elongation/desaturation pathway, the pools of 18-, 20- and 22-carbon intermediates are relatively large so that in vivo labeling experiments using [$^{14}$C]-acetate reveal clear precursor-product kinetics for the predicted intermediates (Gellerman et al., *Biochim. Biophys. Acta* 573:23 (1979)). Furthermore, radiolabeled intermediates provided exogenously to such organisms are converted to the final PUFA products. The present inventors have shown that [1-$^{14}$C]-acetate was rapidly taken up by *Schizochytrium* cells and incorporated into fatty acids, but at the shortest labeling time (1 min), DHA contained 31% of the label recovered in fatty acids, and this percentage remained essentially unchanged during the 10-15 min of [$^{14}$C]-acetate incorporation and the subsequent 24 hours of culture growth (See Example 3). Similarly, DPA represented 10% of the label throughout the experiment. There is no evidence for a precursor-product relationship between 16- or 18-carbon fatty acids and the 22-carbon polyunsaturated fatty acids. These results are consistent with rapid synthesis of DHA from [$^{14}$C]-acetate involving very small (possibly enzyme-bound) pools of intermediates. A cell-free homogenate derived from *Schizochytrium* cultures incorporated [1-$^{14}$C]-malonyl-CoA into DHA, DPA, and saturated fatty acids. The same biosynthetic activities were retained by a 100,000×g supernatant fraction but were not present in the membrane pellet. Thus, DHA and DPA synthesis in *Schizochytrium* does not involve membrane-bound desaturases or fatty acid elongation enzymes like those described for other eukaryotes (Parker-Barnes et al., 2000, supra; Shanklin et al., 1998, supra). These fractionation data contrast with those obtained from the *Shewanella* enzymes (See Metz et al., 2001, supra) and may indicate use of a different (soluble) acyl acceptor molecule, such as CoA, by the *Schizochytrium* enzyme.

In copending U.S. application Ser. No. 09/231,899, a cDNA library from *Schizochytrium* was constructed and approximately 8,000 random clones (ESTs) were sequenced. Within this dataset, only one moderately expressed gene (0.3% of all sequences) was identified as a fatty acid desaturase, although a second putative desaturase was represented by a single clone (0.01%). By contrast, sequences that exhibited homology to 8 of the 11 domains of the *Shewanella* PKS genes shown in FIG. 2 were all identified at frequencies of 0.2-0.5%. In U.S. application Ser. No. 09/231,899, several cDNA clones showing homology to the *Shewanella* PKS genes were sequenced, and various clones were assembled into nucleic acid sequences representing two partial open reading frames and one complete open reading frame. Nucleotides 390-4443 of the cDNA sequence containing the first partial open reading frame described in U.S. application Ser. No. 09/231,899 (denoted therein as SEQ ID NO:69) match nucleotides 4677-8730 (plus the stop codon) of the sequence denoted herein as OrfA (SEQ ID NO:1). Nucleotides 1-4876 of the cDNA sequence containing the second partial open reading frame described in U.S. application Ser. No. 09/231,899 (denoted therein as SEQ ID NO:71) matches nucleotides 1311-6177 (plus the stop codon) of the sequence denoted herein as OrfB (SEQ ID NO:3). Nucleotides 145-4653 of the cDNA sequence containing the complete open reading frame described in U.S. application Ser. No. 09/231,899 (denoted therein as SEQ ID NO:76 and incorrectly designated as a partial open reading frame) match the entire sequence (plus the stop codon) of the sequence denoted herein as OrfC (SEQ ID NO:5).

Figure 2:
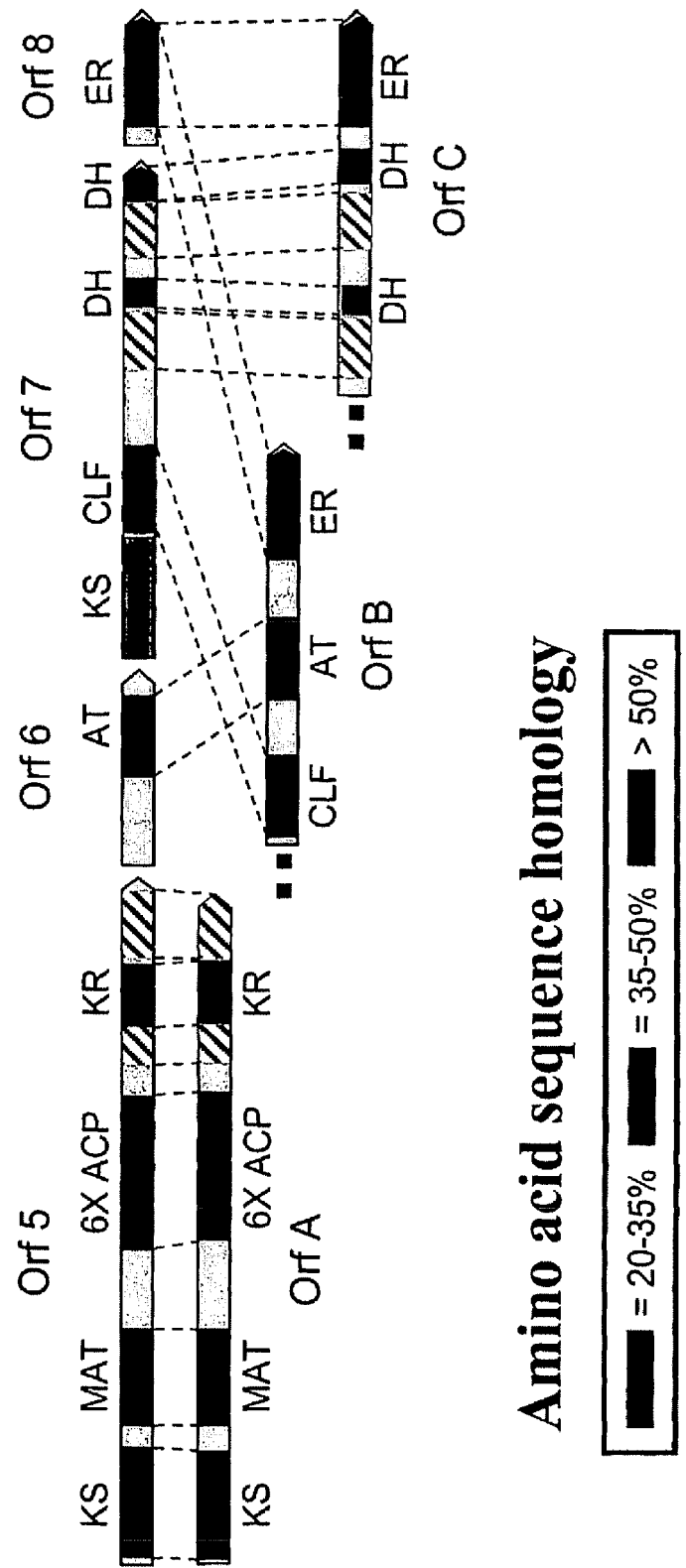
FIG. 2 shows a comparison of PKS domains from *Schizochytrium* and *Shewanella*.

Further sequencing of cDNA and genomic clones by the present inventors allowed the identification of the full-length genomic sequence of each of OrfA, OrfB and OrfC and the complete identification of the domains with homology to those in *Shewanella* (see FIG. 2). It is noted that in *Schizochytrium*, the genomic DNA and cDNA are identical, due to the lack of introns in the organism genome, to the best of the present inventors' knowledge. Therefore, reference to a nucleotide sequence from *Schizochytrium* can refer to genomic DNA or cDNA. Based on the comparison of the *Schizochytrium* PKS domains to *Shewanella*, clearly, the *Schizochytrium* genome encodes proteins that are highly similar to the proteins in *Shewanella* that are capable of catalyzing EPA synthesis. The proteins in *Schizochytrium* constitute a PUFA PKS system that catalyzes DHA and DPA synthesis. As discussed in detail herein, simple modification of the reaction scheme identified for *Shewanella* will allow for DHA synthesis in *Schizochytrium*. The homology between the prokaryotic *Shewanella* and eukaryotic *Schizochytrium* genes suggests that the PUFA PKS has undergone lateral gene transfer.

FIG. 1 is a graphical representation of the three open reading frames from the *Schizochytrium* PUFA PKS system, and includes the domain structure of this PUFA PKS system. As described in Example 1 below, the domain structure of each open reading frame is as follows:

Open Reading Frame A (OrfA):

The complete nucleotide sequence for OrfA is represented herein as SEQ ID NO:1. Nucleotides 4677-8730 of SEQ ID NO:1 correspond to nucleotides 390-4443 of the sequence denoted as SEQ ID NO:69 in U.S. application Ser. No. 09/231,899. Therefore, nucleotides 1-4676 of SEQ ID NO: 1 represent additional sequence that was not disclosed in U.S. application Ser. No. 09/231,899. This novel region of SEQ ID NO:1 encodes the following domains in OrfA: (1) the ORFA-KS domain; (2) the ORFA-MAT domain; and (3) at least a portion of the ACP domain region (e.g., at least ACP domains 1-4). It is noted that nucleotides 1-389 of SEQ ID NO:69 in U.S. application Ser. No. 09/231,899 do not match with the 389 nucleotides that are upstream of position 4677 in SEQ ID NO:1 disclosed herein. Therefore, positions 1-389 of SEQ ID NO:69 in U.S. application Ser. No. 09/231,899 appear to be incorrectly placed next to nucleotides 390-4443 of that sequence. Most of these first 389 nucleotides (about positions 60-389) are a match with an upstream portion of OrfA (SEQ ID NO:1) of the present invention and therefore, it is believed that an error occurred in the effort to prepare the contig of the cDNA constructs in U.S. application Ser. No. 09/231,899. The region in which the alignment error occurred in U.S. application Ser. No. 09/231,899 is within the region of highly repetitive sequence (i.e., the ACP region, discussed below), which probably created some confusion in the assembly of that sequence from various cDNA clones.

OrfA is a 8730 nucleotide sequence (not including the stop codon) which encodes a 2910 amino acid sequence, represented herein as SEQ ID NO:2. Within OrfA are twelve domains: (a) one β-keto acyl-ACP synthase (KS) domain; (b) one malonyl-CoA:ACP acyltransferase (MAT) domain; (c) nine acyl carrier protein (ACP) domains; and (d) one ketoreductase (KR) domain.

The nucleotide sequence for OrfA has been deposited with GenBank as Accession No. AF378327 (amino acid sequence Accession No. AAK728879). OrfA was compared with known sequences in a standard BLAST search (BLAST 2.0 Basic BLAST homology search using blastp for amino acid searches, blastn for nucleic acid searches, and blastX for nucleic acid searches and searches of the translated amino acid sequence in all 6 open reading frames with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety)). At the nucleic acid level, OrfA has no significant homology to any known nucleotide sequence. At the amino acid level, the sequences with the greatest degree of homology to ORFA were: *Nostoc* sp. 7120 heterocyst glycolipid synthase (Accession No. NC_003272), which was 42% identical to ORFA over 1001 amino acid residues; and *Moritella marinus* (*Vibrio marinus*) ORF8 (Accession No. AB025342), which was 40% identical to ORFA over 993 amino acid residues.

The first domain in OrfA is a KS domain, also referred to herein as ORFA-KS. This domain is contained within the nucleotide sequence spanning from a starting point of between about positions 1 and 40 of SEQ ID NO:1 (OrfA) to an ending point of between about positions 1428 and 1500 of SEQ ID NO:1. The nucleotide sequence containing the sequence encoding the ORFA-KS domain is represented herein as SEQ ID NO:7 (positions 1-1500 of SEQ ID NO:1). The amino acid sequence containing the KS domain spans from a starting point of between about positions 1 and 14 of SEQ ID NO:2 (ORFA) to an ending point of between about positions 476 and 500 of SEQ ID NO:2. The amino acid sequence containing the ORFA-KS domain is represented herein as SEQ ID NO:8 (positions 1-500 of SEQ ID NO:2). It is noted that the ORFA-KS domain contains an active site motif: DXAC* (*acyl binding site $C_{215}$).

According to the present invention, a domain or protein having 3-keto acyl-ACP synthase (KS) biological activity (function) is characterized as the enzyme that carries out the initial step of the FAS (and PKS) elongation reaction cycle. The acyl group destined for elongation is linked to a cysteine residue at the active site of the enzyme by a thioester bond. In the multi-step reaction, the acyl-enzyme undergoes condensation with malonyl-ACP to form -keto acyl-ACP, $CO_2$ and free enzyme. The KS plays a key role in the elongation cycle and in many systems has been shown to possess greater substrate specificity than other enzymes of the reaction cycle. For example, *E. coli* has three distinct KS enzymes—each with its own particular role in the physiology of the organism (Magnuson et al., *Microbiol. Rev.* 57, 522 (1993)). The two KS domains of the PUFA-PKS systems could have distinct roles in the PUFA biosynthetic reaction sequence.

As a class of enzymes, KS's have been well characterized. The sequences of many verified KS genes are know, the active site motifs have been identified and the crystal structures of several have been determined. Proteins (or domains of proteins) can be readily identified as belonging to the KS family of enzymes by homology to known KS sequences.

The second domain in OrfA is a MAT domain, also referred to herein as ORFA-MAT. This domain is contained within the nucleotide sequence spanning from a starting point of between about positions 1723 and 1798 of SEQ ID NO:1 (OrfA) to an ending point of between about positions 2805 and 3000 of SEQ ID NO:1. The nucleotide sequence containing the sequence encoding the ORFA-MAT domain is represented herein as SEQ ID NO:9 (positions 1723-3000 of SEQ ID NO:1). The amino acid sequence containing the MAT domain spans from a starting point of between about positions 575 and 600 of SEQ ID NO:2 (ORFA) to an ending point of between about positions 935 and 1000 of SEQ ID NO:2. The amino acid sequence containing the ORFA-MAT domain is represented herein as SEQ ID NO:10 (positions 575-1000 of SEQ ID NO:2). It is noted that the ORFA-MAT domain contains an active site motif: GHS*XG (*acyl binding site $S_{706}$), represented herein as SEQ ID NO:11.

According to the present invention, a domain or protein having malonyl-CoA:ACP acyltransferase (MAT) biological activity (function) is characterized as one that transfers the malonyl moiety from malonyl-CoA to ACP. In addition to the active site motif (GxSxG), these enzymes possess an extended motif ® and Q amino acids in key positions) that identifies them as MAT enzymes (in contrast to the AT domain of *Schizochytrium* Orf B). In some PKS systems (but not the PUFA PKS domain) MAT domains will preferentially load methyl- or ethyl-malonate on to the ACP group (from the corresponding CoA ester), thereby introducing branches into the linear carbon chain. MAT domains can be recognized by their homology to known MAT sequences and by their extended motif structure.

Domains 3-11 of OrfA are nine tandem ACP domains, also referred to herein as ORFA-ACP (the first domain in the sequence is ORFA-ACP 1, the second domain is ORFA-ACP2, the third domain is ORFA-ACP3, etc.). The first ACP domain, ORFA-ACP1, is contained within the nucleotide sequence spanning from about position 3343 to about position 3600 of SEQ ID NO: 1 (OrfA). The nucleotide sequence containing the sequence encoding the ORFA-ACP1 domain is represented herein as SEQ ID NO: 12 (positions 3343-3600 of SEQ ID NO: 1). The amino acid sequence containing the first ACP domain spans from about position 1115 to about position 1200 of SEQ ID NO:2. The amino acid sequence containing the ORFA-ACP1 domain is represented herein as SEQ ID NO: 13 (positions 1115-1200 of SEQ ID NO:2). It is noted that the ORFA-ACP1 domain contains an active site motif: LGIDS* (*pantetheine binding motif $S_{1157}$), represented herein by SEQ ID NO:14.

The nucleotide and amino acid sequences of all nine ACP domains are highly conserved and therefore, the sequence for each domain is not represented herein by an individual sequence identifier. However, based on the information disclosed herein, one of skill in the art can readily determine the sequence containing each of the other eight ACP domains (see discussion below).

All nine ACP domains together span a region of OrfA of from about position 3283 to about position 6288 of SEQ ID NO: 1, which corresponds to amino acid positions of from about 1095 to about 2096 of SEQ ID NO:2. The nucleotide sequence for the entire ACP region containing all nine domains is represented herein as SEQ ID NO:16. The region represented by SEQ ID NO:16 includes the linker segments between individual ACP domains. The repeat interval for the nine domains is approximately every 330 nucleotides of SEQ ID NO:16 (the actual number of amino acids measured between adjacent active site serines ranges from 104 to 116 amino acids). Each of the nine ACP domains contains a pantetheine binding motif LGIDS* (represented herein by SEQ ID NO:14), wherein S* is the pantetheine binding site serine (S). The pantetheine binding site serine (S) is located near the center of each ACP domain sequence. At each end of the ACP domain region and between each ACP domain is a region that is highly enriched for proline (P) and alanine (A), which is believed to be a linker region. For example, between ACP domains 1 and 2 is the sequence: APAPVKAAA-PAAPVASAPAPA, represented herein as SEQ ID NO:15.

The locations of the active site serine residues (i.e., the pantetheine binding site) for each of the nine ACP domains, with respect to the amino acid sequence of SEQ ID NO:2, are as follows: ACP1=$S_{1157}$; ACP2=$S_{1266}$; ACP3=$S_{1377}$; ACP4=$S_{1488}$; ACP5=$S_{1604}$; ACP6=$S_{1715}$; ACP7=$S_{1819}$; ACP8=$S_{1930}$; and ACP9=$S_{2034}$. Given that the average size of an ACP domain is about 85 amino acids, excluding the linker, and about 110 amino acids including the linker, with the active site serine being approximately in the center of the domain, one of skill in the art can readily determine the positions of each of the nine ACP domains in OrfA.

According to the present invention, a domain or protein having acyl carrier protein (ACP) biological activity (function) is characterized as being small polypeptides (typically, 80 to 100 amino acids long), that function as carriers for growing fatty acyl chains via a thioester linkage to a covalently bound co-factor of the protein. They occur as separate units or as domains within larger proteins. ACPs are converted from inactive apo-forms to functional holo-forms by transfer of the phosphopantetheinyl moeity of CoA to a highly conserved serine residue of the ACP. Acyl groups are attached to ACP by a thioester linkage at the free terminus of the phosphopantetheinyl moiety. ACPs can be identified by labeling with radioactive pantetheine and by sequence homology to known ACPs. The presence of variations of the above mentioned motif (LGIDS*) is also a signature of an ACP.

Domain 12 in OrfA is a KR domain, also referred to herein as ORFA-KR. This domain is contained within the nucleotide sequence spanning from a starting point of about position 6598 of SEQ ID NO:1 to an ending point of about position 8730 of SEQ ID NO:1.

The nucleotide sequence containing the sequence encoding the ORFA-KR domain is represented herein as SEQ ID NO:17 (positions 6598-8730 of SEQ ID NO:1). The amino acid sequence containing the KR domain spans from a starting point of about position 2200 of SEQ ID NO:2 (ORFA) to an ending point of about position 2910 of SEQ ID NO:2. The amino acid sequence containing the ORFA-KR domain is represented herein as SEQ ID NO:18 (positions 2200-2910 of SEQ ID NO:2). Within the KR domain is a core region with homology to short chain aldehyde-dehydrogenases (KR is a member of this family). This core region spans from about position 7198 to about position 7500 of SEQ ID NO:1, which corresponds to amino acid positions 2400-2500 of SEQ ID NO:2.

According to the present invention, a domain or protein having ketoreductase activity, also referred to as 3-ketoacyl-ACP reductase (KR) biological activity (function), is characterized as one that catalyzes the pyridine-nucleotide-dependent reduction of 3-keto acyl forms of ACP. It is the first reductive step in the de novo fatty acid biosynthesis elongation cycle and a reaction often performed in polyketide biosynthesis. Significant sequence similarity is observed with one family of enoyl ACP reductases (ER), the other reductase of FAS (but not the ER family present in the PUFA PKS system), and the short-chain alcohol dehydrogenase family. Pfam analysis of the PUFA PKS region indicated above reveals the homology to the short-chain alcohol dehydrogenase family in the core region. Blast analysis of the same region reveals matches in the core area to known KR enzymes as well as an extended region of homology to domains from the other characterized PUFA PKS systems.

Open Reading Frame B (OrfB):

The complete nucleotide sequence for OrfB is represented herein as SEQ ID NO:3. Nucleotides 1311-4242 and 4244-6177 of SEQ ID NO:3 correspond to nucleotides 1-2932 and 2934-4867 of the sequence denoted as SEQ ID NO:71 in U.S. application Ser. No. 09/231,899 (The cDNA sequence in U.S. application Ser. No. 09/231,899 contains about 345 additional nucleotides beyond the stop codon, including a polyA tail). Therefore, nucleotides 1-1310 of SEQ ID NO:1 represent additional sequence that was not disclosed in U.S. application Ser. No. 09/231,899. This novel region of SEQ ID NO:3 contains most of the KS domain encoded by OrfB.

OrfB is a 6177 nucleotide sequence (not including the stop codon) which encodes a 2059 amino acid sequence, represented herein as SEQ ID NO:4. Within OrfB are four domains: (a) one β-keto acyl-ACP synthase (KS) domain; (b) one chain length factor (CLF) domain; (c) one acyl transferase (AT) domain; and, (d) one enoyl ACP-reductase (ER) domain.

The nucleotide sequence for OrfB has been deposited with GenBank as Accession No. AF378328 (amino acid sequence Accession No. AAK728880). OrfB was compared with known sequences in a standard BLAST search as described above. At the nucleic acid level, OrfB has no significant homology to any known nucleotide sequence. At the amino acid level, the sequences with the greatest degree of homology to ORFB were: *Shewanella* sp. hypothetical protein (Accession No. U73935), which was 53% identical to ORFB over 458 amino acid residues; *Moritella marinus* (*Vibrio marinus*) ORF11 (Accession No. AB025342), which was 53% identical to ORFB over 460 amino acid residues; *Photobacterium profundum* omega-3 polyunsaturated fatty acid synthase PfaD (Accession No. AF409100), which was 52% identical to ORFB over 457 amino acid residues; and *Nostoc* sp. 7120 hypothetical protein (Accession No. NC_003272), which was 53% identical to ORFB over 430 amino acid residues.

The first domain in OrfB is a KS domain, also referred to herein as ORFB-KS. This domain is contained within the nucleotide sequence spanning from a starting point of between about positions 1 and 43 of SEQ ID NO:3 (OrfB) to an ending point of between about positions 1332 and 1350 of SEQ ID NO:3. The nucleotide sequence containing the sequence encoding the ORFB-KS domain is represented herein as SEQ ID NO:19 (positions 1-1350 of SEQ ID NO:3). The amino acid sequence containing the KS domain spans from a starting point of between about positions 1 and 15 of SEQ ID NO:4 (ORFB) to an ending point of between about positions 444 and 450 of SEQ ID NO:4. The amino acid sequence containing the ORFB-KS domain is represented herein as SEQ ID NO:20 (positions 1-450 of SEQ ID NO:4). It is noted that the ORFB-KS domain contains an active site motif: DXAC* (*acyl binding site $C_{196}$). KS biological activity and methods of identifying proteins or domains having such activity is described above.

The second domain in OrfB is a CLF domain, also referred to herein as ORFB-CLF. This domain is contained within the nucleotide sequence spanning from a starting point of between about positions 1378 and 1402 of SEQ ID NO:3 (OrfB) to an ending point of between about positions 2682 and 2700 of SEQ ID NO:3. The nucleotide sequence containing the sequence encoding the ORFB-CLF domain is represented herein as SEQ ID NO:21 (positions 1378-2700 of SEQ ID NO:3). The amino acid sequence containing the CLF domain spans from a starting point of between about positions 460 and 468 of SEQ ID NO:4 (ORFB) to an ending point of between about positions 894 and 900 of SEQ ID NO:4. The amino acid sequence containing the ORFB-CLF domain is represented herein as SEQ ID NO:22 (positions 460-900 of SEQ ID NO:4). It is noted that the ORFB-CLF domain contains a KS active site motif without the acyl-binding cysteine.

According to the present invention, a domain or protein is referred to as a chain length factor (CLF) based on the following rationale. The CLF was originally described as characteristic of Type II (dissociated enzymes) PKS systems and was hypothesized to play a role in determining the number of elongation cycles, and hence the chain length, of the end product. CLF amino acid sequences show homology to KS domains (and are thought to form heterodimers with a KS protein), but they lack the active site cysteine. CLF's role in PKS systems is currently controversial. New evidence (C. Bisang et al., *Nature* 401, 502 (1999)) suggests a role in priming (providing the initial acyl group to be elongated) the PKS systems. In this role the CLF domain is thought to decarboxylate malonate (as malonyl-ACP), thus forming an acetate group that can be transferred to the KS active site. This acetate therefore acts as the 'priming' molecule that can undergo the initial elongation (condensation) reaction. Homologues of the Type II CLF have been identified as 'loading' domains in some modular PKS systems. A domain with the sequence features of the CLF is found in all currently identified PUFA PKS systems and in each case is found as part of a multidomain protein.

The third domain in OrfB is an AT domain, also referred to herein as ORFB-AT. This domain is contained within the nucleotide sequence spanning from a starting point of between about positions 2701 and 3598 of SEQ ID NO:3 (OrfB) to an ending point of between about positions 3975 and 4200 of SEQ ID NO:3. The nucleotide sequence containing the sequence encoding the ORFB-AT domain is represented herein as SEQ ID NO:23 (positions 2701-4200 of SEQ ID NO:3). The amino acid sequence containing the AT domain spans from a starting point of between about positions 901 and 1200 of SEQ ID NO:4 (ORFB) to an ending point of between about positions 1325 and 1400 of SEQ ID NO:4. The amino acid sequence containing the ORFB-AT domain is represented herein as SEQ ID NO:24 (positions 901-1400 of SEQ ID NO:4). It is noted that the ORFB-AT domain contains an active site motif of GxS*xG (*acyl binding site $S_{1140}$) that is characteristic of acyltransferse (AT) proteins.

An "acyltransferase" or "AT" refers to a general class of enzymes that can carry out a number of distinct acyl transfer reactions. The *Schizochytrium* domain shows good homology to a domain present in all of the other PUFA PKS systems currently examined and very weak homology to some acyltransferases whose specific functions have been identified (e.g. to malonyl-CoA:ACP acyltransferase, MAT). In spite of the weak homology to MAT, this AT domain is not believed to function as a MAT because it does not possess an extended motif structure characteristic of such enzymes (see MAT domain description, above). For the purposes of this disclosure, the functions of the AT domain in a PUFA PKS system include, but are not limited to: transfer of the fatty acyl group from the ORFA ACP domain(s) to water (i.e. a thioesterase—releasing the fatty acyl group as a free fatty acid), transfer of a fatty acyl group to an acceptor such as CoA, transfer of the acyl group among the various ACP domains, or transfer of the fatty acyl group to a lipophilic acceptor molecule (e.g. to lysophosphadic acid).

The fourth domain in OrfB is an ER domain, also referred to herein as ORFB-ER. This domain is contained within the nucleotide sequence spanning from a starting point of about position 4648 of SEQ ID NO:3 (OrfB) to an ending point of about position 6177 of SEQ ID NO:3. The nucleotide sequence containing the sequence encoding the ORFB-ER domain is represented herein as SEQ ID NO:25 (positions 4648-6177 of SEQ ID NO:3). The amino acid sequence containing the ER domain spans from a starting point of about position 1550 of SEQ ID NO:4 (ORFB) to an ending point of about position 2059 of SEQ ID NO:4. The amino acid sequence containing the ORFB-ER domain is represented herein as SEQ ID NO:26 (positions 1550-2059 of SEQ ID NO:4).

According to the present invention, this domain has enoyl reductase (ER) biological activity. The ER enzyme reduces the trans-double bond (introduced by the DH activity) in the fatty acyl-ACP, resulting in fully saturating those carbons. The ER domain in the PUFA-PKS shows homology to a newly characterized family of ER enzymes (Heath et al., *Nature* 406, 145 (2000)). Heath and Rock identified this new class of ER enzymes by cloning a gene of interest from *Streptococcus pneumoniae*, purifying a protein expressed from that gene, and showing that it had ER activity in an in vitro assay. The sequence of the *Schizochytrium* ER domain of OrfB shows homology to the *S. pneumoniae* ER protein. All of the PUFA PKS systems currently examined contain at least one domain with very high sequence homology to the *Schizochytrium* ER domain. The *Schizochytrium* PUFA PKS system contains two ER domains (one on OrfB and one on OrfC).

Open Reading Frame C (OrfC):

The complete nucleotide sequence for OrfC is represented herein as SEQ ID NO:5. Nucleotides 1-4506 of SEQ ID NO:5 (i.e., the entire open reading frame sequence, not including the stop codon) correspond to nucleotides 145-2768, 2770-2805, 2807-2817, and 2819-4653 of the sequence denoted as SEQ ID NO:76 in U.S. application Ser. No. 09/231,899 (The cDNA sequence in U.S. application Ser. No. 09/231,899 contains about 144 nucleotides upstream of the start codon for OrfC and about 110 nucleotides beyond the stop codon, including a polyA tail). OrfC is a 4506 nucleotide sequence (not including the stop codon) which encodes a 1502 amino acid sequence, represented herein as SEQ ID NO:6. Within OrfC are three domains: (a) two FabA-like β-hydroxy acyl-ACP dehydrase (DH) domains; and (b) one enoyl ACP-reductase (ER) domain.

The nucleotide sequence for OrfC has been deposited with GenBank as Accession No. AF378329 (amino acid sequence Accession No. AAK728881). OrfC was compared with known sequences in a standard BLAST search as described above. At the nucleic acid level, OrfC has no significant homology to any known nucleotide sequence. At the amino acid level (Blastp), the sequences with the greatest degree of homology to ORFC were: *Moritella marinus* (*Vibrio marinus*) ORF11 (Accession No. ABO25342), which is 45% identical to ORFC over 514 amino acid residues, *Shewanella* sp. hypothetical protein 8 (Accession No. U73935), which is 49% identical to ORFC over 447 amino acid residues, *Nostoc* sp. hypothetical protein (Accession No. NC_003272), which is 49% identical to ORFC over 430 amino acid residues, and *Shewanella* sp. hypothetical protein 7 (Accession No. U73935), which is 37% identical to ORFC over 930 amino acid residues.

The first domain in OrfC is a DH domain, also referred to herein as ORFC-DH1. This is one of two DH domains in OrfC, and therefore is designated DH1. This domain is contained within the nucleotide sequence spanning from a starting point of between about positions 1 and 778 of SEQ ID NO:5 (OrfC) to an ending point of between about positions 1233 and 1350 of SEQ ID NO:5. The nucleotide sequence containing the sequence encoding the ORFC-DH1 domain is represented herein as SEQ ID NO:27 (positions 1-1350 of SEQ ID NO:5). The amino acid sequence containing the DH1 domain spans from a starting point of between about positions 1 and 260 of SEQ ID NO:6 (ORFC) to an ending point of between about positions 411 and 450 of SEQ ID NO:6. The amino acid sequence containing the ORFC-DH1 domain is represented herein as SEQ ID NO:28 (positions 1-450 of SEQ ID NO:6).

The characteristics of both the DH domains (see below for DH 2) in the PUFA PKS systems have been described in the preceding sections. This class of enzyme removes HOH from a β-keto acyl-ACP and leaves a trans double bond in the carbon chain. The DH domains of the PUFA PKS systems show homology to bacterial DH enzymes associated with their FAS systems (rather than to the DH domains of other PKS systems). A subset of bacterial DH's, the FabA-like DH's, possesses cis-trans isomerase activity (Heath et al., *J. Biol. Chem.*, 271, 27795 (1996)). It is the homologies to the FabA-like DH's that indicate that one or both of the DH domains is responsible for insertion of the cis double bonds in the PUFA PKS products.

The second domain in OrfC is a DH domain, also referred to herein as ORFC-DH2. This is the second of two DH domains in OrfC, and therefore is designated DH2. This domain is contained within the nucleotide sequence spanning from a starting point of between about positions 1351 and 2437 of SEQ ID NO:5 (OrfC) to an ending point of between about positions 2607 and 2847 of SEQ ID NO:5. The nucleotide sequence containing the sequence encoding the ORFC-DH2 domain is represented herein as SEQ ID NO:29 (positions 1351-2847 of SEQ ID NO:5). The amino acid sequence containing the DH2 domain spans from a starting point of between about positions 451 and 813 of SEQ ID NO:6 (ORFC) to an ending point of between about positions 869 and 949 of SEQ ID NO:6. The amino acid sequence containing the ORFC-DH2 domain is represented herein as SEQ ID NO:30 (positions 451-949 of SEQ ID NO:6). DH biological activity has been described above.

The third domain in OrfC is an ER domain, also referred to herein as ORFC-ER. This domain is contained within the nucleotide sequence spanning from a starting point of about position 2995 of SEQ ID NO:5 (OrfC) to an ending point of about position 4506 of SEQ ID NO:5. The nucleotide sequence containing the sequence encoding the ORFC-ER domain is represented herein as SEQ ID NO:31 (positions 2995-4506 of SEQ ID NO:5). The amino acid sequence containing the ER domain spans from a starting point of about position 999 of SEQ ID NO:6 (ORFC) to an ending point of about position 1502 of SEQ ID NO:6. The amino acid sequence containing the ORFC-ER domain is represented herein as SEQ ID NO:32 (positions 999-1502 of SEQ ID NO:6). ER biological activity has been described above.

One embodiment of the present invention relates to an isolated nucleic acid molecule comprising a nucleic acid sequence from a non-bacterial PUFA PKS system, a homologue thereof, a fragment thereof, and/or a nucleic acid sequence that is complementary to any of such nucleic acid sequences. In one aspect, the present invention relates to an isolated nucleic acid molecule comprising a nucleic acid sequence selected from the group consisting of: (a) a nucleic acid sequence encoding an amino acid sequence selected from the group consisting of: SEQ ID NO:2, SEQ ID NO:4, SEQ ID NO: 6, and biologically active fragments thereof; (b) a nucleic acid sequence encoding an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and biologically active fragments thereof; (c) a nucleic acid sequence encoding an amino acid sequence that is at least about 60% identical to at least 500 consecutive amino acids of said amino acid sequence of (a), wherein said amino acid sequence has a biological activity of at least one domain of a polyunsaturated fatty acid (PUFA) polyketide synthase (PKS) system; (d) a nucleic acid sequence encoding an amino acid sequence that is at least about 60% identical to said amino acid sequence of (b), wherein said amino acid sequence has a biological activity of at least one domain of a polyunsaturated fatty acid (PUFA) polyketide synthase (PKS) system; or (e) a nucleic acid sequence that is fully complementary to the nucleic acid sequence of (a), (b), (c), or (d). In a further embodiment, nucleic acid sequences including a sequence encoding the active site domains or other functional motifs described above for several of the PUFA PKS domains are encompassed by the invention.

According to the present invention, an amino acid sequence that has a biological activity of at least one domain of a PUFA PKS system is an amino acid sequence that has the biological activity of at least one domain of the PUFA PKS system described in detail herein, as exemplified by the *Schizochytrium* PUFA PKS system. The biological activities of the various domains within the *Schizochytrium* PUFA PKS system have been described in detail above. Therefore, an isolated nucleic acid molecule of the present invention can encode the translation product of any PUFA PKS open reading frame, PUFA PKS domain, biologically active fragment thereof, or any homologue of a naturally occurring PUFA PKS open reading frame or domain which has biological activity. A homologue of given protein or domain is a protein or polypeptide that has an amino acid sequence which differs from the naturally occurring reference amino acid sequence (i.e., of the reference protein or domain) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). Preferred homologues of a PUFA PKS protein or domain are described in detail below. It is noted that homologues can include synthetically produced homologues, naturally occurring allelic variants of a given protein or domain, or homologous sequences from organisms other than the organism from which the reference sequence was derived.

In general, the biological activity or biological action of a protein or domain refers to any function(s) exhibited or performed by the protein or domain that is ascribed to the naturally occurring form of the protein or domain as measured or observed in vivo (i.e., in the natural physiological environment of the protein) or in vitro (i.e., under laboratory conditions). Biological activities of PUFA PKS systems and the individual proteins/domains that make up a PUFA PKS system have been described in detail elsewhere herein. Modifications of a protein or domain, such as in a homologue or mimetic (discussed below), may result in proteins or domains having the same biological activity as the naturally occurring protein or domain, or in proteins or domains having decreased or increased biological activity as compared to the naturally occurring protein or domain. Modifications which result in a decrease in expression or a decrease in the activity of the protein or domain, can be referred to as inactivation (complete or partial), down-regulation, or decreased action of a protein or domain. Similarly, modifications which result in an increase in expression or an increase in the activity of the protein or domain, can be referred to as amplification, overproduction, activation, enhancement, up-regulation or increased action of a protein or domain. A functional domain of a PUFA PKS system is a domain (i.e., a domain can be a portion of a protein) that is capable of performing a biological function (i.e., has biological activity).

In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on PUFA PKS system biological activity as described herein. Protein homologues (e.g., proteins encoded by nucleic acid homologues) have been discussed in detail above.

A nucleic acid molecule homologue can be produced using a number of methods known to those skilled in the art (see, for example, Sambrook et al., *Molecular Cloning: A Laboratory Manual*, Cold Spring Harbor Labs Press, 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

The minimum size of a nucleic acid molecule of the present invention is a size sufficient to form a probe or oligonucleotide primer that is capable of forming a stable hybrid (e.g., under moderate, high or very high stringency conditions) with the complementary sequence of a nucleic acid molecule useful in the present invention, or of a size sufficient to encode an amino acid sequence having a biological activity of at least one domain of a PUFA PKS system according to the present invention. As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a sequence sufficient to encode a biologically active fragment of a domain of a PUFA PKS system, an entire domain of a PUFA PKS system, several domains within an open reading frame (Orf) of a PUFA PKS system, an entire Orf of a PUFA PKS system, or more than one Orf of a PUFA PKS system.

In one embodiment of the present invention, an isolated nucleic acid molecule comprises or consists essentially of a nucleic acid sequence selected from the group of: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, or biologically active fragments thereof. In one aspect, the nucleic acid sequence is selected from the group of: SEQ ID NO:1, SEQ ID NO:3, SEQ ID NO:5, SEQ ID NO:7, SEQ ID NO:9, SEQ ID NO:12, SEQ ID NO:17, SEQ ID NO:19, SEQ ID NO:21, SEQ ID NO:23, SEQ ID NO:25, SEQ ID NO:27, SEQ ID NO:29, and SEQ ID NO:31. In one embodiment of the present invention, any of the above-described PUFA PKS amino acid sequences, as well as homologues of such sequences, can be produced with from at least one, and up to about 20, additional heterologous amino acids flanking each of the C- and/or N-terminal end of the given amino acid sequence. The resulting protein or polypeptide can be referred to as "consisting essentially of" a given amino acid sequence. According to the present invention, the heterologous amino acids are a sequence of amino acids that are not naturally found (i.e., not found in nature, in vivo) flanking the given amino acid sequence or which would not be encoded by the nucleotides that flank the naturally occurring nucleic acid sequence encoding the given amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a given amino acid sequence that can be flanked by from at least one, and up to as many as about 60, additional heterologous nucleotides at each of the 5' and/or the 3' end of the nucleic acid sequence encoding the given amino acid sequence. The heterologous nucleotides are not naturally found (i.e., not found in nature, in vivo) flanking the nucleic acid sequence encoding the given amino acid sequence as it occurs in the natural gene.

The present invention also includes an isolated nucleic acid molecule comprising a nucleic acid sequence encoding an amino acid sequence having a biological activity of at least one domain of a PUFA PKS system. In one aspect, such a nucleic acid sequence encodes a homologue of any of the *Schizochytrium* PUFA PKS ORFs or domains, including:

SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, wherein the homologue has a biological activity of at least one domain of a PUFA PKS system as described previously herein.

In one aspect of the invention, a homologue of a *Schizochytrium* PUFA PKS protein or domain encompassed by the present invention comprises an amino acid sequence that is at least about 60% identical to at least 500 consecutive amino acids of an amino acid sequence chosen from: SEQ ID NO:2, SEQ ID NO:4, and SEQ ID NO:6; wherein said amino acid sequence has a biological activity of at least one domain of a PUFA PKS system. In a further aspect, the amino acid sequence of the homologue is at least about 60% identical to at least about 600 consecutive amino acids, and more preferably to at least about 700 consecutive amino acids, and more preferably to at least about 800 consecutive amino acids, and more preferably to at least about 900 consecutive amino acids, and more preferably to at least about 1000 consecutive amino acids, and more preferably to at least about 1100 consecutive amino acids, and more preferably to at least about 1200 consecutive amino acids, and more preferably to at least about 1300 consecutive amino acids, and more preferably to at least about 1400 consecutive amino acids, and more preferably to at least about 1500 consecutive amino acids of any of SEQ ID NO:2, SEQ ID NO:4 and SEQ ID NO:6, or to the full length of SEQ ID NO:6. In a further aspect, the amino acid sequence of the homologue is at least about 60% identical to at least about 1600 consecutive amino acids, and more preferably to at least about 1700 consecutive amino acids, and more preferably to at least about 1800 consecutive amino acids, and more preferably to at least about 1900 consecutive amino acids, and more preferably to at least about 2000 consecutive amino acids of any of SEQ ID NO:2 or SEQ ID NO:4, or to the full length of SEQ ID NO:4. In a further aspect, the amino acid sequence of the homologue is at least about 60% identical to at least about 2100 consecutive amino acids, and more preferably to at least about 2200 consecutive amino acids, and more preferably to at least about 2300 consecutive amino acids, and more preferably to at least about 2400 consecutive amino acids, and more preferably to at least about 2500 consecutive amino acids, and more preferably to at least about 2600 consecutive amino acids, and more preferably to at least about 2700 consecutive amino acids, and more preferably to at least about 2800 consecutive amino acids, and even more preferably, to the full length of SEQ ID NO:2.

In another aspect, a homologue of a *Schizochytrium* PUFA PKS protein or domain encompassed by the present invention comprises an amino acid sequence that is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical to an amino acid sequence chosen from: SEQ ID NO:2, SEQ ID NO:4, or SEQ ID NO:6, over any of the consecutive amino acid lengths described in the paragraph above, wherein the amino acid sequence has a biological activity of at least one domain of a PUFA PKS system.

In one aspect of the invention, a homologue of a *Schizochytrium* PUFA PKS protein or domain encompassed by the present invention comprises an amino acid sequence that is at least about 60% identical to an amino acid sequence chosen from: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, wherein said amino acid sequence has a biological activity of at least one domain of a PUFA PKS system. In a further aspect, the amino acid sequence of the homologue is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical to an amino acid sequence chosen from: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, wherein the amino acid sequence has a biological activity of at least one domain of a PUFA PKS system.

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

As used herein, unless otherwise specified, reference to a percent (%) identity refers to an evaluation of homology which is performed using: (1) a BLAST 2.0 Basic BLAST homology search using blastp for amino acid searches, blastn for nucleic acid searches, and blastX for nucleic acid searches and searches of translated amino acids in all 6 open reading frames, all with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST). It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
 Reward for match=1
 Penalty for mismatch=−2
 Open gap (5) and extension gap (2) penalties
 gap x_dropoff (50) expect (10) word size (11) filter (on)
For blastp, using 0 BLOSUM62 matrix:
 Open gap (11) and extension gap (1) penalties
 gap x_dropoff (50) expect (10) word size (3) filter (on).

In another embodiment of the invention, an amino acid sequence having the biological activity of at least one domain of a PUFA PKS system of the present invention includes an amino acid sequence that is sufficiently similar to a naturally occurring PUFA PKS protein or polypeptide that a nucleic acid sequence encoding the amino acid sequence is capable of hybridizing under moderate, high, or very high stringency conditions (described below) to (i.e., with) a nucleic acid molecule encoding the naturally occurring PUFA PKS protein or polypeptide (i.e., to the complement of the nucleic acid strand encoding the naturally occurring PUFA PKS protein or polypeptide). Preferably, an amino acid sequence having the biological activity of at least one domain of a PUFA PKS system of the present invention is encoded by a nucleic acid sequence that hybridizes under moderate, high or very high stringency conditions to the complement of a nucleic acid sequence that encodes a protein comprising an amino acid sequence represented by any of SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. Methods to deduce a complementary sequence are known to those skilled in the art. It should be noted that since amino acid sequencing and nucleic acid sequencing technologies are not entirely error-free, the sequences presented herein, at best, represent apparent sequences of PUFA PKS domains and proteins of the present invention.

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

Another embodiment of the present invention includes a recombinant nucleic acid molecule comprising a recombinant vector and a nucleic acid molecule comprising a nucleic acid sequence encoding an amino acid sequence having a biological activity of at least one domain of a PUFA PKS system as described herein. Such nucleic acid sequences are described in detail above. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid molecules of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., a PUFA PKS domain) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector which enable the transcription and translation of the nucleic acid sequence within the recombinant host cell.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete or inactivate an endogenous gene within the host cell or microorganism (i.e., used for targeted gene disruption or knock-out technology). Such a vector may also be known in the art as a "knock-out" vector. In one aspect of this embodiment, a portion of the vector, but more typically, the nucleic acid molecule inserted into the vector (i.e., the insert), has a nucleic acid sequence that is homologous to a nucleic acid sequence of a target gene in the host cell (i.e., a gene which is targeted to be deleted or inactivated). The nucleic acid sequence of the vector insert is designed to bind to the target gene such that the target gene and the insert undergo homologous recombination, whereby the endogenous target gene is deleted, inactivated or attenuated (i.e., by at least a portion of the endogenous target gene being mutated or deleted).

Typically, a recombinant nucleic acid molecule includes at least one nucleic acid molecule of the present invention operatively linked to one or more transcription control sequences. As used herein, the phrase "recombinant molecule" or "recombinant nucleic acid molecule" primarily refers to a nucleic acid molecule or nucleic acid sequence operatively linked to a transcription control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to a transcription control sequence in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in a host cell or organism into which the recombinant nucleic acid molecule is to be introduced.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

The present inventors have found that the *Schizochytrium* PUFA PKS Orfs A and B are closely linked in the genome and region between the Orfs has been sequenced. The Orfs are oriented in opposite directions and 4244 base pairs separate the start (ATG) codons (i.e. they are arranged as follows: 3'OrfA5'-4244 bp-5'OrfB3'). Examination of the 4244 bp intergenic region did not reveal any obvious Orfs (no significant matches were found on a BlastX search). Both Orfs A and B are highly expressed in *Schizochytrium*, at least during the time of oil production, implying that active promoter elements are embedded in this intergenic region. These genetic elements are believed to have utility as a bi-directional promoter sequence for transgenic applications. For example, in a preferred embodiment, one could clone this region, place any genes of interest at each end and introduce the construct into *Schizochytrium* (or some other host in which the promoters can be shown to function). It is predicted that the regulatory elements, under the appropriate conditions, would provide for coordinated, high level expression of the two introduced genes. The complete nucleotide sequence for the regulatory region containing *Schizochytrium* PUFA PKS regulatory elements (e.g., a promoter) is represented herein as SEQ ID NO:36.

In a similar manner, OrfC is highly expressed in *Schizochytrium* during the time of oil production and regulatory elements are expected to reside in the region upstream of its start codon. A region of genomic DNA upstream of OrfC has been cloned and sequenced and is represented herein as (SEQ ID NO:37). This sequence contains the 3886 nt immediately upstream of the OrfC start codon. Examination of this region did not reveal any obvious Orfs (i.e., no significant matches were found on a BlastX search). It is believed that regulatory elements contained in this region, under the appropriate conditions, will provide for high-level expression of a gene placed behind them. Additionally, under the appropriate conditions, the level of expression may be coordinated with genes under control of the A-B intergenic region (SEQ ID NO:36).

Therefore, in one embodiment, a recombinant nucleic acid molecule useful in the present invention, as disclosed herein, can include a PUFA PKS regulatory region contained within SEQ ID NO:36 and/or SEQ ID NO:37. Such a regulatory region can include any portion (fragment) of SEQ ID NO:36 and/or SEQ ID NO:37 that has at least basal PUFA PKS transcriptional activity.

One or more recombinant molecules of the present invention can be used to produce an encoded product (e.g., a PUFA PKS domain, protein, or system) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one other recombinant nucleic acid molecule.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass transfection of animal cells, plant cells and transformation of microbial cells, to the extent that the terms pertain to the introduction of exogenous nucleic acids into a cell. Therefore, transfection techniques include, but are not limited to, transformation, particle bombardment, electroporation, microinjection, lipofection, adsorption, infection and protoplast fusion.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts.

General discussion above with regard to recombinant nucleic acid molecules and transfection of host cells is intended to be applied to any recombinant nucleic acid molecule discussed herein, including those encoding any amino acid sequence having a biological activity of at least one domain from a PUFA PKS, those encoding amino acid sequences from other PKS systems, and those encoding other proteins or domains.

This invention also relates to the use of a novel method to identify a microorganism that has a PUFA PKS system that is homologous in structure, domain organization and/or function to a *Schizochytrium* PUFA PKS system. In one embodiment, the microorganism is a non-bacterial microorganism, and preferably, the microorganism identified by this method is a eukaryotic microorganism. In addition, this invention relates to the microorganisms identified by such method and to the use of these microorganisms and the PUFA PKS systems from these microorganisms in the various applications for a PUFA PKS system (e.g., genetically modified organisms and methods of producing bioactive molecules) according to the present invention. The unique screening method described and demonstrated herein enables the rapid identification of new microbial strains containing a PUFA PKS system homologous to the *Schizochytrium* PUFA PKS system of the present invention. Applicants have used this method to discover and disclose herein that a *Thraustochytrium* microorganism contains a PUFA PKS system that is homologous to that found in *Schizochytrium*. This discovery is described in detail in Example 2 below.

Microbial organisms with a PUFA PKS system similar to that found in *Schizochytrium*, such as the *Thraustochytrium* microorganism discovered by the present inventors and described in Example 2, can be readily identified/isolated/screened by the following methods used separately or in any combination of these methods.

In general, the method to identify a non-bacterial microorganism that has a polyunsaturated fatty acid (PUFA) polyketide synthase (PKS) system includes a first step of (a) selecting a microorganism that produces at least one PUFA; and a second step of (b) identifying a microorganism from (a) that has an ability to produce increased PUFAs under dissolved oxygen conditions of less than about 5% of saturation in the fermentation medium, as compared to production of PUFAs by said microorganism under dissolved oxygen conditions of greater than 5% of saturation, more preferably 10% of saturation, more preferably greater than 15% of saturation and more preferably greater than 20% of saturation in the fermentation medium. A microorganism that produces at least one PUFA and has an ability to produce increased PUFAs under dissolved oxygen conditions of less than about 5% of saturation is identified as a candidate for containing a PUFA PKS system. Subsequent to identifying a microorganism that is a strong candidate for containing a PUFA PKS system, the method can include an additional step (c) of detecting whether the organism identified in step (b) comprises a PUFA PKS system.

In one embodiment of the present invention, step (b) is performed by culturing the microorganism selected for the screening process in low oxygen/anoxic conditions and aerobic conditions, and, in addition to measuring PUFA content in the organism, the fatty acid profile is determined, as well as fat content. By comparing the results under low oxygen/anoxic conditions with the results under aerobic conditions, the method provides a strong indication of whether the test microorganism contains a PUFA PKS system of the present invention. This preferred embodiment is described in detail below.

Initially, microbial strains to be examined for the presence of a PUFA PKS system are cultured under aerobic conditions to induce production of a large number of cells (microbial biomass). As one element of the identification process, these cells are then placed under low oxygen or anoxic culture conditions (e.g., dissolved oxygen less than about 5% of saturation, more preferably less than about 2%, even more preferably less than about 1%, and most preferably dissolved oxygen of about 0% of saturation in the culture medium) and allowed to grow for approximately another 24-72 hours. In this process, the microorganisms should be cultured at a temperature greater than about 15° C., and more preferably greater than about 20° C., and even more preferably greater than about 25° C., and even more preferably greater than 30° C. The low or anoxic culture environment can be easily maintained in culture chambers capable of inducing this type of atmospheric environment in the chamber (and thus in the cultures) or by culturing the cells in a manner that induces the low oxygen environment directly in the culture flask/vessel itself.

In a preferred culturing method, the microbes can be cultured in shake flasks which, instead of normally containing a small amount of culture medium—less than about 50% of total capacity and usually less than about 25% of total capacity—to keep the medium aerated as it is shaken on a shaker table, are instead filled to greater than about 50% of their capacity, and more preferably greater than about 60%, and most preferably greater than about 75% of their capacity with culture medium. High loading of the shake flask with culture medium prevents it from mixing very well in the flask when it is placed on a shaker table, preventing oxygen diffusion into the culture. Therefore as the microbes grow, they use up the existing oxygen in the medium and naturally create a low or no oxygen environment in the shake flask.

After the culture period, the cells are harvested and analyzed for content of bioactive compounds of interest (e.g., lipids), but most particularly, for compounds containing two or more unsaturated bonds, and more preferably three or more double bonds, and even more preferably four or more double bonds. For lipids, those strains possessing such compounds at greater than about 5%, and more preferably greater than about 10%, and more preferably greater than about 15%, and even more preferably greater than about 20% of the dry weight of the microorganism are identified as predictably containing a novel PKS system of the type described above. For other bioactive compounds, such as antibiotics or compounds that are synthesized in smaller amounts, those strains possessing such compounds at greater than about 0.5%, and more preferably greater than about 0.1%, and more preferably greater than about 0.25%, and more preferably greater than about 0.5%, and more preferably greater than about 0.75%, and more preferably greater than about 1%, and more preferably greater than about 2.5%, and more preferably greater than about 5% of the dry weight of the microorganism are identified as predictably containing a novel PKS system of the type described above.

Alternatively, or in conjunction with this method, prospective microbial strains containing novel PUFA PKS systems as described herein can be identified by examining the fatty acid profile of the strain (obtained by culturing the organism or through published or other readily available sources). If the microbe contains greater than about 30%, and more preferably greater than about 40%, and more preferably greater than about 45%, and even more preferably greater than about 50% of its total fatty acids as C14:0, C16:0 and/or C16:1, while also producing at least one long chain fatty acid with three or more unsaturated bonds, and more preferably 4 or more double bonds, and more preferably 5 or more double bonds, and even more preferably 6 or more double bonds, then this microbial strain is identified as a likely candidate to possess a novel PUFA PKS system of the type described in this invention. Screening this organism under the low oxygen conditions described above, and confirming production of bioactive molecules containing two or more unsaturated bonds would suggest the existence of a novel PUFA PKS system in the organism, which could be further confirmed by analysis of the microbes' genome.

The success of this method can also be enhanced by screening eukaryotic strains that are known to contain C17:0 and or C17:1 fatty acids (in conjunction with the large percentages of C14:0, C16:0 and C16:1 fatty acids described above)- because the C17:0 and C17:1 fatty acids are potential markers for a bacterial (prokaryotic) based or influenced fatty acid production system. Another marker for identifying strains containing novel PUFA PKS systems is the production of simple fatty acid profiles by the organism. According to the present invention, a "simple fatty acid profile" is defined as 8 or fewer fatty acids being produced by the strain at levels greater than 10% of total fatty acids.

Use of any of these methods or markers (singly or preferably in combination) would enable one of skill in the art to readily identify microbial strains that are highly predicted to contain a novel PUFA PKS system of the type described in this invention.

In a preferred embodiment combining many of the methods and markers described above, a novel biorational screen (using shake flask cultures) has been developed for detecting microorganisms containing PUFA producing PKS systems. This screening system is conducted as follows:

A portion of a culture of the strain/microorganism to be tested is placed in 250 mL baffled shake flask with 50 mL culture media (aerobic treatment), and another portion of culture of the same strain is placed in a 250 mL non-baffled shake flask with 200 mL culture medium (anoxic/low oxygen treatment). Various culture media can be employed depending on the type and strain of microorganism being evaluated. Both flasks are placed on a shaker table at 200 rpm. After 48-72 hr of culture time, the cultures are harvested by centrifugation and the cells are analyzed for fatty acid methyl ester content via gas chromatography to determine the following data for each culture: (1) fatty acid profile; (2) PUFA content; and (3) fat content (approximated as amount total fatty acids/cell dry weight).

These data are then analyzed asking the following five questions (Yes/No):
Comparing the Data from the Low $O_2$/Anoxic Flask with the Data from the Aerobic Flask:

(1) Did the DHA (or other PUFA content) (as % FAME (fatty acid methyl esters)) stay about the same or preferably increased in the low oxygen culture compared to the aerobic culture?

(2) Is C14:0+C16:0+C16:1 greater than about 40% TFA in the anoxic culture?

(3) Are there very little (<1% as FAME) or no precursors (C18:3n-3+C18:2n-6+C18:3n-6) to the conventional oxygen dependent elongase/desaturase pathway in the anoxic culture?

(4) Did fat content (as amount total fatty acids/cell dry weight) increase in the low oxygen culture compared to the aerobic culture?

(5) Did DHA (or other PUFA content) increase as % cell dry weight in the low oxygen culture compared to the aerobic culture?

If the first three questions are answered yes, this is a good indication that the strain contains a PKS genetic system for making long chain PUFAs. The more questions that are answered yes (preferably the first three questions must be answered yes), the stronger the indication that the strain contains such a PKS genetic system. If all five questions are answered yes, then there is a very strong indication that the strain contains a PKS genetic system for making long chain PUFAs. The lack of 18:3n-3/18:2n-6/18:3n-6 would indicate that the low oxygen conditions would have turned off or inhibited the conventional pathway for PUFA synthesis. A high 14:0/16:0/16:1 fatty is an preliminary indicator of a bacterially influenced fatty acid synthesis profile (the presence of C17:0 and 17:1 is also and indicator of this) and of a simple fatty acid profile. The increased PUFA synthesis and PUFA containing fat synthesis under the low oxygen conditions is directly indicative of a PUFA PKS system, since this system does not require oxygen to make highly unsaturated fatty acids.

Finally, in the identification method of the present invention, once a strong candidate is identified, the microbe is preferably screened to detect whether or not the microbe contains a PUFA PKS system. For example, the genome of the microbe can be screened to detect the presence of one or more nucleic acid sequences that encode a domain of a PUFA PKS system as described herein. Preferably, this step of detection includes a suitable nucleic acid detection method, such as hybridization, amplification and or sequencing of one or more nucleic acid sequences in the microbe of interest. The probes and/or primers used in the detection methods can be derived from any known PUFA PKS system, including the marine bacteria PUFA PKS systems described in U.S. Pat. No. 6,140,486, or the Thraustochytrid PUFA PKS systems described in U.S. application Ser. No. 09/231,899 and herein. Once novel PUFA PKS systems are identified, the genetic material from these systems can also be used to detect additional novel PUFA PKS systems. Methods of hybridization, amplification and sequencing of nucleic acids for the purpose of identification and detection of a sequence are well known in the art. Using these detection methods, sequence homology and domain structure (e.g., the presence, number and/or arrangement of various PUFA PKS functional domains) can be evaluated and compared to the known PUFA PKS systems described herein.

In some embodiments, a PUFA PKS system can be identified using biological assays. For example, in U.S. application Ser. No. 09/231,899, Example 7, the results of a key experiment using a well-known inhibitor of some types of fatty acid synthesis systems, i.e., thiolactomycin, is described. The inventors showed that the synthesis of PUFAs in whole cells of *Schizochytrium* could be specifically blocked without blocking the synthesis of short chain saturated fatty acids. The significance of this result is as follows: the inventors knew from analysis of cDNA sequences from *Schizochytrium* that a Type I fatty acid synthase system is present in *Schizochytrium*. It was known that thiolactomycin does not inhibit Type I FAS systems, and this is consistent with the inventors' data—i.e., production of the saturated fatty acids (primarily C14:0 and C16:0 in *Schizochytrium*) was not inhibited by the thiolactomycin treatment. There are no indications in the literature or in the inventors' own data that thiolactomycin has any inhibitory effect on the elongation of C14:0 or C16:0 fatty acids or their desaturation (i.e. the conversion of short chain saturated fatty acids to PUFAs by the classical pathway). Therefore, the fact that the PUFA production in *Schizochytrium* was blocked by thiolactomycin strongly indicates that the classical PUFA synthesis pathway does not produce the PUFAs in *Schizochytrium*, but rather that a different pathway of synthesis is involved. Further, it had previously been determined that the *Shewanella* PUFA PKS system is inhibited by thiolactomycin (note that the PUFA PKS system of the present invention has elements of both Type I and Type II systems), and it was known that thiolactomycin is an inhibitor of Type II FAS systems (such as that found in *E. coli*). Therefore, this experiment indicated that *Schizochytrium* produced PUFAs as a result of a pathway not involving the Type I FAS. A similar rationale and detection step could be used to detect a PUFA PKS system in a microbe identified using the novel screening method disclosed herein.

In addition, Example 3 shows additional biochemical data which provides evidence that PUFAs in *Schizochytrium* are not produced by the classical pathway (i.e., precursor product kinetics between C16:0 and DHA are not observed in whole cells and, in vitro PUFA synthesis can be separated from the membrane fraction—all of the fatty acid desaturases of the classical PUFA synthesis pathway, with the exception of the delta 9 desaturase which inserts the first double bond of the series, are associated with cellular membranes). This type of biochemical data could be used to detect PUFA PKS activity in microbe identified by the novel screening method described above.

Preferred microbial strains to screen using the screening/identification method of the present invention are chosen from the group consisting of: bacteria, algae, fungi, protozoa or protists, but most preferably from the eukaryotic microbes consisting of algae, fungi, protozoa and protists. These microbes are preferably capable of growth and production of the bioactive compounds containing two or more unsaturated bonds at temperatures greater than about 15° C., more preferably greater than about 20° C., even more preferably greater than about 25° C. and most preferably greater than about 30° C.

In some embodiments of this method of the present invention, novel bacterial PUFA PKS systems can be identified in bacteria that produce PUFAs at temperatures exceeding about 20° C., preferably exceeding about 25° C. and even more preferably exceeding about 30° C. As described previously herein, the marine bacteria, *Shewanella* and *Vibrio marinus*, described in U.S. Pat. No. 6,140,486, do not produce PUFAs at higher temperatures, which limits the usefulness of PUFA PKS systems derived from these bacteria, particularly in plant applications under field conditions. Therefore, in one embodiment, the screening method of the present invention can be used to identify bacteria that have a PUFA PKS system which are capable of growth and PUFA production at higher temperatures (e.g., above about 20, 25, or 30° C.). In this embodiment, inhibitors of eukaryotic growth such as nystatin (antifungal) or cycloheximide (inhibitor of eukaryotic protein synthesis) can be added to agar plates used to culture/select initial strains from water samples/soil samples collected from the types of habitats/niches described below. This process would help select for enrichment of bacterial strains without (or minimal) contamination of eukaryotic strains. This selection process, in combination with culturing the plates at elevated temperatures (e.g. 30° C.), and then selecting strains that produce at least one PUFA would initially identify candidate bacterial strains with a PUFA PKS system that is operative at elevated temperatures (as opposed to those bacterial strains in the prior art which only exhibit PUFA production at temperatures less than about 20° C. and more preferably below about 5° C.).

Locations for collection of the preferred types of microbes for screening for a PUFA PKS system according to the present invention include any of the following: low oxygen environments (or locations near these types of low oxygen environments including in the guts of animals including invertebrates that consume microbes or microbe-containing foods (including types of filter feeding organisms), low or non-oxygen containing aquatic habitats (including freshwater, saline and marine), and especially at—or near—low oxygen environments (regions) in the oceans. The microbial strains would preferably not be obligate anaerobes but be adapted to live in both aerobic and low or anoxic environments. Soil environments containing both aerobic and low oxygen or anoxic environments would also excellent environments to find these organisms in and especially in these types of soil in aquatic habitats or temporary aquatic habitats.

A particularly preferred microbial strain would be a strain (selected from the group consisting of algae, fungi (including yeast), protozoa or protists) that, during a portion of its life cycle, is capable of consuming whole bacterial cells (bacterivory) by mechanisms such as phagocytosis, phagotrophic or endocytic capability and/or has a stage of its life cycle in which it exists as an amoeboid stage or naked protoplast. This method of nutrition would greatly increase the potential for transfer of a bacterial PKS system into a eukaryotic cell if a mistake occurred and the bacterial cell (or its DNA) did not get digested and instead are functionally incorporated into the eukaryotic cell.

Strains of microbes (other than the members of the Thraustochytrids) capable of bacterivory (especially by phagocytosis or endocytosis) can be found in the following microbial classes (including but not limited to example genera):

In the algae and algae-like microbes (including stramenopiles): of the class Euglenophyceae (for example genera *Euglena*, and *Peranema*), the class Chrysophyceae (for example the genus *Ochromonas*), the class Dinobryaceae (for example the genera *Dinobryon, Platychysis*, and *Chysochromulina*), the Dinophyceae (including the genera *Cryptheco-dinium, Gymnodinium, Peridinium, Ceratium, Gyrodinium*, and *Oxyrrhis*), the class Cryptophyceae (for example the genera *Cryptomonas*, and *Rhodomonas*), the class Xanthophyceae (for example the genus *Olisthodiscus*) (and including forms of algae in which an amoeboid stage occurs as in the flagellates Rhizochloridaceae, and zoospores/gametes of *Aphanochaete pascheri, Bumilleria stigeoclonium* and *Vaucheria geminata*), the class Eustigmatophyceae, and the class Prymnesiopyceae (including the genera *Prymnesium* and *Diacronema*).

In the Stramenopiles including the: Proteromonads, Opalines, Developayella, Diplophorys, Larbrinthulids, Thraustochytrids, Bicosecids, Oomycetes, Hypochytridiomycetes, Commation, Reticulosphaera, Pelagomonas, Pelapococcus, Ollicola, Aureococcus, Parmales, Raphidiophytes, Synurids, Rhizochromulinaales, Pedinellales, Dictyochales, Chrysomeridales, Sarcinochrysidales, Hydrurales, Hibberdiales, and Chromulinales.

In the Fungi: Class Myxomycetes (form myxamoebae)—slime molds, class Acrasieae including the orders Acrasiceae (for example the genus *Sappinia*), class Guttulinaceae (for example the genera *Guttulinopsis*, and *Guttulina*), class Dictysteliaceae (for example the genera *Acrasis, Dictyostelium, Polysphondylium*, and *Coenonia*), and class Phycomyceae including the orders Chytridiales, Ancylistales, Blastocladiales, Monoblepharidales, Saprolegniales, Peronosporales, Mucorales, and Entomophthorales.

In the Protozoa: Protozoa strains with life stages capable of bacterivory (including by phageocytosis) can be selected from the types classified as ciliates, flagellates or amoebae. Protozoan ciliates include the groups: Chonotrichs, Colpodids, Cyrtophores, Haptorids, Karyorelicts, Oligohymenophora, Polyhymenophora (spirotrichs), Prostomes and Suctoria. Protozoan flagellates include the Biosoecids, Bodonids, Cercomonads, Chrysophytes (for example the genera *Anthophysa, Chrysamoemba, Chrysosphaerella, Dendromonas, Dinobryon, Mallomonas, Ochromonas, Paraphysomonas, Poterioochromonas, Spumella, Syncrypta, Synura*, and *Uroglena*), Collar flagellates, Cryptophytes (for example the genera *Chilomonas, Cryptomonas, Cyanomonas*, and *Goniomonas*), Dinoflagellates, Diplomonads, Euglenoids, Heterolobosea, Pedinellids, Pelobionts, Phalansteriids, Pseudodendromonads, Spongomonads and Volvocales (and other flagellates including the unassigned flagellate genera of *Artodiscus, Clautriavia, Helkesimastix, Kathablepharis* and *Multicilia*). Amoeboid protozoans include the groups: Actinophryids, Centrohelids, Desmothoricids, Diplophryids, Eumamoebae, Heterolobosea, Leptomyxids, Nucleariid filose amoebae, Pelebionts, Testate amoebae and Vampyrellids (and including the unassigned amoebid genera *Gymnophrys, Biomyxa, Microcometes, Reticulomyxa, Belonocystis, Elaeorhanis, Allelogromia, Gromia* or *Lieberkuhnia*). The protozoan orders include the following: Percolomonadeae, Heterolobosea, Lyromonadea, Pseudociliata, Trichomonadea, Hypermastigea, Heteromiteae, Telonemea, Cyathobodonea, Ebridea, Pyytomyxea, Opalinea, Kinetomonadea, Hemimastigea, Protostelea, Myxagastrea, Dictyostelea, Choanomonadea, Apicomonadea, Eogregarinea, Neogregarinea, Coelotrolphea, Eucoccidea, Haemosporea, Piroplasmea, Spirotrichea, Prostomatea, Litostomatea, Phyllopharyngea, Nassophorea, Oligohymenophorea, Colpodea, Karyorelicta, Nucleohelea, Centrohelea, Acantharea, Sticholonchea, Polycystinea, Phaeodarea, Lobosea, Filosea, Athalamea, Monothalamea, Polythalamea, Xenophyophorea, Schizocladea, Holosea, Entamoebea, Myxosporea, Actinomyxea, Halosporea, Paramyxea, Rhombozoa and Orthonectea.

A preferred embodiment of the present invention includes strains of the microorganisms listed above that have been collected from one of the preferred habitats listed above.

One embodiment of the present invention relates to any microorganisms identified using the novel PUFA PKS screening method described above, to the PUFA PKS genes and proteins encoded thereby, and to the use of such microorganisms and/or PUFA PKS genes and proteins (including homologues and fragments thereof) in any of the methods described herein. In particular, the present invention encompasses organisms identified by the screening method of the present invention which are then genetically modified to regulate the production of bioactive molecules by said PUFA PKS system.

Yet another embodiment of the present invention relates to an isolated nucleic acid molecule comprising a nucleic acid sequence encoding at least one biologically active domain or biologically active fragment thereof of a polyunsaturated fatty acid (PUFA) polyketide synthase (PKS) system from a Thraustochytrid microorganism. As discussed above, the present inventors have successfully used the method to identify a non-bacterial microorganism that has a PUFA PKS system to identify additional members of the order Thraustochytriales which contain a PUFA PKS system. The identification of three such microorganisms is described in Example 2. Specifically, the present inventors have used the screening method of the present invention to identify *Thraus-*

*tochytrium* sp. 23B (ATCC 20892) as being highly predicted to contain a PUFA PKS system, followed by detection of sequences in the *Thraustochytrium* sp. 23B genome that hybridize to the *Schizochytrium* PUFA PKS genes disclosed herein. *Schizochytrium limacium* (IFO 32693) and *Ulkenia* (BP-5601) have also been identified as good candidates for containing PUFA PKS systems. Based on these data and on the similarities among members of the order Thraustochytriales, it is believed that many other Thraustochytriales PUFA PKS systems can now be readily identified using the methods and tools provided by the present invention. Therefore, Thraustochytriales PUFA PKS systems and portions and/or homologues thereof (e.g., proteins, domains and fragments thereof), genetically modified organisms comprising such systems and portions and/or homologues thereof, and methods of using such microorganisms and PUFA PKS systems, are encompassed by the present invention.

Developments have resulted in revision of the taxonomy of the Thraustochytrids. Taxonomic theorists place Thraustochytrids with the algae or algae-like protists. However, because of taxonomic uncertainty, it would be best for the purposes of the present invention to consider the strains described in the present invention as Thraustochytrids (Order: Thraustochytriales; Family: Thraustochytriaceae; Genus: *Thraustochytrium, Schizochytrium, Labyrinthuloides*, or *Japonochytrium*). For the present invention, members of the labrinthulids are considered to be included in the Thraustochytrids. Taxonomic changes are summarized below. Strains of certain unicellular microorganisms disclosed herein are members of the order Thraustochytriales. Thraustochytrids are marine eukaryotes with a evolving taxonomic history. Problems with the taxonomic placement of the Thraustochytrids have been reviewed by Moss (1986), Bahnweb and Jackle (1986) and Chamberlain and Moss (1988). According to the present invention, the phrases "Thraustochytrid", "Thraustochytriales microorganism" and "microorganism of the order Thraustochytriales" can be used interchangeably.

For convenience purposes, the Thraustochytrids were first placed by taxonomists with other colorless zoosporic eukaryotes in the Phycomycetes (algae-like fungi). The name Phycomycetes, however, was eventually dropped from taxonomic status, and the Thraustochytrids were retained in the Oomycetes (the biflagellate zoosporic fungi). It was initially assumed that the Oomycetes were related to the heterokont algae, and eventually a wide range of ultrastructural and biochemical studies, summarized by Barr (Barr, 1981, *Biosystems* 14:359-370) supported this assumption. The Oomycetes were in fact accepted by Leedale (Leedale, 1974, *Taxon* 23:261-270) and other phycologists as part of the heterokont algae. However, as a matter of convenience resulting from their heterotrophic nature, the Oomycetes and Thraustochytrids have been largely studied by mycologists (scientists who study fungi) rather than phycologists (scientists who study algae).

From another taxonomic perspective, evolutionary biologists have developed two general schools of thought as to how eukaryotes evolved. One theory proposes an exogenous origin of membrane-bound organelles through a series of endosymbioses (Margulis, 1970, *Origin of Eukaryotic Cells*. Yale University Press, New Haven); e.g., mitochondria were derived from bacterial endosymbionts, chloroplasts from cyanophytes, and flagella from spirochaetes. The other theory suggests a gradual evolution of the membrane-bound organelles from the non-membrane-bounded systems of the prokaryote ancestor via an autogenous process (Cavalier-Smith, 1975, *Nature* (Lond.) 256:462-468). Both groups of evolutionary biologists however, have removed the Oomycetes and Thraustochytrids from the fungi and place them either with the chromophyte algae in the kingdom Chromophyta (Cavalier-Smith, 1981, *BioSystems* 14:461-481) (this kingdom has been more recently expanded to include other protists and members of this kingdom are now called Stramenopiles) or with all algae in the kingdom Protoctista (Margulis and Sagen, 1985, *Biosystems* 18:141-147).

With the development of electron microscopy, studies on the ultrastructure of the zoospores of two genera of Thraustochytrids, *Thraustochytrium* and *Schizochytrium*, (Perkins, 1976, pp. 279-312 in "Recent Advances in Aquatic Mycology" (ed. E. B. G. Jones), John Wiley & Sons, New York; Kazama, 1980, *Can. J. Bot.* 58:2434-2446; Barr, 1981, *Biosystems* 14:359-370) have provided good evidence that the Thraustochytriaceae are only distantly related to the Oomycetes. Additionally, genetic data representing a correspondence analysis (a form of multivariate statistics) of 5 S ribosomal RNA sequences indicate that Thraustochytriales are clearly a unique group of eukaryotes, completely separate from the fungi, and most closely related to the red and brown algae, and to members of the Oomycetes (Mannella, et al., 1987, *Mol. Evol.* 24:228-235). Most taxonomists have agreed to remove the Thraustochytrids from the Oomycetes (Bartnicki-Garcia, 1987, pp. 389-403 in "Evolutionary Biology of the Fungi" (eds. Rayner, A. D. M., Brasier, C. M. & Moore, D.), Cambridge University Press, Cambridge).

In summary, employing the taxonomic system of Cavalier-Smith (Cavalier-Smith, 1981, *BioSystems* 14:461-481, 1983; Cavalier-Smith, 1993, *Microbiol Rev.* 57:953-994), the Thraustochytrids are classified with the chromophyte algae in the kingdom Chromophyta (Stramenopiles). This taxonomic placement has been more recently reaffirmed by Cavalier-Smith et al. using the 18s rRNA signatures of the Heterokonta to demonstrate that Thraustochytrids are chromists not Fungi (Cavalier-Smith et al., 1994, *Phil. Tran. Roy. Soc. London Series BioSciences* 346:387-397). This places them in a completely different kingdom from the fungi, which are all placed in the kingdom Eufungi. The taxonomic placement of the Thraustochytrids is therefore summarized below:

Kingdom: Chromophyta (Stramenopiles)
Phylum: Heterokonta
Order: Thraustochytriales
Family: Thraustochytriaceae
Genus: *Thraustochytrium, Schizochytrium, Labyrinthuloides*, or *Japonochytrium*

Some early taxonomists separated a few original members of the genus *Thraustochytrium* (those with an amoeboid life stage) into a separate genus called *Ulkenia*. However it is now known that most, if not all, Thraustochytrids (including *Thraustochytrium* and *Schizochytrium*), exhibit amoeboid stages and as such, *Ulkenia* is not considered by some to be a valid genus. As used herein, the genus *Thraustochytrium* will include *Ulkenia*.

Despite the uncertainty of taxonomic placement within higher classifications of Phylum and Kingdom, the Thraustochytrids remain a distinctive and characteristic grouping whose members remain classifiable within the order Thraustochytriales.

Polyunsaturated fatty acids (PUFAs) are essential membrane components in higher eukaryotes and the precursors of many lipid-derived signaling molecules. The PUFA PKS system of the present invention uses pathways for PUFA synthesis that do not require desaturation and elongation of saturated fatty acids. The pathways catalyzed by PUFA PKSs that are distinct from previously recognized PKSs in both structure and mechanism. Generation of cis double bonds is suggested to involve position-specific isomerases; these enzymes are believed to be useful in the production of new families of antibiotics.

To produce significantly high yields of various bioactive molecules using the PUFA PKS system of the present invention, an organism, preferably a microorganism or a plant, can be genetically modified to affect the activity of a PUFA PKS system. In one aspect, such an organism can endogenously contain and express a PUFA PKS system, and the genetic modification can be a genetic modification of one or more of the functional domains of the endogenous PUFA PKS system, whereby the modification has some effect on the activity of the PUFA PKS system. In another aspect, such an organism can endogenously contain and express a PUFA PKS system, and the genetic modification can be an introduction of at least one exogenous nucleic acid sequence (e.g., a recombinant nucleic acid molecule), wherein the exogenous nucleic acid sequence encodes at least one biologically active domain or protein from a second PKS system and/or a protein that affects the activity of said PUFA PKS system (e.g., a phosphopantetheinyl transferases (PPTase), discussed below). In yet another aspect, the organism does not necessarily endogenously (naturally) contain a PUFA PKS system, but is genetically modified to introduce at least one recombinant nucleic acid molecule encoding an amino acid sequence having the biological activity of at least one domain of a PUFA PKS system. In this aspect, PUFA PKS activity is affected by introducing or increasing PUFA PKS activity in the organism. Various embodiments associated with each of these aspects will be discussed in greater detail below.

Therefore, according to the present invention, one embodiment relates to a genetically modified microorganism, wherein the microorganism expresses a PKS system comprising at least one biologically active domain of a polyunsaturated fatty acid (PUFA) polyketide synthase (PKS) system. The at least one domain of the PUFA PKS system is encoded by a nucleic acid sequence chosen from: (a) a nucleic acid sequence encoding at least one domain of a polyunsaturated fatty acid (PUFA) polyketide synthase (PKS) system from a Thraustochytrid microorganism; (b) a nucleic acid sequence encoding at least one domain of a PUFA PKS system from a microorganism identified by a screening method of the present invention; (c) a nucleic acid sequence encoding an amino acid sequence that is at least about 60% identical to at least 500 consecutive amino acids of an amino acid sequence selected from the group consisting of: SEQ ID NO:2, SEQ ID NO:4, and SEQ ID NO:6; wherein the amino acid sequence has a biological activity of at least one domain of a PUFA PKS system; and, (d) a nucleic acid sequence encoding an amino acid sequence that is at least about 60% identical to an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; wherein the amino acid sequence has a biological activity of at least one domain of a PUFA PKS system. The genetic modification affects the activity of the PKS system in the organism. The screening process referenced in part (b) has been described in detail above and includes the steps of: (a) selecting a microorganism that produces at least one PUFA; and, (b) identifying a microorganism from (a) that has an ability to produce increased PUFAs under dissolved oxygen conditions of less than about 5% of saturation in the fermentation medium, as compared to production of PUFAs by the microorganism under dissolved oxygen conditions of greater than about 5% of saturation, and preferably about 10%, and more preferably about 15%, and more preferably about 20% of saturation in the fermentation medium. The genetically modified microorganism can include any one or more of the above-identified nucleic acid sequences, and/or any of the other homologues of any of the *Schizochytrium* PUFA PKS ORFs or domains as described in detail above.

As used herein, a genetically modified microorganism can include a genetically modified bacterium, protist, microalgae, fungus, or other microbe, and particularly, any of the genera of the order Thraustochytriales (e.g., a Thraustochytrid) described herein (e.g., *Schizochytrium, Thraustochytrium, Japonochytrium, Labyrinthuloides*). Such a genetically modified microorganism has a genome which is modified (i.e., mutated or changed) from its normal (i.e., wild-type or naturally occurring) form such that the desired result is achieved (i.e., increased or modified PUFA PKS activity and/or production of a desired product using the PKS system). Genetic modification of a microorganism can be accomplished using classical strain development and/or molecular genetic techniques. Such techniques known in the art and are generally disclosed for microorganisms, for example, in Sambrook et al., 1989, *Molecular Cloning: A Laboratory Manual*, Cold Spring Harbor Labs Press. The reference Sambrook et al., ibid., is incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

Preferred microorganism host cells to modify according to the present invention include, but are not limited to, any bacteria, protist, microalga, fungus, or protozoa. In one aspect, preferred microorganisms to genetically modify include, but are not limited to, any microorganism of the order Thraustochytriales. Particularly preferred host cells for use in the present invention could include microorganisms from a genus including, but not limited to: *Thraustochytrium, Labyrinthuloides, Japonochytrium*, and *Schizochytrium*. Preferred species within these genera include, but are not limited to: any *Schizochytrium* species, including *Schizochytrium aggregatum, Schizochytrium limacinum, Schizochytrium minutum*; any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Particularly preferred strains of Thraustochytriales include, but are not limited to: *Schizochytrium* sp. (S31) (ATCC 20888); *Schizochytrium* sp. (S8)(ATCC 20889); *Schizochytrium* sp. (LC-RM)(ATCC 18915); *Schizochytrium* sp. (SR21); *Schizochytrium aggregatum* (Goldstein et Belsky)(ATCC 28209); *Schizochytrium limacinum* (Honda et Yokochi)(IFO 32693); *Thraustochytrium* sp. (23B)(ATCC 20891); *Thraustochytrium striatum* (Schneider)(ATCC 24473); *Thraustochytrium aureum* (Goldstein)(ATCC 34304); *Thraustochytrium roseum* (Goldstein)(ATCC 28210); and *Japonochytrium* sp. (L1)(ATCC 28207). Other examples of suitable host microorganisms for genetic modification include, but are not limited to, yeast including *Saccharomyces cerevisiae, Saccharomyces carlsbergensis*, or other yeast such as *Candida, Kluyveromyces*, or other fungi, for example, filamentous fungi such as *Aspergillus, Neurospora, Penicillium*, etc. Bacterial cells also may be used as hosts. This includes *Escherichia coli*, which can be useful in fermentation processes. Alternatively, a host such as a *Lactobacillus* species or *Bacillus* species can be used as a host.

Another embodiment of the present invention relates to a genetically modified plant, wherein the plant has been genetically modified to recombinantly express a PKS system comprising at least one biologically active domain of a polyunsaturated fatty acid (PUFA) polyketide synthase (PKS) system. The domain is encoded by a nucleic acid sequence chosen from: (a) a nucleic acid sequence encoding at least one domain of a polyunsaturated fatty acid (PUFA) polyketide synthase (PKS) system from a Thraustochytrid microorganism; (b) a nucleic acid sequence encoding at least one domain of a PUFA PKS system from a microorganism identified by the screening and selection method described herein (see brief summary of method in discussion of genetically modified microorganism above); (c) a nucleic acid sequence encoding an amino acid sequence selected from the group consisting of: SEQ ID NO:2, SEQ ID NO:4, SEQ ID NO:6, and biologically active fragments thereof; (d) a nucleic acid sequence encoding an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and biologically active fragments thereof; (e) a nucleic acid sequence encoding an amino acid sequence that is at least about 60% identical to at least 500 consecutive amino acids of an amino acid sequence selected from the group consisting of: SEQ ID NO:2, SEQ ID NO:4, and SEQ ID NO:6; wherein the amino acid sequence has a biological activity of at least one domain of a PUFA PKS system; and/or (f) a nucleic acid sequence encoding an amino acid sequence that is at least about 60% identical to an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; wherein the amino acid sequence has a biological activity of at least one domain of a PUFA PKS system. The genetically modified plant can include any one or more of the above-identified nucleic acid sequences, and/or any of the other homologues of any of the *Schizochytrium* PUFA PKS ORFs or domains as described in detail above.

As used herein, a genetically modified plant can include any genetically modified plant including higher plants and particularly, any consumable plants or plants useful for producing a desired bioactive molecule of the present invention. Such a genetically modified plant has a genome which is modified (i.e., mutated or changed) from its normal (i.e., wild-type or naturally occurring) form such that the desired result is achieved (i.e., increased or modified PUFA PKS activity and/or production of a desired product using the PKS system). Genetic modification of a plant can be accomplished using classical strain development and/or molecular genetic techniques. Methods for producing a transgenic plant, wherein a recombinant nucleic acid molecule encoding a desired amino acid sequence is incorporated into the genome of the plant, are known in the art. A preferred plant to genetically modify according to the present invention is preferably a plant suitable for consumption by animals, including humans.

Preferred plants to genetically modify according to the present invention (i.e., plant host cells) include, but are not limited to any higher plants, and particularly consumable plants, including crop plants and especially plants used for their oils. Such plants can include, for example: canola, soybeans, rapeseed, linseed, corn, safflowers, sunflowers and tobacco. Other preferred plants include those plants that are known to produce compounds used as pharmaceutical agents, flavoring agents, neutraceutical agents, functional food ingredients or cosmetically active agents or plants that are genetically engineered to produce these compounds/agents.

According to the present invention, a genetically modified microorganism or plant includes a microorganism or plant that has been modified using recombinant technology. As used herein, genetic modifications which result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications that result in an increase in gene expression or function can be referred to as amplification, overproduction, overexpression, activation, enhancement, addition, or up-regulation of a gene.

The genetic modification of a microorganism or plant according to the present invention preferably affects the activity of the PKS system expressed by the plant, whether the PKS system is endogenous and genetically modified, endogenous with the introduction of recombinant nucleic acid molecules into the organism, or provided completely by recombinant technology. According to the present invention, to "affect the activity of a PKS system" includes any genetic modification that causes any detectable or measurable change or modification in the PKS system expressed by the organism as compared to in the absence of the genetic modification. A detectable change or modification in the PKS system can include, but is not limited to: the introduction of PKS system activity into an organism such that the organism now has measurable/detectable PKS system activity (i.e., the organism did not contain a PKS system prior to the genetic modification), the introduction into the organism of a functional domain from a different PKS system than a PKS system endogenously expressed by the organism such that the PKS system activity is modified (e.g., a bacterial PUFA PKS domain or a type I PKS domain is introduced into an organism that endogenously expresses a non-bacterial PUFA PKS system), a change in the amount of a bioactive molecule produced by the PKS system (e.g., the system produces more (increased amount) or less (decreased amount) of a given product as compared to in the absence of the genetic modification), a change in the type of a bioactive molecule produced by the PKS system (e.g., the system produces a new or different product, or a variant of a product that is naturally produced by the system), and/or a change in the ratio of multiple bioactive molecules produced by the PKS system (e.g., the system produces a different ratio of one PUFA to another PUFA, produces a completely different lipid profile as compared to in the absence of the genetic modification, or places various PUFAs in different positions in a triacylglycerol as compared to the natural configuration). Such a genetic modification includes any type of genetic modification and specifically includes modifications made by recombinant technology and by classical mutagenesis.

It should be noted that reference to increasing the activity of a functional domain or protein in a PUFA PKS system refers to any genetic modification in the organism containing the domain or protein (or into which the domain or protein is to be introduced) which results in increased functionality of the domain or protein system and can include higher activity of the domain or protein (e.g., specific activity or in vivo enzymatic activity), reduced inhibition or degradation of the domain or protein system, and overexpression of the domain or protein. For example, gene copy number can be increased, expression levels can be increased by use of a promoter that gives higher levels of expression than that of the native promoter, or a gene can be altered by genetic engineering or classical mutagenesis to increase the activity of the domain or protein encoded by the gene.

Similarly, reference to decreasing the activity of a functional domain or protein in a PUFA PKS system refers to any genetic modification in the organism containing such domain or protein (or into which the domain or protein is to be introduced) which results in decreased functionality of the domain or protein and includes decreased activity of the domain or protein, increased inhibition or degradation of the domain or protein and a reduction or elimination of expression of the domain or protein. For example, the action of domain or protein of the present invention can be decreased by blocking or reducing the production of the domain or protein, "knocking out" the gene or portion thereof encoding the domain or protein, reducing domain or protein activity, or inhibiting the activity of the domain or protein. Blocking or reducing the production of an domain or protein can include placing the gene encoding the domain or protein under the control of a promoter that requires the presence of an inducing compound in the growth medium. By establishing conditions such that the inducer becomes depleted from the medium, the expression of the gene encoding the domain or protein (and therefore, of protein synthesis) could be turned off. Blocking or reducing the activity of domain or protein could also include using an excision technology approach similar to that described in U.S. Pat. No. 4,743,546, incorporated herein by reference. To use this approach, the gene encoding the protein of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In one embodiment of the present invention, a genetic modification includes a modification of a nucleic acid sequence encoding an amino acid sequence that has a biological activity of at least one domain of a non-bacterial PUFA PKS system as described herein. Such a modification can be to an amino acid sequence within an endogenously (naturally) expressed non-bacterial PUFA PKS system, whereby a microorganism that naturally contains such a system is genetically modified by, for example, classical mutagenesis and selection techniques and/or molecular genetic techniques, include genetic engineering techniques. Genetic engineering techniques can include, for example, using a targeting recombinant vector to delete a portion of an endogenous gene, or to replace a portion of an endogenous gene with a heterologous sequence. Examples of heterologous sequences that could be introduced into a host genome include sequences encoding at least one functional domain from another PKS system, such as a different non-bacterial PUFA PKS system, a bacterial PUFA PKS system, a type I PKS system, a type II PKS system, or a modular PKS system. Other heterologous sequences to introduce into the genome of a host includes a sequence encoding a protein or functional domain that is not a domain of a PKS system, but which will affect the activity of the endogenous PKS system. For example, one could introduce into the host genome a nucleic acid molecule encoding a phosphopantetheinyl transferase (discussed below). Specific modifications that could be made to an endogenous PUFA PKS system are discussed in detail below.

In another aspect of this embodiment of the invention, the genetic modification can include: (1) the introduction of a recombinant nucleic acid molecule encoding an amino acid sequence having a biological activity of at least one domain of a non-bacterial PUFA PKS system; and/or (2) the introduction of a recombinant nucleic acid molecule encoding a protein or functional domain that affects the activity of a PUFA PKS system, into a host. The host can include: (1) a host cell that does not express any PKS system, wherein all functional domains of a PKS system are introduced into the host cell, and wherein at least one functional domain is from a non-bacterial PUFA PKS system; (2) a host cell that expresses a PKS system (endogenous or recombinant) having at least one functional domain of a non-bacterial PUFA PKS system, wherein the introduced recombinant nucleic acid molecule can encode at least one additional non-bacterial PUFA PKS domain function or another protein or domain that affects the activity of the host PKS system; and (3) a host cell that expresses a PKS system (endogenous or recombinant) which does not necessarily include a domain function from a non-bacterial PUFA PKS, and wherein the introduced recombinant nucleic acid molecule includes a nucleic acid sequence encoding at least one functional domain of a non-bacterial PUFA PKS system. In other words, the present invention intends to encompass any genetically modified organism (e.g., microorganism or plant), wherein the organism comprises at least one non-bacterial PUFA PKS domain function (either endogenously or by recombinant modification), and wherein the genetic modification has a measurable effect on the non-bacterial PUFA PKS domain function or on the PKS system when the organism comprises a functional PKS system.

Therefore, using the non-bacterial PUFA PKS systems of the present invention, which, for example, makes use of genes from Thraustochytrid PUFA PKS systems, gene mixing can be used to extend the range of PUFA products to include EPA, DHA, ARA, GLA, SDA and others, as well as to produce a wide variety of bioactive molecules, including antibiotics, other pharmaceutical compounds, and other desirable products. The method to obtain these bioactive molecules includes not only the mixing of genes from various organisms but also various methods of genetically modifying the non-bacterial PUFA PKS genes disclosed herein. Knowledge of the genetic basis and domain structure of the non-bacterial PUFA PKS system of the present invention provides a basis for designing novel genetically modified organisms which produce a variety of bioactive molecules. Although mixing and modification of any PKS domains and related genes are contemplated by the present inventors, by way of example, various possible manipulations of the PUFA-PKS system are discussed below with regard to genetic modification and bioactive molecule production.

For example, in one embodiment, non-bacterial PUFA-PKS system products, such as those produced by Thraustochytrids, are altered by modifying the CLF (chain length factor) domain. This domain is characteristic of Type II (dissociated enzymes) PKS systems. Its amino acid sequence shows homology to KS (keto synthase pairs) domains, but it lacks the active site cysteine. CLF may function to determine the number of elongation cycles, and hence the chain length, of the end product. In this embodiment of the invention, using the current state of knowledge of FAS and PKS synthesis, a rational strategy for production of ARA by directed modification of the non-bacterial PUFA-PKS system is provided.

There is controversy in the literature concerning the function of the CLF in PKS systems (C. Bisang et al., Nature 401, 502 (1999)) and it is realized that other domains may be involved in determination of the chain length of the end product. However, it is significant that Schizochytrium produces both DHA (C22:6, ω-3) and DPA (C22:5, ω-6). In the PUFA-PKS system the cis double bonds are introduced during synthesis of the growing carbon chain. Since placement of the ω-3 and ω-6 double bonds occurs early in the synthesis of the molecules, one would not expect that they would affect subsequent end-product chain length determination. Thus, without being bound by theory, the present inventors believe that introduction of a factor (e.g. CLF) that directs synthesis of C20 units (instead of C22 units) into the Schizochytrium PUFA-PKS system will result in the production of EPA (C20: 5, ω-3) and ARA (C20:4, ω-6). For example, in heterologous systems, one could exploit the CLF by directly substituting a CLF from an EPA producing system (such as one from Photobacterium) into the Schizochytrium gene set. The fatty acids of the resulting transformants can then be analyzed for alterations in profiles to identify the transformants producing EPA and/or ARA.

In addition to dependence on development of a heterologous system (recombinant system, such as could be introduced into plants), the CLF concept can be exploited in Schizochytrium (i.e., by modification of a Schizochytrium genome). Transformation and homologous recombination has been demonstrated in Schizochytrium. One can exploit this by constructing a clone with the CLF of OrfB replaced with a CLF from a C20 PUFA-PKS system. A marker gene will be inserted downstream of the coding region. One can then transform the wild type cells, select for the marker phenotype and then screen for those that had incorporated the new CLF. Again, one would analyze these for any effects on fatty acid profiles to identify transformants producing EPA and/or ARA. If some factor other than those associated with the CLF are found to influence the chain length of the end product, a similar strategy could be employed to alter those factors.

Another preferred embodiment involving alteration of the PUFA-PKS products involves modification or substitution of the β-hydroxy acyl-ACP dehydrase/keto synthase pairs. During cis-vaccenic acid (C18:1, Δ11) synthesis in E. coli, creation of the cis double bond is believed to depend on a specific DH enzyme, β-hydroxy acyl-ACP dehydrase, the product of the FabA gene. This enzyme removes HOH from a β-keto acyl-ACP and leaves a trans double bond in the carbon chain. A subset of DH's, FabA-like, possess cis-trans isomerase activity (Heath et al., 1996, supra). A novel aspect of bacterial and non-bacterial PUFA-PKS systems is the presence of two FabA-like DH domains. Without being bound by theory, the present inventors believe that one or both of these DH domains will possess cis-trans isomerase activity (manipulation of the DH domains is discussed in greater detail below).

Another aspect of the unsaturated fatty acid synthesis in E. coli is the requirement for a particular KS enzyme, β-ketoacyl-ACP synthase, the product of the FabB gene. This is the enzyme that carries out condensation of a fatty acid, linked to a cysteine residue at the active site (by a thio-ester bond), with a malonyl-ACP. In the multi-step reaction, $CO_2$ is released and the linear chain is extended by two carbons. It is believed that only this KS can extend a carbon chain that contains a double bond. This extension occurs only when the double bond is in the cis configuration; if it is in the trans configuration, the double bond is reduced by enoyl-ACP reductase (ER) prior to elongation (Heath et al., 1996, supra). All of the PUFA-PKS systems characterized so far have two KS domains, one of which shows greater homology to the FabB-like KS of E. coli than the other. Again, without being bound by theory, the present inventors believe that in PUFA-PKS systems, the specificities and interactions of the DH (FabA-like) and KS (FabB-like) enzymatic domains determine the number and placement of cis double bonds in the end products. Because the number of 2-carbon elongation reactions is greater than the number of double bonds present in the PUFA-PKS end products, it can be determined that in some extension cycles complete reduction occurs. Thus the DH and KS domains can be used as targets for alteration of the DHA/DPA ratio or ratios of other long chain fatty acids. These can be modified and/or evaluated by introduction of homologous domains from other systems or by mutagenesis of these gene fragments.

In another embodiment, the ER (enoyl-ACP reductase—an enzyme which reduces the trans-double bond in the fatty acyl-ACP resulting in fully saturated carbons) domains can be modified or substituted to change the type of product made by the PKS system. For example, the present inventors know that Schizochytrium PUFA-PKS system differs from the previously described bacterial systems in that it has two (rather than one) ER domains. Without being bound by theory, the present inventors believe these ER domains can strongly influence the resulting PKS production product. The resulting PKS product could be changed by separately knocking out the individual domains or by modifying their nucleotide sequence or by substitution of ER domains from other organisms.

In another embodiment, nucleic acid molecules encoding proteins or domains that are not part of a PKS system, but which affect a PKS system, can be introduced into an organism. For example, all of the PUFA PKS systems described above contain multiple, tandem, ACP domains. ACP (as a separate protein or as a domain of a larger protein) requires attachment of a phosphopantetheine cofactor to produce the active, holo-ACP. Attachment of phosphopantetheine to the apo-ACP is carried out by members of the superfamily of enzymes—the phosphopantetheinyl transferases (PPTase) (Lambalot R. H., et al., Chemistry and Biology, 3, 923 (1996)).

By analogy to other PKS and FAS systems, the present inventors presume that activation of the multiple ACP domains present in the Schizochytrium ORFA protein is carried out by a specific, endogenous, PPTase. The gene encoding this presumed PPTase has not yet been identified in Schizochytrium. If such a gene is present in Schizochytrium, one can envision several approaches that could be used in an attempt to identify and clone it. These could include (but would not be limited to): generation and partial sequencing of a cDNA library prepared from actively growing Schizochytrium cells (note, one sequence was identified in the currently available Schizochytrium cDNA library set which showed homology to PPTase's; however, it appears to be part of a multidomain FAS protein, and as such may not encode the desired OrfA specific PPTase); use of degenerate oligonucleotide primers designed using amino acid motifs present in many PPTase's in PCR reactions (to obtain a nucleic acid probe molecule to screen genomic or cDNA libraries); genetic approaches based on protein-protein interactions (e.g. a yeast two-hybrid system) in which the ORFA-ACP domains would be used as a "bait" to find a "target" (i.e. the PPTase); and purification and partial sequencing of the enzyme itself as a means to generate a nucleic acid probe for screening of genomic or cDNA libraries.

It is also conceivable that a heterologous PPTase may be capable of activating the Schizochytrium ORFA ACP domains. It has been shown that some PPTases, for example the sfp enzyme of *Bacillus subtilis* (Lambalot et al., supra) and the svp enzyme of *Streptomyces verticillus* (Sanchez et al., 2001, *Chemistry & Biology* 8:725-738), have a broad substrate tolerance. These enzymes can be tested to see if they will activate the *Schizochytrium* ACP domains. Also, a recent publication described the expression of a fungal PKS protein in tobacco (Yalpani et al., 2001, *The Plant Cell* 13:1401-1409). Products of the introduced PKS system (encoded by the 6-methylsalicyclic acid synthase gene of *Penicillium patulum*) were detected in the transgenic plant, even though the corresponding fungal PPTase was not present in those plants. This suggested that an endogenous plant PPTase(s) recognized and activated the fungal PKS ACP domain. Of relevance to this observation, the present inventors have identified two sequences (genes) in the *Arabidopsis* whole genome database that are likely to encode PPTases. These sequences (GenBank Accession numbers; AAG51443 and AAC05345) are currently listed as encoding "Unknown Proteins". They can be identified as putative PPTases based on the presence in the translated protein sequences of several signature motifs including; G(I/V)D and WxxKE(A/S)xxK (SEQ ID NO:33), (listed in Lambalot et al., 1996 as characteristic of all PPTases). In addition, these two putative proteins contain two additional motifs typically found in PPTases typically associated with PKS and non-ribosomal peptide synthesis systems; i.e., FN(I/L/V)SHS (SEQ ID NO:34) and (I/V/L)G(I/L/V)D(I/L/V) (SEQ ID NO:35). Furthermore, these motifs occur in the expected relative positions in the protein sequences. It is likely that homologues of the *Arabidopsis* genes are present in other plants, such as tobacco. Again, these genes can be cloned and expressed to see if the enzymes they encode can activate the *Schizochytrium* ORFA ACP domains, or alternatively, OrfA could be expressed directly in the transgenic plant (either targeted to the plastid or the cytoplasm).

Figure 3:
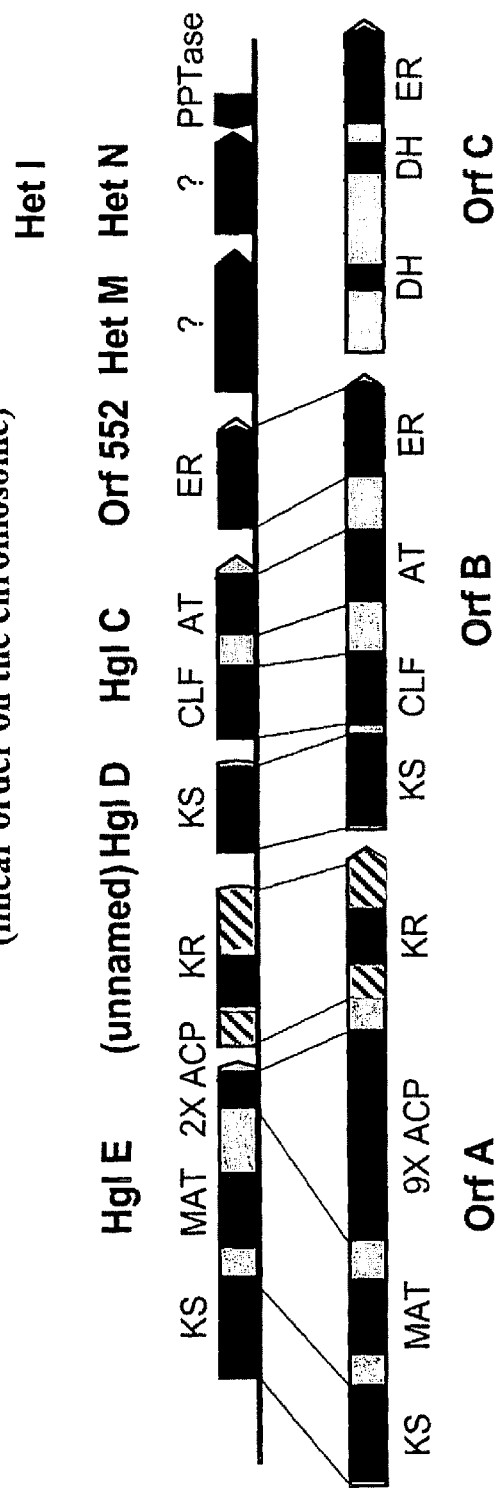
FIG. 3 shows a comparison of PKS domains from *Schizochytrium* and a related PKS system from *Nostoc* whose product is a long chain fatty acid that does not contain any double bonds.

Another heterologous PPTase which may recognize the ORFA ACP domains as substrates is the Het I protein of *Nostoc* sp. PCC 7120 (formerly called *Anabaena* sp. PCC 7120). As noted in U.S. Pat. No. 6,140,486, several of the PUFA-PKS genes of *Shewanella* showed a high degree of homology to protein domains present in a PKS cluster found in *Nostoc* (FIG. 2 of that patent). This *Nostoc* PKS system is associated with the synthesis of long chain (C26 or C28) hydroxy fatty acids that become esterified to sugar moieties and form a part of the heterocyst cell wall. These *Nostoc* PKS domains are also highly homologous to the domains found in Orfs B and C of the *Schizochytrium* PKS proteins (i.e. the same ones that correspond to those found in the *Shewanella* PKS proteins). Until very recently, none of the *Nostoc* PKS domains present in the GenBank databases showed high homology to any of the domains of *Schizochytrium* OrfA (or the homologous *Shewanella* Orf 5 protein). However, the complete genome of *Nostoc* has recently been sequenced and as a result, the sequence of the region just upstream of the PKS gene cluster is now available. In this region are three Orfs that show homology to the domains (KS, MAT, ACP and KR) of OrfA (see FIG. 3). Included in this set are two ACP domains, both of which show high homology to the ORFA ACP domains. At the end of the *Nostoc* PKS cluster is the gene that encodes the Het I PPTase. Previously, it was not obvious what the substrate of the Het I enzyme could be, however the presence of tandem ACP domains in the newly identified Orf (Hgl E) of the cluster strongly suggests to the present inventors that it is those ACPs. The homology of the ACP domains of *Schizochytrium* and *Nostoc*, as well as the tandem arrangement of the domains in both proteins, makes Het I a likely candidate for heterologous activation of the *Schizochytrium* ORFA ACPs. The present inventors are believed to be the first to recognize and contemplate this use for *Nostoc* Het I PPTase.

As indicated in Metz et al., 2001, supra, one novel feature of the PUFA PKS systems is the presence of two dehydratase domains, both of which show homology to the FabA proteins of *E. coli*. With the availability of the new *Nostoc* PKS gene sequences mentioned above, one can now compare the two systems and their products. The sequence of domains in the *Nostoc* cluster (from HglE to Het I) as the present inventors have defined them is (see FIG. 3):

KS-MAT-2×ACP, KR, KS, CLF-AT, ER (HetM, HetN) HetI

In the *Schizochytrium* PUFA-PKS Orfs A, B & C the sequence (OrfA-B-C) is:

KS-MAT-9×ACP-KR KS-CLF-AT-ER DH-DH-ER

One can see the correspondence of the domains sequence (there is also a high amino acid sequence homology). The product of the *Nostoc* PKS system is a long chain hydroxy fatty acid (C26 or C28 with one or two hydroxy groups) that contains no double bonds (cis or trans). The product of the *Schizochytrium* PKS system is a long chain polyunsaturated fatty acid (C22, with 5 or 6 double bonds—all cis). An obvious difference between the two domain sets is the presence of the two DH domains in the *Schizochytrium* proteins—just the domains implicated in the formation of the cis double bonds of DHA and DPA (presumably HetM and HetN in the *Nostoc* system are involved in inclusion of the hydroxyl groups and also contain a DH domain whose origin differs from the those found in the PUFA). Also, the role of the duplicated ER domain in the *Schizochytrium* Orfs B and C is not known (the second ER domain in is not present other characterized PUFA PKS systems). The amino acid sequence homology between the two sets of domains implies an evolutionary relationship. One can conceive of the PUFA PKS gene set being derived from (in an evolutionary sense) an ancestral *Nostoc*-like PKS gene set by incorporation of the DH (FabA-like) domains. The addition of the DH domains would result in the introduction of cis double bonds in the new PKS end product structure.

The comparisons of the *Schizochytrium* and *Nostoc* PKS domain structures as well as the comparison of the domain organization between the *Schizochytrium* and *Shewanella* PUFA-PKS proteins demonstrate nature's ability to alter domain order as well as incorporate new domains to create novel end products. In addition, the genes can now be manipulated in the laboratory to create new products. The implication from these observations is that it should be possible to continue to manipulate the systems in either a directed or random way to influence the end products. For example, in a preferred embodiment, one could envision substituting one of the DH (FabA-like) domains of the PUFA-PKS system for a DH domain that did not posses isomerization activity, potentially creating a molecule with a mix of cis- and trans-double bonds. The current products of the *Schizochytrium* PUFA PKS system are DHA and DPA (C22:5 ω6). If one manipulated the system to produce C20 fatty acids, one would expect the products to be EPA and ARA (C20:4 ω6). This could provide a new source for ARA. One could also substitute domains from related PUFA-PKS systems that produced a different DHA to DPA ratio—for example by using genes from *Thraustochytrium* 23B (the PUFA PKS system of which is identified for the first time herein).

Additionally, one could envision specifically altering one of the ER domains (e.g. removing, or inactivating) in the *Schizochytrium* PUFA PKS system (other PUFA PKS systems described so far do not have two ER domains) to determine its effect on the end product profile. Similar strategies could be attempted in a directed manner for each of the distinct domains of the PUFA-PKS proteins using more or less sophisticated approaches. Of course one would not be limited to the manipulation of single domains. Finally, one could extend the approach by mixing domains from the PUFA-PKS system and other PKS or FAS systems (e.g., type I, type II, modular) to create an entire range of new end products. For example, one could introduce the PUFA-PKS DH domains into systems that do not normally incorporate cis double bonds into their end products.

Accordingly, encompassed by the present invention are methods to genetically modify microbial or plant cells by: genetically modifying at least one nucleic acid sequence in the organism that encodes an amino acid sequence having the biological activity of at least one functional domain of a non-bacterial PUFA PKS system according to the present invention, and/or expressing at least one recombinant nucleic acid molecule comprising a nucleic acid sequence encoding such amino acid sequence. Various embodiments of such sequences, methods to genetically modify an organism, and specific modifications have been described in detail above. Typically, the method is used to produce a particular genetically modified organism that produces a particular bioactive molecule or molecules.

One embodiment of the present invention relates to a recombinant host cell which has been modified to express a polyunsaturated fatty acid (PUFA) polyketide synthase (PKS) system, wherein the PKS catalyzes both iterative and non-iterative enzymatic reactions, and wherein the PUFA PKS system comprises: (a) at least two enoyl ACP-reductase (ER) domains; (b) at least six acyl carrier protein (ACP) domains; (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; and (h) at least one malonyl-CoA:ACP acyltransferase (MAT) domain. In one embodiment, the PUFA PKS system is a eukaryotic PUFA PKS system. In a preferred embodiment, the PUFA PKS system is an algal PUFA PKS system. In a more preferred embodiment, the PUFA PKS system is a Thraustochytriales PUFA PKS system. Such PUFA PKS systems can include, but are not limited to, a *Schizochytrium* PUFA PKS system, and a *Thraustochytrium* PUFA PKS system. In one embodiment, the PUFA PKS system can be expressed in a prokaryotic host cell. In another embodiment, the PUFA PKS system can be expressed in a eukaryotic host cell.

Another embodiment of the present invention relates to a recombinant host cell which has been modified to express a non-bacterial PUFA PKS system, wherein the PKS system catalyzes both iterative and non-iterative enzymatic reactions, and wherein the non-bacterial PUFA PKS system comprises at least the following biologically active domains: (a) at least one enoyl ACP-reductase (ER) domain; (b) multiple acyl carrier protein (ACP) domains (at least four); (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; and (h) at least one malonyl-CoA:ACP acyltransferase (MAT) domain.

One aspect of this embodiment of the invention relates to a method to produce a product containing at least one PUFA, comprising growing a plant comprising any of the recombinant host cells described above, wherein the recombinant host cell is a plant cell, under conditions effective to produce the product. Another aspect of this embodiment of the invention relates to a method to produce a product containing at least one PUFA, comprising culturing a culture containing any of the recombinant host cells described above, wherein the host cell is a microbial cell, under conditions effective to produce the product. In a preferred embodiment, the PKS system in the host cell catalyzes the direct production of triglycerides.

Another embodiment of the present invention relates to a microorganism comprising a non-bacterial, polyunsaturated fatty acid (PUFA) polyketide synthase (PKS) system, wherein the PKS catalyzes both iterative and non-iterative enzymatic reactions, and wherein the PUFA PKS system comprises: (a) at least two enoyl ACP-reductase (ER) domains; (b) at least six acyl carrier protein (ACP) domains; (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; and (h) at least one malonyl-CoA:ACP acyltransferase (MAT) domain. Preferably, the microorganism is a non-bacterial microorganism and more preferably, a eukaryotic microorganism.

Yet another embodiment of the present invention relates to a microorganism comprising a non-bacterial, polyunsaturated fatty acid (PUFA) polyketide synthase (PKS) system, wherein the PKS catalyzes both iterative and non-iterative enzymatic reactions, and wherein the PUFA PKS system comprises: (a) at least one enoyl ACP-reductase (ER) domain; (b) multiple acyl carrier protein (ACP) domains (at least four); (c) at least two β-keto acyl-ACP synthase (KS) domains; (d) at least one acyltransferase (AT) domain; (e) at least one ketoreductase (KR) domain; (f) at least two FabA-like β-hydroxy acyl-ACP dehydrase (DH) domains; (g) at least one chain length factor (CLF) domain; and (h) at least one malonyl-CoA:ACP acyltransferase (MAT) domain.

In one embodiment of the present invention, it is contemplated that a mutagenesis program could be combined with a selective screening process to obtain bioactive molecules of interest. This would include methods to search for a range of bioactive compounds. This search would not be restricted to production of those molecules with cis double bonds. The mutagenesis methods could include, but are not limited to: chemical mutagenesis, gene shuffling, switching regions of the genes encoding specific enzymatic domains, or mutagenesis restricted to specific regions of those genes, as well as other methods.

For example, high throughput mutagenesis methods could be used to influence or optimize production of the desired bioactive molecule. Once an effective model system has been developed, one could modify these genes in a high throughput manner. Utilization of these technologies can be envisioned on two levels. First, if a sufficiently selective screen for production of a product of interest (e.g., ARA) can be devised, it could be used to attempt to alter the system to produce this product (e.g., in lieu of, or in concert with, other strategies such as those discussed above). Additionally, if the strategies outlined above resulted in a set of genes that did produce the product of interest, the high throughput technologies could then be used to optimize the system. For example, if the introduced domain only functioned at relatively low temperatures, selection methods could be devised to permit removing that limitation. In one embodiment of the invention, screening methods are used to identify additional non-bacterial organisms having novel PKS systems similar to the PUFA PKS system of *Schizochytrium*, as described herein (see above). Homologous PKS systems identified in such organisms can be used in methods similar to those described herein for the

*Schizochytrium*, as well as for an additional source of genetic material from which to create, further modify and/or mutate a PKS system for expression in that microorganism, in another microorganism, or in a higher plant, to produce a variety of compounds.

It is recognized that many genetic alterations, either random or directed, which one may introduce into a native (endogenous, natural) PKS system, will result in an inactivation of enzymatic functions. A preferred embodiment of the invention includes a system to select for only those modifications that do not block the ability of the PKS system to produce a product. For example, the FabB− strain of *E. coli* is incapable of synthesizing unsaturated fatty acids and requires supplementation of the medium with fatty acids that can substitute for its normal unsaturated fatty acids in order to grow (see Metz et al., 2001, supra). However, this requirement (for supplementation of the medium) can be removed when the strain is transformed with a functional PUFA-PKS system (i.e. one that produces a PUFA product in the *E. coli* host—see (Metz et al., 2001, supra, FIG. 2A). The transformed FabB− strain now requires a functional PUFA-PKS system (to produce the unsaturated fatty acids) for growth without supplementation. The key element in this example is that production of a wide range of unsaturated fatty acid will suffice (even unsaturated fatty acid substitutes such as branched chain fatty acids). Therefore, in another preferred embodiment of the invention, one could create a large number of mutations in one or more of the PUFA PKS genes disclosed herein, and then transform the appropriately modified FabB− strain (e.g. create mutations in an expression construct containing an ER domain and transform a FabB− strain having the other essential domains on a separate plasmid—or integrated into the chromosome) and select only for those transformants that grow without supplementation of the medium (i.e., that still possessed an ability to produce a molecule that could complement the FabB− defect). Additional screens could be developed to look for particular compounds (e.g. use of GC for fatty acids) being produced in this selective subset of an active PKS system. One could envision a number of similar selective screens for bioactive molecules of interest.

As described above, in one embodiment of the present invention, a genetically modified microorganism or plant includes a microorganism or plant which has an enhanced ability to synthesize desired bioactive molecules (products) or which has a newly introduced ability to synthesize specific products (e.g., to synthesize a specific antibiotic). According to the present invention, "an enhanced ability to synthesize" a product refers to any enhancement, or up-regulation, in a pathway related to the synthesis of the product such that the microorganism or plant produces an increased amount of the product (including any production of a product where there was none before) as compared to the wild-type microorganism or plant, cultured or grown, under the same conditions. Methods to produce such genetically modified organisms have been described in detail above.

One embodiment of the present invention is a method to produce desired bioactive molecules (also referred to as products or compounds) by growing or culturing a genetically modified microorganism or plant of the present invention (described in detail above). Such a method includes the step of culturing in a fermentation medium or growing in a suitable environment, such as soil, a microorganism or plant, respectively, that has a genetic modification as described previously herein and in accordance with the present invention. In a preferred embodiment, method to produce bioactive molecules of the present invention includes the step of culturing under conditions effective to produce the bioactive molecule a genetically modified organism that expresses a PKS system comprising at least one biologically active domain of a polyunsaturated fatty acid (PUFA) polyketide synthase (PKS) system. In this preferred aspect, at least one domain of the PUFA PKS system is encoded by a nucleic acid sequence selected from the group consisting of: (a) a nucleic acid sequence encoding at least one domain of a polyunsaturated fatty acid (PUFA) polyketide synthase (PKS) system from a Thraustochytrid microorganism; (b) a nucleic acid sequence encoding at least one domain of a PUFA PKS system from a microorganism identified by the novel screening method of the present invention (described above in detail); (c) a nucleic acid sequence encoding an amino acid sequence selected from the group consisting of: SEQ ID NO:2, SEQ ID NO:4, SEQ ID NO:6, and biologically active fragments thereof; (d) a nucleic acid sequence encoding an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and biologically active fragments thereof; (e) a nucleic acid sequence encoding an amino acid sequence that is at least about 60% identical to at least 500 consecutive amino acids of an amino acid sequence selected from the group consisting of: SEQ ID NO:2, SEQ ID NO:4, and SEQ ID NO:6; wherein the amino acid sequence has a biological activity of at least one domain of a PUFA PKS system; and, (f) a nucleic acid sequence encoding an amino acid sequence that is at least about 60% identical to an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; wherein the amino acid sequence has a biological activity of at least one domain of a PUFA PKS system. In this preferred aspect of the method, the organism is genetically modified to affect the activity of the PKS system (described in detail above). Preferred host cells for genetic modification related to the PUFA PKS system of the invention are described above.

In the method of production of desired bioactive compounds of the present invention, a genetically modified microorganism is cultured or grown in a suitable medium, under conditions effective to produce the bioactive compound. An appropriate, or effective, medium refers to any medium in which a genetically modified microorganism of the present invention, when cultured, is capable of producing the desired product. Such a medium is typically an aqueous medium comprising assimilable carbon, nitrogen and phosphate sources. Such a medium can also include appropriate salts, minerals, metals and other nutrients. Microorganisms of the present invention can be cultured in conventional fermentation bioreactors. The microorganisms can be cultured by any fermentation process which includes, but is not limited to, batch, fed-batch, cell recycle, and continuous fermentation. Preferred growth conditions for potential host microorganisms according to the present invention are well known in the art. The desired bioactive molecules produced by the genetically modified microorganism can be recovered from the fermentation medium using conventional separation and purification techniques. For example, the fermentation medium can be filtered or centrifuged to remove microorganisms, cell debris and other particulate matter, and the product can be recovered from the cell-free supernatant by conventional methods, such as, for example, ion exchange, chromatography, extraction, solvent extraction, membrane separation, electrodialysis, reverse osmosis, distillation, chemical derivatization and crystallization. Alternatively, microorganisms producing the desired compound, or extracts and various fractions thereof, can be used without removal of the microorganism components from the product.

In the method for production of desired bioactive compounds of the present invention, a genetically modified plant is cultured in a fermentation medium or grown in a suitable medium such as soil. An appropriate, or effective, fermentation medium has been discussed in detail above. A suitable growth medium for higher plants includes any growth medium for plants, including, but not limited to, soil, sand, any other particulate media that support root growth (e.g. vermiculite, perlite, etc.) or Hydroponic culture, as well as suitable light, water and nutritional supplements which optimize the growth of the higher plant. The genetically modified plants of the present invention are engineered to produce significant quantities of the desired product through the activity of the PKS system that is genetically modified according to the present invention. The compounds can be recovered through purification processes which extract the compounds from the plant. In a preferred embodiment, the compound is recovered by harvesting the plant. In this embodiment, the plant can be consumed in its natural state or further processed into consumable products.

As described above, a genetically modified microorganism useful in the present invention can, in one aspect, endogenously contain and express a PUFA PKS system, and the genetic modification can be a genetic modification of one or more of the functional domains of the endogenous PUFA PKS system, whereby the modification has some effect on the activity of the PUFA PKS system. In another aspect, such an organism can endogenously contain and express a PUFA PKS system, and the genetic modification can be an introduction of at least one exogenous nucleic acid sequence (e.g., a recombinant nucleic acid molecule), wherein the exogenous nucleic acid sequence encodes at least one biologically active domain or protein from a second PKS system and/or a protein that affects the activity of said PUFA PKS system (e.g., a phosphopantetheinyl transferases (PPTase), discussed below). In yet another aspect, the organism does not necessarily endogenously (naturally) contain a PUFA PKS system, but is genetically modified to introduce at least one recombinant nucleic acid molecule encoding an amino acid sequence having the biological activity of at least one domain of a PUFA PKS system. In this aspect, PUFA PKS activity is affected by introducing or increasing PUFA PKS activity in the organism. Various embodiments associated with each of these aspects have been discussed in detail above.

In one embodiment of the method to produce bioactive compounds, the genetic modification changes at least one product produced by the endogenous PKS system, as compared to a wild-type organism.

In another embodiment, the organism endogenously expresses a PKS system comprising the at least one biologically active domain of the PUFA PKS system, and the genetic modification comprises transfection of the organism with a recombinant nucleic acid molecule selected from the group consisting of: a recombinant nucleic acid molecule encoding at least one biologically active domain from a second PKS system and a recombinant nucleic acid molecule encoding a protein that affects the activity of the PUFA PKS system. In this embodiment, the genetic modification preferably changes at least one product produced by the endogenous PKS system, as compared to a wild-type organism. A second PKS system can include another PUFA PKS system (bacterial or non-bacterial), a type I PKS system, a type II PKS system, and/or a modular PKS system. Examples of proteins that affect the activity of a PKS system have been described above (e.g., PPTase).

In another embodiment, the organism is genetically modified by transfection with a recombinant nucleic acid molecule encoding the at least one domain of the polyunsaturated fatty acid (PUFA) polyketide synthase (PKS) system. Such recombinant nucleic acid molecules have been described in detail previously herein.

In another embodiment, the organism endogenously expresses a non-bacterial PUFA PKS system, and the genetic modification comprises substitution of a domain from a different PKS system for a nucleic acid sequence encoding at least one domain of the non-bacterial PUFA PKS system. In another embodiment, the organism endogenously expresses a non-bacterial PUFA PKS system that has been modified by transfecting the organism with a recombinant nucleic acid molecule encoding a protein that regulates the chain length of fatty acids produced by the PUFA PKS system. In one aspect, the recombinant nucleic acid molecule encoding a protein that regulates the chain length of fatty acids replaces a nucleic acid sequence encoding a chain length factor in the non-bacterial PUFA PKS system. In another aspect, the protein that regulates the chain length of fatty acids produced by the PUFA PKS system is a chain length factor. In another aspect, the protein that regulates the chain length of fatty acids produced by the PUFA PKS system is a chain length factor that directs the synthesis of C20 units.

In another embodiment, the organism expresses a non-bacterial PUFA PKS system comprising a genetic modification in a domain selected from the group consisting of a domain encoding β-hydroxy acyl-ACP dehydrase (DH) and a domain encoding β-ketoacyl-ACP synthase (KS), wherein the modification alters the ratio of long chain fatty acids produced by the PUFA PKS system as compared to in the absence of the modification. In one aspect of this embodiment, the modification is selected from the group consisting of a deletion of all or a part of the domain, a substitution of a homologous domain from a different organism for the domain, and a mutation of the domain.

In another embodiment, the organism expresses a non-bacterial PUFA PKS system comprising a modification in an enoyl-ACP reductase (ER) domain, wherein the modification results in the production of a different compound as compared to in the absence of the modification. In one aspect of this embodiment, the modification is selected from the group consisting of a deletion of all or a part of the ER domain, a substitution of an ER domain from a different organism for the ER domain, and a mutation of the ER domain.

In one embodiment of the method to produce a bioactive molecule, the organism produces a polyunsaturated fatty acid (PUFA) profile that differs from the naturally occurring organism without a genetic modification.

Many other genetic modifications useful for producing bioactive molecules will be apparent to those of skill in the art, given the present disclosure, and various other modifications have been discussed previously herein. The present invention contemplates any genetic modification related to a PUFA PKS system as described herein which results in the production of a desired bioactive molecule.

Bioactive molecules, according to the present invention, include any molecules (compounds, products, etc.) that have a biological activity, and that can be produced by a PKS system that comprises at least one amino acid sequence having a biological activity of at least one functional domain of a non-bacterial PUFA PKS system as described herein. Such bioactive molecules can include, but are not limited to: a polyunsaturated fatty acid (PUFA), an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, and a cholesterol lowering formulation. One advantage of the non-bacterial PUFA PKS system of the present invention is the ability of such a system to introduce carbon-carbon double bonds in the cis configuration, and molecules including a double bond at every third carbon. This ability can be utilized to produce a variety of compounds.

Preferably, bioactive compounds of interest are produced by the genetically modified microorganism in an amount that is greater than about 0.05%, and preferably greater than about 0.1%, and more preferably greater than about 0.25%, and more preferably greater than about 0.5%, and more preferably greater than about 0.75%, and more preferably greater than about 1%, and more preferably greater than about 2.5%, and more preferably greater than about 5%, and more preferably greater than about 10%, and more preferably greater than about 15%, and even more preferably greater than about 20% of the dry weight of the microorganism. For lipid compounds, preferably, such compounds are produced in an amount that is greater than about 5% of the dry weight of the microorganism. For other bioactive compounds, such as antibiotics or compounds that are synthesized in smaller amounts, those strains possessing such compounds at of the dry weight of the microorganism are identified as predictably containing a novel PKS system of the type described above. In some embodiments, particular bioactive molecules (compounds) are secreted by the microorganism, rather than accumulating. Therefore, such bioactive molecules are generally recovered from the culture medium and the concentration of molecule produced will vary depending on the microorganism and the size of the culture.

One embodiment of the present invention relates to a method to modify an endproduct containing at least one fatty acid, comprising adding to said endproduct an oil produced by a recombinant host cell that expresses at least one recombinant nucleic acid molecule comprising a nucleic acid sequence encoding at least one biologically active domain of a PUFA PKS system. The PUFA PKS system is any non-bacterial PUFA PKS system, and preferably, is selected from the group of: (a) a nucleic acid sequence encoding at least one domain of a polyunsaturated fatty acid (PUFA) polyketide synthase (PKS) system from a Thraustochytrid microorganism; (b) a nucleic acid sequence encoding at least one domain of a PUFA PKS system from a microorganism identified by the novel screening method disclosed herein; (c) a nucleic acid sequence encoding an amino acid sequence selected from the group consisting of: SEQ ID NO:2, SEQ ID NO:4, SEQ ID NO:6, and biologically active fragments thereof; (d) a nucleic acid sequence encoding an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and biologically active fragments thereof; (e) a nucleic acid sequence encoding an amino acid sequence that is at least about 60% identical to at least 500 consecutive amino acids of an amino acid sequence selected from the group consisting of: SEQ ID NO:2, SEQ ID NO:4, and SEQ ID NO:6; wherein the amino acid sequence has a biological activity of at least one domain of a PUFA PKS system; and, (f) a nucleic acid sequence encoding an amino acid sequence that is at least about 60% identical to an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; wherein the amino acid sequence has a biological activity of at least one domain of a PUFA PKS system. Variations of these nucleic acid sequences have been described in detail above.

Preferably, the endproduct is selected from the group consisting of a food, a dietary supplement, a pharmaceutical formulation, a humanized animal milk, and an infant formula. Suitable pharmaceutical formulations include, but are not limited to, an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, and a cholesterol lowering formulation. In one embodiment, the endproduct is used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, and peroxisomal disorder.

Suitable food products include, but are not limited to, fine bakery wares, bread and rolls, breakfast cereals, processed and unprocessed cheese, condiments (ketchup, mayonnaise, etc.), dairy products (milk, yogurt), puddings and gelatine desserts, carbonated drinks, teas, powdered beverage mixes, processed fish products, fruit-based drinks, chewing gum, hard confectionery, frozen dairy products, processed meat products, nut and nut-based spreads, pasta, processed poultry products, gravies and sauces, potato chips and other chips or crisps, chocolate and other confectionery, soups and soup mixes, soya based products (milks, drinks, creams, whiteners), vegetable oil-based spreads, and vegetable-based drinks.

Yet another embodiment of the present invention relates to a method to produce a humanized animal milk. This method includes the steps of genetically modifying milk-producing cells of a milk-producing animal with at least one recombinant nucleic acid molecule comprising a nucleic acid sequence encoding at least one biologically active domain of a PUFA PKS system. The PUFA PKS system is a non-bacterial PUFA PKS system, and preferably, the at least one domain of the PUFA PKS system is encoded by a nucleic acid sequence selected from the group consisting of: (a) a nucleic acid sequence encoding at least one domain of a polyunsaturated fatty acid (PUFA) polyketide synthase (PKS) system from a Thraustochytrid microorganism; (b) a nucleic acid sequence encoding at least one domain of a PUFA PKS system from a microorganism identified by the novel screening method described previously herein; (c) a nucleic acid sequence encoding an amino acid sequence selected from the group consisting of: SEQ ID NO:2, SEQ ID NO:4, SEQ ID NO:6, and biologically active fragments thereof; (d) a nucleic acid sequence encoding an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and biologically active fragments thereof; (e) a nucleic acid sequence encoding an amino acid sequence that is at least about 60% identical to at least 500 consecutive amino acids of an amino acid sequence selected from the group consisting of: SEQ ID NO:2, SEQ ID NO:4, and SEQ ID NO:6; wherein the amino acid sequence has a biological activity of at least one domain of a PUFA PKS system; and/or (f) a nucleic acid sequence encoding an amino acid sequence that is at least about 60% identical to an amino acid sequence selected from the group consisting of: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, and SEQ ID NO:32; wherein the amino acid sequence has a biological activity of at least one domain of a PUFA PKS system.

Methods to genetically modify a host cell and to produce a genetically modified non-human, milk-producing animal, are known in the art. Examples of host animals to modify include cattle, sheep, pigs, goats, yaks, etc., which are amenable to genetic manipulation and cloning for rapid expansion of a transgene expressing population. For animals, PKS-like transgenes can be adapted for expression in target organelles, tissues and body fluids through modification of the gene regulatory regions. Of particular interest is the production of PUFAs in the breast milk of the host animal.

The following examples are provided for the purpose of illustration and are not intended to limit the scope of the present invention.

EXAMPLES

Example 1

The following example describes the further analysis of PKS related sequences from *Schizochytrium*.

The present inventors have sequenced the genomic DNA including the entire length of all three open reading frames (Orfs) in the *Schizochytrium* PUFA PKS system using the general methods outlined in Examples 8 and 9 from PCT Publication No. WO 0042195 and U.S. application Ser. No. 09/231,899. The biologically active domains in the *Schizochytrium* PKS proteins are depicted graphically in FIG. 1. The domain structure of the *Schizochytrium* PUFA PKS system is described more particularly as follows.

Open Reading Frame A (OrfA):

The complete nucleotide sequence for OrfA is represented herein as SEQ ID NO:1. OrfA is a 8730 nucleotide sequence (not including the stop codon) which encodes a 2910 amino acid sequence, represented herein as SEQ ID NO:2. Within OrfA are twelve domains:
 (a) one β-keto acyl-ACP synthase (KS) domain;
 (b) one malonyl-CoA:ACP acyltransferase (MAT) domain;
 (c) nine acyl carrier protein (ACP) domains;
 (d) one ketoreductase (KR) domain.

The domains contained within OrfA have been determined based on:
 (1) results of an analysis with Pfam program (Pfam is a database of multiple alignments of protein domains or conserved protein regions. The alignments represent some evolutionary conserved structure that has implications for the protein's function. Profile hidden Markov models (profile HMMs) built from the Pfam alignments can be very useful for automatically recognizing that a new protein belongs to an existing protein family, even if the homology is weak. Unlike standard pairwise alignment methods (e.g. BLAST, FASTA), Pfam HMMs deal sensibly with multidomain proteins. The reference provided for the Pfam version used is: Bateman A, Birney E, Cerruti L, Durbin R, Etwiller L, Eddy S R, Griffiths-Jones S, Howe K L, Marshall M, Sonnhammer E L (2002) Nucleic Acids Research 30(1):276-280); and/or
 (2) homology comparison to bacterial PUFA-PKS systems (e.g., *Shewanella*) using a BLAST 2.0 Basic BLAST homology search using blastp for amino acid searches with standard default parameters, wherein the query sequence is filtered for low complexity regions by default (described in Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety).

Sequences provided for individual domains are believed to contain the full length of the sequence encoding a functional domain, and may contain additional flanking sequence within the Orf.

ORFA-KS

The first domain in OrfA is a KS domain, also referred to herein as ORFA-KS. This domain is contained within the nucleotide sequence spanning from a starting point of between about positions 1 and 40 of SEQ ID NO:1 (OrfA) to an ending point of between about positions 1428 and 1500 of SEQ ID NO:1. The nucleotide sequence containing the sequence encoding the ORFA-KS domain is represented herein as SEQ ID NO:7 (positions 1-1500 of SEQ ID NO:1). The amino acid sequence containing the KS domain spans from a starting point of between about positions 1 and 14 of SEQ ID NO:2 (ORFA) to an ending point of between about positions 476 and 500 of SEQ ID NO:2. The amino acid sequence containing the ORFA-KS domain is represented herein as SEQ ID NO:8 (positions 1-500 of SEQ ID NO:2). It is noted that the ORFA-KS domain contains an active site motif: DXAC* (*acyl binding site $C_{215}$).

ORFA-MAT

The second domain in OrfA is a MAT domain, also referred to herein as ORFA-MAT. This domain is contained within the nucleotide sequence spanning from a starting point of between about positions 1723 and 1798 of SEQ ID NO:1 (OrfA) to an ending point of between about positions 2805 and 3000 of SEQ ID NO:1. The nucleotide sequence containing the sequence encoding the ORFA-MAT domain is represented herein as SEQ ID NO:9 (positions 1723-3000 of SEQ ID NO:1). The amino acid sequence containing the MAT domain spans from a starting point of between about positions 575 and 600 of SEQ ID NO:2 (ORFA) to an ending point of between about positions 935 and 1000 of SEQ ID NO:2. The amino acid sequence containing the ORFA-MAT domain is represented herein as SEQ ID NO:10 (positions 575-1000 of SEQ ID NO:2). It is noted that the ORFA-MAT domain contains an active site motif: GHS*XG (*acyl binding site $S_{706}$), represented herein as SEQ ID NO:11.

ORFA-ACP#1-9

Domains 3-11 of OrfA are nine tandem ACP domains, also referred to herein as ORFA-ACP (the first domain in the sequence is ORFA-ACP1, the second domain is ORFA-ACP2, the third domain is ORFA-ACP3, etc.). The first ACP domain, ORFA-ACP1, is contained within the nucleotide sequence spanning from about position 3343 to about position 3600 of SEQ ID NO:1 (OrfA). The nucleotide sequence containing the sequence encoding the ORFA-ACP1 domain is represented herein as SEQ ID NO:12 (positions 3343-3600 of SEQ ID NO:1). The amino acid sequence containing the first ACP domain spans from about position 1115 to about position 1200 of SEQ ID NO:2. The amino acid sequence containing the ORFA-ACP1 domain is represented herein as SEQ ID NO:13 (positions 1115-1200 of SEQ ID NO:2). It is noted that the ORFA-ACP1 domain contains an active site motif: LGIDS* (*pantetheine binding motif $S_{1157}$), represented herein by SEQ ID NO:14. The nucleotide and amino acid sequences of all nine ACP domains are highly conserved and therefore, the sequence for each domain is not represented herein by an individual sequence identifier. However, based on this information, one of skill in the art can readily determine the sequence for each of the other eight ACP domains. The repeat interval for the nine domains is approximately about 110 to about 330 nucleotides of SEQ ID NO:1.

All nine ACP domains together span a region of OrfA of from about position 3283 to about position 6288 of SEQ ID NO:1, which corresponds to amino acid positions of from about 1095 to about 2096 of SEQ ID NO:2. This region includes the linker segments between individual ACP domains. Each of the nine ACP domains contains a pantetheine binding motif LGIDS* (represented herein by SEQ ID NO:14), wherein * is the pantetheine binding site S. At each end of the ACP domain region and between each ACP domain is a region that is highly enriched for proline (P) and alanine (A), which is believed to be a linker region. For example, between ACP domains 1 and 2 is the sequence: APAPV-KAAAPAAPVASAPAPA, represented herein as SEQ ID NO:15.

ORFA-KR

Domain 12 in OrfA is a KR domain, also referred to herein as ORFA-KR. This domain is contained within the nucleotide sequence spanning from a starting point of about position 6598 of SEQ ID NO:1 to an ending point of about position 8730 of SEQ ID NO:1. The nucleotide sequence containing the sequence encoding the ORFA-KR domain is represented herein as SEQ ID NO:17 (positions 6598-8730 of SEQ ID NO:1). The amino acid sequence containing the KR domain spans from a starting point of about position 2200 of SEQ ID NO:2 (ORFA) to an ending point of about position 2910 of SEQ ID NO:2. The amino acid sequence containing the ORFA-KR domain is represented herein as SEQ ID NO:18 (positions 2200-2910 of SEQ ID NO:2). Within the KR domain is a core region with homology to short chain aldehyde-dehydrogenases (KR is a member of this family). This core region spans from about position 7198 to about position 7500 of SEQ ID NO:1, which corresponds to amino acid positions 2400-2500 of SEQ ID NO:2.

Open Reading Frame B (OrfB):

The complete nucleotide sequence for OrfB is represented herein as SEQ ID NO:3. OrfB is a 6177 nucleotide sequence (not including the stop codon) which encodes a 2059 amino acid sequence, represented herein as SEQ ID NO:4. Within OrfB are four domains:
(a) β-keto acyl-ACP synthase (KS) domain;
(b) one chain length factor (CLF) domain;
(c) one acyl transferase (AT) domain;
(d) one enoyl ACP-reductase (ER) domain.

The domains contained within ORFB have been determined based on: (1) results of an analysis with Pfam program, described above; and/or (2) homology comparison to bacterial PUFA-PKS systems (e.g., *Shewanella*) using a BLAST 2.0 Basic BLAST homology search, also described above. Sequences provided for individual domains are believed to contain the full length of the sequence encoding a functional domain, and may contain additional flanking sequence within the Orf.

ORFB-KS

The first domain in OrfB is a KS domain, also referred to herein as ORFB-KS. This domain is contained within the nucleotide sequence spanning from a starting point of between about positions 1 and 43 of SEQ ID NO:3 (Orf)B) to an ending point of between about positions 1332 and 1350 of SEQ ID NO:3. The nucleotide sequence containing the sequence encoding the ORFB-KS domain is represented herein as SEQ ID NO:19 (positions 1-1350 of SEQ ID NO:3). The amino acid sequence containing the KS domain spans from a starting point of between about positions 1 and 15 of SEQ ID NO:4 (ORFB) to an ending point of between about positions 444 and 450 of SEQ ID NO:4. The amino acid sequence containing the ORFB-KS domain is represented herein as SEQ ID NO:20 (positions 1-450 of SEQ ID NO:4). It is noted that the ORFB-KS domain contains an active site motif: DXAC* (*acyl binding site $C_{196}$).

ORFB-CLF

The second domain in OrfB is a CLF domain, also referred to herein as ORFB-CLF. This domain is contained within the nucleotide sequence spanning from a starting point of between about positions 1378 and 1402 of SEQ ID NO:3 (OrfB) to an ending point of between about positions 2682 and 2700 of SEQ ID NO:3. The nucleotide sequence containing the sequence encoding the ORFB-CLF domain is represented herein as SEQ ID NO:21 (positions 1378-2700 of SEQ ID NO:3). The amino acid sequence containing the CLF domain spans from a starting point of between about positions 460 and 468 of SEQ ID NO:4 (ORFB) to an ending point of between about positions 894 and 900 of SEQ ID NO:4. The amino acid sequence containing the ORFB-CLF domain is represented herein as SEQ ID NO:22 (positions 460-900 of SEQ ID NO:4). It is noted that the ORFB-CLF domain contains a KS active site motif without the acyl-binding cysteine.

ORFB-AT

The third domain in OrfB is an AT domain, also referred to herein as ORFB-AT. This domain is contained within the nucleotide sequence spanning from a starting point of between about positions 2701 and 3598 of SEQ ID NO:3 (OrfB) to an ending point of between about positions 3975 and 4200 of SEQ ID NO:3. The nucleotide sequence containing the sequence encoding the ORFB-AT domain is represented herein as SEQ ID NO:23 (positions 2701-4200 of SEQ ID NO:3). The amino acid sequence containing the AT domain spans from a starting point of between about positions 901 and 1200 of SEQ ID NO:4 (ORFB) to an ending point of between about positions 1325 and 1400 of SEQ ID NO:4. The amino acid sequence containing the ORFB-AT domain is represented herein as SEQ ID NO:24 (positions 901-1400 of SEQ ID NO:4). It is noted that the ORFB-AT domain contains an AT active site motif of GxS*xG (*acyl binding site $S_{1140}$).

ORFB-ER

The fourth domain in OrfB is an ER domain, also referred to herein as ORFB-ER. This domain is contained within the nucleotide sequence spanning from a starting point of about position 4648 of SEQ ID NO:3 (OrfB) to an ending point of about position 6177 of SEQ ID NO:3. The nucleotide sequence containing the sequence encoding the ORFB-ER domain is represented herein as SEQ ID NO:25 (positions 4648-6177 of SEQ ID NO:3). The amino acid sequence containing the ER domain spans from a starting point of about position 1550 of SEQ ID NO:4 (ORFB) to an ending point of about position 2059 of SEQ ID NO:4. The amino acid sequence containing the ORFB-ER domain is represented herein as SEQ ID NO:26 (positions 1550-2059 of SEQ ID NO:4).

Open Reading Frame C (OrfC):

The complete nucleotide sequence for OrfC is represented herein as SEQ ID NO:5. OrfC is a 4509 nucleotide sequence (not including the stop codon) which encodes a 1503 amino acid sequence, represented herein as SEQ ID NO:6. Within OrfC are three domains:
(a) two FabA-like β-hydroxy acyl-ACP dehydrase (DH) domains;
(b) one enoyl ACP-reductase (ER) domain.

The domains contained within ORFC have been determined based on: (1) results of an analysis with Pfam program, described above; and/or (2) homology comparison to bacterial PUFA-PKS systems (e.g., *Shewanella*) using a BLAST 2.0 Basic BLAST homology search, also described above. Sequences provided for individual domains are believed to contain the full length of the sequence encoding a functional domain, and may contain additional flanking sequence within the Orf.

ORFC-DH1

The first domain in OrfC is a DH domain, also referred to herein as ORFC-DH1. This is one of two DH domains in OrfC, and therefore is designated DH1. This domain is contained within the nucleotide sequence spanning from a starting point of between about positions 1 and 778 of SEQ ID NO:5 (OrfC) to an ending point of between about positions 1233 and 1350 of SEQ ID NO:5. The nucleotide sequence containing the sequence encoding the ORFC-DH1 domain is represented herein as SEQ ID NO:27 (positions 1-1350 of SEQ ID NO:5). The amino acid sequence containing the DH1 domain spans from a starting point of between about positions 1 and 260 of SEQ ID NO:6 (ORFC) to an ending point of between about positions 411 and 450 of SEQ ID NO:6. The amino acid sequence containing the ORFC-DH1 domain is represented herein as SEQ ID NO:28 (positions 1-450 of SEQ ID NO:6).

ORFC-DH2

The second domain in OrfC is a DH domain, also referred to herein as ORFC-DH2. This is the second of two DH domains in OrfC, and therefore is designated DH2. This domain is contained within the nucleotide sequence spanning from a starting point of between about positions 1351 and 2437 of SEQ ID NO:5 (OrfC) to an ending point of between about positions 2607 and 2850 of SEQ ID NO:5. The nucleotide sequence containing the sequence encoding the ORFC-DH2 domain is represented herein as SEQ ID NO:29 (positions 1351-2850 of SEQ ID NO:5). The amino acid sequence containing the DH2 domain spans from a starting point of between about positions 451 and 813 of SEQ ID NO:6 (ORFC) to an ending point of between about positions 869 and 950 of SEQ ID NO:6. The amino acid sequence containing the ORFC-DH2 domain is represented herein as SEQ ID NO:30 (positions 451-950 of SEQ ID NO:6).

ORFC-ER

The third domain in OrfC is an ER domain, also referred to herein as ORFC-ER. This domain is contained within the nucleotide sequence spanning from a starting point of about position 2998 of SEQ ID NO:5 (OrfC) to an ending point of about position 4509 of SEQ ID NO:5. The nucleotide sequence containing the sequence encoding the ORFC-ER domain is represented herein as SEQ ID NO:31 (positions 2998-4509 of SEQ ID NO:5). The amino acid sequence containing the ER domain spans from a starting point of about position 1000 of SEQ ID NO:6 (ORFC) to an ending point of about position 1502 of SEQ ID NO:6. The amino acid sequence containing the ORFC-ER domain is represented herein as SEQ ID NO:32 (positions 1000-1502 of SEQ ID NO:6).

Example 2

The following example describes the use of the screening process of the present invention to identify three other non-bacterial organisms comprising a PUFA PKS system according to the present invention.

*Thraustochytrium* sp. 23B (ATCC 20892) was cultured according to the screening method described in U.S. Provisional Application Ser. No. 60/298,796 and as described in detail herein.

The biorational screen (using shake flask cultures) developed for detecting microorganisms containing PUFA producing PKS systems is as follows:

Two mL of a culture of the strain/microorganism to be tested is placed in 250 mL baffled shake flask with 50 mL culture media (aerobic treatment) and another 2 mL of culture of the same strain is placed in a 250 mL non-baffled shake flask with 200 mL culture medium (anoxic treatment). Both flasks are placed on a shaker table at 200 rpm. After 48-72 hr of culture time, the cultures are harvested by centrifugation and the cells analyzed for fatty acid methyl esters via gas chromatography to determine the following data for each culture: (1) fatty acid profile; (2) PUFA content; (3) fat content (estimated as amount total fatty acids (TFA)).

These data are then analyzed asking the following five questions:

Selection Criteria: Low $O_2$/Anoxic Flask vs. Aerobic Flask (Yes/No)

(1) Did the DHA (or other PUFA content) (as % FAME) stay about the same or preferably increase in the low oxygen culture compared to the aerobic culture?

(2) Is C14:0+C16:0+C16:1 greater than about 40% TFA in the anoxic culture?

(3) Is there very little (>1% as FAME) or no precursors (C18:3n-3+C18:2n-6+C18:3n-6) to the conventional oxygen dependent elongase/desaturase pathway in the anoxic culture?

(4) Did fat content (as amount total fatty acids/cell dry weight) increase in the low oxygen culture compared to the aerobic culture?

(5) Did DHA (or other PUFA content) increase as % cell dry weight in the low oxygen culture compared to the aerobic culture?

If first three questions are answered yes, there is a good indication that the strain contains a PKS genetic system for making long chain PUFAs. The more questions that are answered yes (preferably the first three questions must be answered yes), the stronger the indication that the strain contains such a PKS genetic system. If all five questions are answered yes, then there is a very strong indication that the strain contains a PKS genetic system for making long chain PUFAs.

Following the method outlined above, a frozen vial of *Thraustochytrium* sp. 23B (ATCC 20892) was used to inoculate a 250 mL shake flask containing 50 mL of RCA medium. The culture was shaken on a shaker table (200 rpm) for 72 hr at 25° C. RCA medium contains the following:

| RCA Medium | |
|---|---|
| Deionized water | 1000 mL |
| Reef Crystals ® sea salts | 40 g/L |
| Glucose | 20 g/L |
| Monosodium glutamate (MSG) | 20 g/L |
| Yeast extract | 1 g/L |
| PII metals* | 5 mL/L |
| Vitamin mix* | 1 mL/L |
| pH | 7.0 |

*PII metal mix and vitamin mix are same as those outlined in U.S. Pat. No. 5,130,742, incorporated herein by reference in its entirety.

25 mL of the 72 hr old culture was then used to inoculate another 250 mL shake flask containing 50 mL of low nitrogen RCA medium (10 g/L MSG instead of 20 g/L) and the other 25 mL of culture was used to inoculate a 250 mL shake flask containing 175 mL of low-nitrogen RCA medium. The two flasks were then placed on a shaker table (200 rpm) for 72 hr at 25° C. The cells were then harvested via centrifugation and dried by lyophilization. The dried cells were analyzed for fat content and fatty acid profile and content using standard gas chromatograph procedures (such as those outlined in U.S. Pat. No. 5,130,742).

The screening results for *Thraustochytrium* 23B were as follows:

| | |
|---|---|
| Did DHA as % FAME increase? | Yes (38->44%) |
| C14:0 + C16:0 + C16:1 greater than about 40% TFA? | Yes (44%) |
| No C18:3(n-3) or C18:3(n-6)? | Yes (0%) |
| Did fat content increase? | Yes (2-fold increase) |
| Did DHA (or other HUFA content increase)? | Yes (2.3-fold increase) |

The results, especially the significant increase in DHA content (as % FAME) under low oxygen conditions, conditions, strongly indicates the presence of a PUFA producing PKS system in this strain of *Thraustochytrium*.

In order to provide additional data confirming the presence of a PUFA PKS system, southern blot of *Thraustochytrium* 23B was conducted using PKS probes from *Schizochytrium* strain 20888, a strain which has already been determined to contain a PUFA producing PKS system (i.e., SEQ ID Nos:1-32 described above). Fragments of *Thraustochytrium* 23B genomic DNA which are homologous to hybridization probes from PKS PUFA synthesis genes were detected using the Southern blot technique. *Thraustochytrium* 23B genomic DNA was digested with either ClaI or KpnI restriction endonucleases, separated by agarose gel electrophoresis (0.7% agarose, in standard Tris-Acetate-EDTA buffer), and blotted to a Schleicher & Schuell Nytran Supercharge membrane by capillary transfer. Two digoxigenin labeled hybridization probes were used—one specific for the Enoyl Reductase (ER) region of *Schizochytrium* PKS Orf B (nucleotides 5012-5511 of Orf B; SEQ ID NO:3), and the other specific for a conserved region at the beginning of *Schizochytrium* PKS Orf C (nucleotides 76-549 of OrfC; SEQ ID NO:5).

The OrfB-ER probe detected an approximately 13 kb ClaI fragment and an approximately 3.6 kb KpnI fragment in the *Thraustochytrium* 23B genomic DNA. The OrfC probe detected an approximately 7.5 kb ClaI fragment and an approximately 4.6 kb KpnI fragment in the *Thraustochytrium* 23B genomic DNA.

Finally, a recombinant genomic library, consisting of DNA fragments from *Thraustochytrium* 23B genomic DNA inserted into vector lambda FIX II (Stratagene), was screened using digoxigenin labeled probes corresponding to the following segments of *Schizochytrium* 20888 PUFA-PKS genes: nucleotides 7385-7879 of Orf A (SEQ ID NO:1), nucleotides 5012-5511 of Orf B (SEQ ID NO:3), and nucleotides 76-549 of Orf C (SEQ ID NO:5). Each of these probes detected positive plaques from the *Thraustochytrium* 23B library, indicating extensive homology between the *Schizochytrium* PUFA-PKS genes and the genes of *Thraustochytrium* 23B.

In summary, these results demonstrate that *Thraustochytrium* 23B genomic DNA contains sequences that are homologous to PKS genes from *Schizochytrium* 20888.

This Thraustochytrid microorganism is encompassed herein as an additional sources of these genes for use in the embodiments above.

*Thraustochytrium* 23B (ATCC 20892) is significantly different from *Schizochytrium* sp. (ATCC 20888) in its fatty acid profile. *Thraustochytrium* 23B can have DHA:DPA(n-6) ratios as high as 14:1 compared to only 2-3:1 in *Schizochytrium* (ATCC 20888). *Thraustochytrium* 23B can also have higher levels of C20:5(n-3). Analysis of the domains in the PUFA PKS system of *Thraustochytrium* 23B in comparison to the known *Schizochytrium* PUFA PKS system should provide us with key information on how to modify these domains to influence the ratio and types of PUFA produced using these systems.

The screening method described above has been utilized the identify other potential candidate strains containing a PUFA PKS system. Two additional strains that have been identified by the present inventors to have PUFA PKS systems are *Schizochytrium limacium* (SR21) Honda & Yokochi (IFO32693) and *Ulkenia* (BP-5601). Both were screened as above but in N2 media (glucose: 60 g/L; $KH_2PO_4$: 4.0 µl; yeast extract: 1.0 g/L; corn steep liquor: 1 mL/L; $NH_4NO_3$: 1.0 g/L; artificial sea salts (Reef Crystals): 20 g/L; all above concentrations mixed in deionized water). For both the *Schizochytrium* and *Ulkenia* strains, the answers to the first three screen questions discussed above for *Thraustochytrium* 23B was yes (*Schizochytrium*—DHA % FAME 32->41% aerobic vs anoxic, 58% 14:0/16:0/16:1, 0% precursors) and (*Ulkenia*—DHA % FAME 28->44% aerobic vs anoxic, 63% 14:0/16:0/16:1, 0% precursors), indicating that these strains are good candidates for containing a PUFA PKS system. Negative answers were obtained for the final two questions for each strain: fat decreased from 61% dry wt to 22% dry weight, and DHA from 21-9% dry weight in *S. limacium* and fat decreased from 59 to 21% dry weight in *Ulkenia* and DHA from 16% to 9% dry weight. These Thraustochytrid microorganisms are also claimed herein as additional sources of the genes for use in the embodiments above.

Example 3

The following example demonstrates that DHA and DPA synthesis in *Schizochytrium* does not involve membrane-bound desaturases or fatty acid elongation enzymes like those described for other eukaryotes (Parker-Barnes et al., 2000, supra; Shanklin et al., 1998, supra).

*Schizochytrium* accumulates large quantities of triacylglycerols rich in DHA and docosapentaenoic acid (DPA; 22:566); e.g., 30% DHA+DPA by dry weight. In eukaryotes that synthesize 20- and 22-carbon PUFAs by an elongation/desaturation pathway, the pools of 18-, 20- and 22-carbon intermediates are relatively large so that in vivo labeling experiments using [$^{14}$C]-acetate reveal clear precursor-product kinetics for the predicted intermediates. Furthermore, radiolabeled intermediates provided exogenously to such organisms are converted to the final PUFA products.

[1-$^{14}$C]acetate was supplied to a 2-day-old culture as a single pulse at zero time. Samples of cells were then harvested by centrifugation and the lipids were extracted. In addition, [1-$^{14}$C]acetate uptake by the cells was estimated by measuring the radioactivity of the sample before and after centrifugation. Fatty acid methyl esters derived from the total cell lipids were separated by $AgNO_3$-TLC (solvent, hexane:diethyl ether:acetic acid, 70:30:2 by volume). The identity of the fatty acid bands was verified by gas chromatography, and the radioactivity in them was measured by scintillation counting. Results showed that [1-$^{14}$C]-acetate was rapidly taken up by *Schizochytrium* cells and incorporated into fatty acids, but at the shortest labeling time (1 min) DHA contained 31% of the label recovered in fatty acids and this percentage remained essentially unchanged during the 10-15 min of [$^{14}$C]-acetate incorporation and the subsequent 24 hours of culture growth (data not shown). Similarly, DPA represented 10% of the label throughout the experiment. There is no evidence for a precursor-product relationship between 16- or 18-carbon fatty acids and the 22-carbon polyunsaturated fatty acids. These results are consistent with rapid synthesis of DHA from [$^{14}$C]-acetate involving very small (possibly enzyme-bound) pools of intermediates.

Next, cells were disrupted in 100 mM phosphate buffer (pH 7.2), containing 2 mM DTT, 2 mM EDTA, and 10% glycerol, by vortexing with glass beads. The cell-free homogenate was centrifuged at 100,000 g for 1 hour. Equivalent aliquots of total homogenate, pellet (H-S pellet), and supernatant (H-S super) fractions were incubated in homogenization buffer supplemented with 20 μM acetyl-CoA, 100 μM [1-$^{14}$C]malonyl-CoA (0.9 Gbq/mol), 2 mM NADH, and 2 mM NADPH for 60 min at 25° C. Assays were extracted and fatty acid methyl esters were prepared and separated as described above before detection of radioactivity with an Instantimager (Packard Instruments, Meriden, Conn.). Results showed that a cell-free homogenate derived from *Schizochytrium* cultures incorporated [1-$^{14}$C]-malonyl-CoA into DHA, DPA, and saturated fatty acids (data not shown). The same biosynthetic activities were retained by a 100,000×g supernatant fraction but were not present in the membrane pellet. These data contrast with those obtained during assays of the bacterial enzymes (see Metz et al., 2001, supra) and may indicate use of a different (soluble) acyl acceptor molecule. Thus, DHA and DPA synthesis in *Schizochytrium* does not involve membrane-bound desaturases or fatty acid elongation enzymes like those described for other eukaryotes.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule comprising a nucleic acid sequence encoding a polypeptide comprising the β-keto acyl-ACP synthase (KS), malonyl-CoA:ACP acyltransferase (MAT), acyl carrier protein (ACP), and ketoreductase (KR) activities of SEQ ID NO:2, wherein the polypeptide comprises:
   a) an amino acid sequence that is at least 95% identical to SEQ ID NO:8 and comprises KS activity;
   b) an amino acid sequence that is at least 95% identical to SEQ ID NO:10 and comprises MAT activity;
   c) an amino acid sequence that is at least 95% identical to amino acids 1095-2096 of SEQ ID NO:2 and comprises ACP activity; and
   d) an amino acid sequence that is at least 95% identical to SEQ ID NO:18 and comprises KR activity.

2. A recombinant nucleic acid molecule comprising the nucleic acid molecule of claim 1, operatively linked to at least one transcription control sequence.

3. An isolated recombinant host cell transfected with the recombinant nucleic acid molecule of claim 2.

4. A genetically modified microorganism transfected with the recombinant nucleic acid molecule of claim 2.

5. The genetically modified microorganism of claim 4, wherein the microorganism endogenously expresses a polyunsaturated fatty acid (PUFA) polyketide synthase (PKS) system, and wherein the genetic modification comprises expression of a recombinant nucleic acid molecule encoding a protein that enhances the activity of the PUFA PKS system relative to the unmodified microorganism.

6. A genetically modified plant, wherein the plant has been genetically modified to recombinantly express a PKS system comprising a nucleic acid sequence encoding a polypeptide of a PUFA PKS system, wherein the polypeptide comprises the β-keto acyl-ACP synthase (KS), malonyl-CoA:ACP acyltransferase (MAT), acyl carrier protein (ACP), and ketoreductase (KR) activities of SEQ ID NO:2, and wherein the polypeptide comprises:
   a) an amino acid sequence that is at least 95% identical to SEQ ID NO:8 and comprises KS activity;
   b) an amino acid sequence that is at least 95% identical to SEQ ID NO:10 and comprises MAT activity;
   c) an amino acid sequence that is at least 95% identical to amino acids 1095-2096 of SEQ ID NO:2 and comprises ACP activity; and
   d) an amino acid sequence that is at least 95% identical to SEQ ID NO: 18 and comprises KR activity.

7. A method to produce a plant that has a PUFA profile that differs from the naturally occurring plant, comprising genetically modifying cells of the plant to express a PKS system comprising at least one recombinant nucleic acid molecule comprising a nucleic acid sequence encoding a polypeptide of a PUFA PKS system, wherein the polypeptide comprises the β-keto acyl-ACP synthase (KS), malonyl-CoA:ACP acyltransferase (MAT), acyl carrier protein (ACP), and ketoreductase (KR) activities of SEQ ID NO:2, and wherein the polypeptide comprises:
   a) an amino acid sequence that is at least 95% identical to SEQ ID NO:8 and comprises KS activity;
   b) an amino acid sequence that is at least 95% identical to SEQ ID NO:10 and comprises MAT activity;
   c) an amino acid sequence that is at least 95% identical to amino acids 1095-2096 of SEQ ID NO:2 and comprises ACP activity; and
   d) an amino acid sequence that is at least 95% identical to SEQ ID NO: 18 and comprises KR activity.

8. A method to produce a recombinant microbe, comprising genetically modifying microbial cells to express at least one recombinant nucleic acid molecule comprising a nucleic acid sequence encoding a polypeptide of a PUPA PKS system, wherein the polypeptide comprises the β-keto acyl-ACP synthase (KS), malonyl-CoA:ACP acyltransferase (MAT), acyl carrier protein (ACP), and ketoreductase (KR) activities of SEQ ID NO:2, and wherein the polypeptide comprises:
   a) an amino acid sequence that is at least 95% identical to SEQ ID NO:8 and comprises KS activity;
   b) an amino acid sequence that is at least 95% identical to SEQ ID NO:10 and comprises MAT activity;
   c) an amino acid sequence that is at least 95% identical to amino acids 1095-2096 of SEQ ID NO:2 and comprises ACP activity; and
   d) an amino acid sequence that is at least 95% identical to SEQ ID NO: 18 and comprises KR activity.

* * * * *

SEQUENCE LISTING

```
<160> NUMBER OF SEQ ID NOS: 37

<210> SEQ ID NO 1
<211> LENGTH: 8730
<212> TYPE: DNA
<213> ORGANISM: Schizochytrium sp.
<220> FEATURE:
<221> NAME/KEY: CDS
<222> LOCATION: (1)..(8730)

<400> SEQUENCE: 1 atg gcg gcc cgt ctg cag gag caa aag gga ggc gag atg gat acc cgc      48
Met Ala Ala Arg Leu Gln Glu Gln Lys Gly Gly Glu Met Asp Thr Arg
1               5                   10                  15 att gcc atc atc ggc atg tcg gcc atc ctc ccc tgc ggc acg acc gtg      96
Ile Ala Ile Ile Gly Met Ser Ala Ile Leu Pro Cys Gly Thr Thr Val
            20                  25                  30 cgc gag tcg tgg gag acc atc cgc gcc ggc atc gac tgc ctg tcg gat     144
Arg Glu Ser Trp Glu Thr Ile Arg Ala Gly Ile Asp Cys Leu Ser Asp
        35                  40                  45 ctc ccc gag gac cgc gtc gac gtg acg gcg tac ttt gac ccc gtc aag     192
Leu Pro Glu Asp Arg Val Asp Val Thr Ala Tyr Phe Asp Pro Val Lys
    50                  55                  60 acc acc aag gac aag atc tac tgc aag cgc ggt ggc ttc att ccc gag     240
Thr Thr Lys Asp Lys Ile Tyr Cys Lys Arg Gly Gly Phe Ile Pro Glu
65                  70                  75                  80 tac gac ttt gac gcc cgc gag ttc gga ctc aac atg ttc cag atg gag     288
Tyr Asp Phe Asp Ala Arg Glu Phe Gly Leu Asn Met Phe Gln Met Glu
                85                  90                  95 gac tcg gac gca aac cag acc atc tcg ctt ctc aag gtc aag gag gcc     336
Asp Ser Asp Ala Asn Gln Thr Ile Ser Leu Leu Lys Val Lys Glu Ala
            100                 105                 110 ctc cag gac gcc ggc atc gac gcc ctc ggc aag gaa aag aag aac atc     384
Leu Gln Asp Ala Gly Ile Asp Ala Leu Gly Lys Glu Lys Lys Asn Ile
        115                 120                 125 ggc tgc gtg ctc ggc att ggc ggc ggc caa aag tcc agc cac gag ttc     432
Gly Cys Val Leu Gly Ile Gly Gly Gly Gln Lys Ser Ser His Glu Phe
    130                 135                 140 tac tcg cgc ctt aat tat gtt gtc gtg gag aag gtc ctc cgc aag atg     480
Tyr Ser Arg Leu Asn Tyr Val Val Val Glu Lys Val Leu Arg Lys Met
145                 150                 155                 160 ggc atg ccc gag gag gac gtc aag gtc gcc gtc gaa aag tac aag gcc     528
Gly Met Pro Glu Glu Asp Val Lys Val Ala Val Glu Lys Tyr Lys Ala
                165                 170                 175
```

```
aac ttc ccc gag tgg cgc ctc gac tcc ttc cct ggc ttc ctc ggc aac    576
Asn Phe Pro Glu Trp Arg Leu Asp Ser Phe Pro Gly Phe Leu Gly Asn
        180                 185                 190 gtc acc gcc ggt cgc tgc acc aac acc ttc aac ctc gac ggt atg aac    624
Val Thr Ala Gly Arg Cys Thr Asn Thr Phe Asn Leu Asp Gly Met Asn
        195                 200                 205 tgc gtt gtc gac gcc gca tgc gcc tcg tcc ctc atc gcc gtc aag gtc    672
Cys Val Val Asp Ala Ala Cys Ala Ser Ser Leu Ile Ala Val Lys Val
210                 215                 220 gcc atc gac gag ctg ctc tac ggt gac tgc gac atg atg gtc acc ggt    720
Ala Ile Asp Glu Leu Leu Tyr Gly Asp Cys Asp Met Met Val Thr Gly
225                 230                 235                 240 gcc acc tgc acg gat aac tcc atc ggc atg tac atg gcc ttc tcc aag    768
Ala Thr Cys Thr Asp Asn Ser Ile Gly Met Tyr Met Ala Phe Ser Lys
                245                 250                 255 acc ccc gtg ttc tcc acg gac ccc agc gtg cgc gcc tac gac gaa aag    816
Thr Pro Val Phe Ser Thr Asp Pro Ser Val Arg Ala Tyr Asp Glu Lys
        260                 265                 270 aca aag ggc atg ctc atc ggc gag ggc tcc gcc atg ctc gtc ctc aag    864
Thr Lys Gly Met Leu Ile Gly Glu Gly Ser Ala Met Leu Val Leu Lys
        275                 280                 285 cgc tac gcc gac gcc gtc cgc gac ggc gat gag atc cac gct gtt att    912
Arg Tyr Ala Asp Ala Val Arg Asp Gly Asp Glu Ile His Ala Val Ile
        290                 295                 300 cgc ggc tgc gcc tcc tcc agt gat ggc aag gcc gcc ggc atc tac acg    960
Arg Gly Cys Ala Ser Ser Ser Asp Gly Lys Ala Ala Gly Ile Tyr Thr
305                 310                 315                 320 ccc acc att tcg ggc cag gag gag gcc ctc cgc cgc gcc tac aac cgc   1008
Pro Thr Ile Ser Gly Gln Glu Glu Ala Leu Arg Arg Ala Tyr Asn Arg
                325                 330                 335 gcc tgt gtc gac ccg gcc acc gtc act ctc gtc gag ggt cac ggc acc   1056
Ala Cys Val Asp Pro Ala Thr Val Thr Leu Val Glu Gly His Gly Thr
        340                 345                 350 ggt act ccc gtt ggc gac cgc atc gag ctc acc gcc ttg cgc aac ctc   1104
Gly Thr Pro Val Gly Asp Arg Ile Glu Leu Thr Ala Leu Arg Asn Leu
        355                 360                 365 ttt gac aag gcc tac ggc gag ggc aac acc gaa aag gtc gct gtg ggc   1152
Phe Asp Lys Ala Tyr Gly Glu Gly Asn Thr Glu Lys Val Ala Val Gly
        370                 375                 380 agc atc aag tcc agc atc ggc cat ctc aag gcc gtc gcc ggt ctc gcc   1200
Ser Ile Lys Ser Ser Ile Gly His Leu Lys Ala Val Ala Gly Leu Ala
385                 390                 395                 400 ggt atg atc aag gtc atc atg gcg ctc aag cac aag act ctc ccg ggc   1248
Gly Met Ile Lys Val Ile Met Ala Leu Lys His Lys Thr Leu Pro Gly
                405                 410                 415 acc atc aac gtc gac aac cca ccc aac ctc tac gac aac acg ccc atc   1296
Thr Ile Asn Val Asp Asn Pro Pro Asn Leu Tyr Asp Asn Thr Pro Ile
        420                 425                 430 aac gag tcc tcg ctc tac att aac acc atg aac cgc ccc tgg ttc ccg   1344
Asn Glu Ser Ser Leu Tyr Ile Asn Thr Met Asn Arg Pro Trp Phe Pro
        435                 440                 445 ccc cct ggt gtg ccc cgc cgc gcc ggc att tcg agc ttt ggc ttt ggt   1392
Pro Pro Gly Val Pro Arg Arg Ala Gly Ile Ser Ser Phe Gly Phe Gly
        450                 455                 460 ggc gcc aac tac cac gcc gtc ctc gag gag gcc gag ccc gag cac acg   1440
Gly Ala Asn Tyr His Ala Val Leu Glu Glu Ala Glu Pro Glu His Thr
465                 470                 475                 480 acc gcg tac cgc ctc aac aag cgc ccg cag ccc gtg ctc atg atg gcc   1488
Thr Ala Tyr Arg Leu Asn Lys Arg Pro Gln Pro Val Leu Met Met Ala
        485                 490                 495
```

```
gcc acg ccc gcg gcc ctc cag tcg ctc tgc gag gcc cag ctc aag gag   1536
Ala Thr Pro Ala Ala Leu Gln Ser Leu Cys Glu Ala Gln Leu Lys Glu
            500                 505                 510 ttc gag gcc gcc atc aag gag aac gag acc gtc aag aac acc gcc tac   1584
Phe Glu Ala Ala Ile Lys Glu Asn Glu Thr Val Lys Asn Thr Ala Tyr
            515                 520                 525 atc aag tgc gtc aag ttc ggc gag cag ttc aaa ttc cct ggc tcc atc   1632
Ile Lys Cys Val Lys Phe Gly Glu Gln Phe Lys Phe Pro Gly Ser Ile
        530                 535                 540 ccg gcc aca aac gcg cgc ctc ggc ttc ctc gtc aag gat gct gag gat   1680
Pro Ala Thr Asn Ala Arg Leu Gly Phe Leu Val Lys Asp Ala Glu Asp
545                 550                 555                 560 gcc tgc tcc acc ctc cgt gcc atc tgc gcc caa ttc gcc aag gat gtc   1728
Ala Cys Ser Thr Leu Arg Ala Ile Cys Ala Gln Phe Ala Lys Asp Val
                565                 570                 575 acc aag gag gcc tgg cgc ctc ccc cgc gag ggc gtc agc ttc cgc gcc   1776
Thr Lys Glu Ala Trp Arg Leu Pro Arg Glu Gly Val Ser Phe Arg Ala
            580                 585                 590 aag ggc atc gcc acc aac ggc gct gtc gcc gcg ctc ttc tcc ggc cag   1824
Lys Gly Ile Ala Thr Asn Gly Ala Val Ala Ala Leu Phe Ser Gly Gln
            595                 600                 605 ggc gcg cag tac acg cac atg ttt agc gag gtg gcc atg aac tgg ccc   1872
Gly Ala Gln Tyr Thr His Met Phe Ser Glu Val Ala Met Asn Trp Pro
610                 615                 620 cag ttc cgc cag agc att gcc gcc atg gac gcc gcc cag tcc aag gtc   1920
Gln Phe Arg Gln Ser Ile Ala Ala Met Asp Ala Ala Gln Ser Lys Val
625                 630                 635                 640 gct gga agc gac aag gac ttt gag cgc gtc tcc cag gtc ctc tac ccg   1968
Ala Gly Ser Asp Lys Asp Phe Glu Arg Val Ser Gln Val Leu Tyr Pro
                645                 650                 655 cgc aag ccg tac gag cgt gag ccc gag cag gac cac aag aag atc tcc   2016
Arg Lys Pro Tyr Glu Arg Glu Pro Glu Gln Asp His Lys Lys Ile Ser
            660                 665                 670 ctc acc gcc tac tcg cag ccc tcg acc ctg gcc tgc gct ctc ggt gcc   2064
Leu Thr Ala Tyr Ser Gln Pro Ser Thr Leu Ala Cys Ala Leu Gly Ala
            675                 680                 685 ttt gag atc ttc aag gag gcc ggc ttc acc ccg gac ttt gcc gcc ggc   2112
Phe Glu Ile Phe Lys Glu Ala Gly Phe Thr Pro Asp Phe Ala Ala Gly
690                 695                 700 cat tcg ctc ggt gag ttc gcc gcc ctc tac gcc gcg ggc tgc gtc gac   2160
His Ser Leu Gly Glu Phe Ala Ala Leu Tyr Ala Ala Gly Cys Val Asp
705                 710                 715                 720 cgc gac gag ctc ttt gag ctt gtc tgc cgc cgc gcc cgc atc atg ggc   2208
Arg Asp Glu Leu Phe Glu Leu Val Cys Arg Arg Ala Arg Ile Met Gly
                725                 730                 735 ggc aag gac gca ccg gcc acc ccc aag ggc tgc atg gcc gcc gtc att   2256
Gly Lys Asp Ala Pro Ala Thr Pro Lys Gly Cys Met Ala Ala Val Ile
            740                 745                 750 ggc ccc aac gcc gag aac atc aag gtc cag gcc gcc aac gtc tgg ctc   2304
Gly Pro Asn Ala Glu Asn Ile Lys Val Gln Ala Ala Asn Val Trp Leu
            755                 760                 765 ggc aac tcc aac tcg cct tcg cag acc gtc atc acc ggc tcc gtc gaa   2352
Gly Asn Ser Asn Ser Pro Ser Gln Thr Val Ile Thr Gly Ser Val Glu
770                 775                 780 ggt atc cag gcc gag agc gcc cgc ctc cag aag gag ggc ttc cgc gtc   2400
Gly Ile Gln Ala Glu Ser Ala Arg Leu Gln Lys Glu Gly Phe Arg Val
785                 790                 795                 800 gtg cct ctt gcc tgc gag agc gcc ttc cac tcg ccc cag atg gag aac   2448
Val Pro Leu Ala Cys Glu Ser Ala Phe His Ser Pro Gln Met Glu Asn
                805                 810                 815
```

```
gcc tcg tcg gcc ttc aag gac gtc atc tcc aag gtc tcc ttc cgc acc      2496
Ala Ser Ser Ala Phe Lys Asp Val Ile Ser Lys Val Ser Phe Arg Thr
        820             825             830 ccc aag gcc gag acc aag ctc ttc agc aac gtc tct ggc gag acc tac      2544
Pro Lys Ala Glu Thr Lys Leu Phe Ser Asn Val Ser Gly Glu Thr Tyr
            835             840             845 ccc acg gac gcc cgc gag atg ctt acg cag cac atg acc agc agc gtc      2592
Pro Thr Asp Ala Arg Glu Met Leu Thr Gln His Met Thr Ser Ser Val
850             855             860 aag ttc ctc acc cag gtc cgc aac atg cac cag gcc ggt gcg cgc atc      2640
Lys Phe Leu Thr Gln Val Arg Asn Met His Gln Ala Gly Ala Arg Ile
865             870             875             880 ttt gtc gag ttc gga ccc aag cag gtg ctc tcc aag ctt gtc tcc gag      2688
Phe Val Glu Phe Gly Pro Lys Gln Val Leu Ser Lys Leu Val Ser Glu
                885             890             895 acc ctc aag gat gac ccc tcg gtt gtc acc gtc tct gtc aac ccg gcc      2736
Thr Leu Lys Asp Asp Pro Ser Val Val Thr Val Ser Val Asn Pro Ala
            900             905             910 tcg ggc acg gat tcg gac atc cag ctc cgc gac gcg gcc gtc cag ctc      2784
Ser Gly Thr Asp Ser Asp Ile Gln Leu Arg Asp Ala Ala Val Gln Leu
            915             920             925 gtt gtc gct ggc gtc aac ctt cag ggc ttt gac aag tgg gac gcc ccc      2832
Val Val Ala Gly Val Asn Leu Gln Gly Phe Asp Lys Trp Asp Ala Pro
930             935             940 gat gcc acc cgc atg cag gcc atc aag aag aag cgc act acc ctc cgc      2880
Asp Ala Thr Arg Met Gln Ala Ile Lys Lys Lys Arg Thr Thr Leu Arg
945             950             955             960 ctt tcg gcc gcc acc tac gtc tcg gac aag acc aag aag gtc cgc gac      2928
Leu Ser Ala Ala Thr Tyr Val Ser Asp Lys Thr Lys Lys Val Arg Asp
                965             970             975 gcc gcc atg aac gat ggc cgc tgc gtc acc tac ctc aag ggc gcc gca      2976
Ala Ala Met Asn Asp Gly Arg Cys Val Thr Tyr Leu Lys Gly Ala Ala
            980             985             990 ccg ctc atc aag gcc ccg gag ccc gtt gtc gac gag gcc gcc aag cgc      3024
Pro Leu Ile Lys Ala Pro Glu Pro Val Val Asp Glu Ala Ala Lys Arg
            995             1000            1005 gag gcc gag cgt ctc cag aag gag ctt cag gat gcc cag cgc cag           3069
Glu Ala Glu Arg Leu Gln Lys Glu Leu Gln Asp Ala Gln Arg Gln
    1010            1015            1020 ctc gac gac gcc aag cgc gcc gcc gcc gag gcc aac tcc aag ctc           3114
Leu Asp Asp Ala Lys Arg Ala Ala Ala Glu Ala Asn Ser Lys Leu
    1025            1030            1035 gcc gct gcc aag gag gag gcc aag acc gcc gct gct tcg gcc aag           3159
Ala Ala Ala Lys Glu Glu Ala Lys Thr Ala Ala Ala Ser Ala Lys
    1040            1045            1050 ccc gca gtt gac act gct gtt gtc gaa aag cat cgt gcc atc ctc           3204
Pro Ala Val Asp Thr Ala Val Val Glu Lys His Arg Ala Ile Leu
    1055            1060            1065 aag tcc atg ctc gcg gag ctc gat ggc tac gga tcg gtc gac gct           3249
Lys Ser Met Leu Ala Glu Leu Asp Gly Tyr Gly Ser Val Asp Ala
    1070            1075            1080 tct tcc ctc cag cag cag cag cag cag cag acg gcc ccc gcc ccg           3294
Ser Ser Leu Gln Gln Gln Gln Gln Gln Gln Thr Ala Pro Ala Pro
    1085            1090            1095 gtc aag gct gct gcg cct gcc gcc ccc gtt gcc tcg gcc cct gcc           3339
Val Lys Ala Ala Ala Pro Ala Ala Pro Val Ala Ser Ala Pro Ala
    1100            1105            1110 ccg gct gtc tcg aac gag ctt ctt gag aag gcc gag act gtc gtc           3384
Pro Ala Val Ser Asn Glu Leu Leu Glu Lys Ala Glu Thr Val Val
    1115            1120            1125
```

```
atg gag gtc ctc gcc gcc aag acc ggc tac gag acc gac atg atc      3429
Met Glu Val Leu Ala Ala Lys Thr Gly Tyr Glu Thr Asp Met Ile
    1130                1135                1140 gag gct gac atg gag ctc gag acc gag ctc ggc att gac tcc atc      3474
Glu Ala Asp Met Glu Leu Glu Thr Glu Leu Gly Ile Asp Ser Ile
1145                1150                1155 aag cgt gtc gag atc ctc tcc gag gtc cag gcc atg ctc aat gtc      3519
Lys Arg Val Glu Ile Leu Ser Glu Val Gln Ala Met Leu Asn Val
1160                1165                1170 gag gcc aag gat gtc gat gcc ctc agc cgc act cgc act gtt ggt      3564
Glu Ala Lys Asp Val Asp Ala Leu Ser Arg Thr Arg Thr Val Gly
    1175                1180                1185 gag gtt gtc aac gcc atg aag gcc gag atc gct ggc agc tct gcc      3609
Glu Val Val Asn Ala Met Lys Ala Glu Ile Ala Gly Ser Ser Ala
1190                1195                1200 ccg gcg cct gct gcc gct gct ccg gct ccg gcc aag gct gcc cct      3654
Pro Ala Pro Ala Ala Ala Pro Ala Pro Ala Lys Ala Ala Pro
    1205                1210                1215 gcc gcc gct gcg cct gct gtc tcg aac gag ctt ctc gag aag gcc      3699
Ala Ala Ala Ala Pro Ala Val Ser Asn Glu Leu Leu Glu Lys Ala
1220                1225                1230 gag acc gtc gtc atg gag gtc ctc gcc gcc aag act ggc tac gag      3744
Glu Thr Val Val Met Glu Val Leu Ala Ala Lys Thr Gly Tyr Glu
    1235                1240                1245 act gac atg atc gag tcc gac atg gag ctc gag act gag ctc ggc      3789
Thr Asp Met Ile Glu Ser Asp Met Glu Leu Glu Thr Glu Leu Gly
1250                1255                1260 att gac tcc atc aag cgt gtc gag atc ctc tcc gag gtt cag gcc      3834
Ile Asp Ser Ile Lys Arg Val Glu Ile Leu Ser Glu Val Gln Ala
    1265                1270                1275 atg ctc aac gtc gag gcc aag gac gtc gac gct ctc agc cgc act      3879
Met Leu Asn Val Glu Ala Lys Asp Val Asp Ala Leu Ser Arg Thr
1280                1285                1290 cgc act gtg ggt gag gtc gtc aac gcc atg aag gct gag atc gct      3924
Arg Thr Val Gly Glu Val Val Asn Ala Met Lys Ala Glu Ile Ala
    1295                1300                1305 ggt ggc tct gcc ccg gcg cct gcc gcc gct gcc cca ggt ccg gct      3969
Gly Gly Ser Ala Pro Ala Pro Ala Ala Ala Ala Pro Gly Pro Ala
1310                1315                1320 gct gcc gcc cct gcg cct gcc gcc gcc gcc cct gct gtc tcg aac      4014
Ala Ala Ala Pro Ala Pro Ala Ala Ala Ala Pro Ala Val Ser Asn
    1325                1330                1335 gag ctt ctt gag aag gcc gag acc gtc gtc atg gag gtc ctc gcc      4059
Glu Leu Leu Glu Lys Ala Glu Thr Val Val Met Glu Val Leu Ala
1340                1345                1350 gcc aag act ggc tac gag act gac atg atc gag tcc gac atg gag      4104
Ala Lys Thr Gly Tyr Glu Thr Asp Met Ile Glu Ser Asp Met Glu
    1355                1360                1365 ctc gag acc gag ctc ggc att gac tcc atc aag cgt gtc gag att      4149
Leu Glu Thr Glu Leu Gly Ile Asp Ser Ile Lys Arg Val Glu Ile
1370                1375                1380 ctc tcc gag gtc cag gcc atg ctc aac gtc gag gcc aag gac gtc      4194
Leu Ser Glu Val Gln Ala Met Leu Asn Val Glu Ala Lys Asp Val
    1385                1390                1395 gac gct ctc agc cgc acc cgc act gtt ggc gag gtc gtc gat gcc      4239
Asp Ala Leu Ser Arg Thr Arg Thr Val Gly Glu Val Val Asp Ala
1400                1405                1410 atg aag gcc gag atc gct ggt ggc tct gcc ccg gcg cct gcc gcc      4284
Met Lys Ala Glu Ile Ala Gly Gly Ser Ala Pro Ala Pro Ala Ala
    1415                1420                1425
```

|     |     |     |     |     |     |     |     |     |     |     |     |     |      |
| --- | --- | --- | --- | --- | --- | --- | --- | --- | --- | --- | --- | --- | ---- |
| gct | gct | cct | gct | ccg | gct | gcc | gcc | cct | gcg | cct | gcc | gcc | cct  | 4329 |
| Ala | Ala | Pro | Ala | Pro | Ala | Ala | Ala | Pro | Ala | Pro | Ala | Ala | Pro  |
|     | 1430 |     |     |     | 1435 |     |     |     | 1440 |     |     |     |      |

| gcg | cct | gct | gtc | tcg | agc | gag | ctt | ctc | gag | aag | gcc | gag | act | gtc | 4374 |
| Ala | Pro | Ala | Val | Ser | Ser | Glu | Leu | Leu | Glu | Lys | Ala | Glu | Thr | Val |
| 1445 |     |     |     | 1450 |     |     |     |     | 1455 |     |     |     |     |     |

| gtc | atg | gag | gtc | ctc | gcc | gcc | aag | act | ggc | tac | gag | act | gac | atg | 4419 |
| Val | Met | Glu | Val | Leu | Ala | Ala | Lys | Thr | Gly | Tyr | Glu | Thr | Asp | Met |
|     | 1460 |     |     |     | 1465 |     |     |     | 1470 |     |     |     |     |     |

| atc | gag | tcc | gac | atg | gag | ctc | gag | acc | gag | ctc | ggc | att | gac | tcc | 4464 |
| Ile | Glu | Ser | Asp | Met | Glu | Leu | Glu | Thr | Glu | Leu | Gly | Ile | Asp | Ser |
| 1475 |     |     |     | 1480 |     |     |     |     | 1485 |     |     |     |     |     |

| atc | aag | cgt | gtc | gag | att | ctc | tcc | gag | gtc | cag | gcc | atg | ctc | aac | 4509 |
| Ile | Lys | Arg | Val | Glu | Ile | Leu | Ser | Glu | Val | Gln | Ala | Met | Leu | Asn |
| 1490 |     |     |     | 1495 |     |     |     |     | 1500 |     |     |     |     |     |

| gtc | gag | gcc | aag | gac | gtc | gac | gct | ctc | agc | cgc | acc | cgc | act | gtt | 4554 |
| Val | Glu | Ala | Lys | Asp | Val | Asp | Ala | Leu | Ser | Arg | Thr | Arg | Thr | Val |
| 1505 |     |     |     | 1510 |     |     |     |     | 1515 |     |     |     |     |     |

| ggc | gag | gtc | gtc | gat | gcc | atg | aag | gcc | gag | atc | gct | ggt | ggc | tct | 4599 |
| Gly | Glu | Val | Val | Asp | Ala | Met | Lys | Ala | Glu | Ile | Ala | Gly | Gly | Ser |
| 1520 |     |     |     | 1525 |     |     |     |     | 1530 |     |     |     |     |     |

| gcc | ccg | gcg | cct | gcc | gcc | gct | gct | cct | gct | ccg | gct | gct | gcc | gcc | 4644 |
| Ala | Pro | Ala | Pro | Ala | Ala | Ala | Ala | Pro | Ala | Pro | Ala | Ala | Ala | Ala |
| 1535 |     |     |     | 1540 |     |     |     |     | 1545 |     |     |     |     |     |

| cct | gcg | cct | gcc | gcc | cct | gcg | cct | gcc | gcc | cct | gcg | cct | gct | gtc | 4689 |
| Pro | Ala | Pro | Ala | Ala | Pro | Ala | Pro | Ala | Ala | Pro | Ala | Pro | Ala | Val |
| 1550 |     |     |     | 1555 |     |     |     |     | 1560 |     |     |     |     |     |

| tcg | agc | gag | ctt | ctc | gag | aag | gcc | gag | act | gtc | gtc | atg | gag | gtc | 4734 |
| Ser | Ser | Glu | Leu | Leu | Glu | Lys | Ala | Glu | Thr | Val | Val | Met | Glu | Val |
| 1565 |     |     |     | 1570 |     |     |     |     | 1575 |     |     |     |     |     |

| ctc | gcc | gcc | aag | act | ggc | tac | gag | act | gac | atg | att | gag | tcc | gac | 4779 |
| Leu | Ala | Ala | Lys | Thr | Gly | Tyr | Glu | Thr | Asp | Met | Ile | Glu | Ser | Asp |
| 1580 |     |     |     | 1585 |     |     |     |     | 1590 |     |     |     |     |     |

| atg | gag | ctc | gag | acc | gag | ctc | ggc | att | gac | tcc | atc | aag | cgt | gtc | 4824 |
| Met | Glu | Leu | Glu | Thr | Glu | Leu | Gly | Ile | Asp | Ser | Ile | Lys | Arg | Val |
| 1595 |     |     |     | 1600 |     |     |     |     | 1605 |     |     |     |     |     |

| gag | att | ctc | tcc | gag | gtt | cag | gcc | atg | ctc | aac | gtc | gag | gcc | aag | 4869 |
| Glu | Ile | Leu | Ser | Glu | Val | Gln | Ala | Met | Leu | Asn | Val | Glu | Ala | Lys |
| 1610 |     |     |     | 1615 |     |     |     |     | 1620 |     |     |     |     |     |

| gac | gtc | gac | gct | ctc | agc | cgc | act | cgc | act | gtt | ggt | gag | gtc | gtc | 4914 |
| Asp | Val | Asp | Ala | Leu | Ser | Arg | Thr | Arg | Thr | Val | Gly | Glu | Val | Val |
| 1625 |     |     |     | 1630 |     |     |     |     | 1635 |     |     |     |     |     |

| gat | gcc | atg | aag | gct | gag | atc | gct | ggc | agc | tcc | gcc | tcg | gcg | cct | 4959 |
| Asp | Ala | Met | Lys | Ala | Glu | Ile | Ala | Gly | Ser | Ser | Ala | Ser | Ala | Pro |
| 1640 |     |     |     | 1645 |     |     |     |     | 1650 |     |     |     |     |     |

| gcc | gcc | gct | gct | cct | gct | ccg | gct | gct | gcc | gct | cct | gcg | ccc | gct | 5004 |
| Ala | Ala | Ala | Ala | Pro | Ala | Pro | Ala | Ala | Ala | Ala | Pro | Ala | Pro | Ala |
| 1655 |     |     |     | 1660 |     |     |     |     | 1665 |     |     |     |     |     |

| gcc | gcc | gcc | cct | gct | gtc | tcg | aac | gag | ctt | ctc | gag | aaa | gcc | gag | 5049 |
| Ala | Ala | Ala | Pro | Ala | Val | Ser | Asn | Glu | Leu | Leu | Glu | Lys | Ala | Glu |
| 1670 |     |     |     | 1675 |     |     |     |     | 1680 |     |     |     |     |     |

| act | gtc | gtc | atg | gag | gtc | ctc | gcc | gcc | aag | act | ggc | tac | gag | act | 5094 |
| Thr | Val | Val | Met | Glu | Val | Leu | Ala | Ala | Lys | Thr | Gly | Tyr | Glu | Thr |
| 1685 |     |     |     | 1690 |     |     |     |     | 1695 |     |     |     |     |     |

| gac | atg | atc | gag | tcc | gac | atg | gag | ctc | gag | act | gag | ctc | ggc | att | 5139 |
| Asp | Met | Ile | Glu | Ser | Asp | Met | Glu | Leu | Glu | Thr | Glu | Leu | Gly | Ile |
| 1700 |     |     |     | 1705 |     |     |     |     | 1710 |     |     |     |     |     |

| gac | tcc | atc | aag | cgt | gtc | gag | atc | ctc | tcc | gag | gtt | cag | gcc | atg | 5184 |
| Asp | Ser | Ile | Lys | Arg | Val | Glu | Ile | Leu | Ser | Glu | Val | Gln | Ala | Met |
| 1715 |     |     |     | 1720 |     |     |     |     | 1725 |     |     |     |     |     |

```
ctc aac gtc gag gcc aag gac gtc gat gcc ctc agc cgc acc cgc         5229
Leu Asn Val Glu Ala Lys Asp Val Asp Ala Leu Ser Arg Thr Arg
    1730            1735                1740 act gtt ggc gag gtt gtc gat gcc atg aag gcc gag atc gct ggt         5274
Thr Val Gly Glu Val Val Asp Ala Met Lys Ala Glu Ile Ala Gly
    1745            1750                1755 ggc tct gcc ccg gcg cct gcc gcc gct gcc cct gct ccg gct gcc         5319
Gly Ser Ala Pro Ala Pro Ala Ala Ala Ala Pro Ala Pro Ala Ala
    1760            1765                1770 gcc gcc cct gct gtc tcg aac gag ctt ctc gag aag gcc gag act         5364
Ala Ala Pro Ala Val Ser Asn Glu Leu Leu Glu Lys Ala Glu Thr
    1775            1780                1785 gtc gtc atg gag gtc ctc gcc gcc aag act ggc tac gag acc gac         5409
Val Val Met Glu Val Leu Ala Ala Lys Thr Gly Tyr Glu Thr Asp
    1790            1795                1800 atg atc gag tcc gac atg gag ctc gag acc gag ctc ggc att gac         5454
Met Ile Glu Ser Asp Met Glu Leu Glu Thr Glu Leu Gly Ile Asp
    1805            1810                1815 tcc atc aag cgt gtc gag att ctc tcc gag gtt cag gcc atg ctc         5499
Ser Ile Lys Arg Val Glu Ile Leu Ser Glu Val Gln Ala Met Leu
    1820            1825                1830 aac gtc gag gcc aag gac gtc gat gct ctc agc cgc act cgc act         5544
Asn Val Glu Ala Lys Asp Val Asp Ala Leu Ser Arg Thr Arg Thr
    1835            1840                1845 gtt ggc gag gtc gtc gat gcc atg aag gct gag atc gcc ggc agc         5589
Val Gly Glu Val Val Asp Ala Met Lys Ala Glu Ile Ala Gly Ser
    1850            1855                1860 tcc gcc ccg gcg cct gcc gcc gct gct cct gct ccg gct gct gcc         5634
Ser Ala Pro Ala Pro Ala Ala Ala Ala Pro Ala Pro Ala Ala Ala
    1865            1870                1875 gct cct gcg ccc gct gcc gct gcc cct gct gtc tcg agc gag ctt         5679
Ala Pro Ala Pro Ala Ala Ala Ala Pro Ala Val Ser Ser Glu Leu
    1880            1885                1890 ctc gag aag gcc gag acc gtc gtc atg gag gtc ctc gcc gcc aag         5724
Leu Glu Lys Ala Glu Thr Val Val Met Glu Val Leu Ala Ala Lys
    1895            1900                1905 act ggc tac gag act gac atg att gag tcc gac atg gag ctc gag         5769
Thr Gly Tyr Glu Thr Asp Met Ile Glu Ser Asp Met Glu Leu Glu
    1910            1915                1920 act gag ctc ggc att gac tcc atc aag cgt gtc gag atc ctc tcc         5814
Thr Glu Leu Gly Ile Asp Ser Ile Lys Arg Val Glu Ile Leu Ser
    1925            1930                1935 gag gtt cag gcc atg ctc aac gtc gag gcc aag gac gtc gat gcc         5859
Glu Val Gln Ala Met Leu Asn Val Glu Ala Lys Asp Val Asp Ala
    1940            1945                1950 ctc agc cgc acc cgc act gtt ggc gag gtt gtc gat gcc atg aag         5904
Leu Ser Arg Thr Arg Thr Val Gly Glu Val Val Asp Ala Met Lys
    1955            1960                1965 gcc gag atc gct ggt ggc tct gcc ccg gcg cct gcc gcc gct gcc         5949
Ala Glu Ile Ala Gly Gly Ser Ala Pro Ala Pro Ala Ala Ala Ala
    1970            1975                1980 cct gct ccg gct gcc gcc gcc cct gct gtc tcg aac gag ctt ctt         5994
Pro Ala Pro Ala Ala Ala Ala Pro Ala Val Ser Asn Glu Leu Leu
    1985            1990                1995 gag aag gcc gag acc gtc gtc atg gag gtc ctc gcc gcc aag act         6039
Glu Lys Ala Glu Thr Val Val Met Glu Val Leu Ala Ala Lys Thr
    2000            2005                2010 ggc tac gag acc gac atg atc gag tcc gac atg gag ctc gag acc         6084
Gly Tyr Glu Thr Asp Met Ile Glu Ser Asp Met Glu Leu Glu Thr
    2015            2020                2025
```

| | | | | | | | | | | | |
|---|---|---|---|---|---|---|---|---|---|---|---|
| gag | ctc | ggc | att | gac | tcc | atc | aag | cgt | gtc | gag | att | ctc | tcc | gag | 6129 |
| Glu | Leu | Gly | Ile | Asp | Ser | Ile | Lys | Arg | Val | Glu | Ile | Leu | Ser | Glu | |
| | 2030 | | | | 2035 | | | | | 2040 | | | | | |

| gtt | cag | gcc | atg | ctc | aac | gtc | gag | gcc | aag | gac | gtc | gac | gct | ctc | 6174 |
| Val | Gln | Ala | Met | Leu | Asn | Val | Glu | Ala | Lys | Asp | Val | Asp | Ala | Leu | |
| | 2045 | | | | 2050 | | | | | 2055 | | | | | |

| agc | cgc | act | cgc | act | gtt | ggc | gag | gtc | gtc | gat | gcc | atg | aag | gct | 6219 |
| Ser | Arg | Thr | Arg | Thr | Val | Gly | Glu | Val | Val | Asp | Ala | Met | Lys | Ala | |
| | 2060 | | | | 2065 | | | | | 2070 | | | | | |

| gag | atc | gct | ggt | ggc | tct | gcc | ccg | gcg | cct | gcc | gcc | gct | gct | cct | 6264 |
| Glu | Ile | Ala | Gly | Gly | Ser | Ala | Pro | Ala | Pro | Ala | Ala | Ala | Ala | Pro | |
| | 2075 | | | | 2080 | | | | | 2085 | | | | | |

| gcc | tcg | gct | ggc | gcc | gcg | cct | gcg | gtc | aag | att | gac | tcg | gtc | cac | 6309 |
| Ala | Ser | Ala | Gly | Ala | Ala | Pro | Ala | Val | Lys | Ile | Asp | Ser | Val | His | |
| | 2090 | | | | 2095 | | | | | 2100 | | | | | |

| ggc | gct | gac | tgt | gat | gat | ctt | tcc | ctg | atg | cac | gcc | aag | gtg | gtt | 6354 |
| Gly | Ala | Asp | Cys | Asp | Asp | Leu | Ser | Leu | Met | His | Ala | Lys | Val | Val | |
| | 2105 | | | | 2110 | | | | | 2115 | | | | | |

| gac | atc | cgc | cgc | ccg | gac | gag | ctc | atc | ctg | gag | cgc | ccc | gag | aac | 6399 |
| Asp | Ile | Arg | Arg | Pro | Asp | Glu | Leu | Ile | Leu | Glu | Arg | Pro | Glu | Asn | |
| | 2120 | | | | 2125 | | | | | 2130 | | | | | |

| cgc | ccc | gtt | ctc | gtt | gtc | gat | gac | ggc | agc | gag | ctc | acc | ctc | gcc | 6444 |
| Arg | Pro | Val | Leu | Val | Val | Asp | Asp | Gly | Ser | Glu | Leu | Thr | Leu | Ala | |
| | 2135 | | | | 2140 | | | | | 2145 | | | | | |

| ctg | gtc | cgc | gtc | ctc | ggc | gcc | tgc | gcc | gtt | gtc | ctg | acc | ttt | gag | 6489 |
| Leu | Val | Arg | Val | Leu | Gly | Ala | Cys | Ala | Val | Val | Leu | Thr | Phe | Glu | |
| | 2150 | | | | 2155 | | | | | 2160 | | | | | |

| ggt | ctc | cag | ctc | gct | cag | cgc | gct | ggt | gcc | gct | gcc | atc | cgc | cac | 6534 |
| Gly | Leu | Gln | Leu | Ala | Gln | Arg | Ala | Gly | Ala | Ala | Ala | Ile | Arg | His | |
| | 2165 | | | | 2170 | | | | | 2175 | | | | | |

| gtg | ctc | gcc | aag | gat | ctt | tcc | gcg | gag | agc | gcc | gag | aag | gcc | atc | 6579 |
| Val | Leu | Ala | Lys | Asp | Leu | Ser | Ala | Glu | Ser | Ala | Glu | Lys | Ala | Ile | |
| | 2180 | | | | 2185 | | | | | 2190 | | | | | |

| aag | gag | gcc | gag | cag | cgc | ttt | ggc | gct | ctc | ggc | ggc | ttc | atc | tcg | 6624 |
| Lys | Glu | Ala | Glu | Gln | Arg | Phe | Gly | Ala | Leu | Gly | Gly | Phe | Ile | Ser | |
| | 2195 | | | | 2200 | | | | | 2205 | | | | | |

| cag | cag | gcg | gag | cgc | ttc | gag | ccc | gcc | gaa | atc | ctc | ggc | ttc | acg | 6669 |
| Gln | Gln | Ala | Glu | Arg | Phe | Glu | Pro | Ala | Glu | Ile | Leu | Gly | Phe | Thr | |
| | 2210 | | | | 2215 | | | | | 2220 | | | | | |

| ctc | atg | tgc | gcc | aag | ttc | gcc | aag | gct | tcc | ctc | tgc | acg | gct | gtg | 6714 |
| Leu | Met | Cys | Ala | Lys | Phe | Ala | Lys | Ala | Ser | Leu | Cys | Thr | Ala | Val | |
| | 2225 | | | | 2230 | | | | | 2235 | | | | | |

| gct | ggc | ggc | cgc | ccg | gcc | ttt | atc | ggt | gtg | gcg | cgc | ctt | gac | ggc | 6759 |
| Ala | Gly | Gly | Arg | Pro | Ala | Phe | Ile | Gly | Val | Ala | Arg | Leu | Asp | Gly | |
| | 2240 | | | | 2245 | | | | | 2250 | | | | | |

| cgc | ctc | gga | ttc | act | tcg | cag | ggc | act | tct | gac | gcg | ctc | aag | cgt | 6804 |
| Arg | Leu | Gly | Phe | Thr | Ser | Gln | Gly | Thr | Ser | Asp | Ala | Leu | Lys | Arg | |
| | 2255 | | | | 2260 | | | | | 2265 | | | | | |

| gcc | cag | cgt | ggt | gcc | atc | ttt | ggc | ctc | tgc | aag | acc | atc | ggc | ctc | 6849 |
| Ala | Gln | Arg | Gly | Ala | Ile | Phe | Gly | Leu | Cys | Lys | Thr | Ile | Gly | Leu | |
| | 2270 | | | | 2275 | | | | | 2280 | | | | | |

| gag | tgg | tcc | gag | tct | gac | gtc | ttt | tcc | cgc | ggc | gtg | gac | att | gct | 6894 |
| Glu | Trp | Ser | Glu | Ser | Asp | Val | Phe | Ser | Arg | Gly | Val | Asp | Ile | Ala | |
| | 2285 | | | | 2290 | | | | | 2295 | | | | | |

| cag | ggc | atg | cac | ccc | gag | gat | gcc | gcc | gtg | gcg | att | gtg | cgc | gag | 6939 |
| Gln | Gly | Met | His | Pro | Glu | Asp | Ala | Ala | Val | Ala | Ile | Val | Arg | Glu | |
| | 2300 | | | | 2305 | | | | | 2310 | | | | | |

| atg | gcg | tgc | gct | gac | att | cgc | att | cgc | gag | gtc | ggc | att | ggc | gca | 6984 |
| Met | Ala | Cys | Ala | Asp | Ile | Arg | Ile | Arg | Glu | Val | Gly | Ile | Gly | Ala | |
| | 2315 | | | | 2320 | | | | | 2325 | | | | | |

```
aac cag cag cgc tgc acg atc cgt gcc gcc aag ctc gag acc ggc     7029
Asn Gln Gln Arg Cys Thr Ile Arg Ala Ala Lys Leu Glu Thr Gly
    2330            2335                2340 aac ccg cag cgc cag atc gcc aag gac gac gtg ctg ctc gtt tct     7074
Asn Pro Gln Arg Gln Ile Ala Lys Asp Asp Val Leu Leu Val Ser
2345                2350                2355 ggc ggc gct cgc ggc atc acg cct ctt tgc atc cgg gag atc acg     7119
Gly Gly Ala Arg Gly Ile Thr Pro Leu Cys Ile Arg Glu Ile Thr
        2360            2365                2370 cgc cag atc gcg ggc ggc aag tac att ctg ctt ggc cgc agc aag     7164
Arg Gln Ile Ala Gly Gly Lys Tyr Ile Leu Leu Gly Arg Ser Lys
    2375            2380                2385 gtc tct gcg agc gaa ccg gca tgg tgc gct ggc atc act gac gag     7209
Val Ser Ala Ser Glu Pro Ala Trp Cys Ala Gly Ile Thr Asp Glu
2390                2395                2400 aag gct gtg caa aag gct gct acc cag gag ctc aag cgc gcc ttt     7254
Lys Ala Val Gln Lys Ala Ala Thr Gln Glu Leu Lys Arg Ala Phe
        2405            2410                2415 agc gct ggc gag ggc ccc aag ccc acg ccc cgc gct gtc act aag     7299
Ser Ala Gly Glu Gly Pro Lys Pro Thr Pro Arg Ala Val Thr Lys
    2420            2425                2430 ctt gtg ggc tct gtt ctt ggc gct cgc gag gtg cgc agc tct att     7344
Leu Val Gly Ser Val Leu Gly Ala Arg Glu Val Arg Ser Ser Ile
2435                2440                2445 gct gcg att gaa gcg ctc ggc ggc aag gcc atc tac tcg tcg tgc     7389
Ala Ala Ile Glu Ala Leu Gly Gly Lys Ala Ile Tyr Ser Ser Cys
        2450            2455                2460 gac gtg aac tct gcc gcc gac gtg gcc aag gcc gtg cgc gat gcc     7434
Asp Val Asn Ser Ala Ala Asp Val Ala Lys Ala Val Arg Asp Ala
    2465            2470                2475 gag tcc cag ctc ggt gcc cgc gtc tcg ggc atc gtt cat gcc tcg     7479
Glu Ser Gln Leu Gly Ala Arg Val Ser Gly Ile Val His Ala Ser
2480                2485                2490 ggc gtg ctc cgc gac cgt ctc atc gag aag aag ctc ccc gac gag     7524
Gly Val Leu Arg Asp Arg Leu Ile Glu Lys Lys Leu Pro Asp Glu
        2495            2500                2505 ttc gac gcc gtc ttt ggc acc aag gtc acc ggt ctc gag aac ctc     7569
Phe Asp Ala Val Phe Gly Thr Lys Val Thr Gly Leu Glu Asn Leu
    2510            2515                2520 ctc gcc gcc gtc gac cgc gcc aac ctc aag cac atg gtc ctc ttc     7614
Leu Ala Ala Val Asp Arg Ala Asn Leu Lys His Met Val Leu Phe
2525                2530                2535 agc tcg ctc gcc ggc ttc cac ggc aac gtc ggc cag tct gac tac     7659
Ser Ser Leu Ala Gly Phe His Gly Asn Val Gly Gln Ser Asp Tyr
        2540            2545                2550 gcc atg gcc aac gag gcc ctt aac aag atg ggc ctc gag ctc gcc     7704
Ala Met Ala Asn Glu Ala Leu Asn Lys Met Gly Leu Glu Leu Ala
    2555            2560                2565 aag gac gtc tcg gtc aag tcg atc tgc ttc ggt ccc tgg gac ggt     7749
Lys Asp Val Ser Val Lys Ser Ile Cys Phe Gly Pro Trp Asp Gly
2570                2575                2580 ggc atg gtg acg ccg cag ctc aag aag cag ttc cag gag atg ggc     7794
Gly Met Val Thr Pro Gln Leu Lys Lys Gln Phe Gln Glu Met Gly
        2585            2590                2595 gtg cag atc atc ccc cgc gag ggc ggc gct gat acc gtg gcg cgc     7839
Val Gln Ile Ile Pro Arg Glu Gly Gly Ala Asp Thr Val Ala Arg
    2600            2605                2610 atc gtg ctc ggc tcc tcg ccg gct gag atc ctt gtc ggc aac tgg     7884
Ile Val Leu Gly Ser Ser Pro Ala Glu Ile Leu Val Gly Asn Trp
2615                2620                2625
```

```
cgc acc ccg tcc aag aag gtc ggc tcg gac acc atc acc ctg cac      7929
Arg Thr Pro Ser Lys Lys Val Gly Ser Asp Thr Ile Thr Leu His
        2630            2635                2640 cgc aag att tcc gcc aag tcc aac ccc ttc ctc gag gac cac gtc      7974
Arg Lys Ile Ser Ala Lys Ser Asn Pro Phe Leu Glu Asp His Val
    2645            2650                2655 atc cag ggc cgc cgc gtg ctg ccc atg acg ctg gcc att ggc tcg      8019
Ile Gln Gly Arg Arg Val Leu Pro Met Thr Leu Ala Ile Gly Ser
2660            2665                2670 ctc gcg gag acc tgc ctc ggc ctc ttc ccc ggc tac tcg ctc tgg      8064
Leu Ala Glu Thr Cys Leu Gly Leu Phe Pro Gly Tyr Ser Leu Trp
        2675            2680                2685 gcc att gac gac gcc cag ctc ttc aag ggt gtc act gtc gac ggc      8109
Ala Ile Asp Asp Ala Gln Leu Phe Lys Gly Val Thr Val Asp Gly
    2690            2695                2700 gac gtc aac tgc gag gtg acc ctc acc ccg tcg acg gcg ccc tcg      8154
Asp Val Asn Cys Glu Val Thr Leu Thr Pro Ser Thr Ala Pro Ser
2705            2710                2715 ggc cgc gtc aac gtc cag gcc acg ctc aag acc ttt tcc agc ggc      8199
Gly Arg Val Asn Val Gln Ala Thr Leu Lys Thr Phe Ser Ser Gly
        2720            2725                2730 aag ctg gtc ccg gcc tac cgc gcc gtc atc gtg ctc tcc aac cag      8244
Lys Leu Val Pro Ala Tyr Arg Ala Val Ile Val Leu Ser Asn Gln
    2735            2740                2745 ggc gcg ccc ccg gcc aac gcc acc atg cag ccg ccc tcg ctc gat      8289
Gly Ala Pro Pro Ala Asn Ala Thr Met Gln Pro Pro Ser Leu Asp
2750            2755                2760 gcc gat ccg gcg ctc cag ggc tcc gtc tac gac ggc aag acc ctc      8334
Ala Asp Pro Ala Leu Gln Gly Ser Val Tyr Asp Gly Lys Thr Leu
        2765            2770                2775 ttc cac ggc ccg gcc ttc cgc ggc atc gat gac gtg ctc tcg tgc      8379
Phe His Gly Pro Ala Phe Arg Gly Ile Asp Asp Val Leu Ser Cys
    2780            2785                2790 acc aag agc cag ctt gtg gcc aag tgc agc gct gtc ccc ggc tcc      8424
Thr Lys Ser Gln Leu Val Ala Lys Cys Ser Ala Val Pro Gly Ser
2795            2800                2805 gac gcc gct cgc ggc gag ttt gcc acg gac act gac gcc cat gac      8469
Asp Ala Ala Arg Gly Glu Phe Ala Thr Asp Thr Asp Ala His Asp
        2810            2815                2820 ccc ttc gtg aac gac ctg gcc ttt cag gcc atg ctc gtc tgg gtg      8514
Pro Phe Val Asn Asp Leu Ala Phe Gln Ala Met Leu Val Trp Val
    2825            2830                2835 cgc cgc acg ctc ggc cag gct gcg ctc ccc aac tcg atc cag cgc      8559
Arg Arg Thr Leu Gly Gln Ala Ala Leu Pro Asn Ser Ile Gln Arg
2840            2845                2850 atc gtc cag cac cgc ccg gtc ccg cag gac aag ccc ttc tac att      8604
Ile Val Gln His Arg Pro Val Pro Gln Asp Lys Pro Phe Tyr Ile
        2855            2860                2865 acc ctc cgc tcc aac cag tcg ggc ggt cac tcc cag cac aag cac      8649
Thr Leu Arg Ser Asn Gln Ser Gly Gly His Ser Gln His Lys His
    2870            2875                2880 gcc ctt cag ttc cac aac gag cag ggc gat ctc ttc att gat gtc      8694
Ala Leu Gln Phe His Asn Glu Gln Gly Asp Leu Phe Ile Asp Val
2885            2890                2895 cag gct tcg gtc atc gcc acg gac agc ctt gcc ttc                  8730
Gln Ala Ser Val Ile Ala Thr Asp Ser Leu Ala Phe
        2900            2905                2910

<210> SEQ ID NO 2
<211> LENGTH: 2910
```

```
<212> TYPE: PRT
<213> ORGANISM: Schizochytrium sp.

<400> SEQUENCE: 2

Met Ala Ala Arg Leu Gln Glu Gln Lys Gly Gly Glu Met Asp Thr Arg
1               5                   10                  15

Ile Ala Ile Ile Gly Met Ser Ala Ile Leu Pro Cys Gly Thr Thr Val
            20                  25                  30

Arg Glu Ser Trp Glu Thr Ile Arg Ala Gly Ile Asp Cys Leu Ser Asp
        35                  40                  45

Leu Pro Glu Asp Arg Val Asp Val Thr Ala Tyr Phe Asp Pro Val Lys
    50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
                85                  90                  95

Asp Ser Asp Ala Asn Gln Thr Ile Ser Leu Leu Lys Val Lys Glu Ala
            100                 105                 110

Leu Gln Asp Ala Gly Ile Asp Ala Leu Gly Lys Glu Lys Lys Asn Ile
        115                 120                 125

Gly Cys Val Leu Gly Ile Gly Gly Gln Lys Ser Ser His Glu Phe
    130                 135                 140

Tyr Ser Arg Leu Asn Tyr Val Val Val Glu Lys Val Leu Arg Lys Met
145                 150                 155                 160

Gly Met Pro Glu Glu Asp Val Lys Val Ala Val Glu Lys Tyr Lys Ala
                165                 170                 175

Asn Phe Pro Glu Trp Arg Leu Asp Ser Phe Pro Gly Phe Leu Gly Asn
            180                 185                 190

Val Thr Ala Gly Arg Cys Thr Asn Thr Phe Asn Leu Asp Gly Met Asn
        195                 200                 205

Cys Val Val Asp Ala Ala Cys Ala Ser Ser Leu Ile Ala Val Lys Val
    210                 215                 220

Ala Ile Asp Glu Leu Leu Tyr Gly Asp Cys Asp Met Met Val Thr Gly
225                 230                 235                 240

Ala Thr Cys Thr Asp Asn Ser Ile Gly Met Tyr Met Ala Phe Ser Lys
                245                 250                 255

Thr Pro Val Phe Ser Thr Asp Pro Ser Val Arg Ala Tyr Asp Glu Lys
            260                 265                 270

Thr Lys Gly Met Leu Ile Gly Glu Gly Ser Ala Met Leu Val Leu Lys
        275                 280                 285

Arg Tyr Ala Asp Ala Val Arg Asp Gly Asp Glu Ile His Ala Val Ile
    290                 295                 300

Arg Gly Cys Ala Ser Ser Ser Asp Gly Lys Ala Ala Gly Ile Tyr Thr
305                 310                 315                 320

Pro Thr Ile Ser Gly Gln Glu Glu Ala Leu Arg Arg Ala Tyr Asn Arg
                325                 330                 335

Ala Cys Val Asp Pro Ala Thr Val Thr Leu Val Glu Gly His Gly Thr
            340                 345                 350

Gly Thr Pro Val Gly Asp Arg Ile Glu Leu Thr Ala Leu Arg Asn Leu
        355                 360                 365

Phe Asp Lys Ala Tyr Gly Glu Gly Asn Thr Glu Lys Val Ala Val Gly
    370                 375                 380

Ser Ile Lys Ser Ser Ile Gly His Leu Lys Ala Val Ala Gly Leu Ala
385                 390                 395                 400
```

```
Gly Met Ile Lys Val Ile Met Ala Leu Lys His Lys Thr Leu Pro Gly
                405                 410                 415

Thr Ile Asn Val Asp Asn Pro Pro Asn Leu Tyr Asp Asn Thr Pro Ile
            420                 425                 430

Asn Glu Ser Ser Leu Tyr Ile Asn Thr Met Asn Arg Pro Trp Phe Pro
        435                 440                 445

Pro Pro Gly Val Pro Arg Arg Ala Gly Ile Ser Ser Phe Gly Phe Gly
    450                 455                 460

Gly Ala Asn Tyr His Ala Val Leu Glu Glu Ala Pro Glu His Thr
465                 470                 475                 480

Thr Ala Tyr Arg Leu Asn Lys Arg Pro Gln Pro Val Leu Met Met Ala
                485                 490                 495

Ala Thr Pro Ala Ala Leu Gln Ser Leu Cys Glu Ala Gln Leu Lys Glu
            500                 505                 510

Phe Glu Ala Ala Ile Lys Glu Asn Glu Thr Val Lys Asn Thr Ala Tyr
        515                 520                 525

Ile Lys Cys Val Lys Phe Gly Glu Gln Phe Lys Phe Pro Gly Ser Ile
    530                 535                 540

Pro Ala Thr Asn Ala Arg Leu Gly Phe Leu Val Lys Asp Ala Glu Asp
545                 550                 555                 560

Ala Cys Ser Thr Leu Arg Ala Ile Cys Ala Gln Phe Ala Lys Asp Val
                565                 570                 575

Thr Lys Glu Ala Trp Arg Leu Pro Arg Glu Gly Val Ser Phe Arg Ala
            580                 585                 590

Lys Gly Ile Ala Thr Asn Gly Ala Val Ala Ala Leu Phe Ser Gly Gln
        595                 600                 605

Gly Ala Gln Tyr Thr His Met Phe Ser Glu Val Ala Met Asn Trp Pro
    610                 615                 620

Gln Phe Arg Gln Ser Ile Ala Ala Met Asp Ala Ala Gln Ser Lys Val
625                 630                 635                 640

Ala Gly Ser Asp Lys Asp Phe Glu Arg Val Ser Gln Val Leu Tyr Pro
                645                 650                 655

Arg Lys Pro Tyr Glu Arg Glu Pro Glu Gln Asp His Lys Lys Ile Ser
            660                 665                 670

Leu Thr Ala Tyr Ser Gln Pro Ser Thr Leu Ala Cys Ala Leu Gly Ala
        675                 680                 685

Phe Glu Ile Phe Lys Glu Ala Gly Phe Thr Pro Asp Phe Ala Ala Gly
    690                 695                 700

His Ser Leu Gly Glu Phe Ala Ala Leu Tyr Ala Ala Gly Cys Val Asp
705                 710                 715                 720

Arg Asp Glu Leu Phe Glu Leu Val Cys Arg Arg Ala Arg Ile Met Gly
                725                 730                 735

Gly Lys Asp Ala Pro Ala Thr Pro Lys Gly Cys Met Ala Ala Val Ile
            740                 745                 750

Gly Pro Asn Ala Glu Asn Ile Lys Val Gln Ala Ala Asn Val Trp Leu
        755                 760                 765

Gly Asn Ser Asn Ser Pro Ser Gln Thr Val Ile Thr Gly Ser Val Glu
    770                 775                 780

Gly Ile Gln Ala Glu Ser Ala Arg Leu Gln Lys Glu Gly Phe Arg Val
785                 790                 795                 800

Val Pro Leu Ala Cys Glu Ser Ala Phe His Ser Pro Gln Met Glu Asn
                805                 810                 815

Ala Ser Ser Ala Phe Lys Asp Val Ile Ser Lys Val Ser Phe Arg Thr
            820                 825                 830
```

Pro Lys Ala Glu Thr Lys Leu Phe Ser Asn Val Ser Gly Glu Thr Tyr
835              840                  845

Pro Thr Asp Ala Arg Glu Met Leu Thr Gln His Met Thr Ser Ser Val
850              855                  860

Lys Phe Leu Thr Gln Val Arg Asn Met His Gln Ala Gly Ala Arg Ile
865              870                  875                  880

Phe Val Glu Phe Gly Pro Lys Gln Val Leu Ser Lys Leu Val Ser Glu
                 885                  890                  895

Thr Leu Lys Asp Asp Pro Ser Val Thr Val Ser Val Asn Pro Ala
            900              905                  910

Ser Gly Thr Asp Ser Asp Ile Gln Leu Arg Asp Ala Ala Val Gln Leu
            915                  920                  925

Val Val Ala Gly Val Asn Leu Gln Gly Phe Asp Lys Trp Asp Ala Pro
930                  935                  940

Asp Ala Thr Arg Met Gln Ala Ile Lys Lys Lys Arg Thr Thr Leu Arg
945              950                  955                  960

Leu Ser Ala Ala Thr Tyr Val Ser Asp Lys Thr Lys Lys Val Arg Asp
                 965                  970                  975

Ala Ala Met Asn Asp Gly Arg Cys Val Thr Tyr Leu Lys Gly Ala Ala
            980                  985                  990

Pro Leu Ile Lys Ala Pro Glu Pro Val Val Asp Glu Ala Ala Lys Arg
            995                  1000                     1005

Glu Ala Glu Arg Leu Gln Lys Glu Leu Gln Asp Ala Gln Arg Gln
1010                1015                   1020

Leu Asp Asp Ala Lys Arg Ala Ala Glu Ala Asn Ser Lys Leu
1025                1030                   1035

Ala Ala Ala Lys Glu Glu Ala Lys Thr Ala Ala Ala Ser Ala Lys
1040                1045                   1050

Pro Ala Val Asp Thr Ala Val Val Glu Lys His Arg Ala Ile Leu
1055                1060                   1065

Lys Ser Met Leu Ala Glu Leu Asp Gly Tyr Gly Ser Val Asp Ala
1070                1075                   1080

Ser Ser Leu Gln Gln Gln Gln Gln Gln Thr Ala Pro Ala Pro
1085                1090                   1095

Val Lys Ala Ala Ala Pro Ala Ala Pro Val Ala Ser Ala Pro Ala
1100                1105                   1110

Pro Ala Val Ser Asn Glu Leu Leu Glu Lys Ala Glu Thr Val Val
1115                1120                   1125

Met Glu Val Leu Ala Ala Lys Thr Gly Tyr Glu Thr Asp Met Ile
1130                1135                   1140

Glu Ala Asp Met Glu Leu Glu Thr Glu Leu Gly Ile Asp Ser Ile
1145                1150                   1155

Lys Arg Val Glu Ile Leu Ser Glu Val Gln Ala Met Leu Asn Val
1160                1165                   1170

Glu Ala Lys Asp Val Asp Ala Leu Ser Arg Thr Arg Thr Val Gly
1175                1180                   1185

Glu Val Val Asn Ala Met Lys Ala Glu Ile Ala Gly Ser Ser Ala
1190                1195                   1200

Pro Ala Pro Ala Ala Ala Pro Ala Pro Ala Lys Ala Ala Pro
1205                1210                   1215

Ala Ala Ala Ala Pro Ala Val Ser Asn Glu Leu Leu Glu Lys Ala
1220                1225                   1230

Glu Thr Val Val Met Glu Val Leu Ala Ala Lys Thr Gly Tyr Glu

```
            1235                1240                1245

Thr Asp Met Ile Glu Ser Asp Met Glu Leu Glu Thr Glu Leu Gly
    1250                1255                1260

Ile Asp Ser Ile Lys Arg Val Glu Ile Leu Ser Glu Val Gln Ala
    1265                1270                1275

Met Leu Asn Val Glu Ala Lys Asp Val Asp Ala Leu Ser Arg Thr
    1280                1285                1290

Arg Thr Val Gly Glu Val Val Asn Ala Met Lys Ala Glu Ile Ala
    1295                1300                1305

Gly Gly Ser Ala Pro Ala Pro Ala Ala Ala Ala Pro Gly Pro Ala
    1310                1315                1320

Ala Ala Ala Pro Ala Pro Ala Ala Ala Pro Ala Val Ser Asn
    1325                1330                1335

Glu Leu Leu Glu Lys Ala Glu Thr Val Val Met Glu Val Leu Ala
    1340                1345                1350

Ala Lys Thr Gly Tyr Glu Thr Asp Met Ile Glu Ser Asp Met Glu
    1355                1360                1365

Leu Glu Thr Glu Leu Gly Ile Asp Ser Ile Lys Arg Val Glu Ile
    1370                1375                1380

Leu Ser Glu Val Gln Ala Met Leu Asn Val Glu Ala Lys Asp Val
    1385                1390                1395

Asp Ala Leu Ser Arg Thr Arg Thr Val Gly Glu Val Val Asp Ala
    1400                1405                1410

Met Lys Ala Glu Ile Ala Gly Gly Ser Ala Pro Ala Pro Ala Ala
    1415                1420                1425

Ala Ala Pro Ala Pro Ala Ala Ala Pro Ala Pro Ala Ala Pro
    1430                1435                1440

Ala Pro Ala Val Ser Ser Glu Leu Leu Glu Lys Ala Glu Thr Val
    1445                1450                1455

Val Met Glu Val Leu Ala Ala Lys Thr Gly Tyr Glu Thr Asp Met
    1460                1465                1470

Ile Glu Ser Asp Met Glu Leu Glu Thr Glu Leu Gly Ile Asp Ser
    1475                1480                1485

Ile Lys Arg Val Glu Ile Leu Ser Glu Val Gln Ala Met Leu Asn
    1490                1495                1500

Val Glu Ala Lys Asp Val Asp Ala Leu Ser Arg Thr Arg Thr Val
    1505                1510                1515

Gly Glu Val Val Asp Ala Met Lys Ala Glu Ile Ala Gly Gly Ser
    1520                1525                1530

Ala Pro Ala Pro Ala Ala Ala Ala Pro Ala Pro Ala Ala Ala Ala
    1535                1540                1545

Pro Ala Pro Ala Ala Pro Ala Pro Ala Ala Pro Ala Pro Ala Val
    1550                1555                1560

Ser Ser Glu Leu Leu Glu Lys Ala Glu Thr Val Val Met Glu Val
    1565                1570                1575

Leu Ala Ala Lys Thr Gly Tyr Glu Thr Asp Met Ile Glu Ser Asp
    1580                1585                1590

Met Glu Leu Glu Thr Glu Leu Gly Ile Asp Ser Ile Lys Arg Val
    1595                1600                1605

Glu Ile Leu Ser Glu Val Gln Ala Met Leu Asn Val Glu Ala Lys
        1610                1615                1620

Asp Val Asp Ala Leu Ser Arg Thr Arg Thr Val Gly Glu Val Val
    1625                1630                1635
```

```
Asp Ala Met Lys Ala Glu Ile Ala Gly Ser Ser Ala Ser Ala Pro
    1640            1645                1650
Ala Ala Ala Ala Pro Ala Pro Ala Ala Ala Pro Ala Pro Ala
    1655            1660                1665
Ala Ala Ala Pro Ala Val Ser Asn Glu Leu Leu Glu Lys Ala Glu
    1670            1675                1680
Thr Val Val Met Glu Val Leu Ala Ala Lys Thr Gly Tyr Glu Thr
    1685            1690                1695
Asp Met Ile Glu Ser Asp Met Glu Leu Glu Thr Glu Leu Gly Ile
    1700            1705                1710
Asp Ser Ile Lys Arg Val Glu Ile Leu Ser Glu Val Gln Ala Met
    1715            1720                1725
Leu Asn Val Glu Ala Lys Asp Val Asp Ala Leu Ser Arg Thr Arg
    1730            1735                1740
Thr Val Gly Glu Val Val Asp Ala Met Lys Ala Glu Ile Ala Gly
    1745            1750                1755
Gly Ser Ala Pro Ala Pro Ala Ala Ala Pro Ala Pro Ala Ala
    1760            1765                1770
Ala Ala Pro Ala Val Ser Asn Glu Leu Leu Glu Lys Ala Glu Thr
    1775            1780                1785
Val Val Met Glu Val Leu Ala Ala Lys Thr Gly Tyr Glu Thr Asp
    1790            1795                1800
Met Ile Glu Ser Asp Met Glu Leu Glu Thr Glu Leu Gly Ile Asp
    1805            1810                1815
Ser Ile Lys Arg Val Glu Ile Leu Ser Glu Val Gln Ala Met Leu
    1820            1825                1830
Asn Val Glu Ala Lys Asp Val Asp Ala Leu Ser Arg Thr Arg Thr
    1835            1840                1845
Val Gly Glu Val Val Asp Ala Met Lys Ala Glu Ile Ala Gly Ser
    1850            1855                1860
Ser Ala Pro Ala Pro Ala Ala Ala Pro Ala Pro Ala Ala Ala
    1865            1870                1875
Ala Pro Ala Pro Ala Ala Ala Pro Ala Val Ser Ser Glu Leu
    1880            1885                1890
Leu Glu Lys Ala Glu Thr Val Val Met Glu Val Leu Ala Ala Lys
    1895            1900                1905
Thr Gly Tyr Glu Thr Asp Met Ile Glu Ser Asp Met Glu Leu Glu
    1910            1915                1920
Thr Glu Leu Gly Ile Asp Ser Ile Lys Arg Val Glu Ile Leu Ser
    1925            1930                1935
Glu Val Gln Ala Met Leu Asn Val Glu Ala Lys Asp Val Asp Ala
    1940            1945                1950
Leu Ser Arg Thr Arg Thr Val Gly Glu Val Val Asp Ala Met Lys
    1955            1960                1965
Ala Glu Ile Ala Gly Gly Ser Ala Pro Ala Pro Ala Ala Ala
    1970            1975                1980
Pro Ala Pro Ala Ala Ala Pro Ala Val Ser Asn Glu Leu Leu
    1985            1990                1995
Glu Lys Ala Glu Thr Val Val Met Glu Val Leu Ala Ala Lys Thr
    2000            2005                2010
Gly Tyr Glu Thr Asp Met Ile Glu Ser Asp Met Glu Leu Glu Thr
    2015            2020                2025
Glu Leu Gly Ile Asp Ser Ile Lys Arg Val Glu Ile Leu Ser Glu
    2030            2035                2040
```

```
Val Gln Ala Met Leu Asn Val Glu Ala Lys Asp Val Asp Ala Leu
    2045                2050                2055

Ser Arg Thr Arg Thr Val Gly Glu Val Val Asp Ala Met Lys Ala
    2060                2065                2070

Glu Ile Ala Gly Gly Ser Ala Pro Ala Pro Ala Ala Ala Ala Pro
    2075                2080                2085

Ala Ser Ala Gly Ala Ala Pro Ala Val Lys Ile Asp Ser Val His
    2090                2095                2100

Gly Ala Asp Cys Asp Asp Leu Ser Leu Met His Ala Lys Val Val
    2105                2110                2115

Asp Ile Arg Arg Pro Asp Glu Leu Ile Leu Glu Arg Pro Glu Asn
    2120                2125                2130

Arg Pro Val Leu Val Val Asp Asp Gly Ser Glu Leu Thr Leu Ala
    2135                2140                2145

Leu Val Arg Val Leu Gly Ala Cys Ala Val Val Leu Thr Phe Glu
    2150                2155                2160

Gly Leu Gln Leu Ala Gln Arg Ala Gly Ala Ala Ala Ile Arg His
    2165                2170                2175

Val Leu Ala Lys Asp Leu Ser Ala Glu Ser Ala Glu Lys Ala Ile
    2180                2185                2190

Lys Glu Ala Glu Gln Arg Phe Gly Ala Leu Gly Gly Phe Ile Ser
    2195                2200                2205

Gln Gln Ala Glu Arg Phe Glu Pro Ala Glu Ile Leu Gly Phe Thr
    2210                2215                2220

Leu Met Cys Ala Lys Phe Ala Lys Ala Ser Leu Cys Thr Ala Val
    2225                2230                2235

Ala Gly Gly Arg Pro Ala Phe Ile Gly Val Ala Arg Leu Asp Gly
    2240                2245                2250

Arg Leu Gly Phe Thr Ser Gln Gly Thr Ser Asp Ala Leu Lys Arg
    2255                2260                2265

Ala Gln Arg Gly Ala Ile Phe Gly Leu Cys Lys Thr Ile Gly Leu
    2270                2275                2280

Glu Trp Ser Glu Ser Asp Val Phe Ser Arg Gly Val Asp Ile Ala
    2285                2290                2295

Gln Gly Met His Pro Glu Asp Ala Ala Val Ala Ile Val Arg Glu
    2300                2305                2310

Met Ala Cys Ala Asp Ile Arg Ile Arg Glu Val Gly Ile Gly Ala
    2315                2320                2325

Asn Gln Gln Arg Cys Thr Ile Arg Ala Ala Lys Leu Glu Thr Gly
    2330                2335                2340

Asn Pro Gln Arg Gln Ile Ala Lys Asp Asp Val Leu Leu Val Ser
    2345                2350                2355

Gly Gly Ala Arg Gly Ile Thr Pro Leu Cys Ile Arg Glu Ile Thr
    2360                2365                2370

Arg Gln Ile Ala Gly Gly Lys Tyr Ile Leu Leu Gly Arg Ser Lys
    2375                2380                2385

Val Ser Ala Ser Glu Pro Ala Trp Cys Ala Gly Ile Thr Asp Glu
    2390                2395                2400

Lys Ala Val Gln Lys Ala Ala Thr Gln Glu Leu Lys Arg Ala Phe
    2405                2410                2415

Ser Ala Gly Glu Gly Pro Lys Pro Thr Pro Arg Ala Val Thr Lys
    2420                2425                2430

Leu Val Gly Ser Val Leu Gly Ala Arg Glu Val Arg Ser Ser Ile
```

-continued

```
              2435                2440                2445

Ala Ala Ile Glu Ala Leu Gly Gly Lys Ala Ile Tyr Ser Ser Cys
    2450                2455                2460

Asp Val Asn Ser Ala Ala Asp Val Ala Lys Ala Val Arg Asp Ala
    2465                2470                2475

Glu Ser Gln Leu Gly Ala Arg Val Ser Gly Ile Val His Ala Ser
    2480                2485                2490

Gly Val Leu Arg Asp Arg Leu Ile Glu Lys Lys Leu Pro Asp Glu
    2495                2500                2505

Phe Asp Ala Val Phe Gly Thr Lys Val Thr Gly Leu Glu Asn Leu
    2510                2515                2520

Leu Ala Ala Val Asp Arg Ala Asn Leu Lys His Met Val Leu Phe
    2525                2530                2535

Ser Ser Leu Ala Gly Phe His Gly Asn Val Gly Gln Ser Asp Tyr
    2540                2545                2550

Ala Met Ala Asn Glu Ala Leu Asn Lys Met Gly Leu Glu Leu Ala
    2555                2560                2565

Lys Asp Val Ser Val Lys Ser Ile Cys Phe Gly Pro Trp Asp Gly
    2570                2575                2580

Gly Met Val Thr Pro Gln Leu Lys Lys Gln Phe Gln Glu Met Gly
    2585                2590                2595

Val Gln Ile Ile Pro Arg Glu Gly Gly Ala Asp Thr Val Ala Arg
    2600                2605                2610

Ile Val Leu Gly Ser Ser Pro Ala Glu Ile Leu Val Gly Asn Trp
    2615                2620                2625

Arg Thr Pro Ser Lys Lys Val Gly Ser Asp Thr Ile Thr Leu His
    2630                2635                2640

Arg Lys Ile Ser Ala Lys Ser Asn Pro Phe Leu Glu Asp His Val
    2645                2650                2655

Ile Gln Gly Arg Arg Val Leu Pro Met Thr Leu Ala Ile Gly Ser
    2660                2665                2670

Leu Ala Glu Thr Cys Leu Gly Leu Phe Pro Gly Tyr Ser Leu Trp
    2675                2680                2685

Ala Ile Asp Asp Ala Gln Leu Phe Lys Gly Val Thr Val Asp Gly
    2690                2695                2700

Asp Val Asn Cys Glu Val Thr Leu Thr Pro Ser Thr Ala Pro Ser
    2705                2710                2715

Gly Arg Val Asn Val Gln Ala Thr Leu Lys Thr Phe Ser Ser Gly
    2720                2725                2730

Lys Leu Val Pro Ala Tyr Arg Ala Val Ile Val Leu Ser Asn Gln
    2735                2740                2745

Gly Ala Pro Pro Ala Asn Ala Thr Met Gln Pro Pro Ser Leu Asp
    2750                2755                2760

Ala Asp Pro Ala Leu Gln Gly Ser Val Tyr Asp Gly Lys Thr Leu
    2765                2770                2775

Phe His Gly Pro Ala Phe Arg Gly Ile Asp Asp Val Leu Ser Cys
    2780                2785                2790

Thr Lys Ser Gln Leu Val Ala Lys Cys Ser Ala Val Pro Gly Ser
    2795                2800                2805

Asp Ala Ala Arg Gly Glu Phe Ala Thr Asp Thr Asp Ala His Asp
    2810                2815                2820

Pro Phe Val Asn Asp Leu Ala Phe Gln Ala Met Leu Val Trp Val
    2825                2830                2835
```

```
Arg Arg Thr Leu Gly Gln Ala Ala Leu Pro Asn Ser Ile Gln Arg
    2840                2845                2850

Ile Val Gln His Arg Pro Val Pro Gln Asp Lys Pro Phe Tyr Ile
2855                2860                2865

Thr Leu Arg Ser Asn Gln Ser Gly Gly His Ser Gln His Lys His
    2870                2875                2880

Ala Leu Gln Phe His Asn Glu Gln Gly Asp Leu Phe Ile Asp Val
    2885                2890                2895

Gln Ala Ser Val Ile Ala Thr Asp Ser Leu Ala Phe
    2900                2905                2910

<210> SEQ ID NO 3
<211> LENGTH: 6177
<212> TYPE: DNA
<213> ORGANISM: Schizochytrium sp.
<220> FEATURE:
<221> NAME/KEY: CDS
<222> LOCATION: (1)..(6177)

<400> SEQUENCE: 3
```

| | | | | | | | | | | | | | | | | |
|---|---|---|---|---|---|---|---|---|---|---|---|---|---|---|---|---|
| atg | gcc | gct | cgg | aat | gtg | agc | gcc | gcg | cat | gag | atg | cac | gat | gaa | aag | 48 |
| Met | Ala | Ala | Arg | Asn | Val | Ser | Ala | Ala | His | Glu | Met | His | Asp | Glu | Lys | |
| 1 | | | | 5 | | | | | 10 | | | | | 15 | | |
| cgc | atc | gcc | gtc | gtc | ggc | atg | gcc | gtc | cag | tac | gcc | gga | tgc | aaa | acc | 96 |
| Arg | Ile | Ala | Val | Val | Gly | Met | Ala | Val | Gln | Tyr | Ala | Gly | Cys | Lys | Thr | |
| | | | 20 | | | | | 25 | | | | | 30 | | | |
| aag | gac | gag | ttc | tgg | gag | gtg | ctc | atg | aac | ggc | aag | gtc | gag | tcc | aag | 144 |
| Lys | Asp | Glu | Phe | Trp | Glu | Val | Leu | Met | Asn | Gly | Lys | Val | Glu | Ser | Lys | |
| | | 35 | | | | | 40 | | | | | 45 | | | | |
| gtg | atc | agc | gac | aaa | cga | ctc | ggc | tcc | aac | tac | cgc | gcc | gag | cac | tac | 192 |
| Val | Ile | Ser | Asp | Lys | Arg | Leu | Gly | Ser | Asn | Tyr | Arg | Ala | Glu | His | Tyr | |
| 50 | | | | | 55 | | | | | 60 | | | | | | |
| aaa | gca | gag | cgc | agc | aag | tat | gcc | gac | acc | ttt | tgc | aac | gaa | acg | tac | 240 |
| Lys | Ala | Glu | Arg | Ser | Lys | Tyr | Ala | Asp | Thr | Phe | Cys | Asn | Glu | Thr | Tyr | |
| 65 | | | | | 70 | | | | | 75 | | | | | 80 | |
| ggc | acc | ctt | gac | gag | aac | gag | atc | gac | aac | gag | cac | gaa | ctc | ctc | ctc | 288 |
| Gly | Thr | Leu | Asp | Glu | Asn | Glu | Ile | Asp | Asn | Glu | His | Glu | Leu | Leu | Leu | |
| | | | | 85 | | | | | 90 | | | | | 95 | | |
| aac | ctc | gcc | aag | cag | gca | ctc | gca | gag | aca | tcc | gtc | aaa | gac | tcg | aca | 336 |
| Asn | Leu | Ala | Lys | Gln | Ala | Leu | Ala | Glu | Thr | Ser | Val | Lys | Asp | Ser | Thr | |
| | | | 100 | | | | | 105 | | | | | 110 | | | |
| cgc | tgc | ggc | atc | gtc | agc | ggc | tgc | ctc | tcg | ttc | ccc | atg | gac | aac | ctc | 384 |
| Arg | Cys | Gly | Ile | Val | Ser | Gly | Cys | Leu | Ser | Phe | Pro | Met | Asp | Asn | Leu | |
| | | 115 | | | | | 120 | | | | | 125 | | | | |
| cag | ggt | gaa | ctc | ctc | aac | gtg | tac | caa | aac | cat | gtc | gag | aaa | aag | ctc | 432 |
| Gln | Gly | Glu | Leu | Leu | Asn | Val | Tyr | Gln | Asn | His | Val | Glu | Lys | Lys | Leu | |
| | | 130 | | | | | 135 | | | | | 140 | | | | |
| ggg | gcc | cgc | gtc | ttc | aag | gac | gcc | tcc | cat | tgg | tcc | gaa | cgc | gag | cag | 480 |
| Gly | Ala | Arg | Val | Phe | Lys | Asp | Ala | Ser | His | Trp | Ser | Glu | Arg | Glu | Gln | |
| 145 | | | | | 150 | | | | | 155 | | | | | 160 | |
| tcc | aac | aaa | ccc | gag | gcc | ggt | gac | cgc | cgc | atc | ttc | atg | gac | ccg | gcc | 528 |
| Ser | Asn | Lys | Pro | Glu | Ala | Gly | Asp | Arg | Arg | Ile | Phe | Met | Asp | Pro | Ala | |
| | | | | 165 | | | | | 170 | | | | | 175 | | |
| tcc | ttc | gtc | gcc | gaa | gaa | ctc | aac | ctc | ggc | gcc | ctt | cac | tac | tcc | gtc | 576 |
| Ser | Phe | Val | Ala | Glu | Glu | Leu | Asn | Leu | Gly | Ala | Leu | His | Tyr | Ser | Val | |
| | | | 180 | | | | | 185 | | | | | 190 | | | |
| gac | gca | gca | tgc | gcc | acg | gcg | ctc | tac | gtg | ctc | cgc | ctc | gcg | cag | gat | 624 |
| Asp | Ala | Ala | Cys | Ala | Thr | Ala | Leu | Tyr | Val | Leu | Arg | Leu | Ala | Gln | Asp | |
| | | | 195 | | | | | 200 | | | | | 205 | | | |
| cat | ctc | gtc | tcc | ggc | gcc | gcc | gac | gtc | atg | ctc | tgc | ggt | gcc | acc | tgc | 672 |
| His | Leu | Val | Ser | Gly | Ala | Ala | Asp | Val | Met | Leu | Cys | Gly | Ala | Thr | Cys | |

```
            210                 215                 220
ctg ccg gag ccc ttt ttc atc ctt tcg ggc ttt tcc acc ttc cag gcc    720
Leu Pro Glu Pro Phe Phe Ile Leu Ser Gly Phe Ser Thr Phe Gln Ala
225                 230                 235                 240 atg ccc gtc ggc acg ggc cag aac gtg tcc atg ccg ctg cac aag gac    768
Met Pro Val Gly Thr Gly Gln Asn Val Ser Met Pro Leu His Lys Asp
                245                 250                 255 agc cag ggc ctc acc ccg ggt gag ggc ggc tcc atc atg gtc ctc aag    816
Ser Gln Gly Leu Thr Pro Gly Glu Gly Gly Ser Ile Met Val Leu Lys
            260                 265                 270 cgt ctc gat gat gcc atc cgc gac ggc gac cac atc tac ggc acc ctt    864
Arg Leu Asp Asp Ala Ile Arg Asp Gly Asp His Ile Tyr Gly Thr Leu
                275                 280                 285 ctc ggc gcc aat gtc agc aac tcc ggc aca ggt ctg ccc ctc aag ccc    912
Leu Gly Ala Asn Val Ser Asn Ser Gly Thr Gly Leu Pro Leu Lys Pro
            290                 295                 300 ctt ctc ccc agc gag aaa aag tgc ctc atg gac acc tac acg cgc att    960
Leu Leu Pro Ser Glu Lys Lys Cys Leu Met Asp Thr Tyr Thr Arg Ile
305                 310                 315                 320 aac gtg cac ccg cac aag att cag tac gtc gag tgc cac gcc acc ggc   1008
Asn Val His Pro His Lys Ile Gln Tyr Val Glu Cys His Ala Thr Gly
                325                 330                 335 acg ccc cag ggt gat cgt gtg gaa atc gac gcc gtc aag gcc tgc ttt   1056
Thr Pro Gln Gly Asp Arg Val Glu Ile Asp Ala Val Lys Ala Cys Phe
            340                 345                 350 gaa ggc aag gtc ccc cgt ttc ggt acc aca aag ggc aac ttt gga cac   1104
Glu Gly Lys Val Pro Arg Phe Gly Thr Thr Lys Gly Asn Phe Gly His
                355                 360                 365 acc ctc gtc gca gcc ggc ttt gcc ggt atg tgc aag gtc ctc ctc tcc   1152
Thr Leu Val Ala Ala Gly Phe Ala Gly Met Cys Lys Val Leu Leu Ser
            370                 375                 380 atg aag cat ggc atc atc ccg ccc acc ccg ggt atc gat gac gag acc   1200
Met Lys His Gly Ile Ile Pro Pro Thr Pro Gly Ile Asp Asp Glu Thr
385                 390                 395                 400 aag atg gac cct ctc gtc gtc tcc ggt gag gcc atc cca tgg cca gag   1248
Lys Met Asp Pro Leu Val Val Ser Gly Glu Ala Ile Pro Trp Pro Glu
                405                 410                 415 acc aac ggc gag ccc aag cgc gcc ggt ctc tcg gcc ttt ggc ttt ggt   1296
Thr Asn Gly Glu Pro Lys Arg Ala Gly Leu Ser Ala Phe Gly Phe Gly
            420                 425                 430 ggc acc aac gcc cat gcc gtc ttt gag gag cat gac ccc tcc aac gcc   1344
Gly Thr Asn Ala His Ala Val Phe Glu Glu His Asp Pro Ser Asn Ala
                435                 440                 445 gcc tgc acg ggc cac gac tcc att tct gcg ctc tcg gcc cgc tgc ggc   1392
Ala Cys Thr Gly His Asp Ser Ile Ser Ala Leu Ser Ala Arg Cys Gly
            450                 455                 460 ggt gaa agc aac atg cgc atc gcc atc act ggt atg gac gcc acc ttt   1440
Gly Glu Ser Asn Met Arg Ile Ala Ile Thr Gly Met Asp Ala Thr Phe
465                 470                 475                 480 ggc gct ctc aag gga ctc gac gcc ttc gag cgc gcc att tac acc ggc   1488
Gly Ala Leu Lys Gly Leu Asp Ala Phe Glu Arg Ala Ile Tyr Thr Gly
                485                 490                 495 gct cac ggt gcc atc cca ctc cca gaa aag cgc tgg cgc ttt ctc ggc   1536
Ala His Gly Ala Ile Pro Leu Pro Glu Lys Arg Trp Arg Phe Leu Gly
            500                 505                 510 aag gac aag gac ttt ctt gac ctc tgc ggc gtc aag gcc acc ccg cac   1584
Lys Asp Lys Asp Phe Leu Asp Leu Cys Gly Val Lys Ala Thr Pro His
                515                 520                 525 ggc tgc tac att gaa gat gtt gag gtc gac ttc cag cgc ctc cgc acg   1632
Gly Cys Tyr Ile Glu Asp Val Glu Val Asp Phe Gln Arg Leu Arg Thr
```

```
                   530                535                540
ccc atg acc cct gaa gac atg ctc ctc cct cag cag ctt ctg gcc gtc      1680
Pro Met Thr Pro Glu Asp Met Leu Leu Pro Gln Gln Leu Leu Ala Val
545                 550                555                560 acc acc att gac cgc gcc atc ctc gac tcg gga atg aaa aag ggt ggc      1728
Thr Thr Ile Asp Arg Ala Ile Leu Asp Ser Gly Met Lys Lys Gly Gly
                565                570                575 aat gtc gcc gtc ttt gtc ggc ctc ggc acc gac ctc gag ctc tac cgt      1776
Asn Val Ala Val Phe Val Gly Leu Gly Thr Asp Leu Glu Leu Tyr Arg
            580                585                590 cac cgt gct cgc gtc gct ctc aag gag cgc gtc cgc cct gaa gcc tcc      1824
His Arg Ala Arg Val Ala Leu Lys Glu Arg Val Arg Pro Glu Ala Ser
        595                600                605 aag aag ctc aat gac atg atg cag tac att aac gac tgc ggc aca tcc      1872
Lys Lys Leu Asn Asp Met Met Gln Tyr Ile Asn Asp Cys Gly Thr Ser
    610                615                620 aca tcg tac acc tcg tac att ggc aac ctc gtc gcc acg cgc gtc tcg      1920
Thr Ser Tyr Thr Ser Tyr Ile Gly Asn Leu Val Ala Thr Arg Val Ser
625                630                635                640 tcg cag tgg ggc ttc acg ggc ccc tcc ttt acg atc acc gag ggc aac      1968
Ser Gln Trp Gly Phe Thr Gly Pro Ser Phe Thr Ile Thr Glu Gly Asn
                645                650                655 aac tcc gtc tac cgc tgc gcc gag ctc ggc aag tac ctc ctc gag acc      2016
Asn Ser Val Tyr Arg Cys Ala Glu Leu Gly Lys Tyr Leu Leu Glu Thr
            660                665                670 ggc gag gtc gat ggc gtc gtc gtt gcg ggt gtc gat ctc tgc ggc agt      2064
Gly Glu Val Asp Gly Val Val Val Ala Gly Val Asp Leu Cys Gly Ser
        675                680                685 gcc gaa aac ctt tac gtc aag tct cgc cgc ttc aag gtg tcc acc tcc      2112
Ala Glu Asn Leu Tyr Val Lys Ser Arg Arg Phe Lys Val Ser Thr Ser
    690                695                700 gat acc ccg cgc gcc agc ttt gac gcc gcc gcc gat ggc tac ttt gtc      2160
Asp Thr Pro Arg Ala Ser Phe Asp Ala Ala Ala Asp Gly Tyr Phe Val
705                710                715                720 ggc gag ggc tgc ggt gcc ttt gtg ctc aag cgt gag act agc tgc acc      2208
Gly Glu Gly Cys Gly Ala Phe Val Leu Lys Arg Glu Thr Ser Cys Thr
                725                730                735 aag gac gac cgt atc tac gct tgc atg gat gcc atc gtc cct ggc aac      2256
Lys Asp Asp Arg Ile Tyr Ala Cys Met Asp Ala Ile Val Pro Gly Asn
            740                745                750 gtc cct agc gcc tgc ttg cgc gag gcc ctc gac cag gcg cgc gtc aag      2304
Val Pro Ser Ala Cys Leu Arg Glu Ala Leu Asp Gln Ala Arg Val Lys
        755                760                765 ccg ggc gat atc gag atg ctc gag ctc agc gcc gac tcc gcc cgc cac      2352
Pro Gly Asp Ile Glu Met Leu Glu Leu Ser Ala Asp Ser Ala Arg His
    770                775                780 ctc aag gac ccg tcc gtc ctg ccc aag gag ctc act gcc gag gag gaa      2400
Leu Lys Asp Pro Ser Val Leu Pro Lys Glu Leu Thr Ala Glu Glu Glu
785                790                795                800 atc ggc ggc ctt cag acg atc ctt cgt gac gat gac aag ctc ccg cgc      2448
Ile Gly Gly Leu Gln Thr Ile Leu Arg Asp Asp Asp Lys Leu Pro Arg
                805                810                815 aac gtc gca acg ggc agt gtc aag gcc acc gtc ggt gac acc ggt tat      2496
Asn Val Ala Thr Gly Ser Val Lys Ala Thr Val Gly Asp Thr Gly Tyr
            820                825                830 gcc tct ggt gct gcc agc ctc atc aag gct gcg ctt tgc atc tac aac      2544
Ala Ser Gly Ala Ala Ser Leu Ile Lys Ala Ala Leu Cys Ile Tyr Asn
        835                840                845 cgc tac ctg ccc agc aac ggc gac gac tgg gat gaa ccc gcc cct gag      2592
Arg Tyr Leu Pro Ser Asn Gly Asp Asp Trp Asp Glu Pro Ala Pro Glu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 850 |     |     |     |     | 855 |     |     |     |     |     | 860 |     |     |      |
| gcg | ccc | tgg | gac | agc | acc | ctc | ttt | gcg | tgc | cag | acc | tcg | cgc | gct | tgg | 2640 |
| Ala | Pro | Trp | Asp | Ser | Thr | Leu | Phe | Ala | Cys | Gln | Thr | Ser | Arg | Ala | Trp |      |
| 865 |     |     |     |     | 870 |     |     |     |     | 875 |     |     |     |     | 880 |      |
| ctc | aag | aac | cct | ggc | gag | cgt | cgc | tat | gcg | gcc | gtc | tcg | ggc | gtc | tcc | 2688 |
| Leu | Lys | Asn | Pro | Gly | Glu | Arg | Arg | Tyr | Ala | Ala | Val | Ser | Gly | Val | Ser |      |
|     |     |     |     | 885 |     |     |     |     | 890 |     |     |     |     | 895 |     |      |
| gag | acg | cgc | tcg | tgc | tat | tcc | gtg | ctc | ctc | tcc | gaa | gcc | gag | ggc | cac | 2736 |
| Glu | Thr | Arg | Ser | Cys | Tyr | Ser | Val | Leu | Leu | Ser | Glu | Ala | Glu | Gly | His |      |
|     | 900 |     |     |     |     | 905 |     |     |     |     | 910 |     |     |     |     |      |
| tac | gag | cgc | gag | aac | cgc | atc | tcg | ctc | gac | gag | gag | gcg | ccc | aag | ctc | 2784 |
| Tyr | Glu | Arg | Glu | Asn | Arg | Ile | Ser | Leu | Asp | Glu | Glu | Ala | Pro | Lys | Leu |      |
| 915 |     |     |     |     | 920 |     |     |     |     | 925 |     |     |     |     |     |      |
| att | gtg | ctt | cgc | gcc | gac | tcc | cac | gag | gag | atc | ctt | ggt | cgc | ctc | gac | 2832 |
| Ile | Val | Leu | Arg | Ala | Asp | Ser | His | Glu | Glu | Ile | Leu | Gly | Arg | Leu | Asp |      |
|     | 930 |     |     |     |     | 935 |     |     |     |     | 940 |     |     |     |     |      |
| aag | atc | cgc | gag | cgc | ttc | ttg | cag | ccc | acg | ggc | gcc | gcc | ccg | cgc | gag | 2880 |
| Lys | Ile | Arg | Glu | Arg | Phe | Leu | Gln | Pro | Thr | Gly | Ala | Ala | Pro | Arg | Glu |      |
| 945 |     |     |     |     | 950 |     |     |     |     | 955 |     |     |     |     | 960 |      |
| tcc | gag | ctc | aag | gcg | cag | gcc | cgc | cgc | atc | ttc | ctc | gag | ctc | ctc | ggc | 2928 |
| Ser | Glu | Leu | Lys | Ala | Gln | Ala | Arg | Arg | Ile | Phe | Leu | Glu | Leu | Leu | Gly |      |
|     |     |     |     | 965 |     |     |     |     | 970 |     |     |     |     | 975 |     |      |
| gag | acc | ctt | gcc | cag | gat | gcc | gct | tct | tca | ggc | tcg | caa | aag | ccc | ctc | 2976 |
| Glu | Thr | Leu | Ala | Gln | Asp | Ala | Ala | Ser | Ser | Gly | Ser | Gln | Lys | Pro | Leu |      |
|     |     |     | 980 |     |     |     |     | 985 |     |     |     |     | 990 |     |     |      |
| gct | ctc | agc | ctc | gtc | tcc | acg | ccc | tcc | aag | ctc | cag | cgc | gag | gtc | gag | 3024 |
| Ala | Leu | Ser | Leu | Val | Ser | Thr | Pro | Ser | Lys | Leu | Gln | Arg | Glu | Val | Glu |      |
|     |     | 995 |     |     |     |     | 1000|     |     |     |     | 1005|     |     |     |      |
| ctc | gcg | gcc | aag | ggt | atc | ccg | cgc | tgc | ctc | aag | atg | cgc | cgc | gat |     | 3069 |
| Leu | Ala | Ala | Lys | Gly | Ile | Pro | Arg | Cys | Leu | Lys | Met | Arg | Arg | Asp |     |      |
|     | 1010|     |     |     |     | 1015|     |     |     |     | 1020|     |     |     |     |      |
| tgg | agc | tcc | cct | gct | ggc | agc | cgc | tac | gcg | cct | gag | ccg | ctc | gcc |     | 3114 |
| Trp | Ser | Ser | Pro | Ala | Gly | Ser | Arg | Tyr | Ala | Pro | Glu | Pro | Leu | Ala |     |      |
| 1025|     |     |     |     | 1030|     |     |     |     | 1035|     |     |     |     |     |      |
| agc | gac | cgc | gtc | gcc | ttc | atg | tac | ggc | gaa | ggt | cgc | agc | cct | tac |     | 3159 |
| Ser | Asp | Arg | Val | Ala | Phe | Met | Tyr | Gly | Glu | Gly | Arg | Ser | Pro | Tyr |     |      |
|     | 1040|     |     |     |     | 1045|     |     |     |     | 1050|     |     |     |     |      |
| tac | ggc | atc | acc | caa | gac | att | cac | cgc | att | tgg | ccc | gaa | ctc | cac |     | 3204 |
| Tyr | Gly | Ile | Thr | Gln | Asp | Ile | His | Arg | Ile | Trp | Pro | Glu | Leu | His |     |      |
|     | 1055|     |     |     |     | 1060|     |     |     |     | 1065|     |     |     |     |      |
| gag | gtc | atc | aac | gaa | aag | acg | aac | cgt | ctc | tgg | gcc | gaa | ggc | gac |     | 3249 |
| Glu | Val | Ile | Asn | Glu | Lys | Thr | Asn | Arg | Leu | Trp | Ala | Glu | Gly | Asp |     |      |
|     | 1070|     |     |     |     | 1075|     |     |     |     | 1080|     |     |     |     |      |
| cgc | tgg | gtc | atg | ccg | cgc | gcc | agc | ttc | aag | tcg | gag | ctc | gag | agc |     | 3294 |
| Arg | Trp | Val | Met | Pro | Arg | Ala | Ser | Phe | Lys | Ser | Glu | Leu | Glu | Ser |     |      |
| 1085|     |     |     |     | 1090|     |     |     |     | 1095|     |     |     |     |     |      |
| cag | cag | caa | gag | ttt | gat | cgc | aac | atg | att | gaa | atg | ttc | cgt | ctt |     | 3339 |
| Gln | Gln | Gln | Glu | Phe | Asp | Arg | Asn | Met | Ile | Glu | Met | Phe | Arg | Leu |     |      |
| 1100|     |     |     |     | 1105|     |     |     |     | 1110|     |     |     |     |     |      |
| gga | atc | ctc | acc | tca | att | gcc | ttc | acc | aat | ctg | gcg | cgc | gac | gtt |     | 3384 |
| Gly | Ile | Leu | Thr | Ser | Ile | Ala | Phe | Thr | Asn | Leu | Ala | Arg | Asp | Val |     |      |
| 1115|     |     |     |     | 1120|     |     |     |     | 1125|     |     |     |     |     |      |
| ctc | aac | atc | acg | ccc | aag | gcc | gcc | ttt | ggc | ctc | agt | ctt | ggc | gag |     | 3429 |
| Leu | Asn | Ile | Thr | Pro | Lys | Ala | Ala | Phe | Gly | Leu | Ser | Leu | Gly | Glu |     |      |
| 1130|     |     |     |     | 1135|     |     |     |     | 1140|     |     |     |     |     |      |
| att | tcc | atg | att | ttt | gcc | ttt | tcc | aag | aag | aac | ggt | ctc | atc | tcc |     | 3474 |
| Ile | Ser | Met | Ile | Phe | Ala | Phe | Ser | Lys | Lys | Asn | Gly | Leu | Ile | Ser |     |      |
| 1145|     |     |     |     | 1150|     |     |     |     | 1155|     |     |     |     |     |      |
| gac | cag | ctc | acc | aag | gat | ctt | cgc | gag | tcc | gac | gtg | tgg | aac | aag |     | 3519 |
| Asp | Gln | Leu | Thr | Lys | Asp | Leu | Arg | Glu | Ser | Asp | Val | Trp | Asn | Lys |     |      |

-continued

| | | | | | | | | | | | | | |
|---|---|---|---|---|---|---|---|---|---|---|---|---|---|
| | | | | 1160 | | | | 1165 | | | | 1170 | |
| gct | ctg | gcc | gtt | gaa | ttt | aat | gcg | ctg | cgc | gag | gcc | tgg | ggc | att | 3564 |
| Ala | Leu | Ala | Val | Glu | Phe | Asn | Ala | Leu | Arg | Glu | Ala | Trp | Gly | Ile |
| | 1175 | | | | | 1180 | | | | | 1185 | | | |
| cca | cag | agt | gtc | ccc | aag | gac | gag | ttc | tgg | caa | ggc | tac | att | gtg | 3609 |
| Pro | Gln | Ser | Val | Pro | Lys | Asp | Glu | Phe | Trp | Gln | Gly | Tyr | Ile | Val |
| 1190 | | | | | 1195 | | | | | 1200 | | | | |
| cgc | ggc | acc | aag | cag | gat | atc | gag | gcg | gcc | atc | gcc | ccg | gac | agc | 3654 |
| Arg | Gly | Thr | Lys | Gln | Asp | Ile | Glu | Ala | Ala | Ile | Ala | Pro | Asp | Ser |
| 1205 | | | | | 1210 | | | | | 1215 | | | | |
| aag | tac | gtg | cgc | ctc | acc | atc | atc | aat | gat | gcc | aac | acc | gcc | ctc | 3699 |
| Lys | Tyr | Val | Arg | Leu | Thr | Ile | Ile | Asn | Asp | Ala | Asn | Thr | Ala | Leu |
| 1220 | | | | | 1225 | | | | | 1230 | | | | |
| att | agc | ggc | aag | ccc | gac | gcc | tgc | aag | gct | gcg | atc | gcg | cgt | ctc | 3744 |
| Ile | Ser | Gly | Lys | Pro | Asp | Ala | Cys | Lys | Ala | Ala | Ile | Ala | Arg | Leu |
| 1235 | | | | | 1240 | | | | | 1245 | | | | |
| ggt | ggc | aac | att | cct | gcg | ctt | ccc | gtg | acc | cag | ggc | atg | tgc | ggc | 3789 |
| Gly | Gly | Asn | Ile | Pro | Ala | Leu | Pro | Val | Thr | Gln | Gly | Met | Cys | Gly |
| 1250 | | | | | 1255 | | | | | 1260 | | | | |
| cac | tgc | ccc | gag | gtg | gga | cct | tat | acc | aag | gat | atc | gcc | aag | atc | 3834 |
| His | Cys | Pro | Glu | Val | Gly | Pro | Tyr | Thr | Lys | Asp | Ile | Ala | Lys | Ile |
| 1265 | | | | | 1270 | | | | | 1275 | | | | |
| cat | gcc | aac | ctt | gag | ttc | ccc | gtt | gtc | gac | ggc | ctt | gac | ctc | tgg | 3879 |
| His | Ala | Asn | Leu | Glu | Phe | Pro | Val | Val | Asp | Gly | Leu | Asp | Leu | Trp |
| 1280 | | | | | 1285 | | | | | 1290 | | | | |
| acc | aca | atc | aac | cag | aag | cgc | ctc | gtg | cca | cgc | gcc | acg | ggc | gcc | 3924 |
| Thr | Thr | Ile | Asn | Gln | Lys | Arg | Leu | Val | Pro | Arg | Ala | Thr | Gly | Ala |
| 1295 | | | | | 1300 | | | | | 1305 | | | | |
| aag | gac | gaa | tgg | gcc | cct | tct | tcc | ttt | ggc | gag | tac | gcc | ggc | cag | 3969 |
| Lys | Asp | Glu | Trp | Ala | Pro | Ser | Ser | Phe | Gly | Glu | Tyr | Ala | Gly | Gln |
| 1310 | | | | | 1315 | | | | | 1320 | | | | |
| ctc | tac | gag | aag | cag | gct | aac | ttc | ccc | caa | atc | gtc | gag | acc | att | 4014 |
| Leu | Tyr | Glu | Lys | Gln | Ala | Asn | Phe | Pro | Gln | Ile | Val | Glu | Thr | Ile |
| 1325 | | | | | 1330 | | | | | 1335 | | | | |
| tac | aag | caa | aac | tac | gac | gtc | ttt | gtc | gag | gtt | ggg | ccc | aac | aac | 4059 |
| Tyr | Lys | Gln | Asn | Tyr | Asp | Val | Phe | Val | Glu | Val | Gly | Pro | Asn | Asn |
| 1340 | | | | | 1345 | | | | | 1350 | | | | |
| cac | cgt | agc | acc | gca | gtg | cgc | acc | acg | ctt | ggt | ccc | cag | cgc | aac | 4104 |
| His | Arg | Ser | Thr | Ala | Val | Arg | Thr | Thr | Leu | Gly | Pro | Gln | Arg | Asn |
| 1355 | | | | | 1360 | | | | | 1365 | | | | |
| cac | ctt | gct | ggc | gcc | atc | gac | aag | cag | aac | gag | gat | gct | tgg | acg | 4149 |
| His | Leu | Ala | Gly | Ala | Ile | Asp | Lys | Gln | Asn | Glu | Asp | Ala | Trp | Thr |
| 1370 | | | | | 1375 | | | | | 1380 | | | | |
| acc | atc | gtc | aag | ctt | gtg | gct | tcg | ctc | aag | gcc | cac | ctt | gtt | cct | 4194 |
| Thr | Ile | Val | Lys | Leu | Val | Ala | Ser | Leu | Lys | Ala | His | Leu | Val | Pro |
| 1385 | | | | | 1390 | | | | | 1395 | | | | |
| ggc | gtc | acg | atc | tcg | ccg | ctg | tac | cac | tcc | aag | ctt | gtg | gcg | gag | 4239 |
| Gly | Val | Thr | Ile | Ser | Pro | Leu | Tyr | His | Ser | Lys | Leu | Val | Ala | Glu |
| 1400 | | | | | 1405 | | | | | 1410 | | | | |
| gct | gag | gct | tgc | tac | gct | gcg | ctc | tgc | aag | ggt | gaa | aag | ccc | aag | 4284 |
| Ala | Glu | Ala | Cys | Tyr | Ala | Ala | Leu | Cys | Lys | Gly | Glu | Lys | Pro | Lys |
| 1415 | | | | | 1420 | | | | | 1425 | | | | |
| aag | aac | aag | ttt | gtg | cgc | aag | att | cag | ctc | aac | ggt | cgc | ttc | aac | 4329 |
| Lys | Asn | Lys | Phe | Val | Arg | Lys | Ile | Gln | Leu | Asn | Gly | Arg | Phe | Asn |
| 1430 | | | | | 1435 | | | | | 1440 | | | | |
| agc | aag | gcg | gac | ccc | atc | tcc | tcg | gcc | gat | ctt | gcc | agc | ttt | ccg | 4374 |
| Ser | Lys | Ala | Asp | Pro | Ile | Ser | Ser | Ala | Asp | Leu | Ala | Ser | Phe | Pro |
| 1445 | | | | | 1450 | | | | | 1455 | | | | |
| cct | gcg | gac | cct | gcc | att | gaa | gcc | gcc | atc | tcg | agc | cgc | atc | atg | 4419 |
| Pro | Ala | Asp | Pro | Ala | Ile | Glu | Ala | Ala | Ile | Ser | Ser | Arg | Ile | Met |

```
                1460                1465                1470 aag cct gtc gct ccc aag ttc tac gcg cgt ctc aac att gac gag    4464
Lys Pro Val Ala Pro Lys Phe Tyr Ala Arg Leu Asn Ile Asp Glu
    1475                1480                1485 cag gac gag acc cga gat ccg atc ctc aac aag gac aac gcg ccg    4509
Gln Asp Glu Thr Arg Asp Pro Ile Leu Asn Lys Asp Asn Ala Pro
    1490                1495                1500 tct tct tct tct tct tct tct tct tct tct tct tct tct tct tct    4554
Ser Ser Ser Ser Ser Ser Ser Ser Ser Ser Ser Ser Ser Ser Ser
    1505                1510                1515 ccg tcg cct gct cct tcg gcc ccc gtg caa aag aag gct gct ccc    4599
Pro Ser Pro Ala Pro Ser Ala Pro Val Gln Lys Lys Ala Ala Pro
    1520                1525                1530 gcc gcg gag acc aag gct gtt gct tcg gct gac gca ctt cgc agt    4644
Ala Ala Glu Thr Lys Ala Val Ala Ser Ala Asp Ala Leu Arg Ser
    1535                1540                1545 gcc ctg ctc gat ctc gac agt atg ctt gcg ctg agc tct gcc agt    4689
Ala Leu Leu Asp Leu Asp Ser Met Leu Ala Leu Ser Ser Ala Ser
    1550                1555                1560 gcc tcc ggc aac ctt gtt gag act gcg cct agc gac gcc tcg gtc    4734
Ala Ser Gly Asn Leu Val Glu Thr Ala Pro Ser Asp Ala Ser Val
    1565                1570                1575 att gtg ccg ccc tgc aac att gcg gat ctc ggc agc cgc gcc ttc    4779
Ile Val Pro Pro Cys Asn Ile Ala Asp Leu Gly Ser Arg Ala Phe
    1580                1585                1590 atg aaa acg tac ggt gtt tcg gcg cct ctg tac acg ggc gcc atg    4824
Met Lys Thr Tyr Gly Val Ser Ala Pro Leu Tyr Thr Gly Ala Met
    1595                1600                1605 gcc aag ggc att gcc tct gcg gac ctc gtc att gcc gcc ggc cgc    4869
Ala Lys Gly Ile Ala Ser Ala Asp Leu Val Ile Ala Ala Gly Arg
    1610                1615                1620 cag ggc atc ctt gcg tcc ttt ggc gcc ggc gga ctt ccc atg cag    4914
Gln Gly Ile Leu Ala Ser Phe Gly Ala Gly Gly Leu Pro Met Gln
    1625                1630                1635 gtt gtg cgt gag tcc atc gaa aag att cag gcc gcc ctg ccc aat    4959
Val Val Arg Glu Ser Ile Glu Lys Ile Gln Ala Ala Leu Pro Asn
    1640                1645                1650 ggc ccg tac gct gtc aac ctt atc cat tct ccc ttt gac agc aac    5004
Gly Pro Tyr Ala Val Asn Leu Ile His Ser Pro Phe Asp Ser Asn
    1655                1660                1665 ctc gaa aag ggc aat gtc gat ctc ttc ctc gag aag ggt gtc acc    5049
Leu Glu Lys Gly Asn Val Asp Leu Phe Leu Glu Lys Gly Val Thr
    1670                1675                1680 ttt gtc gag gcc tcg gcc ttt atg acg ctc acc ccg cag gtc gtg    5094
Phe Val Glu Ala Ser Ala Phe Met Thr Leu Thr Pro Gln Val Val
    1685                1690                1695 cgg tac cgc gcg gct ggc ctc acg cgc aac gcc gac ggc tcg gtc    5139
Arg Tyr Arg Ala Ala Gly Leu Thr Arg Asn Ala Asp Gly Ser Val
    1700                1705                1710 aac atc cgc aac cgt atc att ggc aag gtc tcg cgc acc gag ctc    5184
Asn Ile Arg Asn Arg Ile Ile Gly Lys Val Ser Arg Thr Glu Leu
    1715                1720                1725 gcc gag atg ttc atg cgt cct gcg ccc gag cac ctt ctt cag aag    5229
Ala Glu Met Phe Met Arg Pro Ala Pro Glu His Leu Leu Gln Lys
    1730                1735                1740 ctc att gct tcc ggc gag atc aac cag gag cag gcc gag ctc gcc    5274
Leu Ile Ala Ser Gly Glu Ile Asn Gln Glu Gln Ala Glu Leu Ala
    1745                1750                1755 cgc cgt gtt ccc gtc gct gac gac atc gcg gtc gaa gct gac tcg    5319
Arg Arg Val Pro Val Ala Asp Asp Ile Ala Val Glu Ala Asp Ser
```

|   |   |   |   |   |   |   |   |   |   |   |   |   |   |   |   |
|---|---|---|---|---|---|---|---|---|---|---|---|---|---|---|---|
| | | | 1760 | | | | 1765 | | | | 1770 | | | | |
| ggt | ggc | cac | acc | gac | aac | cgc | ccc | atc | cac | gtc | att | ctg | ccc | ctc | 5364 |
| Gly | Gly | His | Thr | Asp | Asn | Arg | Pro | Ile | His | Val | Ile | Leu | Pro | Leu | |
| | | 1775 | | | | 1780 | | | | 1785 | | | | | |
| atc | atc | aac | ctt | cgc | gac | cgc | ctt | cac | cgc | gag | tgc | ggc | tac | ccg | 5409 |
| Ile | Ile | Asn | Leu | Arg | Asp | Arg | Leu | His | Arg | Glu | Cys | Gly | Tyr | Pro | |
| | | 1790 | | | | 1795 | | | | 1800 | | | | | |
| gcc | aac | ctt | cgc | gtc | cgt | gtg | ggc | gcc | ggc | ggt | ggc | att | ggg | tgc | 5454 |
| Ala | Asn | Leu | Arg | Val | Arg | Val | Gly | Ala | Gly | Gly | Gly | Ile | Gly | Cys | |
| | | 1805 | | | | 1810 | | | | 1815 | | | | | |
| ccc | cag | gcg | gcg | ctg | gcc | acc | ttc | aac | atg | ggt | gcc | tcc | ttt | att | 5499 |
| Pro | Gln | Ala | Ala | Leu | Ala | Thr | Phe | Asn | Met | Gly | Ala | Ser | Phe | Ile | |
| | | 1820 | | | | 1825 | | | | 1830 | | | | | |
| gtc | acc | ggc | acc | gtg | aac | cag | gtc | gcc | aag | cag | tcg | ggc | acg | tgc | 5544 |
| Val | Thr | Gly | Thr | Val | Asn | Gln | Val | Ala | Lys | Gln | Ser | Gly | Thr | Cys | |
| | | 1835 | | | | 1840 | | | | 1845 | | | | | |
| gac | aat | gtg | cgc | aag | cag | ctc | gcg | aag | gcc | act | tac | tcg | gac | gta | 5589 |
| Asp | Asn | Val | Arg | Lys | Gln | Leu | Ala | Lys | Ala | Thr | Tyr | Ser | Asp | Val | |
| | | 1850 | | | | 1855 | | | | 1860 | | | | | |
| tgc | atg | gcc | ccg | gct | gcc | gac | atg | ttc | gag | gaa | ggc | gtc | aag | ctt | 5634 |
| Cys | Met | Ala | Pro | Ala | Ala | Asp | Met | Phe | Glu | Glu | Gly | Val | Lys | Leu | |
| | | 1865 | | | | 1870 | | | | 1875 | | | | | |
| cag | gtc | ctc | aag | aag | gga | acc | atg | ttt | ccc | tcg | cgc | gcc | aac | aag | 5679 |
| Gln | Val | Leu | Lys | Lys | Gly | Thr | Met | Phe | Pro | Ser | Arg | Ala | Asn | Lys | |
| | | 1880 | | | | 1885 | | | | 1890 | | | | | |
| ctc | tac | gag | ctc | ttt | tgc | aag | tac | gac | tcg | ttc | gag | tcc | atg | ccc | 5724 |
| Leu | Tyr | Glu | Leu | Phe | Cys | Lys | Tyr | Asp | Ser | Phe | Glu | Ser | Met | Pro | |
| | | 1895 | | | | 1900 | | | | 1905 | | | | | |
| ccc | gca | gag | ctt | gcg | cgc | gtc | gag | aag | cgc | atc | ttc | agc | cgc | gcg | 5769 |
| Pro | Ala | Glu | Leu | Ala | Arg | Val | Glu | Lys | Arg | Ile | Phe | Ser | Arg | Ala | |
| | | 1910 | | | | 1915 | | | | 1920 | | | | | |
| ctc | gaa | gag | gtc | tgg | gac | gag | acc | aaa | aac | ttt | tac | att | aac | cgt | 5814 |
| Leu | Glu | Glu | Val | Trp | Asp | Glu | Thr | Lys | Asn | Phe | Tyr | Ile | Asn | Arg | |
| | | 1925 | | | | 1930 | | | | 1935 | | | | | |
| ctt | cac | aac | ccg | gag | aag | atc | cag | cgc | gcc | gag | cgc | gac | ccc | aag | 5859 |
| Leu | His | Asn | Pro | Glu | Lys | Ile | Gln | Arg | Ala | Glu | Arg | Asp | Pro | Lys | |
| | | 1940 | | | | 1945 | | | | 1950 | | | | | |
| ctc | aag | atg | tcg | ctg | tgc | ttt | cgc | tgg | tac | ctg | agc | ctg | gcg | agc | 5904 |
| Leu | Lys | Met | Ser | Leu | Cys | Phe | Arg | Trp | Tyr | Leu | Ser | Leu | Ala | Ser | |
| | | 1955 | | | | 1960 | | | | 1965 | | | | | |
| cgc | tgg | gcc | aac | act | gga | gct | tcc | gat | cgc | gtc | atg | gac | tac | cag | 5949 |
| Arg | Trp | Ala | Asn | Thr | Gly | Ala | Ser | Asp | Arg | Val | Met | Asp | Tyr | Gln | |
| | | 1970 | | | | 1975 | | | | 1980 | | | | | |
| gtc | tgg | tgc | ggt | cct | gcc | att | ggt | tcc | ttc | aac | gat | ttc | atc | aag | 5994 |
| Val | Trp | Cys | Gly | Pro | Ala | Ile | Gly | Ser | Phe | Asn | Asp | Phe | Ile | Lys | |
| | | 1985 | | | | 1990 | | | | 1995 | | | | | |
| gga | act | tac | ctt | gat | ccg | gcc | gtc | gca | aac | gag | tac | ccg | tgc | gtc | 6039 |
| Gly | Thr | Tyr | Leu | Asp | Pro | Ala | Val | Ala | Asn | Glu | Tyr | Pro | Cys | Val | |
| | | 2000 | | | | 2005 | | | | 2010 | | | | | |
| gtt | cag | att | aac | aag | cag | atc | ctt | cgt | gga | gcg | tgc | ttc | ttg | cgc | 6084 |
| Val | Gln | Ile | Asn | Lys | Gln | Ile | Leu | Arg | Gly | Ala | Cys | Phe | Leu | Arg | |
| | | 2015 | | | | 2020 | | | | 2025 | | | | | |
| cgt | ctc | gaa | att | ctg | cgc | aac | gca | cgc | ctt | tcc | gat | ggc | gct | gcc | 6129 |
| Arg | Leu | Glu | Ile | Leu | Arg | Asn | Ala | Arg | Leu | Ser | Asp | Gly | Ala | Ala | |
| | | 2030 | | | | 2035 | | | | 2040 | | | | | |
| gct | ctt | gtg | gcc | agc | atc | gat | gac | aca | tac | gtc | ccg | gcc | gag | aag | 6174 |
| Ala | Leu | Val | Ala | Ser | Ile | Asp | Asp | Thr | Tyr | Val | Pro | Ala | Glu | Lys | |
| | | 2045 | | | | 2050 | | | | 2055 | | | | | |
| ctg | | | | | | | | | | | | | | | 6177 |
| Leu | | | | | | | | | | | | | | | |

```
<210> SEQ ID NO 4
<211> LENGTH: 2059
<212> TYPE: PRT
<213> ORGANISM: Schizochytrium sp.

<400> SEQUENCE: 4

Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60

Lys Ala Glu Arg Ser Lys Tyr Ala Asp Thr Phe Cys Asn Glu Thr Tyr
65                  70                  75                  80

Gly Thr Leu Asp Glu Asn Glu Ile Asp Asn Glu His Glu Leu Leu Leu
                85                  90                  95

Asn Leu Ala Lys Gln Ala Leu Ala Glu Thr Ser Val Lys Asp Ser Thr
            100                 105                 110

Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
    130                 135                 140

Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
                165                 170                 175

Ser Phe Val Ala Glu Glu Leu Asn Leu Gly Ala Leu His Tyr Ser Val
            180                 185                 190

Asp Ala Ala Cys Ala Thr Ala Leu Tyr Val Leu Arg Leu Ala Gln Asp
        195                 200                 205

His Leu Val Ser Gly Ala Ala Asp Val Met Leu Cys Gly Ala Thr Cys
    210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
                245                 250                 255

Ser Gln Gly Leu Thr Pro Gly Glu Gly Ser Ile Met Val Leu Lys
            260                 265                 270

Arg Leu Asp Asp Ala Ile Arg Asp Gly Asp His Ile Tyr Gly Thr Leu
        275                 280                 285

Leu Gly Ala Asn Val Ser Asn Ser Gly Thr Gly Leu Pro Leu Lys Pro
    290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
                325                 330                 335

Thr Pro Gln Gly Asp Arg Val Glu Ile Asp Ala Val Lys Ala Cys Phe
            340                 345                 350

Glu Gly Lys Val Pro Arg Phe Gly Thr Thr Lys Gly Asn Phe Gly His
        355                 360                 365

Thr Leu Val Ala Ala Gly Phe Ala Gly Met Cys Lys Val Leu Leu Ser
    370                 375                 380
```

```
Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
            405                 410                 415

Thr Asn Gly Glu Pro Lys Arg Ala Gly Leu Ser Ala Phe Gly Phe Gly
            420                 425                 430

Gly Thr Asn Ala His Ala Val Phe Glu Glu His Asp Pro Ser Asn Ala
        435                 440                 445

Ala Cys Thr Gly His Asp Ser Ile Ser Ala Leu Ser Ala Arg Cys Gly
        450                 455                 460

Gly Glu Ser Asn Met Arg Ile Ala Ile Thr Gly Met Asp Ala Thr Phe
465                 470                 475                 480

Gly Ala Leu Lys Gly Leu Asp Ala Phe Glu Arg Ala Ile Tyr Thr Gly
                485                 490                 495

Ala His Gly Ala Ile Pro Leu Pro Glu Lys Arg Trp Arg Phe Leu Gly
                500                 505                 510

Lys Asp Lys Asp Phe Leu Asp Leu Cys Gly Val Lys Ala Thr Pro His
            515                 520                 525

Gly Cys Tyr Ile Glu Asp Val Glu Val Asp Phe Gln Arg Leu Arg Thr
            530                 535                 540

Pro Met Thr Pro Glu Asp Met Leu Leu Pro Gln Gln Leu Leu Ala Val
545                 550                 555                 560

Thr Thr Ile Asp Arg Ala Ile Leu Asp Ser Gly Met Lys Lys Gly Gly
                565                 570                 575

Asn Val Ala Val Phe Val Gly Leu Gly Thr Asp Leu Glu Leu Tyr Arg
                580                 585                 590

His Arg Ala Arg Val Ala Leu Lys Glu Arg Val Arg Pro Glu Ala Ser
            595                 600                 605

Lys Lys Leu Asn Asp Met Met Gln Tyr Ile Asn Asp Cys Gly Thr Ser
            610                 615                 620

Thr Ser Tyr Thr Ser Tyr Ile Gly Asn Leu Val Ala Thr Arg Val Ser
625                 630                 635                 640

Ser Gln Trp Gly Phe Thr Gly Pro Ser Phe Thr Ile Thr Glu Gly Asn
                645                 650                 655

Asn Ser Val Tyr Arg Cys Ala Glu Leu Gly Lys Tyr Leu Leu Glu Thr
                660                 665                 670

Gly Glu Val Asp Gly Val Val Ala Gly Val Asp Leu Cys Gly Ser
            675                 680                 685

Ala Glu Asn Leu Tyr Val Lys Ser Arg Arg Phe Lys Val Ser Thr Ser
            690                 695                 700

Asp Thr Pro Arg Ala Ser Phe Asp Ala Ala Asp Gly Tyr Phe Val
705                 710                 715                 720

Gly Glu Gly Cys Gly Ala Phe Val Leu Lys Arg Glu Thr Ser Cys Thr
                725                 730                 735

Lys Asp Asp Arg Ile Tyr Ala Cys Met Asp Ala Ile Val Pro Gly Asn
            740                 745                 750

Val Pro Ser Ala Cys Leu Arg Glu Ala Leu Asp Gln Ala Arg Val Lys
        755                 760                 765

Pro Gly Asp Ile Glu Met Leu Glu Leu Ser Ala Asp Ser Ala Arg His
        770                 775                 780

Leu Lys Asp Pro Ser Val Leu Pro Lys Glu Leu Thr Ala Glu Glu
785                 790                 795                 800

Ile Gly Gly Leu Gln Thr Ile Leu Arg Asp Asp Asp Lys Leu Pro Arg
```

-continued

Asn Val Ala Thr Gly Ser Val Lys Ala Thr Val Gly Asp Thr Gly Tyr
    805                 810                 815
Ala Ser Gly Ala Ala Ser Leu Ile Lys Ala Ala Leu Cys Ile Tyr Asn
    820                 825                 830
Arg Tyr Leu Pro Ser Asn Gly Asp Trp Asp Glu Pro Ala Pro Glu
835                 840                 845
Ala Pro Trp Asp Ser Thr Leu Phe Ala Cys Gln Thr Ser Arg Ala Trp
                850                 855                 860
Leu Lys Asn Pro Gly Glu Arg Arg Tyr Ala Ala Val Ser Gly Val Ser
865                 870                 875                 880
Glu Thr Arg Ser Cys Tyr Ser Val Leu Leu Ser Glu Ala Glu Gly His
                885                 890                 895
Tyr Glu Arg Glu Asn Arg Ile Ser Leu Asp Glu Glu Ala Pro Lys Leu
    900                 905                 910
Ile Val Leu Arg Ala Asp Ser His Glu Ile Leu Gly Arg Leu Asp
    915                 920                 925
Lys Ile Arg Glu Arg Phe Leu Gln Pro Thr Gly Ala Ala Pro Arg Glu
    930                 935                 940
Ser Glu Leu Lys Ala Gln Ala Arg Arg Ile Phe Leu Glu Leu Leu Gly
945                 950                 955                 960
Glu Thr Leu Ala Gln Asp Ala Ala Ser Ser Gly Ser Gln Lys Pro Leu
                965                 970                 975
Ala Leu Ser Leu Val Ser Thr Pro Ser Lys Leu Gln Arg Glu Val Glu
    980                 985                 990
Leu Ala Ala Lys Gly Ile Pro Arg Cys Leu Lys Met Arg Arg Asp
    995                 1000                1005
Trp Ser Ser Pro Ala Gly Ser Arg Tyr Ala Pro Glu Pro Leu Ala
    1010                1015                1020
Ser Asp Arg Val Ala Phe Met Tyr Gly Glu Gly Arg Ser Pro Tyr
    1025                1030                1035
Tyr Gly Ile Thr Gln Asp Ile His Arg Ile Trp Pro Glu Leu His
    1040                1045                1050
Glu Val Ile Asn Glu Lys Thr Asn Arg Leu Trp Ala Glu Gly Asp
    1055                1060                1065
Arg Trp Val Met Pro Arg Ala Ser Phe Lys Ser Glu Leu Glu Ser
    1070                1075                1080
Gln Gln Gln Glu Phe Asp Arg Asn Met Ile Glu Met Phe Arg Leu
    1085                1090                1095
Gly Ile Leu Thr Ser Ile Ala Phe Thr Asn Leu Ala Arg Asp Val
    1100                1105                1110
Leu Asn Ile Thr Pro Lys Ala Ala Phe Gly Leu Ser Leu Gly Glu
    1115                1120                1125
Ile Ser Met Ile Phe Ala Phe Ser Lys Lys Asn Gly Leu Ile Ser
    1130                1135                1140
Asp Gln Leu Thr Lys Asp Leu Arg Glu Ser Asp Val Trp Asn Lys
    1145                1150                1155
Ala Leu Ala Val Glu Phe Asn Ala Leu Arg Glu Ala Trp Gly Ile
    1160                1165                1170
Pro Gln Ser Val Pro Lys Asp Glu Phe Trp Gln Gly Tyr Ile Val
    1175                1180                1185
Arg Gly Thr Lys Gln Asp Ile Glu Ala Ala Ile Ala Pro Asp Ser
    1190                1195                1200
                    1205                1210                1215

```
Lys Tyr Val Arg Leu Thr Ile Ile Asn Asp Ala Asn Thr Ala Leu
1220                1225                1230

Ile Ser Gly Lys Pro Asp Ala Cys Lys Ala Ala Ile Ala Arg Leu
1235                1240                1245

Gly Gly Asn Ile Pro Ala Leu Pro Val Thr Gln Gly Met Cys Gly
1250                1255                1260

His Cys Pro Glu Val Gly Pro Tyr Thr Lys Asp Ile Ala Lys Ile
1265                1270                1275

His Ala Asn Leu Glu Phe Pro Val Val Asp Gly Leu Asp Leu Trp
1280                1285                1290

Thr Thr Ile Asn Gln Lys Arg Leu Val Pro Arg Ala Thr Gly Ala
1295                1300                1305

Lys Asp Glu Trp Ala Pro Ser Ser Phe Gly Glu Tyr Ala Gly Gln
1310                1315                1320

Leu Tyr Glu Lys Gln Ala Asn Phe Pro Gln Ile Val Glu Thr Ile
1325                1330                1335

Tyr Lys Gln Asn Tyr Asp Val Phe Val Glu Val Gly Pro Asn Asn
1340                1345                1350

His Arg Ser Thr Ala Val Arg Thr Thr Leu Gly Pro Gln Arg Asn
1355                1360                1365

His Leu Ala Gly Ala Ile Asp Lys Gln Asn Glu Asp Ala Trp Thr
1370                1375                1380

Thr Ile Val Lys Leu Val Ala Ser Leu Lys Ala His Leu Val Pro
1385                1390                1395

Gly Val Thr Ile Ser Pro Leu Tyr His Ser Lys Leu Val Ala Glu
1400                1405                1410

Ala Glu Ala Cys Tyr Ala Ala Leu Cys Lys Gly Glu Lys Pro Lys
1415                1420                1425

Lys Asn Lys Phe Val Arg Lys Ile Gln Leu Asn Gly Arg Phe Asn
1430                1435                1440

Ser Lys Ala Asp Pro Ile Ser Ser Ala Asp Leu Ala Ser Phe Pro
1445                1450                1455

Pro Ala Asp Pro Ala Ile Glu Ala Ala Ile Ser Ser Arg Ile Met
1460                1465                1470

Lys Pro Val Ala Pro Lys Phe Tyr Ala Arg Leu Asn Ile Asp Glu
1475                1480                1485

Gln Asp Glu Thr Arg Asp Pro Ile Leu Asn Lys Asp Asn Ala Pro
1490                1495                1500

Ser Ser Ser Ser Ser Ser Ser Ser Ser Ser Ser Ser Ser Ser Ser
1505                1510                1515

Pro Ser Pro Ala Pro Ser Ala Pro Val Gln Lys Lys Ala Ala Pro
1520                1525                1530

Ala Ala Glu Thr Lys Ala Val Ala Ser Ala Asp Ala Leu Arg Ser
1535                1540                1545

Ala Leu Leu Asp Leu Asp Ser Met Leu Ala Leu Ser Ser Ala Ser
1550                1555                1560

Ala Ser Gly Asn Leu Val Glu Thr Ala Pro Ser Asp Ala Ser Val
1565                1570                1575

Ile Val Pro Pro Cys Asn Ile Ala Asp Leu Gly Ser Arg Ala Phe
1580                1585                1590

Met Lys Thr Tyr Gly Val Ser Ala Pro Leu Tyr Thr Gly Ala Met
1595                1600                1605

Ala Lys Gly Ile Ala Ser Ala Asp Leu Val Ile Ala Ala Gly Arg
1610                1615                1620
```

```
Gln Gly Ile Leu Ala Ser Phe Gly Ala Gly Leu Pro Met Gln
    1625                1630                1635

Val Val Arg Glu Ser Ile Glu Lys Ile Gln Ala Leu Pro Asn
    1640                1645                1650

Gly Pro Tyr Ala Val Asn Leu Ile His Ser Pro Phe Asp Ser Asn
    1655                1660                1665

Leu Glu Lys Gly Asn Val Asp Leu Phe Leu Glu Lys Gly Val Thr
    1670                1675                1680

Phe Val Glu Ala Ser Ala Phe Met Thr Leu Thr Pro Gln Val Val
    1685                1690                1695

Arg Tyr Arg Ala Ala Gly Leu Thr Arg Asn Ala Asp Gly Ser Val
    1700                1705                1710

Asn Ile Arg Asn Arg Ile Ile Gly Lys Val Ser Arg Thr Glu Leu
    1715                1720                1725

Ala Glu Met Phe Met Arg Pro Ala Pro Glu His Leu Leu Gln Lys
    1730                1735                1740

Leu Ile Ala Ser Gly Glu Ile Asn Gln Glu Gln Ala Glu Leu Ala
    1745                1750                1755

Arg Arg Val Pro Val Ala Asp Ile Ala Val Glu Ala Asp Ser
    1760                1765                1770

Gly Gly His Thr Asp Asn Arg Pro Ile His Val Ile Leu Pro Leu
    1775                1780                1785

Ile Ile Asn Leu Arg Asp Arg Leu His Arg Glu Cys Gly Tyr Pro
    1790                1795                1800

Ala Asn Leu Arg Val Arg Val Gly Ala Gly Gly Ile Gly Cys
    1805                1810                1815

Pro Gln Ala Ala Leu Ala Thr Phe Asn Met Gly Ala Ser Phe Ile
    1820                1825                1830

Val Thr Gly Thr Val Asn Gln Val Ala Lys Gln Ser Gly Thr Cys
    1835                1840                1845

Asp Asn Val Arg Lys Gln Leu Ala Lys Ala Thr Tyr Ser Asp Val
    1850                1855                1860

Cys Met Ala Pro Ala Ala Asp Met Phe Glu Glu Gly Val Lys Leu
    1865                1870                1875

Gln Val Leu Lys Lys Gly Thr Met Phe Pro Ser Arg Ala Asn Lys
    1880                1885                1890

Leu Tyr Glu Leu Phe Cys Lys Tyr Asp Ser Phe Glu Ser Met Pro
    1895                1900                1905

Pro Ala Glu Leu Ala Arg Val Glu Lys Arg Ile Phe Ser Arg Ala
    1910                1915                1920

Leu Glu Glu Val Trp Asp Glu Thr Lys Asn Phe Tyr Ile Asn Arg
    1925                1930                1935

Leu His Asn Pro Glu Lys Ile Gln Arg Ala Glu Arg Asp Pro Lys
    1940                1945                1950

Leu Lys Met Ser Leu Cys Phe Arg Trp Tyr Leu Ser Leu Ala Ser
    1955                1960                1965

Arg Trp Ala Asn Thr Gly Ala Ser Asp Arg Val Met Asp Tyr Gln
    1970                1975                1980

Val Trp Cys Gly Pro Ala Ile Gly Ser Phe Asn Asp Phe Ile Lys
    1985                1990                1995

Gly Thr Tyr Leu Asp Pro Ala Val Ala Asn Glu Tyr Pro Cys Val
    2000                2005                2010

Val Gln Ile Asn Lys Gln Ile Leu Arg Gly Ala Cys Phe Leu Arg
```

```
                2015                2020                2025
Arg  Leu  Glu  Ile  Leu  Arg  Asn  Ala  Arg  Leu  Ser  Asp  Gly  Ala  Ala
       2030                2035                2040

Ala  Leu  Val  Ala  Ser  Ile  Asp  Asp  Thr  Tyr  Val  Pro  Ala  Glu  Lys
       2045                2050                2055

Leu

<210> SEQ ID NO 5
<211> LENGTH: 4506
<212> TYPE: DNA
<213> ORGANISM: Schizochytrium sp.
<220> FEATURE:
<221> NAME/KEY: CDS
<222> LOCATION: (1)..(4506)

<400> SEQUENCE: 5 atg gcg ctc cgt gtc aag acg aac aag aag cca tgc tgg gag atg acc        48
Met Ala Leu Arg Val Lys Thr Asn Lys Lys Pro Cys Trp Glu Met Thr
1               5                   10                  15 aag gag gag ctg acc agc ggc aag acc gag gtg ttc aac tat gag gaa        96
Lys Glu Glu Leu Thr Ser Gly Lys Thr Glu Val Phe Asn Tyr Glu Glu
            20                  25                  30 ctc ctc gag ttc gca gag ggc gac atc gcc aag gtc ttc gga ccc gag       144
Leu Leu Glu Phe Ala Glu Gly Asp Ile Ala Lys Val Phe Gly Pro Glu
        35                  40                  45 ttc gcc gtc atc gac aag tac ccg cgc cgc gtg cgc ctg ccc gcc cgc       192
Phe Ala Val Ile Asp Lys Tyr Pro Arg Arg Val Arg Leu Pro Ala Arg
    50                  55                  60 gag tac ctg ctc gtg acc cgc gtc acc ctc atg gac gcc gag gtc aac       240
Glu Tyr Leu Leu Val Thr Arg Val Thr Leu Met Asp Ala Glu Val Asn
65                  70                  75                  80 aac tac cgc gtc ggc gcc cgc atg gtc acc gag tac gat ctc ccc gtc       288
Asn Tyr Arg Val Gly Ala Arg Met Val Thr Glu Tyr Asp Leu Pro Val
                85                  90                  95 aac gga gag ctc tcc gag ggc gga gac tgc ccc tgg gcc gtc ctg gtc       336
Asn Gly Glu Leu Ser Glu Gly Gly Asp Cys Pro Trp Ala Val Leu Val
            100                 105                 110 gag agt ggc cag tgc gat ctc atg ctc atc tcc tac atg ggc att gac       384
Glu Ser Gly Gln Cys Asp Leu Met Leu Ile Ser Tyr Met Gly Ile Asp
        115                 120                 125 ttc cag aac cag ggc gac cgc gtc tac cgc ctg ctc aac acc acg ctc       432
Phe Gln Asn Gln Gly Asp Arg Val Tyr Arg Leu Leu Asn Thr Thr Leu
    130                 135                 140 acc ttt tac ggc gtg gcc cac gag ggc gag acc ctc gag tac gac att       480
Thr Phe Tyr Gly Val Ala His Glu Gly Glu Thr Leu Glu Tyr Asp Ile
145                 150                 155                 160 cgc gtc acc ggc ttc gcc aag cgt ctc gac ggc ggc atc tcc atg ttc       528
Arg Val Thr Gly Phe Ala Lys Arg Leu Asp Gly Gly Ile Ser Met Phe
                165                 170                 175 ttc ttc gag tac gac tgc tac gtc aac ggc cgc ctc ctc atc gag atg       576
Phe Phe Glu Tyr Asp Cys Tyr Val Asn Gly Arg Leu Leu Ile Glu Met
            180                 185                 190 cgc gat ggc tgc gcc ggc ttc ttc acc aac gag gag ctc gac gcc ggc       624
Arg Asp Gly Cys Ala Gly Phe Phe Thr Asn Glu Glu Leu Asp Ala Gly
        195                 200                 205 aag ggc gtc gtc ttc acc cgc ggc gac ctc gcc gcc cgc gcc aag atc       672
Lys Gly Val Val Phe Thr Arg Gly Asp Leu Ala Ala Arg Ala Lys Ile
    210                 215                 220 cca aag cag gac gtc tcc ccc tac gcc gtc gcc ccc tgc ctc cac aag       720
Pro Lys Gln Asp Val Ser Pro Tyr Ala Val Ala Pro Cys Leu His Lys
225                 230                 235                 240
```

```
                                                            -continued acc aag ctc aac gaa aag gag atg cag acc ctc gtc gac aag gac tgg     768
Thr Lys Leu Asn Glu Lys Glu Met Gln Thr Leu Val Asp Lys Asp Trp
                245                 250                 255 gca tcc gtc ttt ggc tcc aag aac ggc atg ccg gaa atc aac tac aaa     816
Ala Ser Val Phe Gly Ser Lys Asn Gly Met Pro Glu Ile Asn Tyr Lys
            260                 265                 270 ctc tgc gcg cgt aag atg ctc atg att gac cgc gtc acc agc att gac     864
Leu Cys Ala Arg Lys Met Leu Met Ile Asp Arg Val Thr Ser Ile Asp
        275                 280                 285 cac aag ggc ggt gtc tac ggc ctc ggt cag ctc gtc ggt gaa aag atc     912
His Lys Gly Gly Val Tyr Gly Leu Gly Gln Leu Val Gly Glu Lys Ile
    290                 295                 300 ctc gag cgc gac cac tgg tac ttt ccc tgc cac ttt gtc aag gat cag     960
Leu Glu Arg Asp His Trp Tyr Phe Pro Cys His Phe Val Lys Asp Gln
305                 310                 315                 320 gtc atg gcc gga tcc ctc gtc tcc gac ggc tgc agc cag atg ctc aag    1008
Val Met Ala Gly Ser Leu Val Ser Asp Gly Cys Ser Gln Met Leu Lys
                325                 330                 335 atg tac atg atc tgg ctc ggc ctc cac ctc acc acc gga ccc ttt gac    1056
Met Tyr Met Ile Trp Leu Gly Leu His Leu Thr Thr Gly Pro Phe Asp
            340                 345                 350 ttc cgc ccg gtc aac ggc cac ccc aac aag gtc cgc tgc cgc ggc caa    1104
Phe Arg Pro Val Asn Gly His Pro Asn Lys Val Arg Cys Arg Gly Gln
        355                 360                 365 atc tcc ccg cac aag ggc aag ctc gtc tac gtc atg gag atc aag gag    1152
Ile Ser Pro His Lys Gly Lys Leu Val Tyr Val Met Glu Ile Lys Glu
    370                 375                 380 atg ggc ttc gac gag gac aac gac ccg tac gcc att gcc gac gtc aac    1200
Met Gly Phe Asp Glu Asp Asn Asp Pro Tyr Ala Ile Ala Asp Val Asn
385                 390                 395                 400 atc att gat gtc gac ttc gaa aag ggc cag gac ttt agc ctc gac cgc    1248
Ile Ile Asp Val Asp Phe Glu Lys Gly Gln Asp Phe Ser Leu Asp Arg
                405                 410                 415 atc agc gac tac ggc aag ggc gac ctc aac aag aag atc gtc gtc gac    1296
Ile Ser Asp Tyr Gly Lys Gly Asp Leu Asn Lys Lys Ile Val Val Asp
            420                 425                 430 ttt aag ggc atc gct ctc aag atg cag aag cgc tcc acc aac aag aac    1344
Phe Lys Gly Ile Ala Leu Lys Met Gln Lys Arg Ser Thr Asn Lys Asn
        435                 440                 445 ccc tcc aag gtt cag ccc gtc ttt gcc aac ggc gcc gcc act gtc ggc    1392
Pro Ser Lys Val Gln Pro Val Phe Ala Asn Gly Ala Ala Thr Val Gly
    450                 455                 460 ccc gag gcc tcc aag gct tcc tcc ggc gcc agc gcc agc gcc agc gcc    1440
Pro Glu Ala Ser Lys Ala Ser Ser Gly Ala Ser Ala Ser Ala Ser Ala
465                 470                 475                 480 gcc ccg gcc aag cct gcc ttc agc gcc gat gtt ctt gcg ccc aag ccc    1488
Ala Pro Ala Lys Pro Ala Phe Ser Ala Asp Val Leu Ala Pro Lys Pro
                485                 490                 495 gtt gcc ctt ccc gag cac atc ctc aag ggc gac gcc ctc gcc ccc aag    1536
Val Ala Leu Pro Glu His Ile Leu Lys Gly Asp Ala Leu Ala Pro Lys
            500                 505                 510 gag atg tcc tgg cac ccc atg gcc cgc atc ccg ggc aac ccg acg ccc    1584
Glu Met Ser Trp His Pro Met Ala Arg Ile Pro Gly Asn Pro Thr Pro
        515                 520                 525 tct ttt gcg ccc tcg gcc tac aag ccg cgc aac atc gcc ttt acg ccc    1632
Ser Phe Ala Pro Ser Ala Tyr Lys Pro Arg Asn Ile Ala Phe Thr Pro
    530                 535                 540 ttc ccc ggc aac ccc aac gat aac gac cac acc ccg ggc aag atg ccg    1680
Phe Pro Gly Asn Pro Asn Asp Asn Asp His Thr Pro Gly Lys Met Pro
545                 550                 555                 560
```

| | |
|---|---|
| ctc acc tgg ttc aac atg gcc gag ttc atg gcc ggc aag gtc agc atg<br>Leu Thr Trp Phe Asn Met Ala Glu Phe Met Ala Gly Lys Val Ser Met<br>              565                      570                    575 | 1728 |
| tgc ctc ggc ccc gag ttc gcc aag ttc gac gac tcg aac acc agc cgc<br>Cys Leu Gly Pro Glu Phe Ala Lys Phe Asp Asp Ser Asn Thr Ser Arg<br>        580                      585                    590 | 1776 |
| agc ccc gct tgg gac ctc gct ctc gtc acc cgc gcc gtg tct gtg tct<br>Ser Pro Ala Trp Asp Leu Ala Leu Val Thr Arg Ala Val Ser Val Ser<br>            595                      600                    605 | 1824 |
| gac ctc aag cac gtc aac tac cgc aac atc gac ctc gac ccc tcc aag<br>Asp Leu Lys His Val Asn Tyr Arg Asn Ile Asp Leu Asp Pro Ser Lys<br>610                      615                      620 | 1872 |
| ggt acc atg gtc ggc gag ttc gac tgc ccc gcg gac gcc tgg ttc tac<br>Gly Thr Met Val Gly Glu Phe Asp Cys Pro Ala Asp Ala Trp Phe Tyr<br>625                      630                    635                  640 | 1920 |
| aag ggc gcc tgc aac gat gcc cac atg ccg tac tcg atc ctc atg gag<br>Lys Gly Ala Cys Asn Asp Ala His Met Pro Tyr Ser Ile Leu Met Glu<br>                645                      650                    655 | 1968 |
| atc gcc ctc cag acc tcg ggt gtg ctc acc tcg gtg ctc aag gcg ccc<br>Ile Ala Leu Gln Thr Ser Gly Val Leu Thr Ser Val Leu Lys Ala Pro<br>            660                      665                    670 | 2016 |
| ctg acc atg gag aag gac gac atc ctc ttc cgc aac ctc gac gcc aac<br>Leu Thr Met Glu Lys Asp Asp Ile Leu Phe Arg Asn Leu Asp Ala Asn<br>        675                      680                    685 | 2064 |
| gcc gag ttc gtg cgc gcc gac ctc gac tac cgc ggc aag act atc cgc<br>Ala Glu Phe Val Arg Ala Asp Leu Asp Tyr Arg Gly Lys Thr Ile Arg<br>690                      695                      700 | 2112 |
| aac gtc acc aag tgc act ggc tac agc atg ctc ggc gag atg ggc gtc<br>Asn Val Thr Lys Cys Thr Gly Tyr Ser Met Leu Gly Glu Met Gly Val<br>705                      710                    715                  720 | 2160 |
| cac cgc ttc acc ttt gag ctc tac gtc gat gat gtg ctc ttt tac aag<br>His Arg Phe Thr Phe Glu Leu Tyr Val Asp Asp Val Leu Phe Tyr Lys<br>                725                      730                    735 | 2208 |
| ggc tcg acc tcg ttc ggc tgg ttc gtg ccc gag gtc ttt gcc gcc cag<br>Gly Ser Thr Ser Phe Gly Trp Phe Val Pro Glu Val Phe Ala Ala Gln<br>            740                      745                    750 | 2256 |
| gcc ggc ctc gac aac ggc cgc aag tcg gag ccc tgg ttc att gag aac<br>Ala Gly Leu Asp Asn Gly Arg Lys Ser Glu Pro Trp Phe Ile Glu Asn<br>        755                      760                    765 | 2304 |
| aag gtt ccg gcc tcg cag gtc tcc tcc ttt gac gtg cgc ccc aac ggc<br>Lys Val Pro Ala Ser Gln Val Ser Ser Phe Asp Val Arg Pro Asn Gly<br>        770                      775                    780 | 2352 |
| agc ggc cgc acc gcc atc ttc gcc aac gcc ccc agc ggc gcc cag ctc<br>Ser Gly Arg Thr Ala Ile Phe Ala Asn Ala Pro Ser Gly Ala Gln Leu<br>785                      790                    795                  800 | 2400 |
| aac cgc cgc acg gac cag ggc cag tac ctc gac gcc gtc gac att gtc<br>Asn Arg Arg Thr Asp Gln Gly Gln Tyr Leu Asp Ala Val Asp Ile Val<br>                805                      810                    815 | 2448 |
| tcc ggc agc ggc aag aag agc ctc ggc tac gcc cac ggt tcc aag acg<br>Ser Gly Ser Gly Lys Lys Ser Leu Gly Tyr Ala His Gly Ser Lys Thr<br>            820                      825                    830 | 2496 |
| gtc aac ccg aac gac tgg ttc ttc tcg tgc cac ttt tgg ttt gac tcg<br>Val Asn Pro Asn Asp Trp Phe Phe Ser Cys His Phe Trp Phe Asp Ser<br>        835                      840                    845 | 2544 |
| gtc atg ccc gga agt ctc ggt gtc gag tcc atg ttc cag ctc gtc gag<br>Val Met Pro Gly Ser Leu Gly Val Glu Ser Met Phe Gln Leu Val Glu<br>850                      855                      860 | 2592 |
| gcc atc gcc gcc cac gag gat ctc gct ggc aag cac ggc att gcc aac<br>Ala Ile Ala Ala His Glu Asp Leu Ala Gly Lys His Gly Ile Ala Asn<br>865                      870                    875                  880 | 2640 |

```
ccc acc ttt gtg cac gcc ccg ggc aag atc agc tgg aag tac cgc ggc      2688
Pro Thr Phe Val His Ala Pro Gly Lys Ile Ser Trp Lys Tyr Arg Gly
            885                 890                 895 cag ctc acg ccc aag agc aag aag atg gac tcg gag gtc cac atc gtg      2736
Gln Leu Thr Pro Lys Ser Lys Lys Met Asp Ser Glu Val His Ile Val
        900                 905                 910 tcc gtg gac gcc cac gac ggc gtt gtc gac ctc gtc gcc gac ggc ttc      2784
Ser Val Asp Ala His Asp Gly Val Val Asp Leu Val Ala Asp Gly Phe
    915                 920                 925 ctc tgg gcc gac agc ctc cgc gtc tac tcg gtg agc aac att cgc gtg      2832
Leu Trp Ala Asp Ser Leu Arg Val Tyr Ser Val Ser Asn Ile Arg Val
930                 935                 940 cgc atc gcc tcc ggt gag gcc cct gcc gcc gcc tcc tcc gcc gcc tct      2880
Arg Ile Ala Ser Gly Glu Ala Pro Ala Ala Ala Ser Ser Ala Ala Ser
945                 950                 955                 960 gtg ggc tcc tcg gct tcg tcc gtc gag cgc acg cgc tcg agc ccc gct      2928
Val Gly Ser Ser Ala Ser Ser Val Glu Arg Thr Arg Ser Ser Pro Ala
            965                 970                 975 gtc gcc tcc ggc ccg gcc cag acc atc gac ctc aag cag ctc aag acc      2976
Val Ala Ser Gly Pro Ala Gln Thr Ile Asp Leu Lys Gln Leu Lys Thr
        980                 985                 990 gag ctc ctc gag ctc gat gcc ccg ctc tac ctc tcg cag gac ccg acc      3024
Glu Leu Leu Glu Leu Asp Ala Pro Leu Tyr Leu Ser Gln Asp Pro Thr
    995                 1000                1005 agc ggc cag ctc aag aag cac acc gac gtg gcc tcc ggc cag gcc          3069
Ser Gly Gln Leu Lys Lys His Thr Asp Val Ala Ser Gly Gln Ala
    1010                1015                1020 acc atc gtg cag ccc tgc acg ctc ggc gac ctc ggt gac cgc tcc          3114
Thr Ile Val Gln Pro Cys Thr Leu Gly Asp Leu Gly Asp Arg Ser
1025                1030                1035 ttc atg gag acc tac ggc gtc gtc gcc ccg ctg tac acg ggc gcc          3159
Phe Met Glu Thr Tyr Gly Val Val Ala Pro Leu Tyr Thr Gly Ala
    1040                1045                1050 atg gcc aag ggc att gcc tcg gcg gac ctc gtc atc gcc gcc ggc          3204
Met Ala Lys Gly Ile Ala Ser Ala Asp Leu Val Ile Ala Ala Gly
    1055                1060                1065 aag cgc aag atc ctc ggc tcc ttt ggc gcc ggc ggc ctc ccc atg          3249
Lys Arg Lys Ile Leu Gly Ser Phe Gly Ala Gly Gly Leu Pro Met
1070                1075                1080 cac cac gtg cgc gcc gcc ctc gag aag atc cag gcc gcc ctg cct          3294
His His Val Arg Ala Ala Leu Glu Lys Ile Gln Ala Ala Leu Pro
    1085                1090                1095 cag ggc ccc tac gcc gtc aac ctc atc cac tcg cct ttt gac agc          3339
Gln Gly Pro Tyr Ala Val Asn Leu Ile His Ser Pro Phe Asp Ser
    1100                1105                1110 aac ctc gag aag ggc aac gtc gat ctc ttc ctc gag aag ggc gtc          3384
Asn Leu Glu Lys Gly Asn Val Asp Leu Phe Leu Glu Lys Gly Val
1115                1120                1125 act gtg gtg gag gcc tcg gca ttc atg acc ctc acc ccg cag gtc          3429
Thr Val Val Glu Ala Ser Ala Phe Met Thr Leu Thr Pro Gln Val
    1130                1135                1140 gtg cgc tac cgc gcc gcc ggc ctc tcg cgc aac gcc gac ggt tcg          3474
Val Arg Tyr Arg Ala Ala Gly Leu Ser Arg Asn Ala Asp Gly Ser
    1145                1150                1155 gtc aac atc cgc aac cgc atc atc ggc aag gtc tcg cgc acc gag          3519
Val Asn Ile Arg Asn Arg Ile Ile Gly Lys Val Ser Arg Thr Glu
1160                1165                1170 ctc gcc gag atg ttc atc cgc ccg gcc ccg gag cac ctc ctc gag          3564
Leu Ala Glu Met Phe Ile Arg Pro Ala Pro Glu His Leu Leu Glu
    1175                1180                1185
```

```
aag ctc atc gcc tcg ggc gag atc acc cag gag cag gcc gag ctc      3609
Lys Leu Ile Ala Ser Gly Glu Ile Thr Gln Glu Gln Ala Glu Leu
    1190            1195                1200 gcg cgc cgc gtt ccc gtc gcc gac gat atc gct gtc gag gct gac      3654
Ala Arg Arg Val Pro Val Ala Asp Asp Ile Ala Val Glu Ala Asp
    1205            1210                1215 tcg ggc ggc cac acc gac aac cgc ccc atc cac gtc atc ctc ccg      3699
Ser Gly Gly His Thr Asp Asn Arg Pro Ile His Val Ile Leu Pro
    1220            1225                1230 ctc atc atc aac ctc cgc aac cgc ctg cac cgc gag tgc ggc tac      3744
Leu Ile Ile Asn Leu Arg Asn Arg Leu His Arg Glu Cys Gly Tyr
    1235            1240                1245 ccc gcg cac ctc cgc gtc cgc gtt ggc gcc ggc ggt ggc gtc ggc      3789
Pro Ala His Leu Arg Val Arg Val Gly Ala Gly Gly Gly Val Gly
    1250            1255                1260 tgc ccg cag gcc gcc gcc gcc gcg ctc acc atg ggc gcc gcc ttc      3834
Cys Pro Gln Ala Ala Ala Ala Ala Leu Thr Met Gly Ala Ala Phe
    1265            1270                1275 atc gtc acc ggc act gtc aac cag gtc gcc aag cag tcc ggc acc      3879
Ile Val Thr Gly Thr Val Asn Gln Val Ala Lys Gln Ser Gly Thr
    1280            1285                1290 tgc gac aac gtg cgc aag cag ctc tcg cag gcc acc tac tcg gat      3924
Cys Asp Asn Val Arg Lys Gln Leu Ser Gln Ala Thr Tyr Ser Asp
    1295            1300                1305 atc tgc atg gcc ccg gcc gcc gac atg ttc gag gag ggc gtc aag      3969
Ile Cys Met Ala Pro Ala Ala Asp Met Phe Glu Glu Gly Val Lys
    1310            1315                1320 ctc cag gtc ctc aag aag gga acc atg ttc ccc tcg cgc gcc aac      4014
Leu Gln Val Leu Lys Lys Gly Thr Met Phe Pro Ser Arg Ala Asn
    1325            1330                1335 aag ctc tac gag ctc ttt tgc aag tac gac tcc ttc gac tcc atg      4059
Lys Leu Tyr Glu Leu Phe Cys Lys Tyr Asp Ser Phe Asp Ser Met
    1340            1345                1350 cct cct gcc gag ctc gag cgc atc gag aag cgt atc ttc aag cgc      4104
Pro Pro Ala Glu Leu Glu Arg Ile Glu Lys Arg Ile Phe Lys Arg
    1355            1360                1365 gca ctc cag gag gtc tgg gag gag acc aag gac ttt tac att aac      4149
Ala Leu Gln Glu Val Trp Glu Glu Thr Lys Asp Phe Tyr Ile Asn
    1370            1375                1380 ggt ctc aag aac ccg gag aag atc cag cgc gcc gag cac gac ccc      4194
Gly Leu Lys Asn Pro Glu Lys Ile Gln Arg Ala Glu His Asp Pro
    1385            1390                1395 aag ctc aag atg tcg ctc tgc ttc cgc tgg tac ctt ggt ctt gcc      4239
Lys Leu Lys Met Ser Leu Cys Phe Arg Trp Tyr Leu Gly Leu Ala
    1400            1405                1410 agc cgc tgg gcc aac atg ggc gcc ccg gac cgc gtc atg gac tac      4284
Ser Arg Trp Ala Asn Met Gly Ala Pro Asp Arg Val Met Asp Tyr
    1415            1420                1425 cag gtc tgg tgt ggc ccg gcc att ggc gcc ttc aac gac ttc atc      4329
Gln Val Trp Cys Gly Pro Ala Ile Gly Ala Phe Asn Asp Phe Ile
    1430            1435                1440 aag ggc acc tac ctc gac ccc gct gtc tcc aac gag tac ccc tgt      4374
Lys Gly Thr Tyr Leu Asp Pro Ala Val Ser Asn Glu Tyr Pro Cys
    1445            1450                1455 gtc gtc cag atc aac ctg caa atc ctc cgt ggt gcc tgc tac ctg      4419
Val Val Gln Ile Asn Leu Gln Ile Leu Arg Gly Ala Cys Tyr Leu
    1460            1465                1470 cgc cgt ctc aac gcc ctg cgc aac gac ccg cgc att gac ctc gag      4464
Arg Arg Leu Asn Ala Leu Arg Asn Asp Pro Arg Ile Asp Leu Glu
    1475            1480                1485
```

| acc | gag | gat | gct | gcc | ttt | gtc | tac | gag | ccc | acc | aac | gcg | ctc | 4506 |
| Thr | Glu | Asp | Ala | Ala | Phe | Val | Tyr | Glu | Pro | Thr | Asn | Ala | Leu | |
| | 1490 | | | | 1495 | | | | | 1500 | | | | |

<210> SEQ ID NO 6
<211> LENGTH: 1502
<212> TYPE: PRT
<213> ORGANISM: Schizochytrium sp.

<400> SEQUENCE: 6

```
Met Ala Leu Arg Val Lys Thr Asn Lys Lys Pro Cys Trp Glu Met Thr
1               5                   10                  15

Lys Glu Glu Leu Thr Ser Gly Lys Thr Glu Val Phe Asn Tyr Glu Glu
            20                  25                  30

Leu Leu Glu Phe Ala Glu Gly Asp Ile Ala Lys Val Phe Gly Pro Glu
        35                  40                  45

Phe Ala Val Ile Asp Lys Tyr Pro Arg Arg Val Arg Leu Pro Ala Arg
    50                  55                  60

Glu Tyr Leu Leu Val Thr Arg Val Thr Leu Met Asp Ala Glu Val Asn
65                  70                  75                  80

Asn Tyr Arg Val Gly Ala Arg Met Val Thr Glu Tyr Asp Leu Pro Val
                85                  90                  95

Asn Gly Glu Leu Ser Glu Gly Gly Asp Cys Pro Trp Ala Val Leu Val
            100                 105                 110

Glu Ser Gly Gln Cys Asp Leu Met Leu Ile Ser Tyr Met Gly Ile Asp
        115                 120                 125

Phe Gln Asn Gln Gly Asp Arg Val Tyr Arg Leu Leu Asn Thr Thr Leu
    130                 135                 140

Thr Phe Tyr Gly Val Ala His Glu Gly Glu Thr Leu Glu Tyr Asp Ile
145                 150                 155                 160

Arg Val Thr Gly Phe Ala Lys Arg Leu Asp Gly Gly Ile Ser Met Phe
                165                 170                 175

Phe Phe Glu Tyr Asp Cys Tyr Val Asn Gly Arg Leu Leu Ile Glu Met
            180                 185                 190

Arg Asp Gly Cys Ala Gly Phe Phe Thr Asn Glu Glu Leu Asp Ala Gly
        195                 200                 205

Lys Gly Val Val Phe Thr Arg Gly Asp Leu Ala Ala Arg Ala Lys Ile
    210                 215                 220

Pro Lys Gln Asp Val Ser Pro Tyr Ala Val Ala Pro Cys Leu His Lys
225                 230                 235                 240

Thr Lys Leu Asn Glu Lys Glu Met Gln Thr Leu Val Asp Lys Asp Trp
                245                 250                 255

Ala Ser Val Phe Gly Ser Lys Asn Gly Met Pro Glu Ile Asn Tyr Lys
            260                 265                 270

Leu Cys Ala Arg Lys Met Leu Met Ile Asp Arg Val Thr Ser Ile Asp
        275                 280                 285

His Lys Gly Gly Val Tyr Gly Leu Gly Gln Leu Val Gly Glu Lys Ile
    290                 295                 300

Leu Glu Arg Asp His Trp Tyr Phe Pro Cys His Phe Val Lys Asp Gln
305                 310                 315                 320

Val Met Ala Gly Ser Leu Val Ser Asp Gly Cys Ser Gln Met Leu Lys
                325                 330                 335

Met Tyr Met Ile Trp Leu Gly Leu His Leu Thr Thr Gly Pro Phe Asp
            340                 345                 350

Phe Arg Pro Val Asn Gly His Pro Asn Lys Val Arg Cys Arg Gly Gln
```

```
            355                 360                 365
Ile Ser Pro His Lys Gly Lys Leu Val Tyr Val Met Glu Ile Lys Glu
            370                 375                 380

Met Gly Phe Asp Glu Asp Asn Asp Pro Tyr Ala Ile Ala Asp Val Asn
385                 390                 395                 400

Ile Ile Asp Val Asp Phe Glu Lys Gly Gln Asp Phe Ser Leu Asp Arg
                405                 410                 415

Ile Ser Asp Tyr Gly Lys Gly Asp Leu Asn Lys Lys Ile Val Val Asp
                420                 425                 430

Phe Lys Gly Ile Ala Leu Lys Met Gln Lys Arg Ser Thr Asn Lys Asn
            435                 440                 445

Pro Ser Lys Val Gln Pro Val Phe Ala Asn Gly Ala Ala Thr Val Gly
            450                 455                 460

Pro Glu Ala Ser Lys Ala Ser Ser Gly Ala Ser Ala Ser Ala Ser Ala
465                 470                 475                 480

Ala Pro Ala Lys Pro Ala Phe Ser Ala Asp Val Leu Ala Pro Lys Pro
                485                 490                 495

Val Ala Leu Pro Glu His Ile Leu Lys Gly Asp Ala Leu Ala Pro Lys
            500                 505                 510

Glu Met Ser Trp His Pro Met Ala Arg Ile Pro Gly Asn Pro Thr Pro
            515                 520                 525

Ser Phe Ala Pro Ser Ala Tyr Lys Pro Arg Asn Ile Ala Phe Thr Pro
            530                 535                 540

Phe Pro Gly Asn Pro Asn Asp Asn Asp His Thr Pro Gly Lys Met Pro
545                 550                 555                 560

Leu Thr Trp Phe Asn Met Ala Glu Phe Met Ala Gly Lys Val Ser Met
                565                 570                 575

Cys Leu Gly Pro Glu Phe Ala Lys Phe Asp Asp Ser Asn Thr Ser Arg
                580                 585                 590

Ser Pro Ala Trp Asp Leu Ala Leu Val Thr Arg Ala Val Ser Val Ser
            595                 600                 605

Asp Leu Lys His Val Asn Tyr Arg Asn Ile Asp Leu Asp Pro Ser Lys
            610                 615                 620

Gly Thr Met Val Gly Glu Phe Asp Cys Pro Ala Asp Ala Trp Phe Tyr
625                 630                 635                 640

Lys Gly Ala Cys Asn Asp Ala His Met Pro Tyr Ser Ile Leu Met Glu
                645                 650                 655

Ile Ala Leu Gln Thr Ser Gly Val Leu Thr Ser Val Leu Lys Ala Pro
                660                 665                 670

Leu Thr Met Glu Lys Asp Asp Ile Leu Phe Arg Asn Leu Asp Ala Asn
            675                 680                 685

Ala Glu Phe Val Arg Ala Asp Leu Asp Tyr Arg Gly Lys Thr Ile Arg
            690                 695                 700

Asn Val Thr Lys Cys Thr Gly Tyr Ser Met Leu Gly Glu Met Gly Val
705                 710                 715                 720

His Arg Phe Thr Phe Glu Leu Tyr Val Asp Asp Val Leu Phe Tyr Lys
                725                 730                 735

Gly Ser Thr Ser Phe Gly Trp Phe Val Pro Glu Val Phe Ala Ala Gln
                740                 745                 750

Ala Gly Leu Asp Asn Gly Arg Lys Ser Glu Pro Trp Phe Ile Glu Asn
            755                 760                 765

Lys Val Pro Ala Ser Gln Val Ser Ser Phe Asp Val Arg Pro Asn Gly
            770                 775                 780
```

-continued

Ser Gly Arg Thr Ala Ile Phe Ala Asn Ala Pro Ser Gly Ala Gln Leu
785                 790                 795                 800

Asn Arg Arg Thr Asp Gln Gly Gln Tyr Leu Asp Ala Val Asp Ile Val
            805                 810                 815

Ser Gly Ser Gly Lys Lys Ser Leu Gly Tyr Ala His Gly Ser Lys Thr
        820                 825                 830

Val Asn Pro Asn Asp Trp Phe Phe Ser Cys His Phe Trp Phe Asp Ser
    835                 840                 845

Val Met Pro Gly Ser Leu Gly Val Glu Ser Met Phe Gln Leu Val Glu
850                 855                 860

Ala Ile Ala Ala His Glu Asp Leu Ala Gly Lys His Gly Ile Ala Asn
865                 870                 875                 880

Pro Thr Phe Val His Ala Pro Gly Lys Ile Ser Trp Lys Tyr Arg Gly
                885                 890                 895

Gln Leu Thr Pro Lys Ser Lys Lys Met Asp Ser Glu Val His Ile Val
                900                 905                 910

Ser Val Asp Ala His Asp Gly Val Val Asp Leu Val Ala Asp Gly Phe
            915                 920                 925

Leu Trp Ala Asp Ser Leu Arg Val Tyr Ser Val Ser Asn Ile Arg Val
930                 935                 940

Arg Ile Ala Ser Gly Glu Ala Pro Ala Ala Ser Ser Ala Ala Ser
945                 950                 955                 960

Val Gly Ser Ser Ala Ser Ser Val Glu Arg Thr Arg Ser Ser Pro Ala
            965                 970                 975

Val Ala Ser Gly Pro Ala Gln Thr Ile Asp Leu Lys Gln Leu Lys Thr
            980                 985                 990

Glu Leu Leu Glu Leu Asp Ala Pro Leu Tyr Leu Ser Gln Asp Pro Thr
            995                1000                 1005

Ser Gly Gln Leu Lys Lys His Thr Asp Val Ala Ser Gly Gln Ala
        1010                1015                1020

Thr Ile Val Gln Pro Cys Thr Leu Gly Asp Leu Gly Asp Arg Ser
        1025                1030                1035

Phe Met Glu Thr Tyr Gly Val Val Ala Pro Leu Tyr Thr Gly Ala
        1040                1045                1050

Met Ala Lys Gly Ile Ala Ser Ala Asp Leu Val Ile Ala Ala Gly
        1055                1060                1065

Lys Arg Lys Ile Leu Gly Ser Phe Gly Ala Gly Leu Pro Met
        1070                1075                1080

His His Val Arg Ala Ala Leu Glu Lys Ile Gln Ala Ala Leu Pro
        1085                1090                1095

Gln Gly Pro Tyr Ala Val Asn Leu Ile His Ser Pro Phe Asp Ser
        1100                1105                1110

Asn Leu Glu Lys Gly Asn Val Asp Leu Phe Leu Glu Lys Gly Val
        1115                1120                1125

Thr Val Val Glu Ala Ser Ala Phe Met Thr Leu Thr Pro Gln Val
        1130                1135                1140

Val Arg Tyr Arg Ala Ala Gly Leu Ser Arg Asn Ala Asp Gly Ser
        1145                1150                1155

Val Asn Ile Arg Asn Arg Ile Ile Gly Lys Val Ser Arg Thr Glu
        1160                1165                1170

Leu Ala Glu Met Phe Ile Arg Pro Ala Pro Glu His Leu Leu Glu
        1175                1180                1185

Lys Leu Ile Ala Ser Gly Glu Ile Thr Gln Glu Gln Ala Glu Leu
        1190                1195                1200

| Ala | Arg | Arg | Val | Pro | Val | Asp | Asp | Ile | Ala | Val | Glu | Ala | Asp |
|  | 1205 |  |  |  | 1210 |  |  |  |  | 1215 |  |  |  |

Ala Arg Arg Val Pro Val Asp Asp Ile Ala Val Glu Ala Asp
    1205                1210                1215

Ser Gly Gly His Thr Asp Asn Arg Pro Ile His Val Ile Leu Pro
    1220                1225                1230

Leu Ile Ile Asn Leu Arg Asn Arg Leu His Arg Glu Cys Gly Tyr
    1235                1240                1245

Pro Ala His Leu Arg Val Arg Val Gly Ala Gly Gly Gly Val Gly
    1250                1255                1260

Cys Pro Gln Ala Ala Ala Ala Leu Thr Met Gly Ala Ala Phe
    1265                1270                1275

Ile Val Thr Gly Thr Val Asn Gln Val Ala Lys Gln Ser Gly Thr
    1280                1285                1290

Cys Asp Asn Val Arg Lys Gln Leu Ser Gln Ala Thr Tyr Ser Asp
    1295                1300                1305

Ile Cys Met Ala Pro Ala Ala Asp Met Phe Glu Glu Gly Val Lys
    1310                1315                1320

Leu Gln Val Leu Lys Lys Gly Thr Met Phe Pro Ser Arg Ala Asn
    1325                1330                1335

Lys Leu Tyr Glu Leu Phe Cys Lys Tyr Asp Ser Phe Asp Ser Met
    1340                1345                1350

Pro Pro Ala Glu Leu Glu Arg Ile Glu Lys Arg Ile Phe Lys Arg
    1355                1360                1365

Ala Leu Gln Glu Val Trp Glu Thr Lys Asp Phe Tyr Ile Asn
    1370                1375                1380

Gly Leu Lys Asn Pro Glu Lys Ile Gln Arg Ala Glu His Asp Pro
    1385                1390                1395

Lys Leu Lys Met Ser Leu Cys Phe Arg Trp Tyr Leu Gly Leu Ala
    1400                1405                1410

Ser Arg Trp Ala Asn Met Gly Ala Pro Asp Arg Val Met Asp Tyr
    1415                1420                1425

Gln Val Trp Cys Gly Pro Ala Ile Gly Ala Phe Asn Asp Phe Ile
    1430                1435                1440

Lys Gly Thr Tyr Leu Asp Pro Ala Val Ser Asn Glu Tyr Pro Cys
    1445                1450                1455

Val Val Gln Ile Asn Leu Gln Ile Leu Arg Gly Ala Cys Tyr Leu
    1460                1465                1470

Arg Arg Leu Asn Ala Leu Arg Asn Asp Pro Arg Ile Asp Leu Glu
    1475                1480                1485

Thr Glu Asp Ala Ala Phe Val Tyr Glu Pro Thr Asn Ala Leu
    1490                1495                1500

<210> SEQ ID NO 7
<211> LENGTH: 1500
<212> TYPE: DNA
<213> ORGANISM: Schizochytrium sp.
<220> FEATURE:
<221> NAME/KEY: CDS
<222> LOCATION: (1)..(1500)

<400> SEQUENCE: 7

```
atg gcg gcc cgt ctg cag gag caa aag gga ggc gag atg gat acc cgc      48
Met Ala Ala Arg Leu Gln Glu Gln Lys Gly Gly Glu Met Asp Thr Arg
1               5                   10                  15 att gcc atc atc ggc atg tcg gcc atc ctc ccc tgc ggc acg acc gtg      96
Ile Ala Ile Ile Gly Met Ser Ala Ile Leu Pro Cys Gly Thr Thr Val
            20                  25                  30
```

```
cgc gag tcg tgg gag acc atc cgc gcc ggc atc gac tgc ctg tcg gat    144
Arg Glu Ser Trp Glu Thr Ile Arg Ala Gly Ile Asp Cys Leu Ser Asp
         35                  40                  45 ctc ccc gag gac cgc gtc gac gtg acg gcg tac ttt gac ccc gtc aag    192
Leu Pro Glu Asp Arg Val Asp Val Thr Ala Tyr Phe Asp Pro Val Lys
 50                  55                  60 acc acc aag gac aag atc tac tgc aag cgc ggt ggc ttc att ccc gag    240
Thr Thr Lys Asp Lys Ile Tyr Cys Lys Arg Gly Gly Phe Ile Pro Glu
65                  70                  75                  80 tac gac ttt gac gcc cgc gag ttc gga ctc aac atg ttc cag atg gag    288
Tyr Asp Phe Asp Ala Arg Glu Phe Gly Leu Asn Met Phe Gln Met Glu
             85                  90                  95 gac tcg gac gca aac cag acc atc tcg ctt ctc aag gtc aag gag gcc    336
Asp Ser Asp Ala Asn Gln Thr Ile Ser Leu Leu Lys Val Lys Glu Ala
         100                 105                 110 ctc cag gac gcc ggc atc gac gcc ctc ggc aag gaa aag aag aac atc    384
Leu Gln Asp Ala Gly Ile Asp Ala Leu Gly Lys Glu Lys Lys Asn Ile
     115                 120                 125 ggc tgc gtg ctc ggc att ggc ggc ggc caa aag tcc agc cac gag ttc    432
Gly Cys Val Leu Gly Ile Gly Gly Gly Gln Lys Ser Ser His Glu Phe
130                 135                 140 tac tcg cgc ctt aat tat gtt gtc gtg gag aag gtc ctc cgc aag atg    480
Tyr Ser Arg Leu Asn Tyr Val Val Val Glu Lys Val Leu Arg Lys Met
145                 150                 155                 160 ggc atg ccc gag gag gac gtc aag gtc gcc gtc gaa aag tac aag gcc    528
Gly Met Pro Glu Glu Asp Val Lys Val Ala Val Glu Lys Tyr Lys Ala
                165                 170                 175 aac ttc ccc gag tgg cgc ctc gac tcc ttc cct ggc ttc ctc ggc aac    576
Asn Phe Pro Glu Trp Arg Leu Asp Ser Phe Pro Gly Phe Leu Gly Asn
            180                 185                 190 gtc acc gcc ggt cgc tgc acc aac acc ttc aac ctc gac ggc atg aac    624
Val Thr Ala Gly Arg Cys Thr Asn Thr Phe Asn Leu Asp Gly Met Asn
        195                 200                 205 tgc gtt gtc gac gcc gca tgc gcc tcg tcc ctc atc gcc gtc aag gtc    672
Cys Val Val Asp Ala Ala Cys Ala Ser Ser Leu Ile Ala Val Lys Val
210                 215                 220 gcc atc gac gag ctg ctc tac ggt gac tgc gac atg atg gtc acc ggt    720
Ala Ile Asp Glu Leu Leu Tyr Gly Asp Cys Asp Met Met Val Thr Gly
225                 230                 235                 240 gcc acc tgc acg gat aac tcc atc ggc atg tac atg gcc ttc tcc aag    768
Ala Thr Cys Thr Asp Asn Ser Ile Gly Met Tyr Met Ala Phe Ser Lys
                245                 250                 255 acc ccc gtg ttc tcc acg gac ccc agc gtg cgc gcc tac gac gaa aag    816
Thr Pro Val Phe Ser Thr Asp Pro Ser Val Arg Ala Tyr Asp Glu Lys
            260                 265                 270 aca aag ggc atg ctc atc ggc gag ggc tcc gcc atg ctc gtc ctc aag    864
Thr Lys Gly Met Leu Ile Gly Glu Gly Ser Ala Met Leu Val Leu Lys
        275                 280                 285 cgc tac gcc gac gcc gtc cgc gac ggc gat gag atc cac gct gtt att    912
Arg Tyr Ala Asp Ala Val Arg Asp Gly Asp Glu Ile His Ala Val Ile
290                 295                 300 cgc ggc tgc gcc tcc tcc agt gat ggc aag gcc gcc ggc atc tac acg    960
Arg Gly Cys Ala Ser Ser Ser Asp Gly Lys Ala Ala Gly Ile Tyr Thr
305                 310                 315                 320 ccc acc att tcg ggc cag gag gag gcc ctc cgc cgc gcc tac aac cgc    1008
Pro Thr Ile Ser Gly Gln Glu Glu Ala Leu Arg Arg Ala Tyr Asn Arg
                325                 330                 335 gcc tgt gtc gac ccg gcc acc gtc act ctc gtc gag ggt cac ggc acc    1056
Ala Cys Val Asp Pro Ala Thr Val Thr Leu Val Glu Gly His Gly Thr
            340                 345                 350
```

```
ggt act ccc gtt ggc gac cgc atc gag ctc acc gcc ttg cgc aac ctc      1104
Gly Thr Pro Val Gly Asp Arg Ile Glu Leu Thr Ala Leu Arg Asn Leu
        355                 360                 365 ttt gac aag gcc tac ggc gag ggc aac acc gaa aag gtc gct gtg ggc      1152
Phe Asp Lys Ala Tyr Gly Glu Gly Asn Thr Glu Lys Val Ala Val Gly
    370                 375                 380 agc atc aag tcc agc atc ggc cat ctc aag gcc gtc gcc ggt ctc gcc      1200
Ser Ile Lys Ser Ser Ile Gly His Leu Lys Ala Val Ala Gly Leu Ala
385                 390                 395                 400 ggt atg atc aag gtc atc atg gcg ctc aag cac aag act ctc ccg ggc      1248
Gly Met Ile Lys Val Ile Met Ala Leu Lys His Lys Thr Leu Pro Gly
                405                 410                 415 acc atc aac gtc gac aac cca ccc aac ctc tac gac aac acg ccc atc      1296
Thr Ile Asn Val Asp Asn Pro Pro Asn Leu Tyr Asp Asn Thr Pro Ile
            420                 425                 430 aac gag tcc tcg ctc tac att aac acc atg aac cgc ccc tgg ttc ccg      1344
Asn Glu Ser Ser Leu Tyr Ile Asn Thr Met Asn Arg Pro Trp Phe Pro
        435                 440                 445 ccc cct ggt gtg ccc cgc cgc gcc ggc att tcg agc ttt ggc ttt ggt      1392
Pro Pro Gly Val Pro Arg Arg Ala Gly Ile Ser Ser Phe Gly Phe Gly
    450                 455                 460 ggc gcc aac tac cac gcc gtc ctc gag gag gcc gag ccc gag cac acg      1440
Gly Ala Asn Tyr His Ala Val Leu Glu Glu Ala Glu Pro Glu His Thr
465                 470                 475                 480 acc gcg tac cgc ctc aac aag cgc ccg cag ccc gtg ctc atg atg gcc      1488
Thr Ala Tyr Arg Leu Asn Lys Arg Pro Gln Pro Val Leu Met Met Ala
                485                 490                 495 gcc acg ccc gcg                                                      1500
Ala Thr Pro Ala
            500

<210> SEQ ID NO 8
<211> LENGTH: 500
<212> TYPE: PRT
<213> ORGANISM: Schizochytrium sp.

<400> SEQUENCE: 8

Met Ala Ala Arg Leu Gln Glu Gln Lys Gly Gly Glu Met Asp Thr Arg
1               5                   10                  15

Ile Ala Ile Ile Gly Met Ser Ala Ile Leu Pro Cys Gly Thr Thr Val
            20                  25                  30

Arg Glu Ser Trp Glu Thr Ile Arg Ala Gly Ile Asp Cys Leu Ser Asp
        35                  40                  45

Leu Pro Glu Asp Arg Val Asp Val Thr Ala Tyr Phe Asp Pro Val Lys
    50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
                85                  90                  95

Asp Ser Asp Ala Asn Gln Thr Ile Ser Leu Leu Lys Val Lys Glu Ala
            100                 105                 110

Leu Gln Asp Ala Gly Ile Asp Ala Leu Gly Lys Glu Lys Lys Asn Ile
        115                 120                 125

Gly Cys Val Leu Gly Ile Gly Gly Gln Lys Ser Ser His Glu Phe
    130                 135                 140

Tyr Ser Arg Leu Asn Tyr Val Val Glu Lys Val Leu Arg Lys Met
145                 150                 155                 160

Gly Met Pro Glu Glu Asp Val Lys Val Ala Val Glu Lys Tyr Lys Ala
                165                 170                 175
```

```
Asn Phe Pro Glu Trp Arg Leu Asp Ser Phe Pro Gly Phe Leu Gly Asn
            180                 185                 190
Val Thr Ala Gly Arg Cys Thr Asn Thr Phe Asn Leu Asp Gly Met Asn
        195                 200                 205
Cys Val Val Asp Ala Ala Cys Ala Ser Ser Leu Ile Ala Val Lys Val
    210                 215                 220
Ala Ile Asp Glu Leu Leu Tyr Gly Asp Cys Asp Met Met Val Thr Gly
225                 230                 235                 240
Ala Thr Cys Thr Asp Asn Ser Ile Gly Met Tyr Met Ala Phe Ser Lys
                245                 250                 255
Thr Pro Val Phe Ser Thr Asp Pro Ser Val Arg Ala Tyr Asp Glu Lys
            260                 265                 270
Thr Lys Gly Met Leu Ile Gly Glu Gly Ser Ala Met Leu Val Leu Lys
        275                 280                 285
Arg Tyr Ala Asp Ala Val Arg Asp Gly Asp Glu Ile His Ala Val Ile
    290                 295                 300
Arg Gly Cys Ala Ser Ser Ser Asp Gly Lys Ala Ala Gly Ile Tyr Thr
305                 310                 315                 320
Pro Thr Ile Ser Gly Gln Glu Glu Ala Leu Arg Arg Ala Tyr Asn Arg
                325                 330                 335
Ala Cys Val Asp Pro Ala Thr Val Thr Leu Val Glu Gly His Gly Thr
            340                 345                 350
Gly Thr Pro Val Gly Asp Arg Ile Glu Leu Thr Ala Leu Arg Asn Leu
        355                 360                 365
Phe Asp Lys Ala Tyr Gly Glu Gly Asn Thr Glu Lys Val Ala Val Gly
    370                 375                 380
Ser Ile Lys Ser Ser Ile Gly His Leu Lys Ala Val Ala Gly Leu Ala
385                 390                 395                 400
Gly Met Ile Lys Val Ile Met Ala Leu Lys His Lys Thr Leu Pro Gly
                405                 410                 415
Thr Ile Asn Val Asp Asn Pro Pro Asn Leu Tyr Asp Asn Thr Pro Ile
            420                 425                 430
Asn Glu Ser Ser Leu Tyr Ile Asn Thr Met Asn Arg Pro Trp Phe Pro
        435                 440                 445
Pro Pro Gly Val Pro Arg Arg Ala Gly Ile Ser Ser Phe Gly Phe Gly
    450                 455                 460
Gly Ala Asn Tyr His Ala Val Leu Glu Glu Ala Glu Pro Glu His Thr
465                 470                 475                 480
Thr Ala Tyr Arg Leu Asn Lys Arg Pro Gln Pro Val Leu Met Met Ala
                485                 490                 495
Ala Thr Pro Ala
        500
```

<210> SEQ ID NO 9
<211> LENGTH: 1278
<212> TYPE: DNA
<213> ORGANISM: Schizochytrium sp.
<220> FEATURE:
<221> NAME/KEY: CDS
<222> LOCATION: (1)..(1278)

<400> SEQUENCE: 9

```
gat gtc acc aag gag gcc tgg cgc ctc ccc cgc gag ggc gtc agc ttc      48
Asp Val Thr Lys Glu Ala Trp Arg Leu Pro Arg Glu Gly Val Ser Phe
1               5                  10                  15 cgc gcc aag ggc atc gcc acc aac ggc gct gtc gcc gcg ctc ttc tcc      96
```

```
                Arg Ala Lys Gly Ile Ala Thr Asn Gly Ala Val Ala Ala Leu Phe Ser
                             20                  25                  30 gcc cag ggc gcg cag tac acg cac atg ttt agc gag gtg gcc atg aac       144
Gly Gln Gly Ala Gln Tyr Thr His Met Phe Ser Glu Val Ala Met Asn
             35                  40                  45 tgg ccc cag ttc cgc cag agc att gcc gcc atg gac gcc gcc cag tcc       192
Trp Pro Gln Phe Arg Gln Ser Ile Ala Ala Met Asp Ala Ala Gln Ser
 50                  55                  60 aag gtc gct gga agc gac aag gac ttt gag cgc gtc tcc cag gtc ctc       240
Lys Val Ala Gly Ser Asp Lys Asp Phe Glu Arg Val Ser Gln Val Leu
 65                  70                  75                  80 tac ccg cgc aag ccg tac gag cgt gag ccc gag cag gac cac aag aag       288
Tyr Pro Arg Lys Pro Tyr Glu Arg Glu Pro Glu Gln Asp His Lys Lys
                 85                  90                  95 atc tcc ctc acc gcc tac tcg cag ccc tcg acc ctg gcc tgc gct ctc       336
Ile Ser Leu Thr Ala Tyr Ser Gln Pro Ser Thr Leu Ala Cys Ala Leu
            100                 105                 110 ggt gcc ttt gag atc ttc aag gag gcc ggc ttc acc ccg gac ttt gcc       384
Gly Ala Phe Glu Ile Phe Lys Glu Ala Gly Phe Thr Pro Asp Phe Ala
        115                 120                 125 gcc ggc cat tcg ctc ggt gag ttc gcc gcc ctc tac gcc gcg ggc tgc       432
Ala Gly His Ser Leu Gly Glu Phe Ala Ala Leu Tyr Ala Ala Gly Cys
    130                 135                 140 gtc gac cgc gac gag ctc ttt gag ctt gtc tgc cgc cgc gcc cgc atc       480
Val Asp Arg Asp Glu Leu Phe Glu Leu Val Cys Arg Arg Ala Arg Ile
145                 150                 155                 160 atg ggc ggc aag gac gca ccg gcc acc ccc aag ggc tgc atg gcc gcc       528
Met Gly Gly Lys Asp Ala Pro Ala Thr Pro Lys Gly Cys Met Ala Ala
                165                 170                 175 gtc att ggc ccc aac gcc gag aac atc aag gtc cag gcc gcc aac gtc       576
Val Ile Gly Pro Asn Ala Glu Asn Ile Lys Val Gln Ala Ala Asn Val
            180                 185                 190 tgg ctc ggc aac tcc aac tcg cct tcg cag acc gtc atc acc ggc tcc       624
Trp Leu Gly Asn Ser Asn Ser Pro Ser Gln Thr Val Ile Thr Gly Ser
        195                 200                 205 gtc gaa ggt atc cag gcc gag agc gcc cgc ctc cag aag gag ggc ttc       672
Val Glu Gly Ile Gln Ala Glu Ser Ala Arg Leu Gln Lys Glu Gly Phe
    210                 215                 220 cgc gtc gtg cct ctt gcc tgc gag agc gcc ttc cac tcg ccc cag atg       720
Arg Val Val Pro Leu Ala Cys Glu Ser Ala Phe His Ser Pro Gln Met
225                 230                 235                 240 gag aac gcc tcg tcg gcc ttc aag gac gtc atc tcc aag gtc tcc ttc       768
Glu Asn Ala Ser Ser Ala Phe Lys Asp Val Ile Ser Lys Val Ser Phe
                245                 250                 255 cgc acc ccc aag gcc gag acc aag ctc ttc agc aac gtc tct ggc gag       816
Arg Thr Pro Lys Ala Glu Thr Lys Leu Phe Ser Asn Val Ser Gly Glu
            260                 265                 270 acc tac ccc acg gac gcc cgc gag atg ctt acg cag cac atg acc agc       864
Thr Tyr Pro Thr Asp Ala Arg Glu Met Leu Thr Gln His Met Thr Ser
        275                 280                 285 agc gtc aag ttc ctc acc cag gtc cgc aac atg cac cag gcc ggt gcg       912
Ser Val Lys Phe Leu Thr Gln Val Arg Asn Met His Gln Ala Gly Ala
    290                 295                 300 cgc atc ttt gtc gag ttc gga ccc aag cag gtg ctc tcc aag ctt gtc       960
Arg Ile Phe Val Glu Phe Gly Pro Lys Gln Val Leu Ser Lys Leu Val
305                 310                 315                 320 tcc gag acc ctc aag gat gac ccc tcg gtt gtc acc gtc tct gtc aac      1008
Ser Glu Thr Leu Lys Asp Asp Pro Ser Val Val Thr Val Ser Val Asn
                325                 330                 335 ccg gcc tcg ggc acg gat tcg gac atc cag ctc cgc gac gcg gcc gtc      1056
```

```
Pro Ala Ser Gly Thr Asp Ser Asp Ile Gln Leu Arg Asp Ala Ala Val
            340                 345                 350 cag ctc gtt gtc gct ggc gtc aac ctt cag ggc ttt gac aag tgg gac      1104
Gln Leu Val Val Ala Gly Val Asn Leu Gln Gly Phe Asp Lys Trp Asp
            355                 360                 365 gcc ccc gat gcc acc cgc atg cag gcc atc aag aag aag cgc act acc      1152
Ala Pro Asp Ala Thr Arg Met Gln Ala Ile Lys Lys Lys Arg Thr Thr
        370                 375                 380 ctc cgc ctt tcg gcc gcc acc tac gtc tcg gac aag acc aag aag gtc      1200
Leu Arg Leu Ser Ala Ala Thr Tyr Val Ser Asp Lys Thr Lys Lys Val
385                 390                 395                 400 cgc gac gcc gcc atg aac gat ggc cgc tgc gtc acc tac ctc aag ggc      1248
Arg Asp Ala Ala Met Asn Asp Gly Arg Cys Val Thr Tyr Leu Lys Gly
                405                 410                 415 gcc gca ccg ctc atc aag gcc ccg gag ccc                              1278
Ala Ala Pro Leu Ile Lys Ala Pro Glu Pro
            420                 425

<210> SEQ ID NO 10
<211> LENGTH: 426
<212> TYPE: PRT
<213> ORGANISM: Schizochytrium sp.

<400> SEQUENCE: 10

Asp Val Thr Lys Glu Ala Trp Arg Leu Pro Arg Glu Gly Val Ser Phe
1               5                   10                  15

Arg Ala Lys Gly Ile Ala Thr Asn Gly Ala Val Ala Ala Leu Phe Ser
            20                  25                  30

Gly Gln Gly Ala Gln Tyr Thr His Met Phe Ser Glu Val Ala Met Asn
        35                  40                  45

Trp Pro Gln Phe Arg Gln Ser Ile Ala Ala Met Asp Ala Ala Gln Ser
    50                  55                  60

Lys Val Ala Gly Ser Asp Lys Asp Phe Glu Arg Val Ser Gln Val Leu
65                  70                  75                  80

Tyr Pro Arg Lys Pro Tyr Glu Arg Glu Pro Glu Gln Asp His Lys Lys
                85                  90                  95

Ile Ser Leu Thr Ala Tyr Ser Gln Pro Ser Thr Leu Ala Cys Ala Leu
            100                 105                 110

Gly Ala Phe Glu Ile Phe Lys Glu Ala Gly Phe Thr Pro Asp Phe Ala
        115                 120                 125

Ala Gly His Ser Leu Gly Glu Phe Ala Ala Leu Tyr Ala Ala Gly Cys
    130                 135                 140

Val Asp Arg Asp Glu Leu Phe Glu Leu Val Cys Arg Arg Ala Arg Ile
145                 150                 155                 160

Met Gly Gly Lys Asp Ala Pro Ala Thr Pro Lys Gly Cys Met Ala Ala
                165                 170                 175

Val Ile Gly Pro Asn Ala Glu Asn Ile Lys Val Gln Ala Ala Asn Val
            180                 185                 190

Trp Leu Gly Asn Ser Asn Ser Pro Ser Gln Thr Val Ile Thr Gly Ser
        195                 200                 205

Val Glu Gly Ile Gln Ala Glu Ser Ala Arg Leu Gln Lys Glu Gly Phe
    210                 215                 220

Arg Val Val Pro Leu Ala Cys Glu Ser Ala Phe His Ser Pro Gln Met
225                 230                 235                 240

Glu Asn Ala Ser Ser Ala Phe Lys Asp Val Ile Ser Lys Val Ser Phe
                245                 250                 255

Arg Thr Pro Lys Ala Glu Thr Lys Leu Phe Ser Asn Val Ser Gly Glu
```

```
                 260                 265                 270
Thr Tyr Pro Thr Asp Ala Arg Glu Met Leu Thr Gln His Met Thr Ser
            275                 280                 285

Ser Val Lys Phe Leu Thr Gln Val Arg Asn Met His Gln Ala Gly Ala
        290                 295                 300

Arg Ile Phe Val Glu Phe Gly Pro Lys Gln Val Leu Ser Lys Leu Val
305                 310                 315                 320

Ser Glu Thr Leu Lys Asp Asp Pro Ser Val Val Thr Val Ser Val Asn
                325                 330                 335

Pro Ala Ser Gly Thr Asp Ser Asp Ile Gln Leu Arg Asp Ala Ala Val
            340                 345                 350

Gln Leu Val Val Ala Gly Val Asn Leu Gln Gly Phe Asp Lys Trp Asp
        355                 360                 365

Ala Pro Asp Ala Thr Arg Met Gln Ala Ile Lys Lys Arg Thr Thr
370                 375                 380

Leu Arg Leu Ser Ala Ala Thr Tyr Val Ser Asp Lys Thr Lys Val
385                 390                 395                 400

Arg Asp Ala Ala Met Asn Asp Gly Arg Cys Val Thr Tyr Leu Lys Gly
                405                 410                 415

Ala Ala Pro Leu Ile Lys Ala Pro Glu Pro
            420                 425

<210> SEQ ID NO 11
<211> LENGTH: 5
<212> TYPE: PRT
<213> ORGANISM: Schizochytrium sp.
<220> FEATURE:
<221> NAME/KEY: MISC_FEATURE
<222> LOCATION: (4)..(4)
<223> OTHER INFORMATION: X = any amino acid

<400> SEQUENCE: 11

Gly His Ser Xaa Gly
1               5

<210> SEQ ID NO 12
<211> LENGTH: 258
<212> TYPE: DNA
<213> ORGANISM: Schizochytrium sp.
<220> FEATURE:
<221> NAME/KEY: CDS
<222> LOCATION: (1)..(258)

<400> SEQUENCE: 12 gct gtc tcg aac gag ctt ctt gag aag gcc gag act gtc gtc atg gag      48
Ala Val Ser Asn Glu Leu Leu Glu Lys Ala Glu Thr Val Val Met Glu
1               5                   10                  15 gtc ctc gcc gcc aag acc ggc tac gag acc gac atg atc gag gct gac      96
Val Leu Ala Ala Lys Thr Gly Tyr Glu Thr Asp Met Ile Glu Ala Asp
            20                  25                  30 atg gag ctc gag acc gag ctc ggc att gac tcc atc aag cgt gtc gag     144
Met Glu Leu Glu Thr Glu Leu Gly Ile Asp Ser Ile Lys Arg Val Glu
        35                  40                  45 atc ctc tcc gag gtc cag gcc atg ctc aat gtc gag gcc aag gat gtc     192
Ile Leu Ser Glu Val Gln Ala Met Leu Asn Val Glu Ala Lys Asp Val
50                  55                  60 gat gcc ctc agc cgc act cgc act gtt ggt gag gtt gtc aac gcc atg     240
Asp Ala Leu Ser Arg Thr Arg Thr Val Gly Glu Val Val Asn Ala Met
65                  70                  75                  80 aag gcc gag atc gct ggc                                              258
Lys Ala Glu Ile Ala Gly
```

<210> SEQ ID NO 13
<211> LENGTH: 86
<212> TYPE: PRT
<213> ORGANISM: Schizochytrium sp.

<400> SEQUENCE: 13

Ala Val Ser Asn Glu Leu Leu Glu Lys Ala Glu Thr Val Val Met Glu
1               5                   10                  15

Val Leu Ala Ala Lys Thr Gly Tyr Glu Thr Asp Met Ile Glu Ala Asp
            20                  25                  30

Met Glu Leu Glu Thr Glu Leu Gly Ile Asp Ser Ile Lys Arg Val Glu
        35                  40                  45

Ile Leu Ser Glu Val Gln Ala Met Leu Asn Val Glu Ala Lys Asp Val
    50                  55                  60

Asp Ala Leu Ser Arg Thr Arg Thr Val Gly Glu Val Val Asn Ala Met
65                  70                  75                  80

Lys Ala Glu Ile Ala Gly
                85

<210> SEQ ID NO 14
<211> LENGTH: 5
<212> TYPE: PRT
<213> ORGANISM: Schizochytrium sp.

<400> SEQUENCE: 14

Leu Gly Ile Asp Ser
1               5

<210> SEQ ID NO 15
<211> LENGTH: 21
<212> TYPE: PRT
<213> ORGANISM: Schizochytrium sp.

<400> SEQUENCE: 15

Ala Pro Ala Pro Val Lys Ala Ala Ala Pro Ala Pro Val Ala Ser
1               5                   10                  15

Ala Pro Ala Pro Ala
            20

<210> SEQ ID NO 16
<211> LENGTH: 3006
<212> TYPE: DNA
<213> ORGANISM: Schizochytrium sp.

<400> SEQUENCE: 16
gcccccgccc cggtcaaggc tgctgcgcct ccgccccccg ttgcctcggc ccctgccccg        60
gctgtctcga acgagcttct tgagaaggcc gagactgtcg tcatggaggt cctcgccgcc      120
aagaccggct acgagaccga catgatcgag gctgacatgg agctcgagac cgagctcggc      180
attgactcca tcaagcgtgt cgagatcctc tccgaggtcc aggccatgct caatgtcgag      240
gccaaggatg tcgatgccct cagccgcact cgcactgttg gtgaggttgt caacgccatg      300
aaggccgaga tcgctggcag ctctgccccg gcgcctgctg ccgctgctcc ggctccggcc      360
aaggctgccc ctgccgccgc tgcgcctgct gtctcgaacg agcttctcga aggccgag        420 accgtcgtca tggaggtcct cgccgccaag actggctacg agactgacat gatcgagtcc      480
gacatggagc tcgagactga gctcggcatt gactccatca gcgtgtcga gatcctctcc       540 gaggttcagg ccatgctcaa cgtcgaggcc aaggacgtcg acgctctcag ccgcactcgc      600

```
actgtgggtg aggtcgtcaa cgccatgaag gctgagatcg ctggtggctc tgccccggcg    660
cctgccgccg ctgccccagg tccggctgct gccgcccctg cgcctgccgc cgccgcccct    720
gctgtctcga acgagcttct tgagaaggcc gagaccgtcg tcatggaggt cctcgccgcc    780
aagactggct acgagactga catgatcgag tccgacatgg agctcgagac cgagctcggc    840
attgactcca tcaagcgtgt cgagattctc tccgaggtcc aggccatgct caacgtcgag    900
gccaaggacg tcgacgctct cagccgcacc cgcactgttg gcgaggtcgt cgatgccatg    960
aaggccgaga tcgctggtgg ctctgccccg gcgcctgccg ccgctgctcc tgctccggct    1020
gctgccgccc ctgcgcctgc cgcccctgcg cctgctgtct cgagcgagct tctcgagaag    1080
gccgagactg tcgtcatgga ggtcctcgcc gccaagactg gctacgagac tgacatgatc    1140
gagtccgaca tggagctcga gaccgagctc ggcattgact ccatcaagcg tgtcgagatt    1200
ctctccgagg tccaggccat gctcaacgtc gaggccaagg acgtcgacgc tctcagccgc    1260
acccgcactg ttggcgaggt cgtcgatgcc atgaaggccg agatcgctgg tggctctgcc    1320
ccggcgcctg ccgccgctgc tcctgctccg gctgctgccg cccctgcgcc tgccgcccct    1380
gcgcctgccg cccctgcgcc tgctgtctcg agcgagcttc tcgagaaggc cgagactgtc    1440
gtcatggagg tcctcgccgc caagactggc tacgagactg acatgattga gtccgacatg    1500
gagctcgaga ccgagctcgg cattgactcc atcaagcgtg tcgagattct ctccgaggtt    1560
caggccatgc tcaacgtcga ggccaaggac gtcgacgctc tcagccgcac tcgcactgtt    1620
ggtgaggtcg tcgatgccat gaaggctgag atcgctggca gctccgcctc ggcgcctgcc    1680
gccgctgctc ctgctccggc tgctgccgct cctgcgcccg ctgccgccgc cctgctgtc    1740 tcgaacgagc ttctcgagaa agccgagact gtcgtcatgg aggtcctcgc cgccaagact    1800
ggctacgaga ctgacatgat cgagtccgac atggagctcg agactgagct cggcattgac    1860
tccatcaagc gtgtcgagat cctctccgag gttcaggcca tgctcaacgt cgaggccaag    1920
gacgtcgatg ccctcagccg cacccgcact gttggcgagg ttgtcgatgc catgaaggcc    1980
gagatcgctg tggctctgc cccggcgcct gccgccgctg ccctgctcc ggctgccgcc    2040 gccctgctg tctcgaacga gcttctcgag aaggccgaga ctgtcgtcat ggaggtcctc    2100
gccgccaaga ctggctacga gaccgacatg atcgagtccg acatggagct cgagaccgag    2160
ctcggcattg actccatcaa gcgtgtcgag attctctccg aggttcaggc catgctcaac    2220
gtcgaggcca aggacgtcga tgctctcagc cgcactcgca ctgttggcga ggtcgtcgat    2280
gccatgaagg ctgagatcgc cggcagctcc gccccggcgc ctgccgccgc tgctcctgct    2340
ccggctgctg ccgctcctgc gcccgctgcc gctgcccctg ctgtctcgag cgagcttctc    2400
gagaaggccg agaccgtcgt catggaggtc ctcgccgcca agactggcta cgagactgac    2460
atgattgagt ccgacatgga gctcgagact gagctcggca ttgactccat caagcgtgtc    2520
gagatcctct ccgaggttca ggccatgctc aacgtcgagg ccaaggacgt cgatgccctc    2580
agccgcaccc gcactgttgg cgaggttgtc gatgccatga aggccgagat cgctggtggc    2640
tctgccccgg cgcctgccgc cgctgcccct gctccggctg ccgccgcccc tgctgtctcg    2700
aacgagcttc ttgagaaggc cgagaccgtc gtcatggagg tcctcgccgc caagactggc    2760
tacgagaccg acatgatcga gtccgacatg gagctcgaga ccgagctcgg cattgactcc    2820
atcaagcgtg tcgagattct ctccgaggtt caggccatgc tcaacgtcga ggccaaggac    2880
gtcgacgctc tcagccgcac tcgcactgtt ggcgaggtcg tcgatgccat gaaggctgag    2940
atcgctggtg gctctgcccc ggcgcctgcc gccgctgctc ctgcctcggc tggcgccgcg    3000
```

```
<210> SEQ ID NO 17
<211> LENGTH: 2133
<212> TYPE: DNA
<213> ORGANISM: Schizochytrium sp.
<220> FEATURE:
<221> NAME/KEY: CDS
<222> LOCATION: (1)..(2133)

<400> SEQUENCE: 17
```

| | | | | | | | | | | | | | | | | |
|---|---|---|---|---|---|---|---|---|---|---|---|---|---|---|---|---|
| ttt | ggc | gct | ctc | ggc | ggc | ttc | atc | tcg | cag | cag | gcg | gag | cgc | ttc | gag | 48 |
| Phe | Gly | Ala | Leu | Gly | Gly | Phe | Ile | Ser | Gln | Gln | Ala | Glu | Arg | Phe | Glu | |
| 1 | | | | 5 | | | | | 10 | | | | | 15 | | |
| ccc | gcc | gaa | atc | ctc | ggc | ttc | acg | ctc | atg | tgc | gcc | aag | ttc | gcc | aag | 96 |
| Pro | Ala | Glu | Ile | Leu | Gly | Phe | Thr | Leu | Met | Cys | Ala | Lys | Phe | Ala | Lys | |
| | | | 20 | | | | | 25 | | | | | 30 | | | |
| gct | tcc | ctc | tgc | acg | gct | gtg | gct | ggc | cgc | ccg | gcc | ttt | atc | ggt | | 144 |
| Ala | Ser | Leu | Cys | Thr | Ala | Val | Ala | Gly | Arg | Pro | Ala | Phe | Ile | Gly | | |
| | | 35 | | | | | 40 | | | | | 45 | | | | |
| gtg | gcg | cgc | ctt | gac | ggc | cgc | ctc | gga | ttc | act | tcg | cag | ggc | act | tct | 192 |
| Val | Ala | Arg | Leu | Asp | Gly | Arg | Leu | Gly | Phe | Thr | Ser | Gln | Gly | Thr | Ser | |
| 50 | | | | | 55 | | | | | 60 | | | | | | |
| gac | gcg | ctc | aag | cgt | gcc | cag | cgt | ggt | gcc | atc | ttt | ggc | ctc | tgc | aag | 240 |
| Asp | Ala | Leu | Lys | Arg | Ala | Gln | Arg | Gly | Ala | Ile | Phe | Gly | Leu | Cys | Lys | |
| 65 | | | | 70 | | | | | 75 | | | | | 80 | | |
| acc | atc | ggc | ctc | gag | tgg | tcc | gag | tct | gac | gtc | ttt | tcc | cgc | ggc | gtg | 288 |
| Thr | Ile | Gly | Leu | Glu | Trp | Ser | Glu | Ser | Asp | Val | Phe | Ser | Arg | Gly | Val | |
| | | | 85 | | | | | 90 | | | | | 95 | | | |
| gac | att | gct | cag | ggc | atg | cac | ccc | gag | gat | gcc | gcc | gtg | gcg | att | gtg | 336 |
| Asp | Ile | Ala | Gln | Gly | Met | His | Pro | Glu | Asp | Ala | Ala | Val | Ala | Ile | Val | |
| | | | 100 | | | | | 105 | | | | | 110 | | | |
| cgc | gag | atg | gcg | tgc | gct | gac | att | cgc | att | cgc | gag | gtc | ggc | att | ggc | 384 |
| Arg | Glu | Met | Ala | Cys | Ala | Asp | Ile | Arg | Ile | Arg | Glu | Val | Gly | Ile | Gly | |
| | | 115 | | | | | 120 | | | | | 125 | | | | |
| gca | aac | cag | cag | cgc | tgc | acg | atc | cgt | gcc | gcc | aag | ctc | gag | acc | ggc | 432 |
| Ala | Asn | Gln | Gln | Arg | Cys | Thr | Ile | Arg | Ala | Ala | Lys | Leu | Glu | Thr | Gly | |
| 130 | | | | | 135 | | | | | 140 | | | | | | |
| aac | ccg | cag | cgc | cag | atc | gcc | aag | gac | gac | gtg | ctg | ctc | gtt | tct | ggc | 480 |
| Asn | Pro | Gln | Arg | Gln | Ile | Ala | Lys | Asp | Asp | Val | Leu | Leu | Val | Ser | Gly | |
| 145 | | | | 150 | | | | | 155 | | | | | 160 | | |
| ggc | gct | cgc | ggc | atc | acg | cct | ctt | tgc | atc | cgg | gag | atc | acg | cgc | cag | 528 |
| Gly | Ala | Arg | Gly | Ile | Thr | Pro | Leu | Cys | Ile | Arg | Glu | Ile | Thr | Arg | Gln | |
| | | | 165 | | | | | 170 | | | | | 175 | | | |
| atc | gcg | ggc | ggc | aag | tac | att | ctg | ctt | ggc | cgc | agc | aag | gtc | tct | gcg | 576 |
| Ile | Ala | Gly | Gly | Lys | Tyr | Ile | Leu | Leu | Gly | Arg | Ser | Lys | Val | Ser | Ala | |
| | | | 180 | | | | | 185 | | | | | 190 | | | |
| agc | gaa | ccg | gca | tgg | tgc | gct | ggc | atc | act | gac | gag | aag | gct | gtg | caa | 624 |
| Ser | Glu | Pro | Ala | Trp | Cys | Ala | Gly | Ile | Thr | Asp | Glu | Lys | Ala | Val | Gln | |
| | | 195 | | | | | 200 | | | | | 205 | | | | |
| aag | gct | gct | acc | cag | gag | ctc | aag | cgc | gcc | ttt | agc | gct | ggc | gag | ggc | 672 |
| Lys | Ala | Ala | Thr | Gln | Glu | Leu | Lys | Arg | Ala | Phe | Ser | Ala | Gly | Glu | Gly | |
| 210 | | | | | 215 | | | | | 220 | | | | | | |
| ccc | aag | ccc | acg | ccc | cgc | gct | gtc | act | aag | ctt | gtg | ggc | tct | gtt | ctt | 720 |
| Pro | Lys | Pro | Thr | Pro | Arg | Ala | Val | Thr | Lys | Leu | Val | Gly | Ser | Val | Leu | |
| 225 | | | | 230 | | | | | 235 | | | | | 240 | | |
| ggc | gct | cgc | gag | gtg | cgc | agc | tct | att | gct | gcg | att | gaa | gcg | ctc | ggc | 768 |
| Gly | Ala | Arg | Glu | Val | Arg | Ser | Ser | Ile | Ala | Ala | Ile | Glu | Ala | Leu | Gly | |
| | | | 245 | | | | | 250 | | | | | 255 | | | |
| ggc | aag | gcc | atc | tac | tcg | tcg | tgc | gac | gtg | aac | tct | gcc | gcc | gac | gtg | 816 |
| Gly | Lys | Ala | Ile | Tyr | Ser | Ser | Cys | Asp | Val | Asn | Ser | Ala | Ala | Asp | Val | | cctgcg 3006

-continued

```
                    260                 265                 270
gcc aag gcc gtg cgc gat gcc gag tcc cag ctc ggt gcc cgc gtc tcg      864
Ala Lys Ala Val Arg Asp Ala Glu Ser Gln Leu Gly Ala Arg Val Ser
        275                 280                 285 ggc atc gtt cat gcc tcg ggc gtg ctc cgc gac cgt ctc atc gag aag      912
Gly Ile Val His Ala Ser Gly Val Leu Arg Asp Arg Leu Ile Glu Lys
    290                 295                 300 aag ctc ccc gac gag ttc gac gcc gtc ttt ggc acc aag gtc acc ggt      960
Lys Leu Pro Asp Glu Phe Asp Ala Val Phe Gly Thr Lys Val Thr Gly
305                 310                 315                 320 ctc gag aac ctc ctc gcc gcc gtc gac cgc gcc aac ctc aag cac atg     1008
Leu Glu Asn Leu Leu Ala Ala Val Asp Arg Ala Asn Leu Lys His Met
                325                 330                 335 gtc ctc ttc agc tcg ctc gcc ggc ttc cac ggc aac gtc ggc cag tct     1056
Val Leu Phe Ser Ser Leu Ala Gly Phe His Gly Asn Val Gly Gln Ser
            340                 345                 350 gac tac gcc atg gcc aac gag gcc ctt aac aag atg ggc ctc gag ctc     1104
Asp Tyr Ala Met Ala Asn Glu Ala Leu Asn Lys Met Gly Leu Glu Leu
        355                 360                 365 gcc aag gac gtc tcg gtc aag tcg atc tgc ttc ggt ccc tgg gac ggt     1152
Ala Lys Asp Val Ser Val Lys Ser Ile Cys Phe Gly Pro Trp Asp Gly
    370                 375                 380 ggc atg gtg acg ccg cag ctc aag aag cag ttc cag gag atg ggc gtg     1200
Gly Met Val Thr Pro Gln Leu Lys Lys Gln Phe Gln Glu Met Gly Val
385                 390                 395                 400 cag atc atc ccc cgc gag ggc ggc gct gat acc gtg gcg cgc atc gtg     1248
Gln Ile Ile Pro Arg Glu Gly Gly Ala Asp Thr Val Ala Arg Ile Val
                405                 410                 415 ctc ggc tcc tcg ccg gct gag atc ctt gtc ggc aac tgg cgc acc ccg     1296
Leu Gly Ser Ser Pro Ala Glu Ile Leu Val Gly Asn Trp Arg Thr Pro
            420                 425                 430 tcc aag aag gtc ggc tcg gac acc atc acc ctg cac cgc aag att tcc     1344
Ser Lys Lys Val Gly Ser Asp Thr Ile Thr Leu His Arg Lys Ile Ser
        435                 440                 445 gcc aag tcc aac ccc ttc ctc gag gac cac gtc atc cag ggc cgc cgc     1392
Ala Lys Ser Asn Pro Phe Leu Glu Asp His Val Ile Gln Gly Arg Arg
    450                 455                 460 gtg ctg ccc atg acg ctg gcc att ggc tcg ctc gcg gag acc tgc ctc     1440
Val Leu Pro Met Thr Leu Ala Ile Gly Ser Leu Ala Glu Thr Cys Leu
465                 470                 475                 480 ggc ctc ttc ccc ggc tac tcg ctc tgg gcc att gac gac gcc cag ctc     1488
Gly Leu Phe Pro Gly Tyr Ser Leu Trp Ala Ile Asp Asp Ala Gln Leu
                485                 490                 495 ttc aag ggt gtc act gtc gac ggc gac gtc aac tgc gag gtg acc ctc     1536
Phe Lys Gly Val Thr Val Asp Gly Asp Val Asn Cys Glu Val Thr Leu
            500                 505                 510 acc ccg tcg acg gcg ccc tcg ggc cgc gtc aac gtc cag gcc acg ctc     1584
Thr Pro Ser Thr Ala Pro Ser Gly Arg Val Asn Val Gln Ala Thr Leu
        515                 520                 525 aag acc ttt tcc agc ggc aag ctg gtc ccg gcc tac cgc gcc gtc atc     1632
Lys Thr Phe Ser Ser Gly Lys Leu Val Pro Ala Tyr Arg Ala Val Ile
    530                 535                 540 gtg ctc tcc aac cag ggc gcg ccc ccg gcc aac gcc acc atg cag ccg     1680
Val Leu Ser Asn Gln Gly Ala Pro Pro Ala Asn Ala Thr Met Gln Pro
545                 550                 555                 560 ccc tcg ctc gat gcc gat ccg gcg ctc cag ggc tcc gtc tac gac ggc     1728
Pro Ser Leu Asp Ala Asp Pro Ala Leu Gln Gly Ser Val Tyr Asp Gly
                565                 570                 575 aag acc ctc ttc cac ggc ccg gcc ttc cgc ggc atc gat gac gtg ctc     1776
Lys Thr Leu Phe His Gly Pro Ala Phe Arg Gly Ile Asp Asp Val Leu
```

```
                    580                 585                 590
tcg tgc acc aag agc cag ctt gtg gcc aag tgc agc gct gtc ccc ggc      1824
Ser Cys Thr Lys Ser Gln Leu Val Ala Lys Cys Ser Ala Val Pro Gly
        595                 600                 605 tcc gac gcc gct cgc ggc gag ttt gcc acg gac act gac gcc cat gac      1872
Ser Asp Ala Ala Arg Gly Glu Phe Ala Thr Asp Thr Asp Ala His Asp
610                 615                 620 ccc ttc gtg aac gac ctg gcc ttt cag gcc atg ctc gtc tgg gtg cgc      1920
Pro Phe Val Asn Asp Leu Ala Phe Gln Ala Met Leu Val Trp Val Arg
625                 630                 635                 640 cgc acg ctc ggc cag gct gcg ctc ccc aac tcg atc cag cgc atc gtc      1968
Arg Thr Leu Gly Gln Ala Ala Leu Pro Asn Ser Ile Gln Arg Ile Val
            645                 650                 655 cag cac cgc ccg gtc ccg cag gac aag ccc ttc tac att acc ctc cgc      2016
Gln His Arg Pro Val Pro Gln Asp Lys Pro Phe Tyr Ile Thr Leu Arg
        660                 665                 670 tcc aac cag tcg ggc ggt cac tcc cag cac aag cac gcc ctt cag ttc      2064
Ser Asn Gln Ser Gly Gly His Ser Gln His Lys His Ala Leu Gln Phe
    675                 680                 685 cac aac gag cag ggc gat ctc ttc att gat gtc cag gct tcg gtc atc      2112
His Asn Glu Gln Gly Asp Leu Phe Ile Asp Val Gln Ala Ser Val Ile
690                 695                 700 gcc acg gac agc ctt gcc ttc                                          2133
Ala Thr Asp Ser Leu Ala Phe
705                 710

<210> SEQ ID NO 18
<211> LENGTH: 711
<212> TYPE: PRT
<213> ORGANISM: Schizochytrium sp.

<400> SEQUENCE: 18

Phe Gly Ala Leu Gly Gly Phe Ile Ser Gln Gln Ala Glu Arg Phe Glu
1               5                   10                  15

Pro Ala Glu Ile Leu Gly Phe Thr Leu Met Cys Ala Lys Phe Ala Lys
            20                  25                  30

Ala Ser Leu Cys Thr Ala Val Ala Gly Gly Arg Pro Ala Phe Ile Gly
        35                  40                  45

Val Ala Arg Leu Asp Gly Arg Leu Gly Phe Thr Ser Gln Gly Thr Ser
    50                  55                  60

Asp Ala Leu Lys Arg Ala Gln Arg Gly Ala Ile Phe Gly Leu Cys Lys
65                  70                  75                  80

Thr Ile Gly Leu Glu Trp Ser Glu Ser Asp Val Phe Ser Arg Gly Val
                85                  90                  95

Asp Ile Ala Gln Gly Met His Pro Glu Asp Ala Ala Val Ala Ile Val
            100                 105                 110

Arg Glu Met Ala Cys Ala Asp Ile Arg Ile Arg Glu Val Gly Ile Gly
        115                 120                 125

Ala Asn Gln Gln Arg Cys Thr Ile Arg Ala Ala Lys Leu Glu Thr Gly
    130                 135                 140

Asn Pro Gln Arg Gln Ile Ala Lys Asp Asp Val Leu Leu Val Ser Gly
145                 150                 155                 160

Gly Ala Arg Gly Ile Thr Pro Leu Cys Ile Arg Glu Ile Thr Arg Gln
                165                 170                 175

Ile Ala Gly Gly Lys Tyr Ile Leu Leu Gly Arg Ser Lys Val Ser Ala
            180                 185                 190

Ser Glu Pro Ala Trp Cys Ala Gly Ile Thr Asp Glu Lys Ala Val Gln
        195                 200                 205
```

```
Lys Ala Ala Thr Gln Glu Leu Lys Arg Ala Phe Ser Ala Gly Glu Gly
    210                 215                 220

Pro Lys Pro Thr Pro Arg Ala Val Thr Lys Leu Val Gly Ser Val Leu
225                 230                 235                 240

Gly Ala Arg Glu Val Arg Ser Ser Ile Ala Ala Ile Glu Ala Leu Gly
                245                 250                 255

Gly Lys Ala Ile Tyr Ser Ser Cys Asp Val Asn Ser Ala Ala Asp Val
            260                 265                 270

Ala Lys Ala Val Arg Asp Ala Glu Ser Gln Leu Gly Ala Arg Val Ser
    275                 280                 285

Gly Ile Val His Ala Ser Gly Val Leu Arg Asp Arg Leu Ile Glu Lys
        290                 295                 300

Lys Leu Pro Asp Glu Phe Asp Ala Val Phe Gly Thr Lys Val Thr Gly
305                 310                 315                 320

Leu Glu Asn Leu Leu Ala Ala Val Asp Arg Ala Asn Leu Lys His Met
                325                 330                 335

Val Leu Phe Ser Ser Leu Ala Gly Phe His Gly Asn Val Gly Gln Ser
            340                 345                 350

Asp Tyr Ala Met Ala Asn Glu Ala Leu Asn Lys Met Gly Leu Glu Leu
    355                 360                 365

Ala Lys Asp Val Ser Val Lys Ser Ile Cys Phe Gly Pro Trp Asp Gly
        370                 375                 380

Gly Met Val Thr Pro Gln Leu Lys Lys Gln Phe Gln Glu Met Gly Val
385                 390                 395                 400

Gln Ile Ile Pro Arg Glu Gly Gly Ala Asp Thr Val Ala Arg Ile Val
                405                 410                 415

Leu Gly Ser Ser Pro Ala Glu Ile Leu Val Gly Asn Trp Arg Thr Pro
            420                 425                 430

Ser Lys Lys Val Gly Ser Asp Thr Ile Thr Leu His Arg Lys Ile Ser
    435                 440                 445

Ala Lys Ser Asn Pro Phe Leu Glu Asp His Val Ile Gln Gly Arg Arg
        450                 455                 460

Val Leu Pro Met Thr Leu Ala Ile Gly Ser Leu Ala Glu Thr Cys Leu
465                 470                 475                 480

Gly Leu Phe Pro Gly Tyr Ser Leu Trp Ala Ile Asp Asp Ala Gln Leu
                485                 490                 495

Phe Lys Gly Val Thr Val Asp Gly Asp Val Asn Cys Glu Val Thr Leu
            500                 505                 510

Thr Pro Ser Thr Ala Pro Ser Gly Arg Val Asn Val Gln Ala Thr Leu
    515                 520                 525

Lys Thr Phe Ser Ser Gly Lys Leu Val Pro Ala Tyr Arg Ala Val Ile
        530                 535                 540

Val Leu Ser Asn Gln Gly Ala Pro Pro Ala Asn Ala Thr Met Gln Pro
545                 550                 555                 560

Pro Ser Leu Asp Ala Asp Pro Ala Leu Gln Gly Ser Val Tyr Asp Gly
                565                 570                 575

Lys Thr Leu Phe His Gly Pro Ala Phe Arg Gly Ile Asp Asp Val Leu
            580                 585                 590

Ser Cys Thr Lys Ser Gln Leu Val Ala Lys Cys Ser Ala Val Pro Gly
    595                 600                 605

Ser Asp Ala Ala Arg Gly Glu Phe Ala Thr Thr Asp Ala His Asp
        610                 615                 620

Pro Phe Val Asn Asp Leu Ala Phe Gln Ala Met Leu Val Trp Val Arg
```

```
                625                 630                 635                 640
Arg Thr Leu Gly Gln Ala Ala Leu Pro Asn Ser Ile Gln Arg Ile Val
                    645                 650                 655

Gln His Arg Pro Val Pro Gln Asp Lys Pro Phe Tyr Ile Thr Leu Arg
                    660                 665                 670

Ser Asn Gln Ser Gly Gly His Ser Gln His Lys His Ala Leu Gln Phe
                    675                 680                 685

His Asn Glu Gln Gly Asp Leu Phe Ile Asp Val Gln Ala Ser Val Ile
                    690                 695                 700

Ala Thr Asp Ser Leu Ala Phe
705                 710

<210> SEQ ID NO 19
<211> LENGTH: 1350
<212> TYPE: DNA
<213> ORGANISM: Schizochytrium sp.
<220> FEATURE:
<221> NAME/KEY: CDS
<222> LOCATION: (1)..(1350)

<400> SEQUENCE: 19 atg gcc gct cgg aat gtg agc gcc gcg cat gag atg cac gat gaa aag      48
Met Ala Ala Arg Asn Val Ser Ala Ala His Glu Met His Asp Glu Lys
1               5                   10                  15 cgc atc gcc gtc gtc ggc atg gcc gtc cag tac gcc gga tgc aaa acc      96
Arg Ile Ala Val Val Gly Met Ala Val Gln Tyr Ala Gly Cys Lys Thr
                20                  25                  30 aag gac gag ttc tgg gag gtg ctc atg aac ggc aag gtc gag tcc aag     144
Lys Asp Glu Phe Trp Glu Val Leu Met Asn Gly Lys Val Glu Ser Lys
            35                  40                  45 gtg atc agc gac aaa cga ctc ggc tcc aac tac cgc gcc gag cac tac     192
Val Ile Ser Asp Lys Arg Leu Gly Ser Asn Tyr Arg Ala Glu His Tyr
        50                  55                  60 aaa gca gag cgc agc aag tat gcc gac acc ttt tgc aac gaa acg tac     240
Lys Ala Glu Arg Ser Lys Tyr Ala Asp Thr Phe Cys Asn Glu Thr Tyr
65                  70                  75                  80 ggc acc ctt gac gag aac gag atc gac aac gag cac gaa ctc ctc ctc     288
Gly Thr Leu Asp Glu Asn Glu Ile Asp Asn Glu His Glu Leu Leu Leu
                85                  90                  95 aac ctc gcc aag cag gca ctc gca gag aca tcc gtc aaa gac tcg aca     336
Asn Leu Ala Lys Gln Ala Leu Ala Glu Thr Ser Val Lys Asp Ser Thr
            100                 105                 110 cgc tgc ggc atc gtc agc ggc tgc ctc tcg ttc ccc atg gac aac ctc     384
Arg Cys Gly Ile Val Ser Gly Cys Leu Ser Phe Pro Met Asp Asn Leu
        115                 120                 125 cag ggt gaa ctc ctc aac gtg tac caa aac cat gtc gag aaa aag ctc     432
Gln Gly Glu Leu Leu Asn Val Tyr Gln Asn His Val Glu Lys Lys Leu
    130                 135                 140 ggg gcc cgc gtc ttc aag gac gcc tcc cat tgg tcc gaa cgc gag cag     480
Gly Ala Arg Val Phe Lys Asp Ala Ser His Trp Ser Glu Arg Glu Gln
145                 150                 155                 160 tcc aac aaa ccc gag gcc ggt gac cgc cgc atc ttc atg gac ccg gcc     528
Ser Asn Lys Pro Glu Ala Gly Asp Arg Arg Ile Phe Met Asp Pro Ala
                165                 170                 175 tcc ttc gtc gcc gaa gaa ctc aac ctc ggc gcc ctt cac tac tcc gtc     576
Ser Phe Val Ala Glu Glu Leu Asn Leu Gly Ala Leu His Tyr Ser Val
            180                 185                 190 gac gca gca tgc gcc acg gcg ctc tac gtg ctc cgc ctc gcg cag gat     624
Asp Ala Ala Cys Ala Thr Ala Leu Tyr Val Leu Arg Leu Ala Gln Asp
        195                 200                 205
```

| | | |
|---|---|---|
| cat ctc gtc tcc ggc gcc gcc gac gtc atg ctc tgc ggt gcc acc tgc<br>His Leu Val Ser Gly Ala Ala Asp Val Met Leu Cys Gly Ala Thr Cys<br>210                        215                        220 | | 672 |
| ctg ccg gag ccc ttt ttc atc ctt tcg ggc ttt tcc acc ttc cag gcc<br>Leu Pro Glu Pro Phe Phe Ile Leu Ser Gly Phe Ser Thr Phe Gln Ala<br>225                      230                      235                      240 | | 720 |
| atg ccc gtc ggc acg ggc cag aac gtg tcc atg ccg ctg cac aag gac<br>Met Pro Val Gly Thr Gly Gln Asn Val Ser Met Pro Leu His Lys Asp<br>                        245                      250                      255 | | 768 |
| agc cag ggc ctc acc ccg ggt gag ggc ggc tcc atc atg gtc ctc aag<br>Ser Gln Gly Leu Thr Pro Gly Glu Gly Gly Ser Ile Met Val Leu Lys<br>                260                      265                      270 | | 816 |
| cgt ctc gat gat gcc atc cgc gac ggc gac cac att tac ggc acc ctt<br>Arg Leu Asp Asp Ala Ile Arg Asp Gly Asp His Ile Tyr Gly Thr Leu<br>275                        280                      285 | | 864 |
| ctc ggc gcc aat gtc agc aac tcc ggc aca ggt ctg ccc ctc aag ccc<br>Leu Gly Ala Asn Val Ser Asn Ser Gly Thr Gly Leu Pro Leu Lys Pro<br>                        290                      295                      300 | | 912 |
| ctt ctc ccc agc gag aaa aag tgc ctc atg gac acc tac acg cgc att<br>Leu Leu Pro Ser Glu Lys Lys Cys Leu Met Asp Thr Tyr Thr Arg Ile<br>305                        310                      315                      320 | | 960 |
| aac gtg cac ccg cac aag att cag tac gtc gag tgc cac gcc acc ggc<br>Asn Val His Pro His Lys Ile Gln Tyr Val Glu Cys His Ala Thr Gly<br>                        325                      330                      335 | | 1008 |
| acg ccc cag ggt gat cgt gtg gaa atc gac gcc gtc aag gcc tgc ttt<br>Thr Pro Gln Gly Asp Arg Val Glu Ile Asp Ala Val Lys Ala Cys Phe<br>                        340                      345                      350 | | 1056 |
| gaa ggc aag gtc ccc cgt ttc ggt acc aca aag ggc aac ttt gga cac<br>Glu Gly Lys Val Pro Arg Phe Gly Thr Thr Lys Gly Asn Phe Gly His<br>                        355                      360                      365 | | 1104 |
| acc cts gyc gca gcc ggc ttt gcc ggt atg tgc aag gtc ctc ctc tcc<br>Thr Xaa Xaa Ala Ala Gly Phe Ala Gly Met Cys Lys Val Leu Leu Ser<br>370                        375                      380 | | 1152 |
| atg aag cat ggc atc atc ccg ccc acc ccg ggt atc gat gac gag acc<br>Met Lys His Gly Ile Ile Pro Pro Thr Pro Gly Ile Asp Asp Glu Thr<br>385                        390                      395                      400 | | 1200 |
| aag atg gac cct ctc gtc gtc tcc ggt gag gcc atc cca tgg cca gag<br>Lys Met Asp Pro Leu Val Val Ser Gly Glu Ala Ile Pro Trp Pro Glu<br>                        405                      410                      415 | | 1248 |
| acc aac ggc gag ccc aag cgc gcc ggt ctc tcg gcc ttt ggc ttt ggt<br>Thr Asn Gly Glu Pro Lys Arg Ala Gly Leu Ser Ala Phe Gly Phe Gly<br>                        420                      425                      430 | | 1296 |
| ggc acc aac gcc cat gcc gtc ttt gag gag cat gac ccc tcc aac gcc<br>Gly Thr Asn Ala His Ala Val Phe Glu Glu His Asp Pro Ser Asn Ala<br>                        435                      440                      445 | | 1344 |
| gcc tgc<br>Ala Cys<br>      450 | | 1350 |

```
<210> SEQ ID NO 20
<211> LENGTH: 450
<212> TYPE: PRT
<213> ORGANISM: Schizochytrium sp.
<220> FEATURE:
<221> NAME/KEY: misc_feature
<222> LOCATION: (370)..(370)
<223> OTHER INFORMATION: The 'Xaa' at location 370 stands for Leu.
<220> FEATURE:
<221> NAME/KEY: misc_feature
<222> LOCATION: (371)..(371)
<223> OTHER INFORMATION: The 'Xaa' at location 371 stands for Ala, or
      Val.

<400> SEQUENCE: 20
```

```
Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60

Lys Ala Glu Arg Ser Lys Tyr Ala Asp Thr Phe Cys Asn Glu Thr Tyr
65                  70                  75                  80

Gly Thr Leu Asp Glu Asn Glu Ile Asp Asn Glu His Glu Leu Leu Leu
                85                  90                  95

Asn Leu Ala Lys Gln Ala Leu Ala Glu Thr Ser Val Lys Asp Ser Thr
            100                 105                 110

Arg Cys Gly Ile Val Ser Gly Cys Leu Ser Phe Pro Met Asp Asn Leu
            115                 120                 125

Gln Gly Glu Leu Leu Asn Val Tyr Gln Asn His Val Glu Lys Lys Leu
        130                 135                 140

Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
            165                 170                 175

Ser Phe Val Ala Glu Glu Leu Asn Leu Gly Ala Leu His Tyr Ser Val
            180                 185                 190

Asp Ala Ala Cys Ala Thr Ala Leu Tyr Val Leu Arg Leu Ala Gln Asp
            195                 200                 205

His Leu Val Ser Gly Ala Ala Asp Val Met Leu Cys Gly Ala Thr Cys
    210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
            245                 250                 255

Ser Gln Gly Leu Thr Pro Gly Glu Gly Ser Ile Met Val Leu Lys
            260                 265                 270

Arg Leu Asp Asp Ala Ile Arg Asp Gly Asp His Ile Tyr Gly Thr Leu
    275                 280                 285

Leu Gly Ala Asn Val Ser Asn Ser Gly Thr Gly Leu Pro Leu Lys Pro
    290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
            325                 330                 335

Thr Pro Gln Gly Asp Arg Val Glu Ile Asp Ala Val Lys Ala Cys Phe
            340                 345                 350

Glu Gly Lys Val Pro Arg Phe Gly Thr Thr Lys Gly Asn Phe Gly His
            355                 360                 365

Thr Xaa Xaa Ala Ala Gly Phe Ala Gly Met Cys Lys Val Leu Leu Ser
    370                 375                 380

Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
            405                 410                 415

Thr Asn Gly Glu Pro Lys Arg Ala Gly Leu Ser Ala Phe Gly Phe Gly
```

```
                     420                 425                 430
Gly Thr Asn Ala His Ala Val Phe Glu Glu His Asp Pro Ser Asn Ala
            435                 440                 445
Ala Cys
    450

<210> SEQ ID NO 21
<211> LENGTH: 1323
<212> TYPE: DNA
<213> ORGANISM: Schizochytrium sp.
<220> FEATURE:
<221> NAME/KEY: CDS
<222> LOCATION: (1)..(1323)

<400> SEQUENCE: 21 tcg gcc cgc tgc ggc ggt gaa agc aac atg cgc atc gcc atc act ggt         48
Ser Ala Arg Cys Gly Gly Glu Ser Asn Met Arg Ile Ala Ile Thr Gly
1               5                   10                  15 atg gac gcc acc ttt ggc gct ctc aag gga ctc gac gcc ttc gag cgc         96
Met Asp Ala Thr Phe Gly Ala Leu Lys Gly Leu Asp Ala Phe Glu Arg
            20                  25                  30 gcc att tac acc ggc gct cac ggt gcc atc cca ctc cca gaa aag cgc        144
Ala Ile Tyr Thr Gly Ala His Gly Ala Ile Pro Leu Pro Glu Lys Arg
        35                  40                  45 tgg cgc ttt ctc ggc aag gac aag gac ttt ctt gac ctc tgc ggc gtc        192
Trp Arg Phe Leu Gly Lys Asp Lys Asp Phe Leu Asp Leu Cys Gly Val
    50                  55                  60 aag gcc acc ccg cac ggc tgc tac att gaa gat gtt gag gtc gac ttc        240
Lys Ala Thr Pro His Gly Cys Tyr Ile Glu Asp Val Glu Val Asp Phe
65                  70                  75                  80 cag cgc ctc cgc acg ccc atg acc cct gaa gac atg ctc ctc cct cag        288
Gln Arg Leu Arg Thr Pro Met Thr Pro Glu Asp Met Leu Leu Pro Gln
                85                  90                  95 cag ctt ctg gcc gtc acc acc att gac cgc gcc atc ctc gac tcg gga        336
Gln Leu Leu Ala Val Thr Thr Ile Asp Arg Ala Ile Leu Asp Ser Gly
            100                 105                 110 atg aaa aag ggt ggc aat gtc gcc gtc ttt gtc ggc ctc ggc acc gac        384
Met Lys Lys Gly Gly Asn Val Ala Val Phe Val Gly Leu Gly Thr Asp
        115                 120                 125 ctc gag ctc tac cgt cac cgt gct cgc gtc gct ctc aag gag cgc gtc        432
Leu Glu Leu Tyr Arg His Arg Ala Arg Val Ala Leu Lys Glu Arg Val
    130                 135                 140 cgc cct gaa gcc tcc aag aag ctc aat gac atg atg cag tac att aac        480
Arg Pro Glu Ala Ser Lys Lys Leu Asn Asp Met Met Gln Tyr Ile Asn
145                 150                 155                 160 gac tgc ggc aca tcc aca tcg tac acc tcg tac att ggc aac ctc gtc        528
Asp Cys Gly Thr Ser Thr Ser Tyr Thr Ser Tyr Ile Gly Asn Leu Val
                165                 170                 175 gcc acg cgc gtc tcg tcg cag tgg ggc ttc acg ggc ccc tcc ttt acg        576
Ala Thr Arg Val Ser Ser Gln Trp Gly Phe Thr Gly Pro Ser Phe Thr
            180                 185                 190 atc acc gag ggc aac aac tcc gtc tac cgc tgc gcc gag ctc ggc aag        624
Ile Thr Glu Gly Asn Asn Ser Val Tyr Arg Cys Ala Glu Leu Gly Lys
        195                 200                 205 tac ctc ctc gag acc ggc gag gtc gat ggc gtc gtc gtt gcg ggt gtc        672
Tyr Leu Leu Glu Thr Gly Glu Val Asp Gly Val Val Val Ala Gly Val
    210                 215                 220 gat ctc tgc ggc agt gcc gaa aac ctt tac gtc aag tct cgc cgc ttc        720
Asp Leu Cys Gly Ser Ala Glu Asn Leu Tyr Val Lys Ser Arg Arg Phe
225                 230                 235                 240 aag gtg tcc acc tcc gat acc ccg cgc gcc agc ttt gac gcc gcc gcc        768
```

```
Lys Val Ser Thr Ser Asp Thr Pro Arg Ala Ser Phe Asp Ala Ala Ala
            245                 250                 255 gat ggc tac ttt gtc ggc gag ggc tgc ggt gcc ttt gtg ctc aag cgt    816
Asp Gly Tyr Phe Val Gly Glu Gly Cys Gly Ala Phe Val Leu Lys Arg
            260                 265                 270 gag act agc tgc acc aag gac gac cgt atc tac gct tgc atg gat gcc    864
Glu Thr Ser Cys Thr Lys Asp Asp Arg Ile Tyr Ala Cys Met Asp Ala
            275                 280                 285 atc gtc cct ggc aac gtc cct agc gcc tgc ttg cgc gag gcc ctc gac    912
Ile Val Pro Gly Asn Val Pro Ser Ala Cys Leu Arg Glu Ala Leu Asp
            290                 295                 300 cag gcg cgc gtc aag ccg ggc gat atc gag atg ctc gag ctc agc gcc    960
Gln Ala Arg Val Lys Pro Gly Asp Ile Glu Met Leu Glu Leu Ser Ala
305                 310                 315                 320 gac tcc gcc cgc cac ctc aag gac ccg tcc gtc ctg ccc aag gag ctc   1008
Asp Ser Ala Arg His Leu Lys Asp Pro Ser Val Leu Pro Lys Glu Leu
                325                 330                 335 act gcc gag gag gaa atc ggc ggc ctt cag acg atc ctt cgt gac gat   1056
Thr Ala Glu Glu Glu Ile Gly Gly Leu Gln Thr Ile Leu Arg Asp Asp
            340                 345                 350 gac aag ctc ccg cgc aac gtc gca acg ggc agt gtc aag gcc acc gtc   1104
Asp Lys Leu Pro Arg Asn Val Ala Thr Gly Ser Val Lys Ala Thr Val
            355                 360                 365 ggt gac acc ggt tat gcc tct ggt gct gcc agc ctc atc aag gct gcg   1152
Gly Asp Thr Gly Tyr Ala Ser Gly Ala Ala Ser Leu Ile Lys Ala Ala
            370                 375                 380 ctt tgc atc tac aac cgc tac ctg ccc agc aac ggc gac gac tgg gat   1200
Leu Cys Ile Tyr Asn Arg Tyr Leu Pro Ser Asn Gly Asp Asp Trp Asp
385                 390                 395                 400 gaa ccc gcc cct gag gcg ccc tgg gac agc acc ctc ttt gcg tgc cag   1248
Glu Pro Ala Pro Glu Ala Pro Trp Asp Ser Thr Leu Phe Ala Cys Gln
                405                 410                 415 acc tcg cgc gct tgg ctc aag aac cct ggc gag cgt cgc tat gcg gcc   1296
Thr Ser Arg Ala Trp Leu Lys Asn Pro Gly Glu Arg Arg Tyr Ala Ala
            420                 425                 430 gtc tcg ggc gtc tcc gag acg cgc tcg                              1323
Val Ser Gly Val Ser Glu Thr Arg Ser
            435                 440

<210> SEQ ID NO 22
<211> LENGTH: 441
<212> TYPE: PRT
<213> ORGANISM: Schizochytrium sp.

<400> SEQUENCE: 22

Ser Ala Arg Cys Gly Gly Glu Ser Asn Met Arg Ile Ala Ile Thr Gly
1               5                   10                  15

Met Asp Ala Thr Phe Gly Ala Leu Lys Gly Leu Asp Ala Phe Glu Arg
            20                  25                  30

Ala Ile Tyr Thr Gly Ala His Gly Ala Ile Pro Leu Pro Glu Lys Arg
        35                  40                  45

Trp Arg Phe Leu Gly Lys Asp Lys Asp Phe Leu Asp Leu Cys Gly Val
    50                  55                  60

Lys Ala Thr Pro His Gly Cys Tyr Ile Glu Asp Val Glu Val Asp Phe
65                  70                  75                  80

Gln Arg Leu Arg Thr Pro Met Thr Pro Glu Asp Met Leu Leu Pro Gln
                85                  90                  95

Gln Leu Leu Ala Val Thr Thr Ile Asp Arg Ala Ile Leu Asp Ser Gly
            100                 105                 110
```

```
Met Lys Lys Gly Gly Asn Val Ala Val Phe Val Gly Leu Gly Thr Asp
        115                 120                 125
Leu Glu Leu Tyr Arg His Arg Ala Arg Val Ala Leu Lys Glu Arg Val
130                 135                 140
Arg Pro Glu Ala Ser Lys Lys Leu Asn Asp Met Met Gln Tyr Ile Asn
145                 150                 155                 160
Asp Cys Gly Thr Ser Ser Tyr Ser Tyr Ile Gly Asn Leu Val
                165                 170                 175
Ala Thr Arg Val Ser Ser Gln Trp Gly Phe Thr Gly Pro Ser Phe Thr
                180                 185                 190
Ile Thr Glu Gly Asn Asn Ser Val Tyr Arg Cys Ala Glu Leu Gly Lys
        195                 200                 205
Tyr Leu Leu Glu Thr Gly Glu Val Asp Gly Val Val Ala Gly Val
210                 215                 220
Asp Leu Cys Gly Ser Ala Glu Asn Leu Tyr Val Lys Ser Arg Arg Phe
225                 230                 235                 240
Lys Val Ser Thr Ser Asp Thr Pro Arg Ala Ser Phe Asp Ala Ala
                245                 250                 255
Asp Gly Tyr Phe Val Gly Glu Gly Cys Gly Ala Phe Val Leu Lys Arg
                260                 265                 270
Glu Thr Ser Cys Thr Lys Asp Asp Arg Ile Tyr Ala Cys Met Asp Ala
        275                 280                 285
Ile Val Pro Gly Asn Val Pro Ser Ala Cys Leu Arg Glu Ala Leu Asp
290                 295                 300
Gln Ala Arg Val Lys Pro Gly Asp Ile Glu Met Leu Glu Leu Ser Ala
305                 310                 315                 320
Asp Ser Ala Arg His Leu Lys Asp Pro Ser Val Leu Pro Lys Glu Leu
                325                 330                 335
Thr Ala Glu Glu Ile Gly Gly Leu Gln Thr Ile Leu Arg Asp Asp
                340                 345                 350
Asp Lys Leu Pro Arg Asn Val Ala Thr Gly Ser Val Lys Ala Thr Val
        355                 360                 365
Gly Asp Thr Gly Tyr Ala Ser Gly Ala Ala Ser Leu Ile Lys Ala Ala
        370                 375                 380
Leu Cys Ile Tyr Asn Arg Tyr Leu Pro Ser Asn Gly Asp Asp Trp Asp
385                 390                 395                 400
Glu Pro Ala Pro Glu Ala Pro Trp Asp Ser Thr Leu Phe Ala Cys Gln
                405                 410                 415
Thr Ser Arg Ala Trp Leu Lys Asn Pro Gly Glu Arg Tyr Ala Ala
                420                 425                 430
Val Ser Gly Val Ser Glu Thr Arg Ser
        435                 440

<210> SEQ ID NO 23
<211> LENGTH: 1500
<212> TYPE: DNA
<213> ORGANISM: Schizochytrium sp.
<220> FEATURE:
<221> NAME/KEY: CDS
<222> LOCATION: (1)..(1500)

<400> SEQUENCE: 23 tgc tat tcc gtg ctc ctc tcc gaa gcc gag ggc cac tac gag cgc gag      48
Cys Tyr Ser Val Leu Leu Ser Glu Ala Glu Gly His Tyr Glu Arg Glu
1               5                   10                  15 aac cgc atc tcg ctc gac gag gag gcg ccc aag ctc att gtg ctt cgc      96
Asn Arg Ile Ser Leu Asp Glu Glu Ala Pro Lys Leu Ile Val Leu Arg
```

```
                  20                  25                  30
gcc gac tcc cac gag gag atc ctt ggt cgc ctc gac aag atc cgc gag    144
Ala Asp Ser His Glu Glu Ile Leu Gly Arg Leu Asp Lys Ile Arg Glu
             35                  40                  45 cgc ttc ttg cag ccc acg ggc gcc ccg cgc gag tcc gag ctc aag        192
Arg Phe Leu Gln Pro Thr Gly Ala Ala Pro Arg Glu Ser Glu Leu Lys
 50                  55                  60 gcg cag gcc cgc cgc atc ttc ctc gag ctc ctc ggc gag acc ctt gcc    240
Ala Gln Ala Arg Arg Ile Phe Leu Glu Leu Leu Gly Glu Thr Leu Ala
 65                  70                  75                  80 cag gat gcc gct tct tca ggc tcg caa aag ccc ctc gct ctc agc ctc    288
Gln Asp Ala Ala Ser Ser Gly Ser Gln Lys Pro Leu Ala Leu Ser Leu
                 85                  90                  95 gtc tcc acg ccc tcc aag ctc cag cgc gag gtc gag ctc gcg gcc aag    336
Val Ser Thr Pro Ser Lys Leu Gln Arg Glu Val Glu Leu Ala Ala Lys
             100                 105                 110 ggt atc ccg cgc tgc ctc aag atg cgc cgc gat tgg agc tcc cct gct    384
Gly Ile Pro Arg Cys Leu Lys Met Arg Arg Asp Trp Ser Ser Pro Ala
         115                 120                 125 ggc agc cgc tac gcg cct gag ccg ctc gcc agc gac cgc gtc gcc ttc    432
Gly Ser Arg Tyr Ala Pro Glu Pro Leu Ala Ser Asp Arg Val Ala Phe
     130                 135                 140 atg tac ggc gaa ggt cgc agc cct tac tac ggc atc acc caa gac att    480
Met Tyr Gly Glu Gly Arg Ser Pro Tyr Tyr Gly Ile Thr Gln Asp Ile
145                 150                 155                 160 cac cgc att tgg ccc gaa ctc cac gag gtc atc aac gaa aag acg aac    528
His Arg Ile Trp Pro Glu Leu His Glu Val Ile Asn Glu Lys Thr Asn
                 165                 170                 175 cgt ctc tgg gcc gaa ggc gac cgc tgg gtc atg ccg cgc gcc agc ttc    576
Arg Leu Trp Ala Glu Gly Asp Arg Trp Val Met Pro Arg Ala Ser Phe
             180                 185                 190 aag tcg gag ctc gag agc cag cag caa gag ttt gat cgc aac atg att    624
Lys Ser Glu Leu Glu Ser Gln Gln Gln Glu Phe Asp Arg Asn Met Ile
         195                 200                 205 gaa atg ttc cgt ctt gga atc ctc acc tca att gcc ttc acc aat ctg    672
Glu Met Phe Arg Leu Gly Ile Leu Thr Ser Ile Ala Phe Thr Asn Leu
     210                 215                 220 gcg cgc gac gtt ctc aac atc acg ccc aag gcc gcc ttt ggc ctc agt    720
Ala Arg Asp Val Leu Asn Ile Thr Pro Lys Ala Ala Phe Gly Leu Ser
225                 230                 235                 240 ctt ggc gag att tcc atg att ttt gcc ttt tcc aag aag aac ggt ctc    768
Leu Gly Glu Ile Ser Met Ile Phe Ala Phe Ser Lys Lys Asn Gly Leu
                 245                 250                 255 atc tcc gac cag ctc acc aag gat ctt cgc gag tcc gac gtg tgg aac    816
Ile Ser Asp Gln Leu Thr Lys Asp Leu Arg Glu Ser Asp Val Trp Asn
             260                 265                 270 aag gct ctg gcc gtt gaa ttt aat gcg ctg cgc gag gcc tgg ggc att    864
Lys Ala Leu Ala Val Glu Phe Asn Ala Leu Arg Glu Ala Trp Gly Ile
         275                 280                 285 cca cag agt gtc ccc aag gac gag ttc tgg caa ggc tac att gtg cgc    912
Pro Gln Ser Val Pro Lys Asp Glu Phe Trp Gln Gly Tyr Ile Val Arg
     290                 295                 300 ggc acc aag cag gat atc gag gcg gcc atc gcc ccg gac agc aag tac    960
Gly Thr Lys Gln Asp Ile Glu Ala Ala Ile Ala Pro Asp Ser Lys Tyr
305                 310                 315                 320 gtg cgc ctc acc atc atc aat gat gcc aac acc gcc ctc att agc ggc    1008
Val Arg Leu Thr Ile Ile Asn Asp Ala Asn Thr Ala Leu Ile Ser Gly
                 325                 330                 335 aag ccc gac gcc tgc aag gct gcg atc gcg cgt ctc ggt ggc aac att    1056
Lys Pro Asp Ala Cys Lys Ala Ala Ile Ala Arg Leu Gly Gly Asn Ile
```

```
                    340                 345                 350
cct gcg ctt ccc gtg acc cag ggc atg tgc ggc cac tgc ccc gag gtg       1104
Pro Ala Leu Pro Val Thr Gln Gly Met Cys Gly His Cys Pro Glu Val
        355                 360                 365 gga cct tat acc aag gat atc gcc aag atc cat gcc aac ctt gag ttc       1152
Gly Pro Tyr Thr Lys Asp Ile Ala Lys Ile His Ala Asn Leu Glu Phe
370                 375                 380 ccc gtt gtc gac ggc ctt gac ctc tgg acc aca atc aac cag aag cgc       1200
Pro Val Val Asp Gly Leu Asp Leu Trp Thr Thr Ile Asn Gln Lys Arg
385                 390                 395                 400 ctc gtg cca cgc gcc acg ggc gcc aag gac gaa tgg gcc cct tct tcc       1248
Leu Val Pro Arg Ala Thr Gly Ala Lys Asp Glu Trp Ala Pro Ser Ser
        405                 410                 415 ttt ggc gag tac gcc ggc cag ctc tac gag aag cag gct aac ttc ccc       1296
Phe Gly Glu Tyr Ala Gly Gln Leu Tyr Glu Lys Gln Ala Asn Phe Pro
        420                 425                 430 caa atc gtc gag acc att tac aag caa aac tac gac gtc ttt gtc gag       1344
Gln Ile Val Glu Thr Ile Tyr Lys Gln Asn Tyr Asp Val Phe Val Glu
        435                 440                 445 gtt ggg ccc aac aac cac cgt agc acc gca gtg cgc acc acg ctt ggt       1392
Val Gly Pro Asn Asn His Arg Ser Thr Ala Val Arg Thr Thr Leu Gly
450                 455                 460 ccc cag cgc aac cac ctt gct ggc gcc atc gac aag cag aac gag gat       1440
Pro Gln Arg Asn His Leu Ala Gly Ala Ile Asp Lys Gln Asn Glu Asp
465                 470                 475                 480 gct tgg acg acc atc gtc aag ctt gtg gct tcg ctc aag gcc cac ctt       1488
Ala Trp Thr Thr Ile Val Lys Leu Val Ala Ser Leu Lys Ala His Leu
        485                 490                 495 gtt cct ggc gtc                                                        1500
Val Pro Gly Val
        500

<210> SEQ ID NO 24
<211> LENGTH: 500
<212> TYPE: PRT
<213> ORGANISM: Schizochytrium sp.

<400> SEQUENCE: 24

Cys Tyr Ser Val Leu Ser Glu Ala Glu Gly His Tyr Glu Arg Glu
1               5                   10                  15

Asn Arg Ile Ser Leu Asp Glu Glu Ala Pro Lys Leu Ile Val Leu Arg
            20                  25                  30

Ala Asp Ser His Glu Glu Ile Leu Gly Arg Leu Asp Lys Ile Arg Glu
        35                  40                  45

Arg Phe Leu Gln Pro Thr Gly Ala Ala Pro Arg Glu Ser Glu Leu Lys
    50                  55                  60

Ala Gln Ala Arg Arg Ile Phe Leu Glu Leu Leu Gly Glu Thr Leu Ala
65                  70                  75                  80

Gln Asp Ala Ala Ser Ser Gly Ser Gln Lys Pro Leu Ala Leu Ser Leu
                85                  90                  95

Val Ser Thr Pro Ser Lys Leu Gln Arg Glu Val Glu Leu Ala Ala Lys
            100                 105                 110

Gly Ile Pro Arg Cys Leu Lys Met Arg Arg Asp Trp Ser Ser Pro Ala
        115                 120                 125

Gly Ser Arg Tyr Ala Pro Glu Pro Leu Ala Ser Asp Arg Val Ala Phe
    130                 135                 140

Met Tyr Gly Glu Gly Arg Ser Pro Tyr Tyr Gly Ile Thr Gln Asp Ile
145                 150                 155                 160
```

```
His Arg Ile Trp Pro Glu Leu His Glu Val Ile Asn Glu Lys Thr Asn
                165                 170                 175
Arg Leu Trp Ala Glu Gly Asp Arg Trp Val Met Pro Arg Ala Ser Phe
            180                 185                 190
Lys Ser Glu Leu Glu Ser Gln Gln Gln Glu Phe Asp Arg Asn Met Ile
        195                 200                 205
Glu Met Phe Arg Leu Gly Ile Leu Thr Ser Ile Ala Phe Thr Asn Leu
    210                 215                 220
Ala Arg Asp Val Leu Asn Ile Thr Pro Lys Ala Ala Phe Gly Leu Ser
225                 230                 235                 240
Leu Gly Glu Ile Ser Met Ile Phe Ala Phe Ser Lys Lys Asn Gly Leu
                245                 250                 255
Ile Ser Asp Gln Leu Thr Lys Asp Leu Arg Glu Ser Asp Val Trp Asn
            260                 265                 270
Lys Ala Leu Ala Val Glu Phe Asn Ala Leu Arg Glu Ala Trp Gly Ile
        275                 280                 285
Pro Gln Ser Val Pro Lys Asp Glu Phe Trp Gln Gly Tyr Ile Val Arg
    290                 295                 300
Gly Thr Lys Gln Asp Ile Glu Ala Ala Ile Ala Pro Asp Ser Lys Tyr
305                 310                 315                 320
Val Arg Leu Thr Ile Ile Asn Asp Ala Asn Thr Ala Leu Ile Ser Gly
                325                 330                 335
Lys Pro Asp Ala Cys Lys Ala Ala Ile Ala Arg Leu Gly Gly Asn Ile
            340                 345                 350
Pro Ala Leu Pro Val Thr Gln Gly Met Cys Gly His Cys Pro Glu Val
        355                 360                 365
Gly Pro Tyr Thr Lys Asp Ile Ala Lys Ile His Ala Asn Leu Glu Phe
    370                 375                 380
Pro Val Val Asp Gly Leu Asp Leu Trp Thr Thr Ile Asn Gln Lys Arg
385                 390                 395                 400
Leu Val Pro Arg Ala Thr Gly Ala Lys Asp Glu Trp Ala Pro Ser Ser
                405                 410                 415
Phe Gly Glu Tyr Ala Gly Gln Leu Tyr Glu Lys Gln Ala Asn Phe Pro
            420                 425                 430
Gln Ile Val Glu Thr Ile Tyr Lys Gln Asn Tyr Asp Val Phe Val Glu
        435                 440                 445
Val Gly Pro Asn Asn His Arg Ser Thr Ala Val Arg Thr Thr Leu Gly
    450                 455                 460
Pro Gln Arg Asn His Leu Ala Gly Ala Ile Asp Lys Gln Asn Glu Asp
465                 470                 475                 480
Ala Trp Thr Thr Ile Val Lys Leu Val Ala Ser Leu Lys Ala His Leu
                485                 490                 495
Val Pro Gly Val
            500

<210> SEQ ID NO 25
<211> LENGTH: 1530
<212> TYPE: DNA
<213> ORGANISM: Schizochytrium sp.
<220> FEATURE:
<221> NAME/KEY: CDS
<222> LOCATION: (1)..(1530)

<400> SEQUENCE: 25 ctg ctc gat ctc gac agt atg ctt gcg ctg agc tct gcc agt gcc tcc    48
Leu Leu Asp Leu Asp Ser Met Leu Ala Leu Ser Ser Ala Ser Ala Ser
1               5                   10                  15
```

| | |
|---|---|
| ggc aac ctt gtt gag act gcg cct agc gac gcc tcg gtc att gtg ccg<br>Gly Asn Leu Val Glu Thr Ala Pro Ser Asp Ala Ser Val Ile Val Pro<br>      20                        25                   30 | 96 |
| ccc tgc aac att gcg gat ctc ggc agc cgc gcc ttc atg aaa acg tac<br>Pro Cys Asn Ile Ala Asp Leu Gly Ser Arg Ala Phe Met Lys Thr Tyr<br>          35                   40                   45 | 144 |
| ggt gtt tcg gcg cct ctg tac acg ggc gcc atg gcc aag ggc att gcc<br>Gly Val Ser Ala Pro Leu Tyr Thr Gly Ala Met Ala Lys Gly Ile Ala<br>50                   55                   60 | 192 |
| tct gcg gac ctc gtc att gcc gcc ggc cgc cag ggc atc ctt gcg tcc<br>Ser Ala Asp Leu Val Ile Ala Ala Gly Arg Gln Gly Ile Leu Ala Ser<br>65                   70                   75                   80 | 240 |
| ttt ggc gcc ggc gga ctt ccc atg cag gtt gtg cgt gag tcc atc gaa<br>Phe Gly Ala Gly Gly Leu Pro Met Gln Val Val Arg Glu Ser Ile Glu<br>                   85                   90                   95 | 288 |
| aag att cag gcc gcc ctg ccc aat ggc ccg tac gct gtc aac ctt atc<br>Lys Ile Gln Ala Ala Leu Pro Asn Gly Pro Tyr Ala Val Asn Leu Ile<br>             100                  105                 110 | 336 |
| cat tct ccc ttt gac agc aac ctc gaa aag ggc aat gtc gat ctc ttc<br>His Ser Pro Phe Asp Ser Asn Leu Glu Lys Gly Asn Val Asp Leu Phe<br>           115                  120                 125 | 384 |
| ctc gag aag ggt gtc acc ttt gtc gag gcc tcg gcc ttt atg acg ctc<br>Leu Glu Lys Gly Val Thr Phe Val Glu Ala Ser Ala Phe Met Thr Leu<br>130                  135                 140 | 432 |
| acc ccg cag gtc gtg cgg tac cgc gcg gct ggc ctc acg cgc aac gcc<br>Thr Pro Gln Val Val Arg Tyr Arg Ala Ala Gly Leu Thr Arg Asn Ala<br>145                  150                155              160 | 480 |
| gac ggc tcg gtc aac atc cgc aac cgt atc att ggc aag gtc tcg cgc<br>Asp Gly Ser Val Asn Ile Arg Asn Arg Ile Ile Gly Lys Val Ser Arg<br>                   165                  170                 175 | 528 |
| acc gag ctc gcc gag atg ttc atg cgt cct gcg ccc gag cac ctt ctt<br>Thr Glu Leu Ala Glu Met Phe Met Arg Pro Ala Pro Glu His Leu Leu<br>           180                  185                 190 | 576 |
| cag aag ctc att gct tcc ggc gag atc aac cag gag cag gcc gag ctc<br>Gln Lys Leu Ile Ala Ser Gly Glu Ile Asn Gln Glu Gln Ala Glu Leu<br>             195                  200                 205 | 624 |
| gcc cgc cgt gtt ccc gtc gct gac gac atc gcg gtc gaa gct gac tcg<br>Ala Arg Arg Val Pro Val Ala Asp Asp Ile Ala Val Glu Ala Asp Ser<br>210                  215                220 | 672 |
| ggt ggc cac acc gac aac cgc ccc atc cac gtc att ctg ccc ctc atc<br>Gly Gly His Thr Asp Asn Arg Pro Ile His Val Ile Leu Pro Leu Ile<br>225                  230                235              240 | 720 |
| atc aac ctt cgc gac cgc ctt cac cgc gag tgc ggc tac ccg gcc aac<br>Ile Asn Leu Arg Asp Arg Leu His Arg Glu Cys Gly Tyr Pro Ala Asn<br>                   245                  250                 255 | 768 |
| ctt cgc gtc cgt gtg ggc gcc ggc ggt ggc att ggg tgc ccc cag gcg<br>Leu Arg Val Arg Val Gly Ala Gly Gly Gly Ile Gly Cys Pro Gln Ala<br>           260                  265                 270 | 816 |
| gcg ctg gcc acc ttc aac atg ggt gcc tcc ttt att gtc acc ggc acc<br>Ala Leu Ala Thr Phe Asn Met Gly Ala Ser Phe Ile Val Thr Gly Thr<br>             275                  280                 285 | 864 |
| gtg aac cag gtc gcc aag cag tcg ggc acg tgc gac aat gtg cgc aag<br>Val Asn Gln Val Ala Lys Gln Ser Gly Thr Cys Asp Asn Val Arg Lys<br>290                  295                300 | 912 |
| cag ctc gcg aag gcc act tac tcg gac gta tgc atg gcc ccg gct gcc<br>Gln Leu Ala Lys Ala Thr Tyr Ser Asp Val Cys Met Ala Pro Ala Ala<br>305                  310                315              320 | 960 |
| gac atg ttc gag gaa ggc gtc aag ctt cag gtc ctc aag aag gga acc<br>Asp Met Phe Glu Glu Gly Val Lys Leu Gln Val Leu Lys Lys Gly Thr<br>                   325                  330                 335 | 1008 |

```
atg ttt ccc tcg cgc gcc aac aag ctc tac gag ctc ttt tgc aag tac    1056
Met Phe Pro Ser Arg Ala Asn Lys Leu Tyr Glu Leu Phe Cys Lys Tyr
            340                 345                 350 gac tcg ttc gag tcc atg ccc ccc gca gag ctt gcg cgc gtc gag aag    1104
Asp Ser Phe Glu Ser Met Pro Pro Ala Glu Leu Ala Arg Val Glu Lys
        355                 360                 365 cgc atc ttc agc cgc gcg ctc gaa gag gtc tgg gac gag acc aaa aac    1152
Arg Ile Phe Ser Arg Ala Leu Glu Glu Val Trp Asp Glu Thr Lys Asn
    370                 375                 380 ttt tac att aac cgt ctt cac aac ccg gag aag atc cag cgc gcc gag    1200
Phe Tyr Ile Asn Arg Leu His Asn Pro Glu Lys Ile Gln Arg Ala Glu
385                 390                 395                 400 cgc gac ccc aag ctc aag atg tcg ctg tgc ttt cgc tgg tac ctg agc    1248
Arg Asp Pro Lys Leu Lys Met Ser Leu Cys Phe Arg Trp Tyr Leu Ser
                405                 410                 415 ctg gcg agc cgc tgg gcc aac act gga gct tcc gat cgc gtc atg gac    1296
Leu Ala Ser Arg Trp Ala Asn Thr Gly Ala Ser Asp Arg Val Met Asp
            420                 425                 430 tac cag gtc tgg tgc ggt cct gcc att ggt tcc ttc aac gat ttc atc    1344
Tyr Gln Val Trp Cys Gly Pro Ala Ile Gly Ser Phe Asn Asp Phe Ile
        435                 440                 445 aag gga act tac ctt gat ccg gcc gtc gca aac gag tac ccg tgc gtc    1392
Lys Gly Thr Tyr Leu Asp Pro Ala Val Ala Asn Glu Tyr Pro Cys Val
    450                 455                 460 gtt cag att aac aag cag atc ctt cgt gga gcg tgc ttc ttg cgc cgt    1440
Val Gln Ile Asn Lys Gln Ile Leu Arg Gly Ala Cys Phe Leu Arg Arg
465                 470                 475                 480 ctc gaa att ctg cgc aac gca cgc ctt tcc gat ggc gct gcc gct ctt    1488
Leu Glu Ile Leu Arg Asn Ala Arg Leu Ser Asp Gly Ala Ala Ala Leu
                485                 490                 495 gtg gcc agc atc gat gac aca tac gtc ccg gcc gag aag ctg            1530
Val Ala Ser Ile Asp Asp Thr Tyr Val Pro Ala Glu Lys Leu
            500                 505                 510

<210> SEQ ID NO 26
<211> LENGTH: 510
<212> TYPE: PRT
<213> ORGANISM: Schizochytrium sp.

<400> SEQUENCE: 26

Leu Leu Asp Leu Asp Ser Met Leu Ala Leu Ser Ser Ala Ser Ala Ser
1               5                   10                  15

Gly Asn Leu Val Glu Thr Ala Pro Ser Asp Ala Ser Val Ile Val Pro
            20                  25                  30

Pro Cys Asn Ile Ala Asp Leu Gly Ser Arg Ala Phe Met Lys Thr Tyr
        35                  40                  45

Gly Val Ser Ala Pro Leu Tyr Thr Gly Ala Met Ala Lys Gly Ile Ala
    50                  55                  60

Ser Ala Asp Leu Val Ile Ala Ala Gly Arg Gln Gly Ile Leu Ala Ser
65                  70                  75                  80

Phe Gly Ala Gly Gly Leu Pro Met Gln Val Val Arg Glu Ser Ile Glu
                85                  90                  95

Lys Ile Gln Ala Ala Leu Pro Asn Gly Pro Tyr Ala Val Asn Leu Ile
            100                 105                 110

His Ser Pro Phe Asp Ser Asn Leu Glu Lys Gly Asn Val Asp Leu Phe
        115                 120                 125

Leu Glu Lys Gly Val Thr Phe Val Glu Ala Ser Ala Phe Met Thr Leu
    130                 135                 140
```

```
Thr Pro Gln Val Val Arg Tyr Arg Ala Ala Gly Leu Thr Arg Asn Ala
145                 150                 155                 160

Asp Gly Ser Val Asn Ile Arg Asn Arg Ile Ile Gly Lys Val Ser Arg
                165                 170                 175

Thr Glu Leu Ala Glu Met Phe Met Arg Pro Ala Pro Glu His Leu Leu
            180                 185                 190

Gln Lys Leu Ile Ala Ser Gly Glu Ile Asn Gln Glu Gln Ala Glu Leu
        195                 200                 205

Ala Arg Arg Val Pro Val Ala Asp Ile Ala Val Glu Ala Asp Ser
    210                 215                 220

Gly Gly His Thr Asp Asn Arg Pro Ile His Val Ile Leu Pro Leu Ile
225                 230                 235                 240

Ile Asn Leu Arg Asp Arg Leu His Arg Glu Cys Gly Tyr Pro Ala Asn
                245                 250                 255

Leu Arg Val Arg Val Gly Ala Gly Gly Ile Gly Cys Pro Gln Ala
            260                 265                 270

Ala Leu Ala Thr Phe Asn Met Gly Ala Ser Phe Ile Val Thr Gly Thr
        275                 280                 285

Val Asn Gln Val Ala Lys Gln Ser Gly Thr Cys Asp Asn Val Arg Lys
290                 295                 300

Gln Leu Ala Lys Ala Thr Tyr Ser Asp Val Cys Met Ala Pro Ala Ala
305                 310                 315                 320

Asp Met Phe Glu Glu Gly Val Lys Leu Gln Val Leu Lys Lys Gly Thr
                325                 330                 335

Met Phe Pro Ser Arg Ala Asn Lys Leu Tyr Glu Leu Cys Lys Tyr
            340                 345                 350

Asp Ser Phe Glu Ser Met Pro Pro Ala Glu Leu Ala Arg Val Glu Lys
        355                 360                 365

Arg Ile Phe Ser Arg Ala Leu Glu Glu Val Trp Asp Glu Thr Lys Asn
    370                 375                 380

Phe Tyr Ile Asn Arg Leu His Asn Pro Glu Lys Ile Gln Arg Ala Glu
385                 390                 395                 400

Arg Asp Pro Lys Leu Lys Met Ser Leu Cys Phe Arg Trp Tyr Leu Ser
                405                 410                 415

Leu Ala Ser Arg Trp Ala Asn Thr Gly Ala Ser Asp Arg Val Met Asp
            420                 425                 430

Tyr Gln Val Trp Cys Gly Pro Ala Ile Gly Ser Phe Asn Asp Phe Ile
        435                 440                 445

Lys Gly Thr Tyr Leu Asp Pro Ala Val Ala Asn Glu Tyr Pro Cys Val
    450                 455                 460

Val Gln Ile Asn Lys Gln Ile Leu Arg Gly Ala Cys Phe Leu Arg Arg
465                 470                 475                 480

Leu Glu Ile Leu Arg Asn Ala Arg Leu Ser Asp Gly Ala Ala Ala Leu
                485                 490                 495

Val Ala Ser Ile Asp Asp Thr Tyr Val Pro Ala Glu Lys Leu
            500                 505                 510

<210> SEQ ID NO 27
<211> LENGTH: 1350
<212> TYPE: DNA
<213> ORGANISM: Schizochytrium sp.
<220> FEATURE:
<221> NAME/KEY: CDS
<222> LOCATION: (1)..(1350)

<400> SEQUENCE: 27
```

```
atg gcc gct cgg aat gtg agc gcc gcg cat gag atg cac gat gaa aag      48
Met Ala Ala Arg Asn Val Ser Ala Ala His Glu Met His Asp Glu Lys
1               5                   10                  15 cgc atc gcc gtc gtc ggc atg gcc gtc cag tac gcc gga tgc aaa acc      96
Arg Ile Ala Val Val Gly Met Ala Val Gln Tyr Ala Gly Cys Lys Thr
            20                  25                  30 aag gac gag ttc tgg gag gtc ctc atg aac ggc aag gtc gag tcc aag     144
Lys Asp Glu Phe Trp Glu Val Leu Met Asn Gly Lys Val Glu Ser Lys
        35                  40                  45 gtg atc agc gac aaa cga ctc ggc tcc aac tac cgc gcc gag cac tac     192
Val Ile Ser Asp Lys Arg Leu Gly Ser Asn Tyr Arg Ala Glu His Tyr
    50                  55                  60 aaa gca gag cgc agc aag tat gcc gac acc ttt tgc aac gaa acg tac     240
Lys Ala Glu Arg Ser Lys Tyr Ala Asp Thr Phe Cys Asn Glu Thr Tyr
65              70                  75                  80 ggc acc ctt gac gag aac gag atc gac aac gag cac gaa ctc ctc ctc     288
Gly Thr Leu Asp Glu Asn Glu Ile Asp Asn Glu His Glu Leu Leu Leu
                85                  90                  95 aac ctc gcc aag cag gca ctc gca gag aca tcc gtc aaa gac tcg aca     336
Asn Leu Ala Lys Gln Ala Leu Ala Glu Thr Ser Val Lys Asp Ser Thr
            100                 105                 110 cgc tgc ggc atc gtc agc ggc tgc ctc tcg ttc ccc atg gac aac ctc     384
Arg Cys Gly Ile Val Ser Gly Cys Leu Ser Phe Pro Met Asp Asn Leu
        115                 120                 125 cag ggt gaa ctc ctc aac gtg tac caa aac cat gtc gag aaa aag ctc     432
Gln Gly Glu Leu Leu Asn Val Tyr Gln Asn His Val Glu Lys Lys Leu
    130                 135                 140 ggg gcc cgc gtc ttc aag gac gcc tcc cat tgg tcc gaa cgc gag cag     480
Gly Ala Arg Val Phe Lys Asp Ala Ser His Trp Ser Glu Arg Glu Gln
145                 150                 155                 160 tcc aac aaa ccc gag gcc ggt gac cgc cgc atc ttc atg gac ccg gcc     528
Ser Asn Lys Pro Glu Ala Gly Asp Arg Arg Ile Phe Met Asp Pro Ala
                165                 170                 175 tcc ttc gtc gcc gaa gaa ctc aac ctc ggc gcc ctt cac tac tcc gtc     576
Ser Phe Val Ala Glu Glu Leu Asn Leu Gly Ala Leu His Tyr Ser Val
            180                 185                 190 gac gca gca tgc gcc acg gcg ctc tac gtg ctc cgc ctc gcg cag gat     624
Asp Ala Ala Cys Ala Thr Ala Leu Tyr Val Leu Arg Leu Ala Gln Asp
        195                 200                 205 cat ctc gtc tcc ggc gcc gcc gac gtc atg ctc tgc ggt gcc acc tgc     672
His Leu Val Ser Gly Ala Ala Asp Val Met Leu Cys Gly Ala Thr Cys
    210                 215                 220 ctg ccg gag ccc ttt ttc atc ctt tcg ggc ttt tcc acc ttc cag gcc     720
Leu Pro Glu Pro Phe Phe Ile Leu Ser Gly Phe Ser Thr Phe Gln Ala
225                 230                 235                 240 atg ccc gtc ggc acg ggc cag aac gtg tcc atg ccg ctg cac aag gac     768
Met Pro Val Gly Thr Gly Gln Asn Val Ser Met Pro Leu His Lys Asp
                245                 250                 255 agc cag ggc ctc acc ccg ggt gag ggc ggc tcc atc atg gtc ctc aag     816
Ser Gln Gly Leu Thr Pro Gly Glu Gly Gly Ser Ile Met Val Leu Lys
            260                 265                 270 cgt ctc gat gat gcc atc cgc gac ggc gac cac att tac ggc acc ctt     864
Arg Leu Asp Asp Ala Ile Arg Asp Gly Asp His Ile Tyr Gly Thr Leu
        275                 280                 285 ctc ggc gcc aat gtc agc aac tcc ggc aca ggt ctg ccc ctc aag ccc     912
Leu Gly Ala Asn Val Ser Asn Ser Gly Thr Gly Leu Pro Leu Lys Pro
    290                 295                 300 ctt ctc ccc agc gag aaa aag tgc ctc atg gac acc tac acg cgc att     960
Leu Leu Pro Ser Glu Lys Lys Cys Leu Met Asp Thr Tyr Thr Arg Ile
305                 310                 315                 320
```

```
aac gtg cac ccg cac aag att cag tac gtc gag tgc cac gcc acc ggc   1008
Asn Val His Pro His Lys Ile Gln Tyr Val Glu Cys His Ala Thr Gly
            325                 330                 335 acg ccc cag ggt gat cgt gtg gaa atc gac gcc gtc aag gcc tgc ttt   1056
Thr Pro Gln Gly Asp Arg Val Glu Ile Asp Ala Val Lys Ala Cys Phe
            340                 345                 350 gaa ggc aag gtc ccc cgt ttc ggt acc aca aag ggc aac ttt gga cac   1104
Glu Gly Lys Val Pro Arg Phe Gly Thr Thr Lys Gly Asn Phe Gly His
            355                 360                 365 acc cts gyc gca gcc ggc ttt gcc ggt atg tgc aag gtc ctc ctc tcc   1152
Thr Xaa Xaa Ala Ala Gly Phe Ala Gly Met Cys Lys Val Leu Leu Ser
    370                 375                 380 atg aag cat ggc atc atc ccg ccc acc ccg ggt atc gat gac gag acc   1200
Met Lys His Gly Ile Ile Pro Pro Thr Pro Gly Ile Asp Asp Glu Thr
385                 390                 395                 400 aag atg gac cct ctc gtc gtc tcc ggt gag gcc atc cca tgg cca gag   1248
Lys Met Asp Pro Leu Val Val Ser Gly Glu Ala Ile Pro Trp Pro Glu
                405                 410                 415 acc aac ggc gag ccc aag cgc gcc ggt ctc tcg gcc ttt ggc ttt ggt   1296
Thr Asn Gly Glu Pro Lys Arg Ala Gly Leu Ser Ala Phe Gly Phe Gly
            420                 425                 430 ggc acc aac gcc cat gcc gtc ttt gag gag cat gac ccc tcc aac gcc   1344
Gly Thr Asn Ala His Ala Val Phe Glu Glu His Asp Pro Ser Asn Ala
            435                 440                 445 gcc tgc                                                            1350
Ala Cys
    450

<210> SEQ ID NO 28
<211> LENGTH: 450
<212> TYPE: PRT
<213> ORGANISM: Schizochytrium sp.
<220> FEATURE:
<221> NAME/KEY: misc_feature
<222> LOCATION: (370)..(370)
<223> OTHER INFORMATION: The 'Xaa' at location 370 stands for Leu.
<220> FEATURE:
<221> NAME/KEY: misc_feature
<222> LOCATION: (371)..(371)
<223> OTHER INFORMATION: The 'Xaa' at location 371 stands for Ala, or
      Val.

<400> SEQUENCE: 28

Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60

Lys Ala Glu Arg Ser Lys Tyr Ala Asp Thr Phe Cys Asn Glu Thr Tyr
65                  70                  75                  80

Gly Thr Leu Asp Glu Asn Glu Ile Asp Asn Glu His Glu Leu Leu Leu
                85                  90                  95

Asn Leu Ala Lys Gln Ala Leu Ala Glu Thr Ser Val Lys Asp Ser Thr
            100                 105                 110

Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
    130                 135                 140
```

```
Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
            165                 170                 175

Ser Phe Val Ala Glu Glu Leu Asn Leu Gly Ala Leu His Tyr Ser Val
        180                 185                 190

Asp Ala Ala Cys Ala Thr Ala Leu Tyr Val Leu Arg Leu Ala Gln Asp
    195                 200                 205

His Leu Val Ser Gly Ala Ala Asp Val Met Leu Cys Gly Ala Thr Cys
210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
            245                 250                 255

Ser Gln Gly Leu Thr Pro Gly Glu Gly Gly Ser Ile Met Val Leu Lys
        260                 265                 270

Arg Leu Asp Asp Ala Ile Arg Asp Gly Asp His Ile Tyr Gly Thr Leu
    275                 280                 285

Leu Gly Ala Asn Val Ser Asn Ser Gly Thr Gly Leu Pro Leu Lys Pro
290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
            325                 330                 335

Thr Pro Gln Gly Asp Arg Val Glu Ile Asp Ala Val Lys Ala Cys Phe
        340                 345                 350

Glu Gly Lys Val Pro Arg Phe Gly Thr Thr Lys Gly Asn Phe Gly His
    355                 360                 365

Thr Xaa Xaa Ala Ala Gly Phe Ala Gly Met Cys Lys Val Leu Leu Ser
370                 375                 380

Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
            405                 410                 415

Thr Asn Gly Glu Pro Lys Arg Ala Gly Leu Ser Ala Phe Gly Phe Gly
        420                 425                 430

Gly Thr Asn Ala His Ala Val Phe Glu Glu His Asp Pro Ser Asn Ala
    435                 440                 445

Ala Cys
450

<210> SEQ ID NO 29
<211> LENGTH: 1497
<212> TYPE: DNA
<213> ORGANISM: Schizochytrium sp.
<220> FEATURE:
<221> NAME/KEY: CDS
<222> LOCATION: (1)..(1497)

<400> SEQUENCE: 29 aag gtt cag ccc gtc ttt gcc aac ggc gcc gcc act gtc ggc ccc gag     48
Lys Val Gln Pro Val Phe Ala Asn Gly Ala Ala Thr Val Gly Pro Glu
1               5                   10                  15 gcc tcc aag gct tcc tcc ggc gcc agc gcc agc gcc agc gcc gcc ccg     96
Ala Ser Lys Ala Ser Ser Gly Ala Ser Ala Ser Ala Ser Ala Ala Pro
            20                  25                  30 gcc aag cct gcc ttc agc gcc gat gtt ctt gcg ccc aag ccc gtt gcc    144
```

-continued

```
                Ala Lys Pro Ala Phe Ser Ala Asp Val Leu Ala Pro Lys Pro Val Ala
                         35                  40                  45 ctt ccc gag cac atc ctc aag ggc gac gcc ctc gcc ccc aag gag atg          192
Leu Pro Glu His Ile Leu Lys Gly Asp Ala Leu Ala Pro Lys Glu Met
 50                  55                  60 tcc tgg cac ccc atg gcc cgc atc ccg ggc aac ccg acg ccc tct ttt          240
Ser Trp His Pro Met Ala Arg Ile Pro Gly Asn Pro Thr Pro Ser Phe
 65                  70                  75                  80 gcg ccc tcg gcc tac aag ccg cgc aac atc gcc ttt acg ccc ttc ccc          288
Ala Pro Ser Ala Tyr Lys Pro Arg Asn Ile Ala Phe Thr Pro Phe Pro
                 85                  90                  95 ggc aac ccc aac gat aac gac cac acc ccg ggc aag atg ccg ctc acc          336
Gly Asn Pro Asn Asp Asn Asp His Thr Pro Gly Lys Met Pro Leu Thr
            100                 105                 110 tgg ttc aac atg gcc gag ttc atg gcc ggc aag gtc agc atg tgc ctc          384
Trp Phe Asn Met Ala Glu Phe Met Ala Gly Lys Val Ser Met Cys Leu
        115                 120                 125 ggc ccc gag ttc gcc aag ttc gac gac tcg aac acc agc cgc agc ccc          432
Gly Pro Glu Phe Ala Lys Phe Asp Asp Ser Asn Thr Ser Arg Ser Pro
    130                 135                 140 gct tgg gac ctc gct ctc gtc acc cgc gcc gtg tct gtg tct gac ctc          480
Ala Trp Asp Leu Ala Leu Val Thr Arg Ala Val Ser Val Ser Asp Leu
145                 150                 155                 160 aag cac gtc aac tac cgc aac atc gac ctc gac ccc tcc aag ggt acc          528
Lys His Val Asn Tyr Arg Asn Ile Asp Leu Asp Pro Ser Lys Gly Thr
                165                 170                 175 atg gtc ggc gag ttc gac tgc ccc gcg gac gcc tgg ttc tac aag ggc          576
Met Val Gly Glu Phe Asp Cys Pro Ala Asp Ala Trp Phe Tyr Lys Gly
            180                 185                 190 gcc tgc aac gat gcc cac atg ccg tac tcg atc ctc atg gag atc gcc          624
Ala Cys Asn Asp Ala His Met Pro Tyr Ser Ile Leu Met Glu Ile Ala
        195                 200                 205 ctc cag acc tcg ggt gtg ctc acc tcg gtg ctc aag gcg ccc ctg acc          672
Leu Gln Thr Ser Gly Val Leu Thr Ser Val Leu Lys Ala Pro Leu Thr
    210                 215                 220 atg gag aag gac gac atc ctc ttc cgc aac ctc gac gcc aac gcc gag          720
Met Glu Lys Asp Asp Ile Leu Phe Arg Asn Leu Asp Ala Asn Ala Glu
225                 230                 235                 240 ttc gtg cgc gcc gac ctc gac tac cgc ggc aag act atc cgc aac gtc          768
Phe Val Arg Ala Asp Leu Asp Tyr Arg Gly Lys Thr Ile Arg Asn Val
                245                 250                 255 acc aag tgc act ggc tac agc atg ctc ggc gag atg ggc gtc cac cgc          816
Thr Lys Cys Thr Gly Tyr Ser Met Leu Gly Glu Met Gly Val His Arg
            260                 265                 270 ttc acc ttt gag ctc tac gtc gat gat gtg ctc ttt tac aag ggc tcg          864
Phe Thr Phe Glu Leu Tyr Val Asp Asp Val Leu Phe Tyr Lys Gly Ser
        275                 280                 285 acc tcg ttc ggc tgg ttc gtg ccc gag gtc ttt gcc gcc cag gcc ggc          912
Thr Ser Phe Gly Trp Phe Val Pro Glu Val Phe Ala Ala Gln Ala Gly
    290                 295                 300 ctc gac aac ggc cgc aag tcg gag ccc tgg ttc att gag aac aag gtt          960
Leu Asp Asn Gly Arg Lys Ser Glu Pro Trp Phe Ile Glu Asn Lys Val
305                 310                 315                 320 ccg gcc tcg cag gtc tcc tcc ttt gac gtg cgc ccc aac ggc agc ggc         1008
Pro Ala Ser Gln Val Ser Ser Phe Asp Val Arg Pro Asn Gly Ser Gly
                325                 330                 335 cgc acc gcc atc ttc gcc aac gcc ccc agc ggc gcc cag ctc aac cgc         1056
Arg Thr Ala Ile Phe Ala Asn Ala Pro Ser Gly Ala Gln Leu Asn Arg
            340                 345                 350 cgc acg gac cag ggc cag tac ctc gac gcc gtc gac att gtc tcc ggc         1104
```

```
Arg Thr Asp Gln Gly Gln Tyr Leu Asp Ala Val Asp Ile Val Ser Gly
        355                 360                 365 agc ggc aag aag agc ctc ggc tac gcc cac ggt tcc aag acg gtc aac      1152
Ser Gly Lys Lys Ser Leu Gly Tyr Ala His Gly Ser Lys Thr Val Asn
370                 375                 380 ccg aac gac tgg ttc ttc tcg tgc cac ttt tgg ttt gac tcg gtc atg      1200
Pro Asn Asp Trp Phe Phe Ser Cys His Phe Trp Phe Asp Ser Val Met
385                 390                 395                 400 ccc gga agt ctc ggt gtc gag tcc atg ttc cag ctc gtc gag gcc atc      1248
Pro Gly Ser Leu Gly Val Glu Ser Met Phe Gln Leu Val Glu Ala Ile
                405                 410                 415 gcc gcc cac gag gat ctc gct ggc aag cac ggc att gcc aac ccc acc      1296
Ala Ala His Glu Asp Leu Ala Gly Lys His Gly Ile Ala Asn Pro Thr
            420                 425                 430 ttt gtg cac gcc ccg ggc aag atc agc tgg aag tac cgc ggc cag ctc      1344
Phe Val His Ala Pro Gly Lys Ile Ser Trp Lys Tyr Arg Gly Gln Leu
        435                 440                 445 acg ccc aag agc aag aag atg gac tcg gag gtc cac atc gtg tcc gtg      1392
Thr Pro Lys Ser Lys Lys Met Asp Ser Glu Val His Ile Val Ser Val
450                 455                 460 gac gcc cac gac ggc gtt gtc gac ctc gtc gcc gac ggc ttc ctc tgg      1440
Asp Ala His Asp Gly Val Val Asp Leu Val Ala Asp Gly Phe Leu Trp
465                 470                 475                 480 gcc gac agc ctc cgc gtc tac tcg gtc agc aac att cgc gtg cgc atc      1488
Ala Asp Ser Leu Arg Val Tyr Ser Val Ser Asn Ile Arg Val Arg Ile
                485                 490                 495 gcc tcc ggt                                                          1497
Ala Ser Gly <210> SEQ ID NO 30
<211> LENGTH: 499
<212> TYPE: PRT
<213> ORGANISM: Schizochytrium sp.

<400> SEQUENCE: 30

Lys Val Gln Pro Val Phe Ala Asn Gly Ala Ala Thr Val Gly Pro Glu
1               5                   10                  15

Ala Ser Lys Ala Ser Ser Gly Ala Ser Ala Ser Ala Ser Ala Ala Pro
            20                  25                  30

Ala Lys Pro Ala Phe Ser Ala Asp Val Leu Ala Pro Lys Pro Val Ala
        35                  40                  45

Leu Pro Glu His Ile Leu Lys Gly Asp Ala Leu Ala Pro Lys Glu Met
    50                  55                  60

Ser Trp His Pro Met Ala Arg Ile Pro Gly Asn Pro Thr Pro Ser Phe
65                  70                  75                  80

Ala Pro Ser Ala Tyr Lys Pro Arg Asn Ile Ala Phe Thr Pro Phe Pro
                85                  90                  95

Gly Asn Pro Asn Asp Asn Asp His Thr Pro Gly Lys Met Pro Leu Thr
            100                 105                 110

Trp Phe Asn Met Ala Glu Phe Met Ala Gly Lys Val Ser Met Cys Leu
        115                 120                 125

Gly Pro Glu Phe Ala Lys Phe Asp Asp Ser Asn Thr Ser Arg Ser Pro
    130                 135                 140

Ala Trp Asp Leu Ala Leu Val Thr Arg Ala Val Ser Val Ser Asp Leu
145                 150                 155                 160

Lys His Val Asn Tyr Arg Asn Ile Asp Leu Asp Pro Ser Lys Gly Thr
                165                 170                 175

Met Val Gly Glu Phe Asp Cys Pro Ala Asp Ala Trp Phe Tyr Lys Gly
```

```
                    180                 185                 190
Ala Cys Asn Asp Ala His Met Pro Tyr Ser Ile Leu Met Glu Ile Ala
            195                 200                 205

Leu Gln Thr Ser Gly Val Leu Thr Ser Val Leu Lys Ala Pro Leu Thr
        210                 215                 220

Met Glu Lys Asp Asp Ile Leu Phe Arg Asn Leu Asp Ala Asn Ala Glu
225                 230                 235                 240

Phe Val Arg Ala Asp Leu Asp Tyr Arg Gly Lys Thr Ile Arg Asn Val
            245                 250                 255

Thr Lys Cys Thr Gly Tyr Ser Met Leu Gly Glu Met Gly Val His Arg
        260                 265                 270

Phe Thr Phe Glu Leu Tyr Val Asp Asp Val Leu Phe Tyr Lys Gly Ser
    275                 280                 285

Thr Ser Phe Gly Trp Phe Val Pro Glu Val Phe Ala Ala Gln Ala Gly
        290                 295                 300

Leu Asp Asn Gly Arg Lys Ser Glu Pro Trp Phe Ile Glu Asn Lys Val
305                 310                 315                 320

Pro Ala Ser Gln Val Ser Ser Phe Asp Val Arg Pro Asn Gly Ser Gly
            325                 330                 335

Arg Thr Ala Ile Phe Ala Asn Ala Pro Ser Gly Ala Gln Leu Asn Arg
        340                 345                 350

Arg Thr Asp Gln Gly Gln Tyr Leu Asp Ala Val Asp Ile Val Ser Gly
    355                 360                 365

Ser Gly Lys Lys Ser Leu Gly Tyr Ala His Gly Ser Lys Thr Val Asn
        370                 375                 380

Pro Asn Asp Trp Phe Phe Ser Cys His Phe Trp Phe Asp Ser Val Met
385                 390                 395                 400

Pro Gly Ser Leu Gly Val Glu Ser Met Phe Gln Leu Val Glu Ala Ile
            405                 410                 415

Ala Ala His Glu Asp Leu Ala Gly Lys His Gly Ile Ala Asn Pro Thr
        420                 425                 430

Phe Val His Ala Pro Gly Lys Ile Ser Trp Lys Tyr Arg Gly Gln Leu
    435                 440                 445

Thr Pro Lys Ser Lys Lys Met Asp Ser Glu Val His Ile Val Ser Val
450                 455                 460

Asp Ala His Asp Gly Val Asp Leu Val Ala Asp Gly Phe Leu Trp
            470                 475                 480
465

Ala Asp Ser Leu Arg Val Tyr Ser Val Ser Asn Ile Arg Val Arg Ile
        485                 490                 495

Ala Ser Gly

<210> SEQ ID NO 31
<211> LENGTH: 1512
<212> TYPE: DNA
<213> ORGANISM: Schizochytrium sp.
<220> FEATURE:
<221> NAME/KEY: CDS
<222> LOCATION: (1)..(1512)

<400> SEQUENCE: 31 gcc ccg ctc tac ctc tcg cag gac ccg acc agc ggc cag ctc aag aag     48
Ala Pro Leu Tyr Leu Ser Gln Asp Pro Thr Ser Gly Gln Leu Lys Lys
1               5                   10                  15 cac acc gac gtg gcc tcc ggc cag gcc acc atc gtg cag ccc tgc acg     96
His Thr Asp Val Ala Ser Gly Gln Ala Thr Ile Val Gln Pro Cys Thr
            20                  25                  30
```

```
ctc ggc gac ctc ggt gac cgc tcc ttc atg gag acc tac ggc gtc gtc      144
Leu Gly Asp Leu Gly Asp Arg Ser Phe Met Glu Thr Tyr Gly Val Val
        35                  40                  45 gcc ccg ctg tac acg ggc gcc atg gcc aag ggc att gcc tcg gcg gac      192
Ala Pro Leu Tyr Thr Gly Ala Met Ala Lys Gly Ile Ala Ser Ala Asp
 50                  55                  60 ctc gtc atc gcc gcc ggc aag cgc aag atc ctc ggc tcc ttt ggc gcc      240
Leu Val Ile Ala Ala Gly Lys Arg Lys Ile Leu Gly Ser Phe Gly Ala
65                  70                  75                  80 ggc ggc ctc ccc atg cac cac gtg cgc gcc gcc ctc gag aag atc cag      288
Gly Gly Leu Pro Met His His Val Arg Ala Ala Leu Glu Lys Ile Gln
                    85                  90                  95 gcc gcc ctg cct cag ggc ccc tac gcc gtc aac ctc atc cac tcg cct      336
Ala Ala Leu Pro Gln Gly Pro Tyr Ala Val Asn Leu Ile His Ser Pro
                100                 105                 110 ttt gac agc aac ctc gag aag ggc aac gtc gat ctc ttc ctc gag aag      384
Phe Asp Ser Asn Leu Glu Lys Gly Asn Val Asp Leu Phe Leu Glu Lys
            115                 120                 125 ggc gtc act gtg gtg gag gcc tcg gca ttc atg acc ctc acc ccg cag      432
Gly Val Thr Val Val Glu Ala Ser Ala Phe Met Thr Leu Thr Pro Gln
130                 135                 140 gtc gtg cgc tac cgc gcc gcc ggc ctc tcg cgc aac gcc gac ggt tcg      480
Val Val Arg Tyr Arg Ala Ala Gly Leu Ser Arg Asn Ala Asp Gly Ser
145                 150                 155                 160 gtc aac atc cgc aac cgc atc atc ggc aag gtc tcg cgc acc gag ctc      528
Val Asn Ile Arg Asn Arg Ile Ile Gly Lys Val Ser Arg Thr Glu Leu
                165                 170                 175 gcc gag atg ttc atc cgc ccg gcc ccg gag cac ctc ctc gag aag ctc      576
Ala Glu Met Phe Ile Arg Pro Ala Pro Glu His Leu Leu Glu Lys Leu
            180                 185                 190 atc gcc tcg ggc gag atc acc cag gag cag gcc gag ctc gcg cgc cgc      624
Ile Ala Ser Gly Glu Ile Thr Gln Glu Gln Ala Glu Leu Ala Arg Arg
        195                 200                 205 gtt ccc gtc gcc gac gat atc gct gtc gag gct gac tcg ggc ggc cac      672
Val Pro Val Ala Asp Asp Ile Ala Val Glu Ala Asp Ser Gly Gly His
210                 215                 220 acc gac aac cgc ccc atc cac gtc atc ctc ccg ctc atc atc aac ctc      720
Thr Asp Asn Arg Pro Ile His Val Ile Leu Pro Leu Ile Ile Asn Leu
225                 230                 235                 240 cgc aac cgc ctg cac cgc gag tgc ggc tac ccc gcg cac ctc cgc gtc      768
Arg Asn Arg Leu His Arg Glu Cys Gly Tyr Pro Ala His Leu Arg Val
                245                 250                 255 cgc gtt ggc gcc ggc ggt ggc gtc ggc tgc ccg cag gcc gcc gcc gcc      816
Arg Val Gly Ala Gly Gly Gly Val Gly Cys Pro Gln Ala Ala Ala Ala
            260                 265                 270 gcg ctc acc atg ggc gcc gcc ttc atc gtc acc ggc act gtc aac cag      864
Ala Leu Thr Met Gly Ala Ala Phe Ile Val Thr Gly Thr Val Asn Gln
        275                 280                 285 gtc gcc aag cag tcc ggc acc tgc gac aac gtg cgc aag cag ctc tcg      912
Val Ala Lys Gln Ser Gly Thr Cys Asp Asn Val Arg Lys Gln Leu Ser
290                 295                 300 cag gcc acc tac tcg gat atc tgc atg gcc ccg gcc gcc gac atg ttc      960
Gln Ala Thr Tyr Ser Asp Ile Cys Met Ala Pro Ala Ala Asp Met Phe
305                 310                 315                 320 gag gag ggc gtc aag ctc cag gtc ctc aag aag gga acc atg ttc ccc     1008
Glu Glu Gly Val Lys Leu Gln Val Leu Lys Lys Gly Thr Met Phe Pro
                325                 330                 335 tcg cgc gcc aac aag ctc tac gag ctc ttt tgc aag tac gac tcc ttc     1056
Ser Arg Ala Asn Lys Leu Tyr Glu Leu Phe Cys Lys Tyr Asp Ser Phe
            340                 345                 350
```

```
gac tcc atg cct cct gcc gag ctc gag cgt atc gag aag cgt atc ttc    1104
Asp Ser Met Pro Pro Ala Glu Leu Glu Arg Ile Glu Lys Arg Ile Phe
        355                 360                 365 aag cgc gca ctc cag gag gtc tgg gag gag acc aag gac ttt tac att    1152
Lys Arg Ala Leu Gln Glu Val Trp Glu Glu Thr Lys Asp Phe Tyr Ile
    370                 375                 380 aac ggt ctc aag aac ccg gag aag atc cag cgc gcc gag cac gac ccc    1200
Asn Gly Leu Lys Asn Pro Glu Lys Ile Gln Arg Ala Glu His Asp Pro
385                 390                 395                 400 aag ctc aag atg tcg ctc tgc ttc cgc tgg tac ctt ggt ctt gcc agc    1248
Lys Leu Lys Met Ser Leu Cys Phe Arg Trp Tyr Leu Gly Leu Ala Ser
            405                 410                 415 cgc tgg gcc aac atg ggc gcc ccg gac cgc gtc atg gac tac cag gtc    1296
Arg Trp Ala Asn Met Gly Ala Pro Asp Arg Val Met Asp Tyr Gln Val
        420                 425                 430 tgg tgt ggc ccg gcc att ggc gcc ttc aac gac ttc atc aag ggc acc    1344
Trp Cys Gly Pro Ala Ile Gly Ala Phe Asn Asp Phe Ile Lys Gly Thr
    435                 440                 445 tac ctc gac ccc gct gtc tcc aac gag tac ccc tgt gtc gtc cag atc    1392
Tyr Leu Asp Pro Ala Val Ser Asn Glu Tyr Pro Cys Val Val Gln Ile
450                 455                 460 aac ctg caa atc ctc cgt ggt gcc tgc tac ctg cgc cgt ctc aac gcc    1440
Asn Leu Gln Ile Leu Arg Gly Ala Cys Tyr Leu Arg Arg Leu Asn Ala
            470                 475                 480 ctg cgc aac gac ccg cgc att gac ctc gag acc gag gat gct gcc ttt    1488
Leu Arg Asn Asp Pro Arg Ile Asp Leu Glu Thr Glu Asp Ala Ala Phe
        485                 490                 495 gtc tac gag ccc acc aac gcg ctc                                    1512
Val Tyr Glu Pro Thr Asn Ala Leu
            500

<210> SEQ ID NO 32
<211> LENGTH: 504
<212> TYPE: PRT
<213> ORGANISM: Schizochytrium sp.

<400> SEQUENCE: 32

Ala Pro Leu Tyr Leu Ser Gln Asp Pro Thr Ser Gly Gln Leu Lys Lys
1               5                   10                  15

His Thr Asp Val Ala Ser Gly Gln Ala Thr Ile Val Gln Pro Cys Thr
            20                  25                  30

Leu Gly Asp Leu Gly Asp Arg Ser Phe Met Glu Thr Tyr Gly Val Val
        35                  40                  45

Ala Pro Leu Tyr Thr Gly Ala Met Ala Lys Gly Ile Ala Ser Ala Asp
    50                  55                  60

Leu Val Ile Ala Ala Gly Lys Arg Lys Ile Leu Gly Ser Phe Gly Ala
65                  70                  75                  80

Gly Gly Leu Pro Met His His Val Arg Ala Ala Leu Glu Lys Ile Gln
                85                  90                  95

Ala Ala Leu Pro Gln Gly Pro Tyr Ala Val Asn Leu Ile His Ser Pro
            100                 105                 110

Phe Asp Ser Asn Leu Glu Lys Gly Asn Val Asp Leu Phe Leu Glu Lys
        115                 120                 125

Gly Val Thr Val Val Glu Ala Ser Ala Phe Met Thr Leu Thr Pro Gln
    130                 135                 140

Val Val Arg Tyr Arg Ala Ala Gly Leu Ser Arg Asn Ala Asp Gly Ser
145                 150                 155                 160

Val Asn Ile Arg Asn Arg Ile Ile Gly Lys Val Ser Arg Thr Glu Leu
                165                 170                 175
```

Ala Glu Met Phe Ile Arg Pro Ala Pro Glu His Leu Leu Glu Lys Leu
            180                 185                 190

Ile Ala Ser Gly Glu Ile Thr Gln Glu Gln Ala Glu Leu Ala Arg Arg
            195                 200                 205

Val Pro Val Ala Asp Asp Ile Ala Val Glu Ala Asp Ser Gly Gly His
210                 215                 220

Thr Asp Asn Arg Pro Ile His Val Ile Leu Pro Leu Ile Ile Asn Leu
225                 230                 235                 240

Arg Asn Arg Leu His Arg Glu Cys Gly Tyr Pro Ala His Leu Arg Val
                245                 250                 255

Arg Val Gly Ala Gly Gly Val Gly Cys Pro Gln Ala Ala Ala Ala
                260                 265                 270

Ala Leu Thr Met Gly Ala Ala Phe Ile Val Thr Gly Val Asn Gln
            275                 280                 285

Val Ala Lys Gln Ser Gly Thr Cys Asp Asn Val Arg Lys Gln Leu Ser
290                 295                 300

Gln Ala Thr Tyr Ser Asp Ile Cys Met Ala Pro Ala Ala Asp Met Phe
305                 310                 315                 320

Glu Glu Gly Val Lys Leu Gln Val Leu Lys Lys Gly Thr Met Phe Pro
                325                 330                 335

Ser Arg Ala Asn Lys Leu Tyr Glu Leu Phe Cys Lys Tyr Asp Ser Phe
                340                 345                 350

Asp Ser Met Pro Pro Ala Glu Leu Glu Arg Ile Glu Lys Arg Ile Phe
                355                 360                 365

Lys Arg Ala Leu Gln Glu Val Trp Glu Glu Thr Lys Asp Phe Tyr Ile
370                 375                 380

Asn Gly Leu Lys Asn Pro Glu Lys Ile Gln Arg Ala Glu His Asp Pro
385                 390                 395                 400

Lys Leu Lys Met Ser Leu Cys Phe Arg Trp Tyr Leu Gly Leu Ala Ser
                405                 410                 415

Arg Trp Ala Asn Met Gly Ala Pro Asp Arg Val Met Asp Tyr Gln Val
                420                 425                 430

Trp Cys Gly Pro Ala Ile Gly Ala Phe Asn Asp Phe Ile Lys Gly Thr
            435                 440                 445

Tyr Leu Asp Pro Ala Val Ser Asn Glu Tyr Pro Cys Val Val Gln Ile
450                 455                 460

Asn Leu Gln Ile Leu Arg Gly Ala Cys Tyr Leu Arg Arg Leu Asn Ala
465                 470                 475                 480

Leu Arg Asn Asp Pro Arg Ile Asp Leu Glu Thr Glu Asp Ala Ala Phe
                485                 490                 495

Val Tyr Glu Pro Thr Asn Ala Leu
            500

```
<210> SEQ ID NO 33
<211> LENGTH: 9
<212> TYPE: PRT
<213> ORGANISM: Artificial sequence
<220> FEATURE:
<223> OTHER INFORMATION: motif
<220> FEATURE:
<221> NAME/KEY: MISC_FEATURE
<222> LOCATION: (2)..(3)
<223> OTHER INFORMATION: x = any amino acid
<220> FEATURE:
<221> NAME/KEY: MISC_FEATURE
<222> LOCATION: (6)..(6)
<223> OTHER INFORMATION: x = A or S
<220> FEATURE:
```

```
<221> NAME/KEY: MISC_FEATURE
<222> LOCATION: (7)..(8)
<223> OTHER INFORMATION: x = any amino acid

<400> SEQUENCE: 33

Trp Xaa Xaa Lys Glu Xaa Xaa Xaa Lys
1               5

<210> SEQ ID NO 34
<211> LENGTH: 6
<212> TYPE: PRT
<213> ORGANISM: Artificial sequence
<220> FEATURE:
<223> OTHER INFORMATION: motif
<220> FEATURE:
<221> NAME/KEY: MISC_FEATURE
<222> LOCATION: (3)..(3)
<223> OTHER INFORMATION: x = I or L or V

<400> SEQUENCE: 34

Phe Asn Xaa Ser His Ser
1               5

<210> SEQ ID NO 35
<211> LENGTH: 5
<212> TYPE: PRT
<213> ORGANISM: Artificial sequence
<220> FEATURE:
<223> OTHER INFORMATION: motif
<220> FEATURE:
<221> NAME/KEY: MISC_FEATURE
<222> LOCATION: (1)..(5)
<223> OTHER INFORMATION: x = I or L or V

<400> SEQUENCE: 35

Xaa Gly Xaa Asp Xaa
1               5

<210> SEQ ID NO 36
<211> LENGTH: 4244
<212> TYPE: DNA
<213> ORGANISM: Schizochytrium sp.

<400> SEQUENCE: 36
tttctctctc tcgagctgtt gctgctgctg ctgctgctgc tgcttccttg ctggttctca      60
cgtccgttcg atcaagcgct cgctcgctcg accgatcggt gcgtgcgtgc gtgcgtgagt     120
cttgttgcca ggcagccgca ggctgtctgt ctgtttgtgt agtttttaccc tcggggttcg    180
gggtctgcct gcctcccgct cccgcccgcc gccgcccgta tccacccgc tcgcctccgc      240
ccatcgggcc tcgcctcctc gcgccgcacg catcgcgcgc atcgcatgca tcatgctgcc     300
acgcacgggg ggacgcgcgc cccgcgtccc ccgccgccgc cgtcgtcgtc tggcgatgcc     360
gtcgccgccc tccttccttc cctcgcctcc tcttcctccc gagccccccct gtcttccttc    420
gcccccgcag cggcgcgcag gaagcgagga gagcggggag gagagaagaa aagaaaagaa     480
aagaaaagaa aataacagcg ccgtctcgcg cagacgcgcg cggccgcgtg cgaggcggcg     540
tgatggggct tctcgtggcg cggctgcggc ctggcccggc ctcgcctttg aggtgcaggc     600
tttgggagag aagagtggga cgcggagaag ataagatggt gccatggcgc aggacggaga     660
ggttgctgaa acttcttcga gcggcacagg cgatggcgag agaccgacag ctgccggcgc     720
ggagggatg gataccctccc gaggctggca tggacgagct ggccgcgcgg atctggctgg     780
ccgcgcggcg gtgggtccgg aggcgcgagg ttggtttct tcatacctga taccatacgg     840
tattcattct tcctctccag gaaggaagca agtcacatag agtatcacta gcctaatgat     900
```

-continued

```
ggactctatg ttttagggca cgtcggagca gaaggcgcga gcgattcgaa tgcgagcgat    960
agatacagca cagagacctt gccggcgacg cggatgcagg cgagcacgca cgcaccgcac   1020
gcacggcagc ggtgcacgcg ctcctcggca gatgcacggt tctgcgccgc gcctttacat   1080
tttttgattt taggtggtgt gcctgccact ttgaacatca tccacaagtc aacgcagcat   1140
caagaggcaa gcaagtacat acatccattc gaattcaagt tcaagagacg cagcaacagc   1200
cgccgctccg ctcaagctgc agctagctgg ctgacagggc tcgctggctg tagtggaaaa   1260
ttccattcac ttttctgcat ccgcggccag caggcccgta cgcacgttct ctcgtttgtt   1320
tgttcgttcg tgcgtgcgtg cgtgcgtccc agctgcctgt ctaatctgcc gcgcgatcca   1380
acgaccctcg gtcgtcgccg caagcgaaac ccgacgccga cctggccaat gccgcaagaa   1440
tgctaagcgc gcagcaatgc tgagagtaat cttcagccca ccaagtcatt atcgctgccc   1500
aagtctccat cgcagccaca ttcaggcttt ctctctctct ccctccctct ctttctgccg   1560
ggagagaagg aaagacccgc cgccgccgcc tctgcgcctg tgacgggctg tccgttgtaa   1620
gccctcttag acagttccta ggtgccgggc gccgccgcgc ctccgtcgca ggcacacgta   1680
ggcggccacg ggttccccccc gcaccttcca caccttcttc ccccgcagcc ggaccgcgcg   1740
ccgtctgctt acgcacttcg cgcggccgcc gcccgcgaac ccgagcgcgt gctgtgggcg   1800
ccgtcttccg gccgcgtcgg aggtcgtccc cgcgccgcgc tactccgggt cctgtgcggt   1860
acgtacttaa tattaacagt gggacctcgc acaggacctg acggcagcac agacgtcgcc   1920
gcctcgcatc gctggggacg caggcgaggc atcccgcgc ggccccgcac cggggaggct   1980
gcggggcggc ctcttccggc cggcggccgc atcaggcgga tgacgcaaga gccctcgcag   2040
tcgctcgctc gcgggagcgc agcgcggcgc cagcgtggcc aagctcccgc cccttctggc   2100
tggctgcatg cctgcctgcc tgcctgcctg cgtgcgtgcg tgcgtgcgtg ccttcgtgcg   2160
tgcctgcctt cgtgcgtgcg tgcgtgagtg cggcggaaga gggatcatgc gaggatcaat   2220
cacccgccgc acctcgactt ttgaagaagc cgcgatgcga tgcgatgcga tgcgatgcga   2280
cgcgataccg tgcgaggcta cgaagcgagt ctggccggcc gtcatacaac gcacgttttc   2340
gagaaggagg gctggcggag gcgtgcatgc cggcgaccat tgcgaacgcg cgtctcgtg   2400
gctggcgaag gtgcctggag gatctaacga tcgctgctat gatgctatag ctgtgctgat   2460
ccccggtcca ttccaccacg tctgtgcctg ccgcctgacc tgcgcttggc tttccttcaa   2520
gttctcctcc gccgggcctt caggaccgag acgagacctg cagctgcagc tagactcgcg   2580
ctcgctcgcg gaggattcgc cggccgccgg gccggacggg actcgcgagg tcacacggcc   2640
gccggcgatc gcgatggctg tgctgacgta ctcgtgcgtg gcagccgtac gtcagcgacg   2700
ccgcctccgt attgtggatt cgttagttgg ttgttggttg atttgttgat taatttttt    2760
gttcgtaggc ttggttatag ctaatagttt agtttatact ggtgctcttc ggtgctgatt   2820
tagctcgact tgggtccaca ccactgcccc tctactgtga atggatcaat ggacgcacga   2880
cgggccgacg aaagtgcgcg agtgaggtaa cctaagcaac ggcggtcttc agagggacg    2940
cacgccctcc gtcgcagtca gtccagacag gcagaaaagc gtcttaggga ccacgcacgc   3000
acgcacgcac gcacgcacgc ccgcacgcac gctccctccc tcgcgtgcct attttttag    3060
gcttccttcc gcacgggcct acctctcgct ccctcgcctc gccgcaccag gcggcagcag   3120
cgatacctgc cggtgccgcc tccgtcacgc gctcagccgc agctcagccc agccgcgagc   3180
tagggttgt tcgtcctgaa ttgtttgatt tgatttgatt tgatttgatc cgatccgatc   3240
cgatctgatc tgatttgctt tgctttgctt tgtctccctc ccggcgcgga ccaagcgtcc   3300
```

```
gtctgcgcgc cgcagcttcc cttcttctcc cagccctcct tctgctcccg cctctcgcgc    3360
aagcacgcag cttcgccgcc gcatccggtc ggtcggtcgg tcgatcgacc cgcctgccgc    3420
tgctgctgtg gccgggcttt tctccatcgg cgactctttc ttctccatac gtcctactac    3480
gtacatacat actgccggct tcctcctctt ccagcgcggc gacggcggca ggctgcgacg    3540
tcgtcgccgc cgcgggcgcc gcgcgcgccg ccgccgccgc ccgcgtcgca gggcctcgtc    3600
gccgccgccg ctccgctccg ctccgaggcc gcgagagggc cgcggcggcg cgatggatgg    3660
atggatggat ggatggatgg atggattttg ttgatcgatg gcggcgcatg gcggagatg     3720 agcgaggacg agcgcgcgag cgcggcagcc ggattcgcag ggcctcgctc gcctcgcgcc    3780
cgctgccgcg cccgccttgc gagcctgcgc cgcgagcgag cgagcgagcg agcggggctt    3840
tctttgtctc gcgcgccgct tggcctcgtg tgtcttgtgc ttgcgtagcg ggcgccgcgg    3900
tggaagatgg ctcattcaat cgacccattc acgcacgcac tccggcgcgc agagaaggcc    3960
gaggaggagc agcaagcaaa ccaaaagctc tcgcgctcgc ggtctcgggc tcgagcggtc    4020
tcggagagag agtcttgcgg cgaccaccgg cagcagcagc agcagcagca gcgctgtcga    4080
gcacgagcac gagcacgagc acgagcacga gcattcgagc aagaggacag acacggttgt    4140
cagcgcctag ctcgctcgat acagaaagag gcgggttggg cgtaaaaaaa aaggagcacg    4200
caagccgcca gccagccagc tagctagcca gcctgcctgc caaa                     4244

<210> SEQ ID NO 37
<211> LENGTH: 3886
<212> TYPE: DNA
<213> ORGANISM: Schizochytrium sp.
<220> FEATURE:
<221> NAME/KEY: misc_feature
<222> LOCATION: (2115)..(2115)
<223> OTHER INFORMATION: n = a, c, g, or t

<400> SEQUENCE: 37
gatcttgatt gccaagctct ggattgtcga ttccgatgaa tcgagctctt tgttgtcgag      60
ctctggcttg ccgagctttc agaaatagac aaaattgccg agttcctgat tgcgggctc     120 tcgattgcca aggtctggtg gattctcgaa ctctcgattg tcaaaatctt ggtcgtctcg    180
tcggattctt tcctgatttg tttttgtcaag accttgagat tgtgcaaaac cttgatcgtt    240
gacaaaccct tgatcgacag cagcctttca tcacgctcag ctcttgtcat tgattatatt    300
ccccctgaca gccaacacct tgatgcaggg tctcaacctt gattttttgga ggccatcatc    360 agcatcacgc cccggcactc accctcaaca ttcgacagcc aacgcttttt tttcttcgac    420
taggatctga gaataaaagc aggtcaccac gaccgtaggc caacgcgaca accatggaaa    480
taaagtgaca acgaacgact tgcaagttta aatgtaaaga gcagcaattg cccgcccaca    540
gacaaatgaa agcaggcgcc gagtcttatt tgaggaggtg ggcctgtggc aatgggcgaa    600
agaaaatcaa ggacaaggag agcaggttac gtaccggtat actggtatac gtacatggat    660
ggttcttggc aagttgacgg gatgtgtgcg agtgaccgtg gtagttaacg aaagagccgc    720
aagggcaagg aaagcaagag aatgcagact tttccacagg atggatgggt ccgcagcttg    780
ccgcatgatg aaacgctgta tttcacctgg cacgtggtgg cgcacgcgcc cacatatgat    840
cgcggcggcg ggtgtattat acattttccc cctcaggtct actgccatcc ctccatgcgt    900
cgctcgtgcg aacgacgcaa gcctttcgca tcgtgcagcc tctttctggt aaggcaagag    960
ctaaacccaa acctaaacga aagaacattt ttacctctct ctctctccca ttggtcgcgt   1020
gcgctccgcc gctcgctcct cctcctgcca gtgtcgcgcc ctaacttccc ccctccctcc   1080
```

-continued

```
ctccctccct ccctccctct ctcctgccac cgcccctctc tccgcgctgc gtgcggtgct    1140
gccctggacc aatggcatgc tgctgcacgc tcggcggatg acgcaagccg cttcgcaatt    1200
tccggatcag atctcggcgg ggcgtgcgcc gcggggtcac tgcggacctg ccgcggcccc    1260
tgcttctttc acatccatca tgtcctccaa acctccgcct cctccacgca cgtacgcacg    1320
cccgctcgca cgcgcgcact gccgctgcga aagcaagcgc ccgcccgccg cccggcgacg    1380
ggaaggcggc cgcggtctcc ctccgcggtt gcctcgctcc cgcgcggggc tgggcgggca    1440
gcagaaggcg ggtggcggcg gcggcttccg tcttcgtcag cggcctacgt cggcggcggc    1500
gcgcgagact acgcatgccc ttgcgtcatg cgctcgcagg tagccgccgc gggcctagcg    1560
tttccgctgg cgccgcgcct aagccccgg cgcgcacggt attgccgcga taccgtacgg     1620
ccaagaccgc cgcagacgtc ggccctctcg cggccagcca ccagcagcg cagcggagga     1680 agagcgcgca ggcgcggcgg gagggcggcc gcggagcagc gcagagcggg gcggagcagc    1740
gcggagcaga acgggcagac tcggagcggg cagggcgggc agagctttgg ggtttaagga    1800
ccgggttacc ggcgaagtga gcggctgcgg ggagcggctg tgggaggggt gagtacgcaa    1860
gcacgatgcg agcgagagag agacgctgcc gcgaatcaag aaggtaggcg cgctgcgagg    1920
cgcggcggcg gagcggagcg agggagaggg agagggagag agaggagggg agacgtcgcc    1980
gcggcggggc ctgcctggc ctggtttggc ttggtcagcg cggccttgtc cgagcgtgca     2040
gctggagttg ggtggattca tttggatttt cttttgtttt tgtttttctc tctttcccgg    2100
aaagtgttgg ccggncggtg ttctttgttt tgatttcttc aaaagttttg gtggttggtt    2160
ctctctcttg gctctctgtc aggcggtccg gtccacgccc cggcctctcc tctcctctcc    2220
tctcctctcc tctccgtgcg tatacgtacg tacgtttgta tacgtacata catcccgccc    2280
gccgtgccgg cgagggtttg ctcagcctgg agcaatgcga tgcgatgcga tgcgatgcga    2340
cgcgacgcga cgcgagtcac tggttcgcgc tgtggctgtg gcttgcttgc ttacttgctt    2400
tcgagctctc ccgctttctt ctttccttct cacgccacca ccaacgaaag aagatcggcc    2460
ccggcacgcc gctgagaagg gctggcggcg atgacggcac gcgcgcccgc tgccacgttg    2520
gcgctcgctg ctgctgctgc tgctgctgct gctgctgctg ctgctgctgc tgctgcttct    2580
gcgcgcaggc tttgccacga ggccggcgtg ctggccgctg ccgcttccag tccgcgtgga    2640
gagatcgaat gagagataaa ctggatggat tcatcgaggg atgaatgaac gatggttgga    2700 tgccttttt cttttttcagg tccacagcgg gaagcaggag cgcgtgaatc tgccgccatc    2760
cgcatacgtc tgcatcgcat cgcatcgcat gcacgcatcg ctcgccggga ccacagacg     2820 ggcgacaggg cggccagcca gccaggcagc cagccaggca ggcaccagag ggccagagag    2880
cgcgcctcac gcacgcgccg cagtgcgcgc atcgctcgca gtgcagacct tgattccccg    2940
cgcggatctc cgcgagcccg aaacgaagag cgccgtacgg gcccatccta gcgtcgcctc    3000
gcaccgcatc gcatcgcatc gcgttcccta gagagtagta ctcgacgaag gcaccatttc    3060
cgcgctcctc ttcggcgcga tcgaggcccc ggcgccgcg acgatcgcgg cggccgcggc     3120
gctggcggcg gccctggcgc tcgcgctggc ggccgccgcg ggcgtctggc cctgcgcgc     3180 gcgggcgccg caggaggagc ggcagcggct gctcgccgcc agagaagagc gcgccgggcc    3240
cggggaggga cggggaggag aaggagaagg cgcgcaaggc ggccccgaaa gagaagaccc    3300
tggacttgaa cgcgaagaag aagaagaagg agaagaagtt gaagaagaag aagaagaagg    3360
agaggaagtt gaagaagacg aggagcaggc gcgttccaag gcgcgttctc ttccggaggc    3420
gcgttccagc tgcggcggcg gggcgggctg cggggcgggc gcgggcgcgg gtgcgggcag    3480
```

```
aggggacgcg cgcgcggagg cggaggggc cgagcgggag cccctgctgc tgcggggcgc    3540
ccgggccgca ggtgtggcgc gcgcgacgac ggaggcgacg acgccagcgg ccgcgacgac    3600
aaggccggcg gcgtcggcgg gcggaaggcc ccgcgcggag caggggcggg agcaggacaa    3660
ggcgcaggag caggagcagg gccgggagcg ggagcggag cgggcggcgg agcccgaggc    3720
agaacccaat cgagatccag agcgagcaga ggccggccgc gagcccgagc ccgcgccgca    3780
gatcactagt accgctgcgg aatcacagca gcagcagcag cagcagcagc agcagcagca    3840
gcagcagcag ccacgagagg gagataaaga aaaagcggca gagacg                  3886
```